(12) United States Patent
Maw et al.

(10) Patent No.: US 11,484,613 B2
(45) Date of Patent: Nov. 1, 2022

(54) TECHNOLOGIES FOR SANITIZING MEDICAL DEVICES

(71) Applicant: SOCLEAN, INC., Peterborough, NH (US)

(72) Inventors: Kurt Michael Maw, Salem, MA (US); Ashley James Nye Legg, Newton, MA (US); Robert Wilkins, Peterborough, NH (US); Robert A. Charles, New Boston, NH (US); Alex Chaves, Hudson, NH (US)

(73) Assignee: SOCLEAN INC., Peterborough, NH (US)

( * ) Notice: Subject to any disclaimer, the term of this patent is extended or adjusted under 35 U.S.C. 154(b) by 0 days.

(21) Appl. No.: 17/464,154

(22) Filed: Sep. 1, 2021

(65) Prior Publication Data
US 2021/0393838 A1  Dec. 23, 2021

Related U.S. Application Data

(63) Continuation of application No. 17/013,280, filed as application No. PCT/US2020/023631 on Mar. 19, 2020.

(60) Provisional application No. 62/979,551, filed on Feb. 21, 2020, provisional application No. 62/896,117, (Continued)

(51) Int. Cl.
A61L 2/26 (2006.01)
A61L 2/20 (2006.01)
A61L 2/24 (2006.01)
A61M 16/08 (2006.01)

(52) U.S. Cl.
CPC ............... *A61L 2/26* (2013.01); *A61L 2/202* (2013.01); *A61L 2/24* (2013.01); *A61M 16/0816* (2013.01); *A61M 16/0875* (2013.01); *A61L 2202/11* (2013.01); *A61L 2202/14* (2013.01); *A61L 2202/15* (2013.01); *A61L 2202/24* (2013.01); (Continued)

(58) Field of Classification Search
CPC .................................. A61L 2/26; A61L 2/202
See application file for complete search history.

(56) References Cited

U.S. PATENT DOCUMENTS

| 4,019,986 A | 4/1977 | Burris |
| 4,035,657 A | 7/1977 | Carlson |
| 4,110,419 A | 8/1978 | Miller |

(Continued)

FOREIGN PATENT DOCUMENTS

| CN | 1377708 | 11/2002 |
| CN | 2710637 | 4/2005 |

(Continued)

OTHER PUBLICATIONS

Office Action dated Apr. 28, 2021 in JP 2019-201674, 3 pages.
(Continued)

*Primary Examiner* — Kevin Joyner
(74) *Attorney, Agent, or Firm* — Grossman, Tucker, Perreault & Pfleger, PLLC

(57) ABSTRACT

Technologies for sanitizing medical devices are described. In particular, sanitizing systems, components of sanitizing systems, and methods for sanitizing medical devices such as continuous positive airway pressure (CPAP) equipment are described. In embodiments, the sanitizing systems include a sanitizing gas generator and a base including at least one exhaust port and a filter.

19 Claims, 61 Drawing Sheets

Related U.S. Application Data filed on Sep. 5, 2019, provisional application No. 62/820,624, filed on Mar. 19, 2019.

(52) U.S. Cl.
CPC . *A61M 2202/0208* (2013.01); *A61M 2209/10* (2013.01)

(56) References Cited

U.S. PATENT DOCUMENTS

| | | | |
|---|---|---|---|
| 4,207,291 A | 6/1980 | Byrd | |
| 4,465,522 A | 8/1984 | Taldo | |
| 4,517,159 A | 5/1985 | Karlson | |
| D295,074 S | 4/1988 | Jerge | |
| 4,743,275 A | 5/1988 | Flanagan | |
| 4,787,980 A | 11/1988 | Ackermann | |
| 5,029,879 A | 7/1991 | Strang | |
| 5,120,512 A | 6/1992 | Masuda | |
| 5,207,237 A | 5/1993 | Langford | |
| 5,344,622 A | 9/1994 | Faddis | |
| 5,508,006 A | 4/1996 | Gabele | |
| 5,520,893 A | 5/1996 | Kasting | |
| D371,203 S | 6/1996 | Deeds | |
| D390,645 S | 2/1998 | Hanrahan | |
| 5,761,069 A | 6/1998 | Webber | |
| 5,920,075 A | 7/1999 | Whitehead | |
| 6,024,066 A | 2/2000 | Nakayama | |
| 6,134,806 A | 10/2000 | Dhaemers | |
| 6,158,784 A | 12/2000 | Lavender | |
| 6,276,304 B1 | 8/2001 | Tai | |
| 6,280,633 B1 | 8/2001 | Conrad | |
| 6,365,601 B1 | 4/2002 | Fournier | |
| 6,379,617 B1 | 4/2002 | Spickermann | |
| 6,379,632 B1 | 4/2002 | Kinoshita | |
| D476,423 S | 6/2003 | Picot | |
| 6,576,190 B1 | 6/2003 | Park | |
| 6,605,260 B1 | 8/2003 | Busted | |
| D487,315 S | 3/2004 | Picot | |
| 6,752,151 B2 | 6/2004 | Hill | |
| 7,022,225 B1 | 4/2006 | Clawson | |
| 7,461,321 B2 | 12/2008 | Lesartre | |
| 7,520,910 B2 | 4/2009 | Tilley | |
| 7,527,603 B2 | 5/2009 | An | |
| 7,676,276 B2 | 3/2010 | Karell | |
| 7,767,168 B2 | 8/2010 | Namespetra | |
| 7,794,522 B2 | 9/2010 | Bliss | |
| 7,845,350 B1 | 12/2010 | Kayyali | |
| 8,051,853 B2 | 11/2011 | Berthon-Jones | |
| 8,146,946 B1 | 4/2012 | Emond | |
| 8,176,771 B2 | 5/2012 | Onishi | |
| 8,215,465 B2 | 7/2012 | Iceberg | |
| 8,431,075 B2 | 4/2013 | Fraundorfer | |
| D692,155 S | 10/2013 | Matoba | |
| 8,770,198 B2 | 7/2014 | Yee | |
| 8,815,164 B1 | 8/2014 | Al Azemi | |
| D719,673 S | 12/2014 | Leyva | |
| D719,674 S | 12/2014 | Leyva | |
| 8,915,380 B2 | 12/2014 | Sowerby | |
| 9,022,247 B2 | 5/2015 | Enigmann | |
| D733,315 S | 6/2015 | Lui | |
| D733,316 S | 6/2015 | Lui | |
| D748,280 S | 1/2016 | Lui | |
| 9,358,311 B2 | 6/2016 | Leyva | |
| D761,142 S | 7/2016 | Golta | |
| 9,402,928 B2 | 8/2016 | Tremblay | |
| D776,290 S | 1/2017 | Wan | |
| 9,610,373 B2 | 4/2017 | Leyva | |
| 9,616,147 B2 | 4/2017 | Leyva | |
| 9,669,124 B2 | 6/2017 | Leyva | |
| D802,788 S | 11/2017 | Cormier | |
| 9,895,461 B2 | 2/2018 | Leyva | |
| 9,907,872 B2 | 3/2018 | Schmidt | |
| D819,190 S | 5/2018 | Cormier | |
| 10,052,397 B2 | 8/2018 | Leyva | |
| 10,232,072 B2 | 3/2019 | Leyva | |
| 10,264,913 B2 | 4/2019 | Leyva | |
| 10,398,797 B2 | 9/2019 | Leyva | |
| 10,427,961 B2 | 10/2019 | Leyva | |
| 10,434,204 B2 | 10/2019 | Leyva | |
| 10,434,205 B2 | 10/2019 | Leyva | |
| 10,456,492 B2 | 10/2019 | Leyva | |
| 10,485,888 B2 | 11/2019 | Schmidt | |
| 10,842,897 B2 | 11/2020 | Schwartz | |
| 10,980,905 B2 | 4/2021 | Bohman | |
| 11,000,611 B1 | 5/2021 | He | |
| 2003/0000966 A1 | 1/2003 | Shelton | |
| 2003/0063997 A1 | 4/2003 | Fryer | |
| 2003/0065292 A1 | 4/2003 | Darouiche | |
| 2003/0065297 A1 | 4/2003 | Davis | |
| 2003/0071069 A1 | 4/2003 | Shelton | |
| 2004/0007000 A1 | 1/2004 | Takeda | |
| 2004/0251125 A1 | 12/2004 | Yu | |
| 2005/0017380 A1 | 1/2005 | Namespetra | |
| 2005/0019237 A1 | 1/2005 | Riley | |
| 2005/0168907 A1 | 8/2005 | Sekoguchi | |
| 2005/0186108 A1 | 8/2005 | Fields | |
| 2005/0220665 A1 | 10/2005 | Ding | |
| 2006/0130834 A1 | 6/2006 | Chen | |
| 2006/0272682 A1 | 12/2006 | Langford | |
| 2007/0031778 A1 | 2/2007 | Helfenbein | |
| 2007/0065335 A1 | 3/2007 | Bedard | |
| 2008/0050290 A1 | 2/2008 | Yui | |
| 2008/0118411 A1 | 5/2008 | D'Arinzo | |
| 2009/0004047 A1* | 1/2009 | Hunter | A61L 9/205 422/4 |
| 2009/0080809 A1 | 3/2009 | Pham | |
| 2009/0267242 A1 | 10/2009 | Nichols | |
| 2010/0047116 A1 | 2/2010 | Garner | |
| 2010/0059431 A1* | 3/2010 | Cho | C02F 9/005 210/235 |
| 2010/0111792 A1 | 5/2010 | Nelson | |
| 2010/0112677 A1 | 5/2010 | Onishi | |
| 2010/0147302 A1 | 6/2010 | Selvarajan | |
| 2011/0031081 A1 | 2/2011 | Iceberg | |
| 2012/0164025 A1 | 6/2012 | Stockley, III et al. | |
| 2012/0227745 A1 | 9/2012 | Arcilla | |
| 2013/0177475 A1 | 7/2013 | Finch | |
| 2013/0239994 A1 | 9/2013 | Przyjemski | |
| 2014/0112837 A1 | 4/2014 | Huang | |
| 2014/0154134 A1 | 6/2014 | Leyva | |
| 2014/0193294 A1* | 7/2014 | Kain | A61L 2/202 422/111 |
| 2015/0004061 A1 | 1/2015 | Kain | |
| 2016/0235875 A1 | 8/2016 | Schmidt | |
| 2017/0165443 A1 | 6/2017 | Leyva | |
| 2017/0202990 A1 | 7/2017 | Leyva | |
| 2017/0209610 A1 | 7/2017 | Leyva | |
| 2017/0224857 A1 | 8/2017 | Leyva | |
| 2017/0225985 A1 | 8/2017 | Leyva | |
| 2017/0370013 A1 | 12/2017 | Bahar | |
| 2018/0028770 A1 | 2/2018 | Parrish | |
| 2018/0161466 A1 | 6/2018 | Schmidt | |
| 2018/0207307 A1 | 7/2018 | Schwartz | |
| 2018/0264157 A1 | 9/2018 | Benedek | |
| 2018/0311391 A1 | 11/2018 | Leyva | |
| 2018/0311595 A1 | 11/2018 | Leyva | |
| 2019/0076561 A1 | 3/2019 | Leyva | |
| 2019/0076562 A1 | 3/2019 | Schmidt | |
| 2019/0083668 A1 | 3/2019 | Schmidt | |
| 2019/0151487 A1 | 5/2019 | Leyva | |
| 2019/0167828 A1 | 6/2019 | Leyva | |
| 2019/0336627 A1 | 11/2019 | Lucio | |
| 2019/0388575 A1 | 12/2019 | Leyva et al. | |
| 2020/0000950 A1 | 1/2020 | Bohman | |
| 2020/0024167 A1 | 1/2020 | Leyva et al. | |
| 2020/0069362 A1 | 3/2020 | Paesch | |

FOREIGN PATENT DOCUMENTS

| | | |
|---|---|---|
| CN | 1951507 | 4/2007 |
| CN | 2905066 | 5/2007 |
| CN | 201156965 | 12/2008 |
| CN | 103781498 | 5/2014 |
| CN | 105031693 | 11/2015 |

(56) References Cited

FOREIGN PATENT DOCUMENTS

| | | |
|---|---|---|
| CN | 2731632 | 8/2017 |
| JP | S 62230601 | 10/1987 |
| JP | H0724064 | 1/1995 |
| JP | 00288091 | 10/2000 |
| JP | 2005270589 | 10/2005 |
| JP | 131354 | 6/2009 |
| JP | 2014523327 | 1/2013 |
| KR | 1020040098412 | 11/2004 |
| KR | 101839063 | 3/2018 |
| WO | 3068274 | 8/2003 |
| WO | 2008116165 | 9/2008 |
| WO | 2011058472 | 5/2011 |
| WO | 2013012696 | 1/2013 |
| WO | 2015171730 | 11/2015 |
| WO | 2017189916 | 2/2017 |
| WO | 2017189915 | 11/2017 |
| WO | 2018200525 | 11/2018 |

OTHER PUBLICATIONS

First Examination Report issued in Indian Patent Application No. 60/MUMNP/2014, dated Jul. 10, 2019, 6 pages.
Office Action dated Nov. 18, 2020 in CN 201780025983.6.
Office Action dated May 18, 2021 in CN 201780025983.6.
Office Action dated Nov. 1, 2020 in KR 10-2020-7026960, 2 pages.
Office Action dated Jul. 26, 2021, issued in Chinese Patent Application No. 2017101790472, 4 pages.
Office Action dated May 29, 2020, issued in Chinese Patent Application No. 2017101795495, 4 pages.
Office Action dated Jul. 1, 2020, issued in Chinese Patent Application No. 2017101790472, 4 pages.
Office Action dated Jul. 3, 2020, issued in Chinese Patent Application No. 2017101786388, 8 pages.
Restriction Requirement issued in related U.S. Appl. No. 17/025,634, dated Aug. 2, 2021 (6 pages).
Office Action dated May 11, 2021 in BR112018-071444-5.
China Office Action from related matter CN201780025983.6 dated May 9, 2020.
China Office Action from related matter CN201710179459.5 dated May 29, 2020.
International Search Report and Written Opinion from related matter PCT/US20/23631 dated Jun. 3, 2020.
China Office Action from related application CN 201710186091 dated Jul. 1, 2020.
China Office Action from related application CN 20171017904.2 dated Jul. 1, 2020.
U.S. Office Action from related matter U.S. Appl. No. 16/191,059 dated Jun. 11, 2020.
U.S. Final Office Action from related matter U.S. Appl. No. 16/294,097 dated Jun. 11, 2020.
U.S. Office Action from related matter U.S. Appl. No. 15/880,962 dated Jun. 11, 2020.
Office Action dated Jul. 29, 2019, issued in Chinese Patent Application No. 2017101786091, 10 pages.
Office Action dated Jul. 29, 2019, issued in Chinese Patent Application No. 2017101790472, 8 pages.
Office Action dated Aug. 6, 2019, issued in Chinese Patent Application No. 2017101795495, 9 pages.
Notice of Allowance dated Aug. 8, 2019, issued in U.S. Appl. No. 15/141,152, 8 pages.
Examination Report dated Aug. 13, 2019, issued in Australian Patent Application No. 2018200514, 6 pages.
Notice of Acceptance dated Aug. 14, 2019, issued in Australian Patent Application No. 2017228723, 4 pages.
Notice of Allowance dated Oct. 8, 2019, issued in Japanese Application No. 2017-149891, 4 pages.
Examination Report dated Jun. 7, 2019, issued in Canadian Patent Application No. 3,005,981, 3 pages.
Preliminary Report on Patentability dated Nov. 7, 2019, issued in PCT Patent Application No. PCT/US2018/029140, 11 pages.
Notice of Allowance dated Nov. 15, 2019, issued in Australian Patent Application No. 2018200514, 4 pages.
Extended Search Report dated Nov. 29, 2019, issued in European Patent Application No. 17790471.1, 9 pages.
Examination Report dated Jan. 13, 2020, issued in Chilean Patent Application No. 201803063, 17 pages. English language machine translation included.
Office Action dated Feb. 3, 2020, issued in U.S. Appl. No. 16/190,996, 9 pages.
Office Action dated Feb. 18, 2020, issued in Canadian Patent Application No. 3,005,981, 3 pages.
Office Action dated Mar. 19, 2020, issued in Korean Patent Application No. 10-2020-7003298, 4 pages.
Office Action dated Apr. 7, 2020, issued in U.S. Appl. No. 16/780,492, 13 pages.
Office Action dated Apr. 13, 2020, issued in U.S. Appl. No. 16/782,892, 15 pages.
Notice of Allowance dated Apr. 28, 2020, issued in U.S. Appl. No. 16/780,492, 7 pages.
Office Action dated Apr. 23, 2020, issued in U.S. Appl. No. 16/780,355, 14 pages.
Final Office Action dated Feb. 5, 2019, issued in U.S. Appl. No. 15/141,152, 14 pages.
Examination Report dated Feb. 15, 2019, issued in Australian Patent Application No. 2018200514, 5 pages.
Notice of Allowance dated Apr. 30, 2019, issued in U.S. Appl. No. 15/441,929, 5 pages.
Office Action dated Mar. 4, 2019, issued in U.S. Appl. No. 16/257,898, 13 pages.
Office Action dated Mar. 14, 2019, issued in U.S. Appl. No. 16/270,141, 12 pages.
Notice of Allowance dated Mar. 19, 2019, issued in U.S. Appl. No. 15/499,456, 12 pages.
U.S. Appl. No. 16/257,898, filed Jan. 25, 2019.
Office Action dated Apr. 2, 2019, issued in Japanese Patent Application No. 2017-0149891, 7 pages.
Office Action dated Oct. 30, 2018, issued in U.S. Appl. No. 15/499,456, 13 pages.
Notice of Allowance dated Oct. 31, 2018, issued in U.S. Appl. No. 15/873,506, 8 pages.
Office Action amendment dated Oct. 31, 2018, issued in U.S. Appl. No. 15/499,456, 13 pages.
Office Action dated Nov. 6, 2018, issued in U.S. Appl. No. 15/499,378, 18 pages.
Keep your CPAP machine clean and safe, Oct. 18, 2010—Available at https://www.cpap.co.uk/2010/10/keep-your-cpap-machine-clean-and-safe.
GoodKnight H20 Heated Humidifier User's Manual, 2006 Nellcor Puritan Bennett.
Hoffrichter Trend II User's Manual (date unknown).
Hudson RCI Product Catalog (2004-2005).
KnightStar(R) 330 User's Manual, 2006, Nellcor Puritan Bennett.
DeVilbiss® DV54 AutoAdjust CPAP Series (DeVilbiss® SleepCube Positive Airway Pressure Device) User Manual (2009). Available at https://www.manualslib.com/manual/1577762/Devilbiss-Intellipap-Dv54.html.
Sunset Healthcare Solutions, Inc's Preliminary Patent Disclosures Pursuant to Local Rule 16.6(d)(4) in *SoClean, Inc.* v *Sunset Healthcare Solutions, Inc*, in Civil Action No. 1:20-cv-10351-IT.
Sunset Healthcare Solutions, Inc's Second Amended Counterclaims in *SoClean, Inc.* v. *Sunset Healthcare Solutions, Inc*, in Civil Action No. 1:20-cv-10351-IT and Consolidated Case No. 1:21-cv-1013IT.
Memorandum in Support of SoClean's Motion to Dismiss Counts Eight and Nine of Sunset's Second Amended Counterclaims, *SoClean, Inc.* v. *Sunset Healthcare Solutions, Inc*, in Civil Action No. 1:20-cv-10351-IT and Consolidated Case No. 1:21-cv-1013IT.
Defendant Sunset's Memorandum in Opposition to SoClean's Motion to Dismiss Counts Eight and Nine of Sunset's Second Amended Counterclaims. C.A No. 1:20-cv-10351-IT. Filed Aug. 6, 2021.
ResMed VPAP III ST-A with QuickNav Clinical Guide, copyright 2008 ("ResMed Guide"). Cited by opposing counsel in connection with *SoClean Inc.* v. *Sunset Healthcare Solutions, Inc.*, Civil action No. 1:20-cv-10351-IT (U.S. Dist. Ct. Massachusetts).

(56) References Cited

OTHER PUBLICATIONS

VPAP IV and VPAP IV ST Product Training ("ResMed Presentation"). Cited by opposing counsel in connection with *SoClean Inc. v. Sunset Healthcare Solutions, Inc.*, Civil action No. 1:20-cv-10351-IT (U.S. Dist. Ct. Massachusetts). Publication Date is unknown to Applicant, but was asserted by opposing counsel in the noted litigation to be in 2008.
Lenntech "Ozone Generation", Wayback Machine Capture, Mar. 28, 2010, (Year 2010), 3 pages.
Ozone MSDS (Material Safety Data Sheets), Ozone Solutions, Jun. 1, 2000, http://www.ozoneapplications.com/info/ozone_msds.htm, 5 pages.
Tornado, New Kind of CPAP Guardian, User Manual, 8 pages.
Murphy, "Ozone—The Latest Advance in Sterilization of Medical Developments", Canadian Operating Room Nursing Journal; Jun. 2006 (6 pages).
9055 Series DeVilbiss RPM Bilevel CPAP System Instruction Manual, 66 pages.
Ishizaki, "Inactivation of Bacillus spores by gaseous ozone", J Appl Bact 1986:60, 67-72, 6 pages.
Al Ashry, et al. "Humidification during Mechanical Ventilation in the Adult Patient", vol. 2014, Article ID 715434, Hindawi Publishing Corporation, BioMed Research International.
Preliminary Report on Patentability dated Nov. 8, 2018, issued in PCT International Patent Application No. PCT/US2017/029949, 9 pages.
Preliminary Report on Patentability dated Nov. 8, 2018, issued in PCT International Patent Application No. PCT/US2017/029950, 9 pages.
Office Action dated Jan. 16, 2019, issued in Korean Patent Application No. 10-2018-7009274, 5 pages. English anguage translation provided.
Notice of Allowance dated Jan. 18, 2019, issued in U.S. Appl. No. 15/441,929, 7 pages.
Office Action dated Jan. 22, 2019, issued in U.S. Appl. No. 16/190,996, 10 pages.
Examination Report dated May 15, 2019, issued in Australian Patent Application No. 2017228723, 5 pages.
Notice of Allowance dated May 17, 2019, issued in U.S. Appl. No. 16/270,141, 7 pages.
Notice of Allowability dated May 22, 2019, issued in U.S. Appl. No. 15/499,456, 5 pages.
Notice of Allowance dated May 28, 2019, issued in U.S. Appl. No. 15/499,378, 7 pages.
Notice of Allowance dated Jun. 20, 2019, issued in U.S. Appl. No. 16/257,898, 8 pages.
U.S. Office Action dated Jul. 26, 2019, issued in U.S. Appl. No. 16/190,996, 12 pages.
International Search Report and Written Opinion dated Jul. 13, 2018, issued in PCT International Patent Application No. PCT/US18/29140, 12 pages.
Office Action dated Aug. 9, 2018, issued in Japanese Patent Application No. 2014-520352, 5 pages.
Office Action dated Sep. 5, 2018, issued in Chinese Patent Application No. 2016105175158, 10 pages.
Office Action dated Sep. 17, 2018, issued in U.S. Appl. No. 15/441,929, 10 pages.
Examination Report dated Sep. 26, 2018, issued in Australian Patent Application No. 2017228723, 6 pages.
U.S. Final Office Action dated Feb. 4, 2018, issued in U.S. Appl. No. 15/141,152, 16 pages.
U.S. Office Action dated Apr. 3, 2018, issued in U.S. Appl. No. 15/873,506, 7 pages.
U.S. Notice of Allowance dated Apr. 27, 2018, issued in U.S. Appl. No. 15/142,085, 8 pages.
U.S. Office Action dated Jun. 13, 2017, issued in U.S. Appl. No. 15/481,919, 10 pages.
International Search Report and Written Opinion dated Aug. 2, 2017, issued in PCT Patent Application No. PCT/US17/29949, 11 pages.
U.S. Office Action dated Aug. 3, 2017, issued in U.S. Appl. No. 15/141,152, 14 pages.
International Search Report and Written Opinion dated Aug. 16, 2017, issued in PCT Patent Application No. PCT/US17/29950, 11 pages.
International Search Report and Written Opinion dated Sep. 17, 2012, issued in PCT Application No. PCT/US12/46593, 6 pages.
International Search Report and Written Opinion dated Jul. 24, 2015, issued in PCT Application No. PCT/US15/29418, 9 pages.
U.S. Office Action dated Jun. 30, 2016, issued in U.S. Appl. No. 15/141,216, 13 pages.
U.S. Office Action dated Jul. 13, 2016, issued in U.S. Appl. No. 15/142,060, 18 pages.
U.S. Office Action dated Jul. 14, 2016, issued in U.S. Appl. No. 15/142,111, 10 pages.
U.S. Office Action dated Jul. 28, 2016, issued in U.S. Appl. No. 15/142,085, 15 pages.
U.S. Office Action dated Oct. 6, 2016, issued in U.S. Appl. No. 15/141,152, 11 pages.
U.S. Office Action dated Nov. 23, 2016, issued in U.S. Appl. No. 15/141,216, 9 pages.
U.S. Office Action dated Nov. 23, 2016, issued in U.S. Appl. No. 15/142,085, 8 pages.
U.S. Office Action dated Feb. 23, 2017, issued in U.S. Appl. No. 29/562,755, 8 pages.
U.S. Office Action dated Feb. 27, 2017, issued in U.S. Appl. No. 29/562,756, 7 pages.
U.S. Office Action dated Mar. 17, 2017, issued in U.S. Appl. No. 15/141,152, 14 pages.
Office Action dated Sep. 21, 2017, issued in U.S. Appl. No. 15/142,085, 9 pages.
Notice of Allowance dated Oct. 13, 2017, issued in U.S. Appl. No. 15/481,919, 7 pages.
Office Action dated Mar. 4, 2019, issued in U.S. Appl. No. 15/444,916, 16 pages.
Office Action dated Apr. 28, 2019, issued in Chinese Patent Application No. 2017101790491, 10 pages.
Office Action dated Sep. 17, 2019, issued in U.S. Appl. No. 15/444,916, 17 pages.
Office Action dated Apr. 15, 2020, issued in U.S. Appl. No. 15/444,916, 16 pages.
Office Action dated May 17, 2021, issued in Indonesian Patent Application No. PID201808782, 2 pages.
Office Action dated Jan. 8, 2021, issued in Chinese Patent Application No. 2017101786388, 8 pages.
Office Action dated Oct. 20, 2021 in U.S. Appl. No. 17/025,634. 9 pages.
Office Action dated Mar. 23, 2020, issued in Chinese Patent Application No. 2017101790491, 8 pages.
Goodknight 420G Patient Manual, 2005 Nellcor Puritan Bennett Inc.
SoClean 2 PAP Disinfecting Device User Guide Copyright 2011-2014, Inceptus, Inc.
CPAP Guardian TB-316, America Tyson Industrial Group (Asia Pacific) Limited, http://www.ecvv.com/products/2314441.html, Nov. 91, 2009, downloaded from Internet Jul. 8, 2016, 3 pages.
Chaunet et al., "The sterilization technology for the 21st century," TS03, Inc. 2007.
Ohkawa et al. "High grade disinfection using high-density ozone," J Adv Oxid Tech, 7, 154-160, (2004).

* cited by examiner

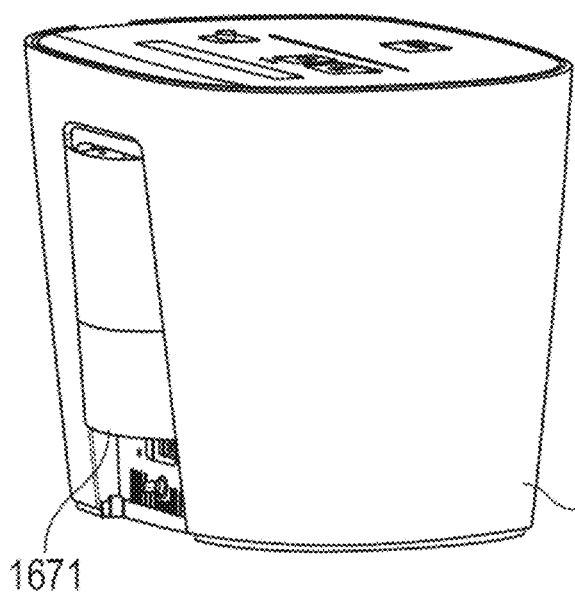
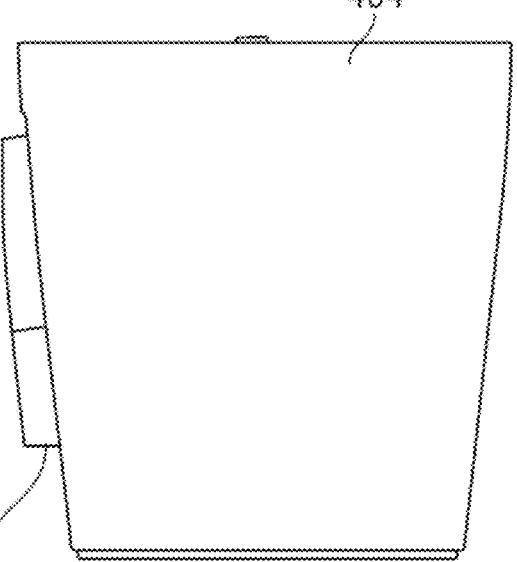
FIG. 16D
FIG. 16E
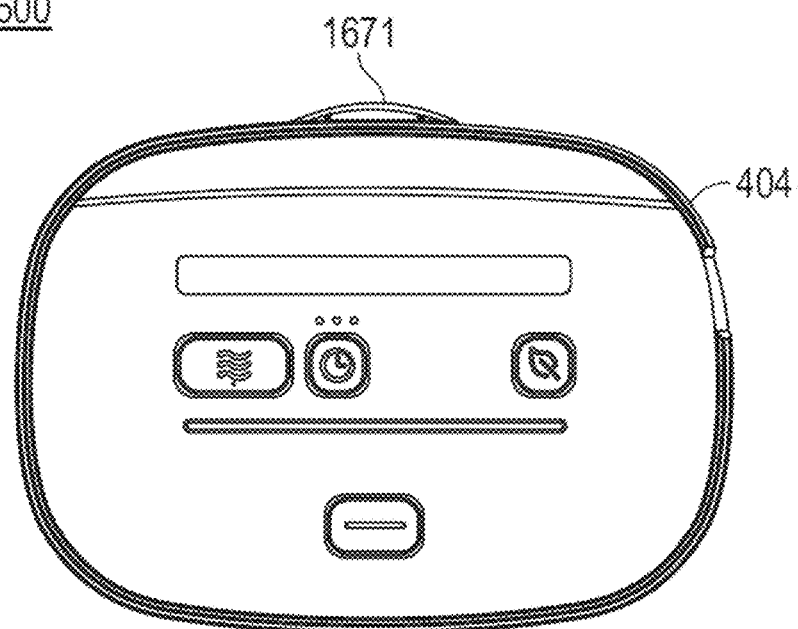
FIG. 16F

TECHNOLOGIES FOR SANITIZING MEDICAL DEVICES

CROSS-REFERENCE TO RELATED APPLICATIONS

This application is a Continuation of U.S. application Ser. No. 17/013,280 filed Sep. 4, 2020, which is a national stage entry of and claims priority to International (PCT) Application No. PCT/US20/023631, filed Mar. 19, 2020, which claims priority to U.S. Provisional Application No. 62/979,551, filed Feb. 21, 2020, U.S. Provisional Application No. 62/896,117 filed Sep. 5, 2019, and U.S. Provisional Application No. 62/820,624, filed Mar. 19, 2019, the entire content of each of which is incorporated herein by reference.

FIELD

The present disclosure generally relates to technologies for sanitizing medical devices, including but not limited to medical and other devices that include a hose. In particular, the present disclosure relates to technologies for sanitizing continuous positive airway pressure (CPAP) equipment, such as CPAP devices and components thereof. Components of such systems and methods of sanitizing a medical device are also described.

BACKGROUND

Sleep apnea is often treated with continuous positive airway pressure (CPAP) equipment, such as a CPAP device. A CPAP device can address symptoms of sleep apnea (e.g., reduced oxygen levels in the blood, sleep loss, etc.) by delivering a stream of pressurized air through a hose to a nasal pillow or facemask surrounding a user's nose. By blowing air at a prescribed pressure for a user, the CPAP device can help keep the user's breathing passageways open and unobstructed as the user sleeps.

Many CPAP devices include a water reservoir that adds humidity to air that is blown into the user's nose or mouth during use of the device. A warm and humid environment may therefore be present in various components of a CPAP device, such as the water reservoir, hose, facemask and/or nasal pillow. Such an environment can facilitate the maintenance and/or growth of bacteria and other pathogens, potentially presenting a health hazard to the user. Even if a CPAP device does not include a reservoir, the growth/presence of bacteria and other pathogens may be promoted by the fact that a user often exhales into the into the facemask and/or nose pillow of a CPAP device. Bacteria and other pathogens may therefore be conveyed from the user's mouth and/or skin to within passageways within the mask, nose pillow, hose, etc. of the CPAP device—where they may proliferate.

Like many medical devices, CPAP devices generally require periodic cleaning and/or maintenance to ensure that they are sanitary for continued use. Many CPAP device manufacturers recommend that users perform daily and weekly maintenance on their devices to prevent growth and build-up of bacteria, mold and/or other pathogens in various components of the device, such as the face mask (or nasal pillow), the hoses, the water reservoir, etc. Such maintenance may require each part of the CPAP device to be cleaned individually, which many users find difficult and time consuming. Consequently, many patients resist using a CPAP device, and/or avoid cleaning their CPAP device on a regular basis.

BRIEF DESCRIPTION OF THE DRAWINGS

Features and advantages of embodiments of the claimed subject matter will become apparent as the following Detailed Description proceeds, and upon reference to the Drawings, wherein like numerals depict like parts, and in which:

FIGS. 16A-16G depict various views of an example of a sanitizing device including an auxiliary fan, consistent with the present disclosure;

DETAILED DESCRIPTION

Figure 1A:
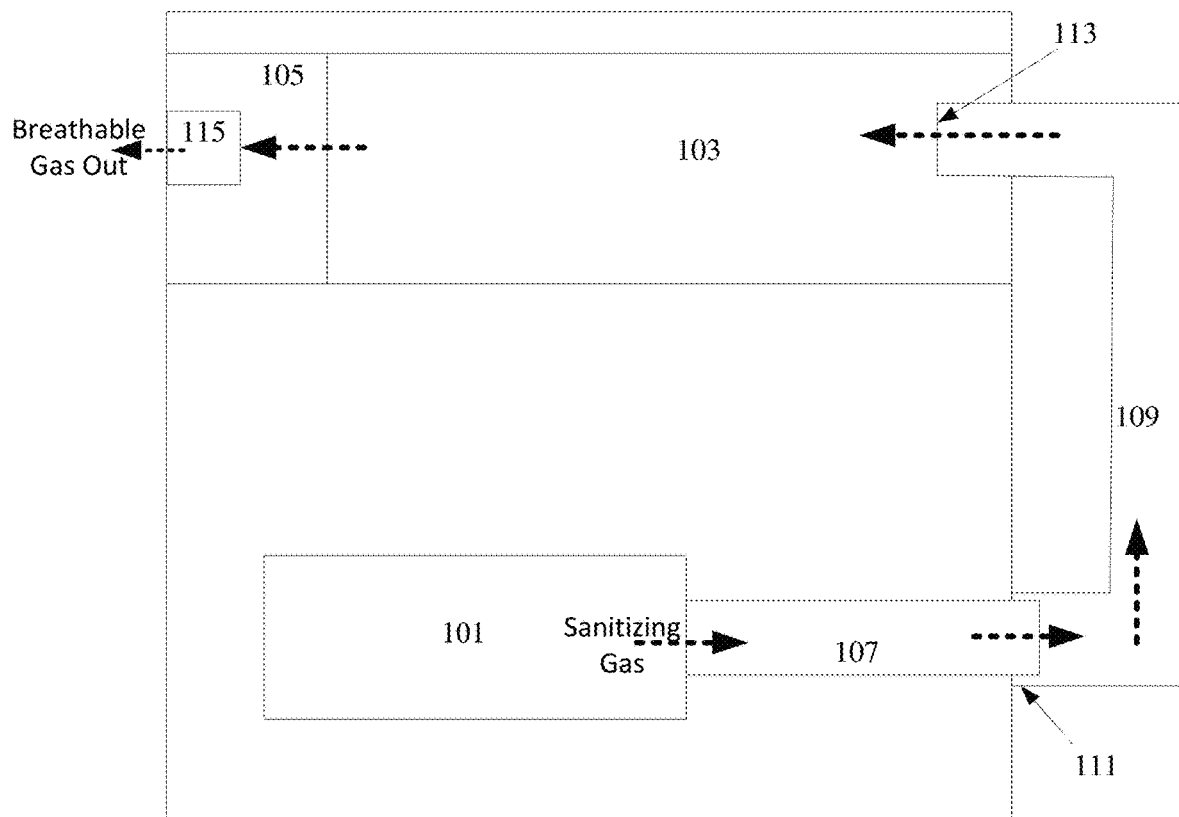
FIG. 1A is a block diagram of one example of a sanitizing device.

CPAP and other medical devices often require varying degrees of cleaning, disinfection, and/or sterilization so that they are sanitary to use. While there are various known methods for cleaning and sanitizing medical devices such as CPAP devices, such methods are often considered inconvenient, messy, and/or time-consuming Consequently, users often resist cleaning CPAP and other medical devices or rush through cleaning protocols, potentially leading to inadequate sanitization.

Systems for sanitizing CPAP and other medical devices with a sanitizing gas such as ozone ($O_3$) have been developed. Although such systems can effectively sanitize CPAP and other medical devices, leakage of the sanitizing gas from the sanitizing system may expose the user to the sanitizing gas. Likewise, a user may be exposed to the sanitizing gas if a sanitization cycle is executed while the sanitizing system is in an unsafe condition. Exposure to the sanitizing gas may present a health hazard to the user, and thus should be avoided.

Existing sanitization systems may be configured such that parts of the medical devices or components may be obscured during a sanitization cycle. For example, portions of components within a sanitizing chamber may be obscured at the point(s) where they touch another component, the walls of the chamber, or the bottom of the chamber. Obscured portions of such components may not be exposed or may be insufficiently exposed to the sanitizing gas during a sanitization cycle—potentially leading to inadequate sanitization thereof.

Some sanitizing systems are configured to deliver a sanitizing agent such as a sanitizing gas to multiple parts of a medical device. In some instances, however, it may not be necessary to distribute the sanitizing agent/gas to one or more of the parts of a medical device while still sanitizing other parts of the medical device. For example, many CPAP devices do not include a reservoir. As the growth and/or presence of bacteria and other pathogens in a CPAP device that does not include a reservoir may be limited, introduction of a sanitizing agent such as a sanitizing gas into such a CPAP device may not be needed. But it may still be desirable to sanitize a CPAP hose and/or mask that fluidly couple to the CPAP device for the reasons discussed above. With that in mind, aspects of the present disclosure relates to technologies for distributing a sanitization agent such as a sanitizing gas into a subset of components of medical device, such as CPAP equipment. In embodiments the systems and methods of the present disclosure relate to systems and methods for sanitizing CPAP equipment including a CPAP device, a CPAP hose, and optionally a CPAP mask. Such systems and methods enable the distribution of a sanitizing agent such as a sanitizing gas into the CPAP hose and optionally a CPAP mask, while limiting or even preventing distribution of the sanitizing agent into the CPAP device.

The present disclosure also relates to technologies for sanitizing CPAP and other medical devices with a sanitizing gas. As will be described below, the technologies of the present disclosure may include one or more safety features that hinder or prevent leakage of the sanitizing gas, and/or execution of a sanitization cycle while a sanitizing device is in an unsafe condition. The technologies of the present disclosure may also include one or more positioning elements configured to facilitate or enhance exposure of components of a medical device to the sanitizing gas. Additionally, aspects of the present disclosure relate to various improvements to a sanitizing system, including improved sanitizing chambers, improved sanitizing gas filters, improved sealing systems, improved sanitizing controllers, improved control methods, and combinations thereof.

Although the technologies described herein can be used with many sanitizing gases, the present disclosure focuses on the use of ozone as a sanitizing gas. This is because ozone ($O_3$) gas is an effective sanitizer yet is relatively safe for consumer use. Because of its strongly oxidizing properties, ozone can effectively kill or otherwise remove a wide range of organic and inorganic contaminants such as yeasts, bacteria, molds, viruses, other pathogens, and/or pollutants with which it comes into contact, e.g., via oxidation. Naturally over time and/or as it oxidizes contaminants, ozone may be chemically reduced to oxygen ($O_2$), which is safe for human consumption and for release into the environment. Ozone is also relatively easy to generate on site (and thus does not require the use of a storage tank), and leaves little or no chemical residue. For those and other reasons, ozone has been identified as a safe and effective sanitizing gas for use in the present disclosure. It should be understood, however, that the technologies described herein are not limited to the use of ozone and may be employed with a wide variety of sanitizing agents/gases.

For the sake of illustration and ease of understanding the present disclosure illustrates and describes various sanitizing systems in a configured state, i.e., in which they are coupled to one or more components of a medical device (e.g., a CPAP hose, CPAP mask, CPAP reservoir, etc.). The present disclosure is not limited to such configurations, and encompasses each individual component of a sanitizing system (e.g., a base, sanitizing chamber, sanitizing gas generator, filter, sealing system, etc.) independent of any connection with a medical device such as a CPAP hose, CPAP reservoir, and the like. Put differently, the term "sanitizing system" encompasses embodiments in which a medical device (e.g., hose, reservoir, etc.) is coupled to one or more other components (e.g. a base, sanitizing chamber, distribution line, etc.), and embodiments in which such components are not coupled to a medical device.

FIG. 1A schematically illustrates one example of a system 100 for sanitizing a medical device with a sanitizing gas. As shown, system 100 includes an ozone operating system 101, a sanitizing chamber 103, and an exhaust port 105. The ozone operating system 101 is coupled to a distribution line 107, which in turn is coupled to a proximal end 111 of a hose 109 of a medical device. Hose 109 may be any suitable medical device hose, such as a hose of a CPAP device.

During a sanitization cycle a distal end 113 of hose 109 is disposed within sanitizing chamber 103, and ozone operating system 101 generates ozone. In embodiments, ozone operating system 101 includes or is in the form of any of a wide range of known ozone generators, including ozone generators that generate ozone from air. A fan or pump (not shown) may cause the ozone to flow in the manner generally shown by the dashed arrows in FIG. 1A. More specifically, the ozone flows from ozone operating system 101 into the distribution line 107 and then into the hose 109, where it will sanitize the interior of the hose 109. Remaining ozone is conveyed into the sanitizing chamber 103, where it will sanitize the interior of sanitizing chamber 103 and any medical devices, components, etc., therein (e.g., a CPAP mask). The sanitization cycle may continue for enough time to attain desired sanitization of hose 109, sanitizing chamber 103, and any components within sanitizing chamber 103.

During or following the sanitization cycle, ozone may convert to oxygen naturally or in another manner. For example and as shown in FIG. 1A, system 100 may include an exhaust port 105 that may include or be coupled to a filter 115. Filter 115 includes or is formed from a material (e.g., a catalyst) that is configured to convert or facilitate the conversion of ozone to oxygen or another breathable gas. Activated carbon and magnesium oxide (either alone or in combination with activated carbon) are non-limiting examples of such materials, but other materials that facilitate and/or catalyze the conversion of the sanitizing gas (e.g., ozone) to breathable gas (e.g., oxygen) may also be used. In instances where ozone is used as the sanitizing gas, ozone within sanitizing chamber 103 may be conveyed to filter 115 via exhaust port 105 and converted to oxygen, which may be safely exhausted into the environment.

Figure 1B:
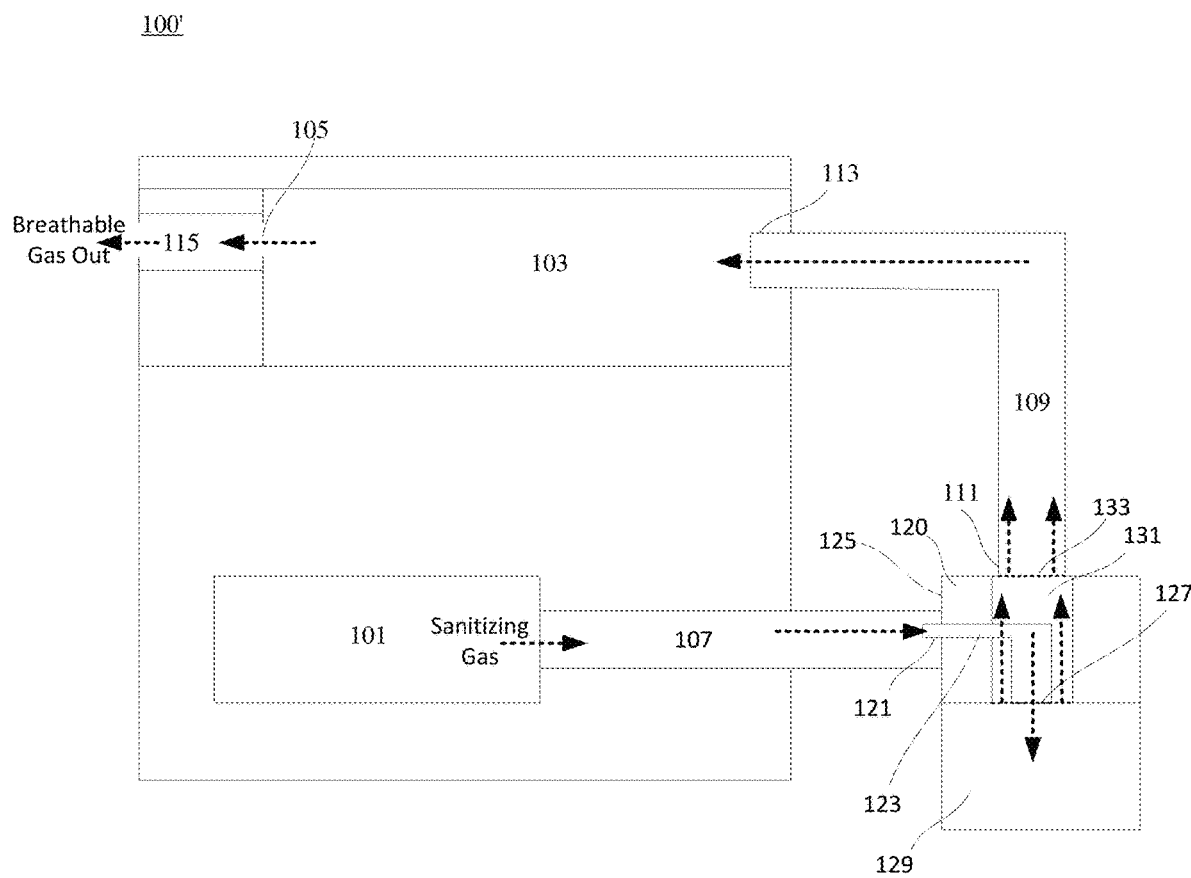
FIG. 1B is a block diagram of another example of a sanitizing device.

FIG. 1B schematically illustrates another example embodiment of a system for sanitizing a medical device. Like system 100, system 100' includes an ozone operating system 101, gas tight compartment, exhaust port 105, and filter 115. Ozone operating system 101 is coupled to a proximal end of distribution line 107, and the distal end of distribution line is coupled to a connector unit 120. In general, connector unit 120 is configured to distribute sanitizing gas (e.g., ozone) from distribution line 107 into one or multiple components of a medical device, such as a CPAP device. In this embodiment, connector unit 120 is configured to fluidly couple distribution line 107 to a medical device 129 (e.g., a reservoir or other component), and to fluidly couple the medical device 129 to a hose 109.

More specifically, connector unit 120 includes a first connector 121 (e.g., a first end), a second connector 127 (e.g., a second end), and a third connector 133 (e.g., a third end). The first connector 121 is configured to couple to distribution line 107, the second connector 127 is configured to couple to a medical device 129 (e.g., a reservoir or other component), and the third connector 133 is configured to couple to a hose 109 (or another component) of the medical device. The connector unit further includes a first passageway 123 and a second passageway 131. As shown in this and various other embodiments the first, second, and third connectors 121, 127, 133) are integral with connector unit 120. While such a configuration has several advantages (e.g., allowing connector unit 120 to be connected in the air flow path from the CPAP device while also being fluidly coupled to ozone operating system 101 and a CPAP device; eliminating interfaces (i.e., potential leak points) between the first, second, and third connectors 121, 127, 133 and the body of connector unit 120, etc.), it should be understood that such a configuration is not required. For example, one or more of the first, second, and third connectors 121, 127, and 133 may be separate from but fluidly coupled to connector unit 120 or, more specifically, to corresponding first and second passageways 123, 131 of connector unit 120. In such instances the connector unit 120 and the first, second, and third connectors 121, 127, 133 may be configured to couple to one another in any suitable manner, while minimizing or preventing leakage of a sanitizing gas at interfaces there between.

First connector 121 is configured to couple to distribution line 107 in any suitable manner. In the illustrated embodiment first connector 121 is in the form of a first port (e.g. a first barb or nipple) that is configured to fluidly couple to a distal end of distribution line 107. For example distribution line may slip over first connector 121 or may otherwise be coupled to first connector 121 in any suitable manner (e.g., threading, compression fitting, mechanical fasteners, combinations thereof, and the like). In any case, first connector 121 forms part of or is fluidly coupled to a first passageway 123. Thus, when first connector 121 is coupled to distribution line 107, first connector 121 fluidly couples distribution line 107 to first passageway 123.

First passageway 123 is generally configured to fluidly couple the distribution line 107 with a medical device or a component thereof. In the embodiment of FIG. 1B, first passageway 123 includes an open end that is oriented towards medical device 129. As such, the first passageway 123 in this embodiment may fluidly couple ozone operating system 101 (and/or distribution line 107) with medical device 129 and/or hose 109. In embodiments medical device 129 is a CPAP device or a component thereof, such as a CPAP reservoir. In such embodiments first passageway 123 may fluidly couple ozone operating system 101 (and/or distribution line 107) with the CPAP device/reservoir. It should be understood, however, that the present disclosure is not limited to sanitizing CPAP devices and, thus, medical device 129 is not limited to CPAP devices and/or CPAP reservoirs. For example, medical device 129 may be a different medical device, and/or may include any suitable type of reservoir. In embodiments at least part of a proximal end of the first passageway 123 extends through (e.g., within) a sidewall 125 of connector unit 120. In such instances first connector 121 may be integral with the first passageway 123. Alternatively, first connector 121 may be discrete from and coupled to first passageway 123. In such instances first connector may include a fluid passageway that extends through sidewall 125, and which is fluidly coupled to first passageway 123 in any suitable manner.

Figure 1C:
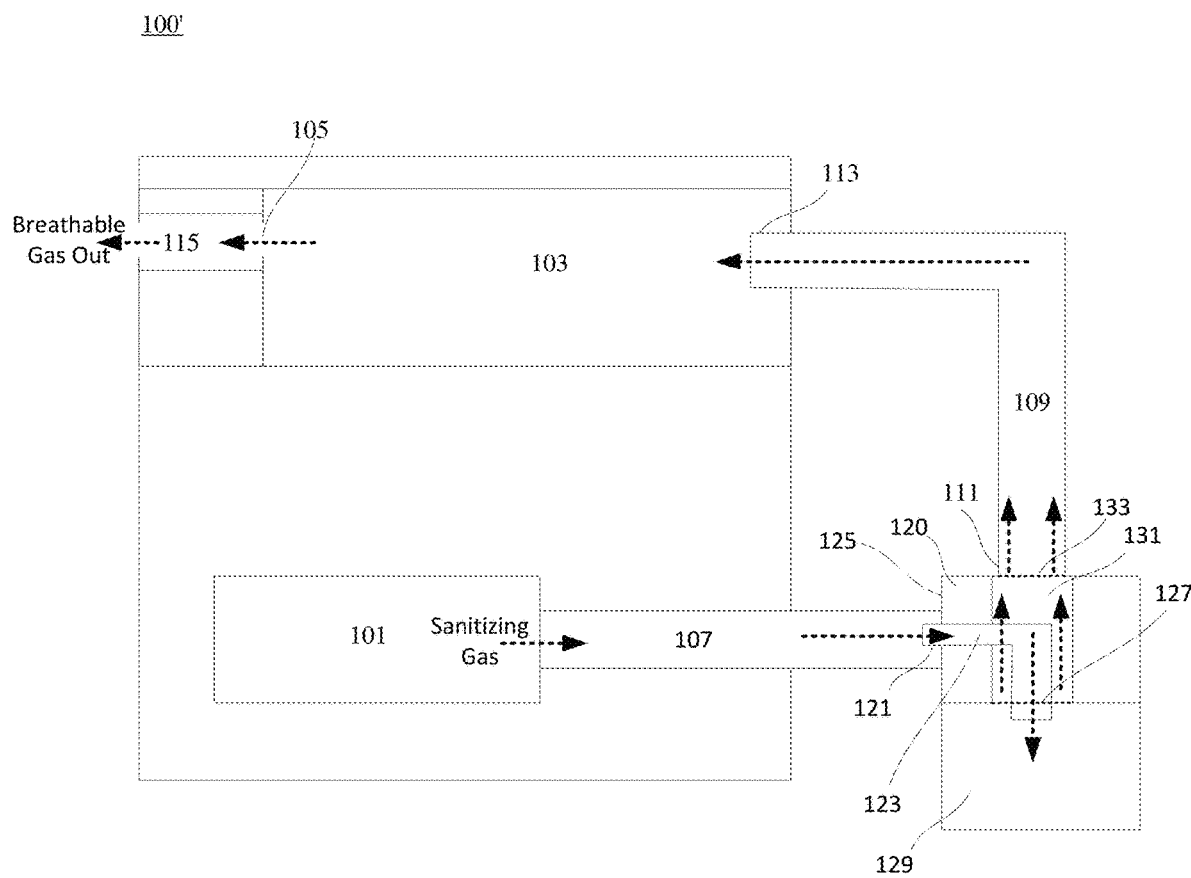
FIG. 1C is a block diagram of another example of a sanitizing device.
Figure 1D:
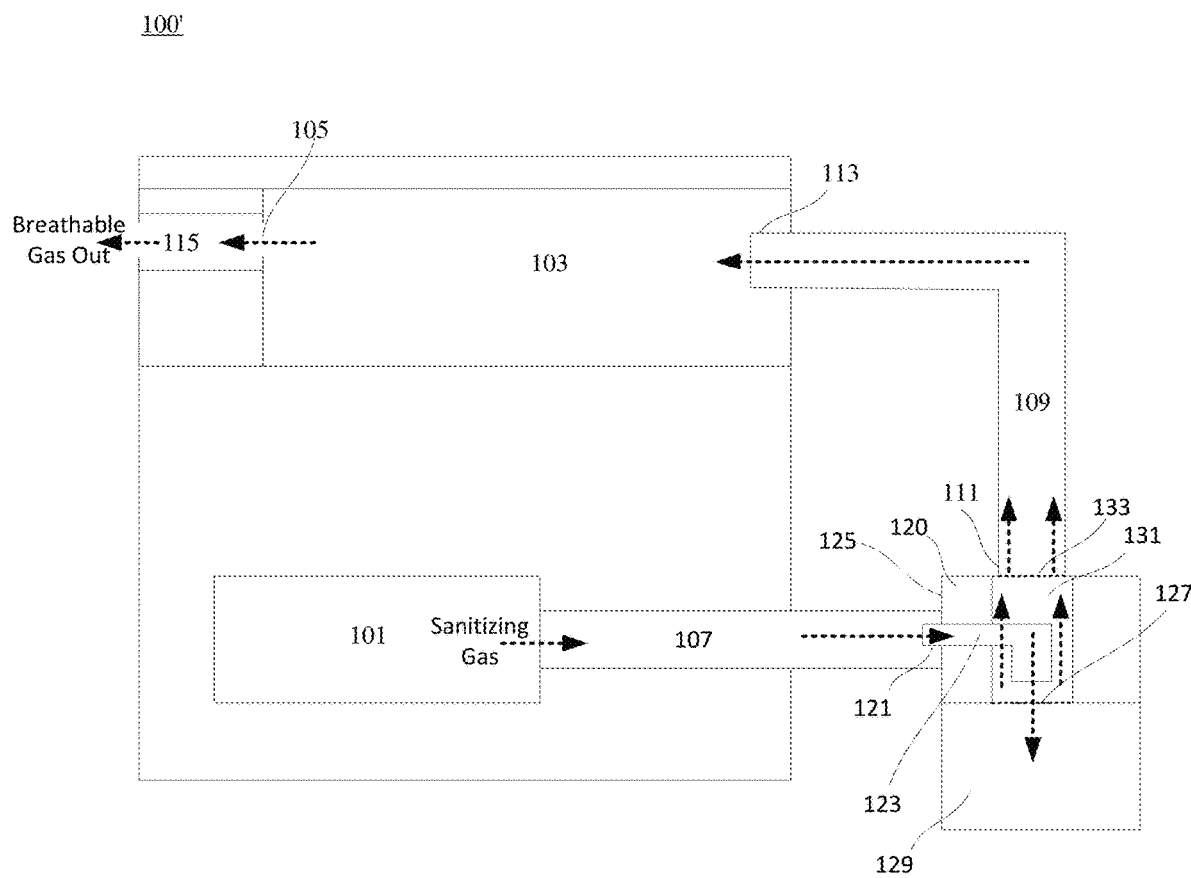
FIG. 1D is a block diagram of another example of a sanitizing device.

As shown, first passageway 123 extends from first connector 121 to or through a first opening in (or defined at least in part by) second connector 127. In embodiments, first passageway 123 extends through a first opening in second connector 127 such that a distal end of first passageway 123 extends to within medical device 129 (e.g., to within a CPAP reservoir and/or to below a level of a liquid (if any) contained therein). Alternatively, the distal end of first passageway 123 may terminate at or proximate to the first opening in second connector 127. For example, in some embodiments the opening in the distal end of the of first passageway 123 may be located proximate the first opening in or defined by the second connector 127, as shown in FIG. 1B. Still further, in embodiments the first passageway 123 may extend through the opening in the second connector 127 such that the distal end of the first passageway 123 is located outside of the second passageway 131, as shown in FIG. 1C. In still further embodiments, the first passageway 123 may terminate within the second passageway, i.e., such that the opening in the distal end of the first passageway 123 is located within the second passageway 131, as shown in FIG. 1D.

In any or all of such embodiments, a proximal end of a second (optional) distribution line (not shown) may be fluidly coupled to the distal end of first passageway 123. In such embodiments the second distribution line may extend such that a distal end thereof is within medical device 129. Coupling of the distal end of first passageway 123 with the proximal end of the second distribution line may occur in any suitable manner. For example, the distal end of first passageway 123 may be in the form of a second port (e.g., a second barb or nipple), and the second distribution line may slip over or otherwise couple thereto in any suitable manner (e.g., by threading, compression fitting, mechanical fasteners, combinations thereof, and the like).

Connector unit 120 further includes a second passageway 131 that extends between second connector 127 and third connector 133. In the illustrated embodiment, second passageway 131 is defined at least in part by sidewall 125 of connector unit 120, and extends between a first opening (e.g., defined in or at least in part by second connector 127) and a second opening (e.g., defined in or at least in part by third connector 133). In embodiments and as shown in FIG. 1B, at least a portion of the first passageway 123 (e.g., a surface of a wall of the first passageway 123) may extend within the second passageway 131. In such embodiments connector unit 120 may be understood to define a "passageway within a passageway" structure. Thus, in embodiments the first opening extends around at least a portion of the first passageway. In such instances a fluid (e.g., gas) flow within first passageway 123 is discrete from a fluid (e.g., gas) flow within second passageway 131. For example, in embodiments gas flow within first passageway 123 is towards medical device 129 (e.g. towards a reservoir thereof), and gas flow within second passageway 131 is away from medical device (e.g., away from a reservoir thereof).

While FIG. 1B depicts an embodiment in which first passageway 123 is at least partially disposed within second passageway 131, such a configuration is not required, and the present disclosure envisions embodiments in which connector unit 120 includes two or more discrete passageways in any suitable manner. For example, connector unit 120 may include a first passageway 123 and a second passageway 131, wherein the first passageway 123 is entirely discrete from second passageway 131. That is, in such instances, no part of the first passageway 123 is disposed within the second passageway 131. Moreover, while the embodiment of FIG. 1B illustrates an embodiment in which both first passageway 123 and second passageway 131 are at least partially disposed through, within and/or defined by an inward facing side of sidewall 125, such a configuration is not required. Indeed the present disclosure envisions embodiments in which connector unit 120 is configured such that one or both first passageway 123 and/or second passageway 131 are disposed outside of sidewall 125, and/or are defined at least in part by an outward facing side of sidewall 125.

During a sanitization cycle ozone operating system 101 may generate a sanitizing gas such as ozone as described above in connection with FIG. 1A. The generated ozone may be conveyed (by a pump, fan, or combination thereof) from ozone operating system 101 into distribution line 107. The ozone may flow from distribution line 107 into first passageway 123, thereby introducing ozone into the connector unit 120. Once introduced into connector unit 120, ozone may flow into medical device 129, into hose 109, or a combination thereof. The ozone may be introduced into medical device 129 in any suitable manner, e.g., via a distal end of the first passageway 123 or via a second distribution line coupled to the distal end of the first passageway 123 as discussed above. Ozone introduced into the medical device 129 will sanitize the interior of the medical device. For example, where medical device 129 is or includes a reservoir such as a CPAP reservoir, sanitizing gas such as ozone flowing into the reservoir may sanitize the interior of the reservoir and optionally any liquid contained therein. In embodiments, medical device 129 is or includes a CPAP reservoir and sanitizing gas such as ozone may be introduced below the surface of any liquid within the CPAP reservoir. Introducing sanitizing gas in that manner may facilitate distribution of the sanitizing gas into the liquid and the sanitization thereof. When medical device 129 includes a reservoir that contains liquid, at least a portion of ozone introduced into the medical device 129 may evolve from the liquid contained in the reservoir, whereupon it may sanitize the interior of the reservoir or be conveyed to other parts of system 100'.

At least a portion of ozone introduced into the connector unit 120 will flow into second passageway 131 and into hose 109, where it may sanitize the interior of hose 109. At least a portion of the ozone entering hose 109 will flow through hose 109 and into sanitizing chamber 103, where it may sanitize the interior of sanitizing chamber 103 and any medical devices or components thereof disposed therein. The sanitization cycle may continue for enough time to attain desired sanitization of medical device 129, hose 109, sanitizing chamber 103, and any components within sanitizing chamber 103. During or following the sanitization cycle, ozone may convert to oxygen naturally or in another manner. For example, ozone within sanitizing chamber 103 may be conveyed through exhaust port 105 to filter 115, which may facilitate conversion of ozone to oxygen or other breathable gas in any suitable manner.

It is noted that FIGS. 1A and 1B depict embodiments in which filter 115 is downstream of exhaust port 105, and thus receives a gas flow containing a sanitizing gas (e.g., ozone) from exhaust port 105. Such a configuration is not required, and the present disclosure envisions and encompasses embodiments in which filter 115 receives a flow of sanitizing gas in another manner. For example, in embodiments filter 115 may be disposed within sanitizing chamber 103 and coupled to a downstream exhaust port 105. That is, filter 115 may be disposed upstream of exhaust port 105. In such instances filter 115 may convert ozone (or other sanitizing gas) to breathable gas, which is then conveyed from filter 115 to exhaust port 105.

It is further noted that FIG. 1B depicts an embodiment wherein distribution line 107 is coupled to first connector 121, which forms part of or is in fluid communication with first passageway 123. Such a configuration is for the sake of example only, and other configurations are envisioned by the present disclosure. For example, first connector 121 may be configured as an opening through which distribution line 107 may be inserted. In such instances distribution line 107 may extend within first passageway 123 and/or within second passageway 131. In embodiments, distribution line 107 extends through an opening in second connector 127 until a distal end thereof is disposed within medical device 129 and/or a reservoir thereof. Alternatively or additionally, the distal end of distribution line 107 may be disposed proximate the opening in second connector 127. In such instances a second distribution line may be fluidly coupled to distribution line 107 in any suitable manner, and the second distribution line may extend from distribution line 107 to within medical device 129 (e.g., to within a reservoir thereof).

Figure 2:
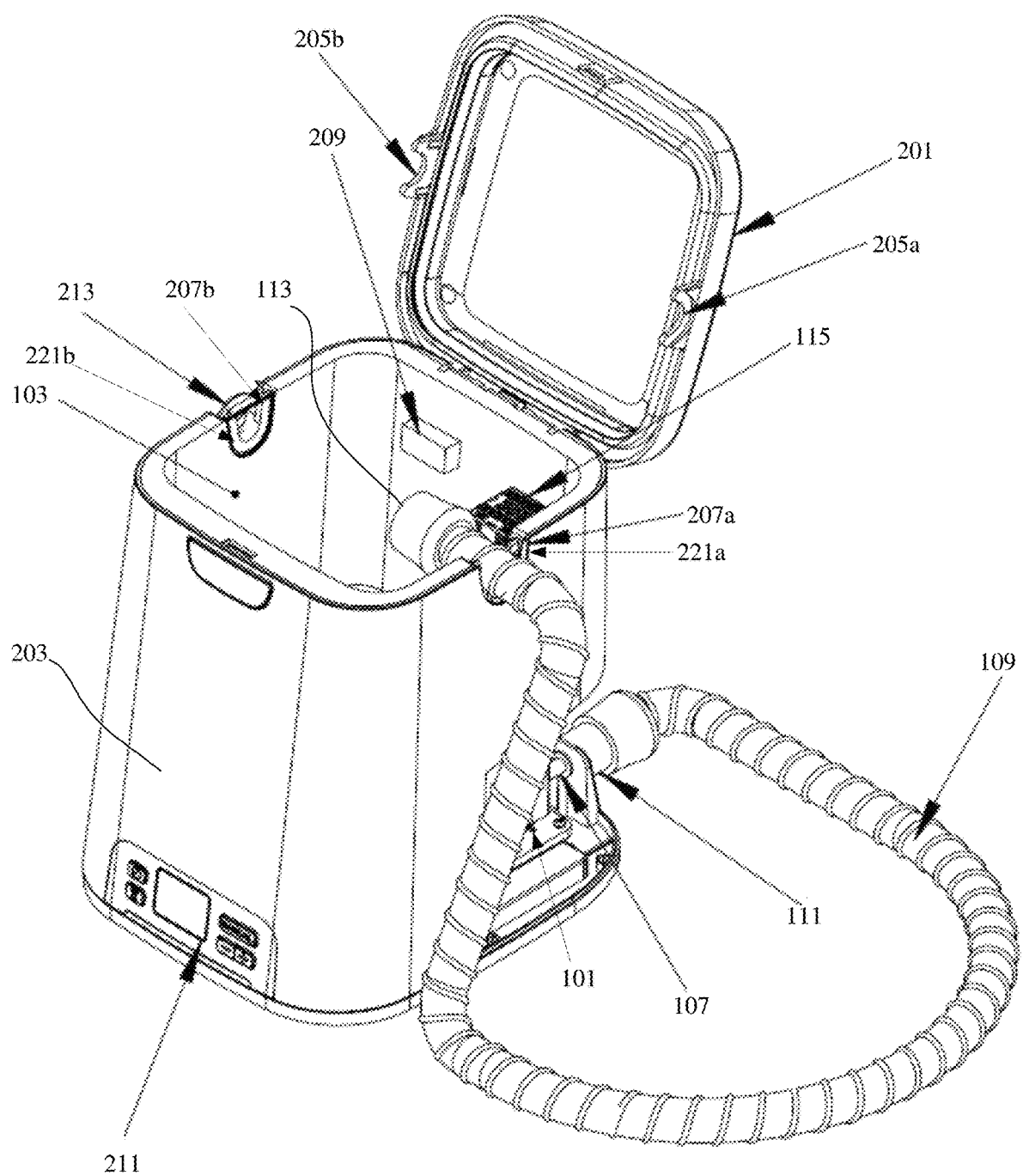
FIG. 2 is a perspective view of one example of a sanitizing device coupled to a medical device hose, consistent with the block diagram of FIG. 1A.

FIG. 2 depicts one example of a system 200 for sanitizing a medical device consistent with FIG. 1A. Like system 100, system 200 includes an ozone operating system 101, sanitizing chamber 103, filter 115, and an exhaust port (not shown). The ozone operating system 101 is coupled to a distribution line 107 that in turn is coupled to a proximal end 111 of a hose 109 (e.g., a medical device hose, such as a CPAP hose). The distal end 113 of hose 109 is disposed within the gas tight compartment as shown. System 200 further includes a lid 201 and a base 203. The lid 201 is movable between an open and a closed position while the distal end 113 of hose 109 is disposed within the sanitizing chamber 103.

The base 203 includes at least one sidewall (not labeled) having a receptacle (221a, 221b) for receiving an intermediate portion of the hose 109 formed therethrough. In the illustrated embodiment, the base 203 includes four sidewalls, though any suitable number of sidewalls (e.g., 1, 2, 3, 4, or more) may be used. Moreover, the illustrated embodiment includes two receptacles 221a, 221b that can receive an intermediate part of the hose 109, though any suitable number of such receptacles (e.g., 1, 2, 3, 4, or more) may be used.

In general, system 200 is (or, more specifically, lid 201 and receptacles 221a and 221b are) configured to engage and form a seal around an intermediate portion of hose 109. In embodiments lid 201 includes upper seal members 205a, 205b, and receptacles 221a, 221b include lower seal members 207a, 207b, respectively. In operation the upper seal members 205a, 205b and lower seal members 207a, 207b engage and form a seal against an intermediate portion of the hose 109. In the illustrated embodiment, when lid 201 is closed the hose 109 is urged against lower seal member 207a such that lower seal member 207a forms a first seal with a first (e.g., lower) part of the intermediate portion of the hose 109. Likewise, the upper seal member 205a is urged against and forms a seal with a second (e.g., upper) part of the intermediate portion of the hose 109. In those or other embodiments, at least a portion of upper seal member 205a may urge against and form a seal with a portion of lower seal member 207a. Upper seal member 205b and lower seal member 207b may function in the same manner when another hose 109 is disposed through receptacle 221b.

In instances where a single hose is used, one of the receptacles 221a, 221b may be obstructed with a plug 213, as shown. In any case the upper and lower seal members cooperatively form a seal against the intermediate portion of the hose 109. The seal formed by the upper and lower seal members (with the hose or plug) may inhibit or prevent flow of a sanitizing gas such as ozone from sanitizing chamber 103 through receptacles 221a, 221b.

To conduct a sanitizing operation with system 200, lid 201 may be moved from the open position (shown) to a closed position (not shown). In the closed position lid 201 causes upper seal member 205a and lower seal member 207a to seal against corresponding parts of the intermediate portion of hose 109, as discussed above. Lid 201 may also cause upper seal member 205b and lower seal member 207b to seal against corresponding parts of plug 213. A user may then initiate a sanitization cycle via user interface 211.

During the sanitization cycle ozone operating system 101 generates ozone gas. The generated ozone gas is conveyed (e.g., by a fan or pump) through distribution line 107, into hose 109, and ultimately into sanitizing chamber 103. Ozone within sanitizing chamber 103 is converted to oxygen naturally and/or by filter 115 as previously described in connection with FIG. 1A. The resulting oxygen may then be conveyed through an exhaust port (not shown) and exhausted into the surrounding environment. Sanitizing gas within the sanitizing chamber 103 may be detected by an optional sanitizing gas sensor 209.

Figure 3:
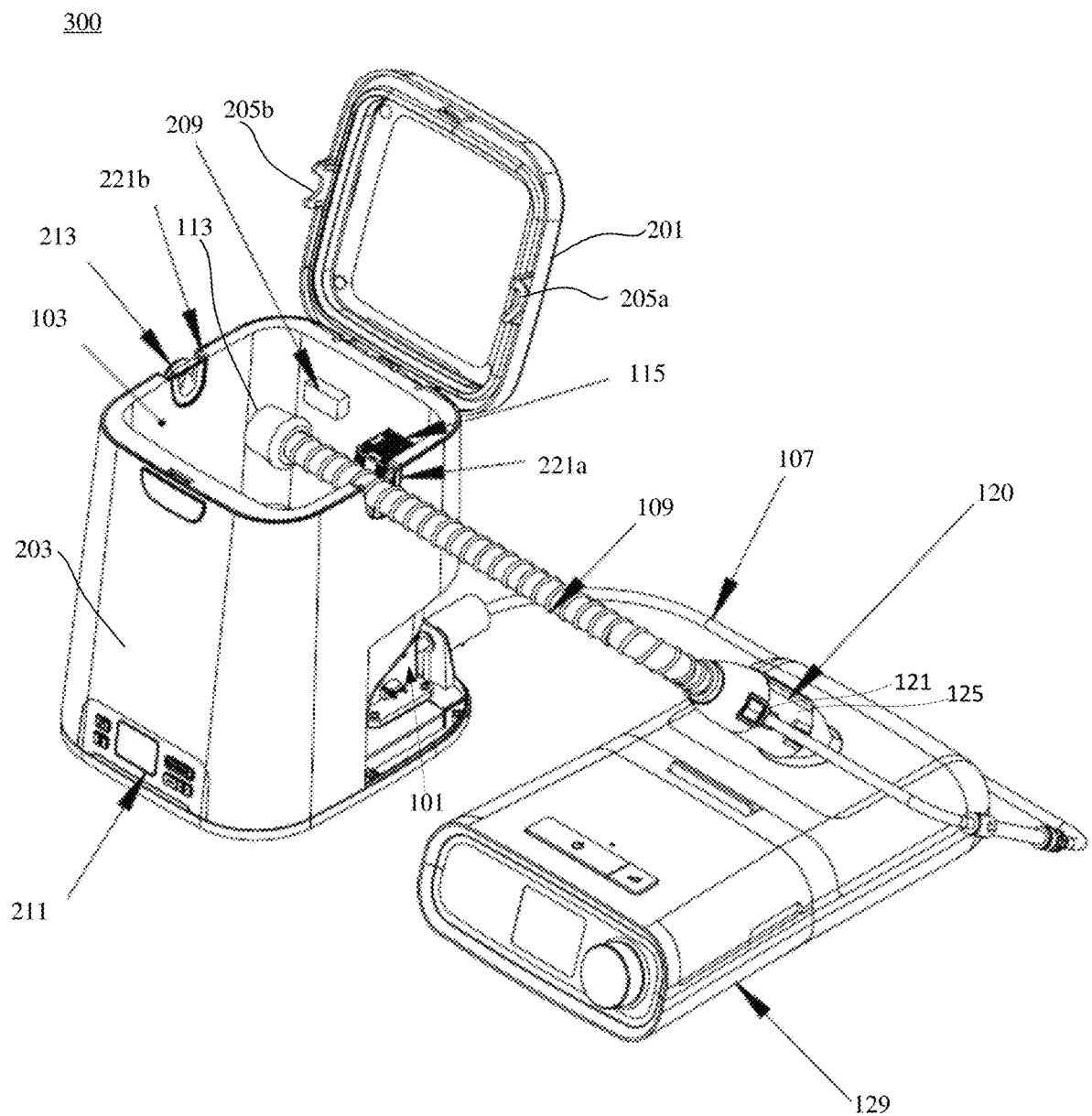
FIG. 3 is a perspective view of one example of a sanitizing device coupled to a medical device reservoir and hose, consistent with the block diagrams of FIGS. 1B-1D.

FIG. 3 depicts one example of a system 300 for sanitizing a medical device consistent with system 100' of FIG. 1B. Like system 100', system 300 includes an ozone operating system 101, sanitizing chamber 103, filter 115, connector unit 120, and an exhaust port (not shown). The ozone operating system 101 is coupled to a distribution line 107. The distal end of distribution line 107 is coupled to first connector 121 of connector unit 120 as described above in connection with FIG. 1B. The first connector 121 is coupled to a first passageway (not shown), at least a portion of which extends through sidewall 125 as discussed above. At least a portion of the first passageway is disposed within a second passageway (not shown) in connector unit 120, as discussed above in connection with FIG. 1B. The second connector is coupled to a medical device 129, such as a CPAP device or, more particularly, a reservoir of a CPAP device.

The second passageway extends between the first opening and a second opening (not shown) in a third connector (not labeled) of connector unit 120. The third connector is coupled to hose 109 of a medical device, such as a CPAP hose. The distal end 113 of hose 109 is disposed within the sanitizing chamber 103 as shown. System 300 also includes a lid 201 and a base 203, the nature, components, and function of which are the same as discussed above in connection with FIG. 2.

To perform a sanitizing operation with system 300, lid 201 may be moved from the open position (shown) to a closed position (not shown). In the closed position, lid 201 causes upper seal member 205a and a corresponding lower seal member 207a (not shown in FIG. 3) to seal against corresponding parts of the intermediate portion of hose 109. Similarly, lid 201 causes upper seal member 205b and a corresponding lower seal member 207b (also not shown in FIG. 3) to seal against corresponding parts of plug 213. A user may then initiate a sanitization cycle via user interface 211.

During the sanitization cycle ozone operating system 101 generates ozone gas. The generated ozone gas is conveyed (e.g., by a fan or pump) through distribution line 107, into the first passageway within connector unit 120. After it is introduced into the first passageway, the ozone may flow into medical device 129 (e.g., into a CPAP reservoir), into hose 109, or a combination thereof. Ozone flowing into medical device 129 may sanitize the interior (and/or a reservoir) thereof. Ozone introduced into hose 109 may sanitize the interior of hose 109. In embodiments, ozone flows from the distribution line 107 into the first passageway of the connector unit 120. Thereafter, ozone may flow into the medical device and/or hose 109. For example, ozone may flow into the medical device 129, and from the medical device 129 into the second passageway and then into the hose 109. Ozone within hose 109 is conveyed into sanitizing chamber 103, where it may sanitize the interior of sanitizing chamber 103 and any components therein. Ozone within sanitizing chamber 103 may then be converted to oxygen, e.g., naturally and/or by a filter 115 (or a catalyst material therein) as previously described. The resulting oxygen may then be conveyed to an exhaust port (not shown) and exhausted into the environment.

FIGS. 2 and 3 depict systems 200 and 300 as including a lid 201 and base 203 that are configured to form a seal around an intermediate portion of hose 109. While such a configuration has some advantages (e.g., enabling a distal end 113 of hose 109 to be disposed within sanitizing chamber 103 while coupled to another component of medical device 129, e.g., a CPAP mask) such a configuration is not required. In alternative configurations systems 200 and 300 may include base 203 with a port (not shown) that extends through a sidewall thereof. The port may include a first end and a second end with a fluid passageway therebetween, wherein the fluid passageway enables the flow of fluid (e.g., sanitizing gas) from a position outside base 203 to the sanitizing chamber 103. A block diagram of such a system is shown, for example, in FIGS. 4K and 4L, which are described later. The first end of the port may be configured to fluidly couple with the distal end 113 of hose 109. In such instances upper seal members 205a, 205b, lower seal members 207a, 207b, and receptacles 221a, 221b may be eliminated from system 200. Moreover, in such embodiments lid 201 may include a lower peripheral surface that is configured to sealingly engage with an upper peripheral surface of base 203.

In those alternative configuration, the distal end 113 may be coupled to the first end of the port in base 203. In operation, when lid 201 is in a closed position a sanitizing gas such as ozone may be introduced into the connector unit 120. The sanitizing gas introduced into the connector unit 120 may migrate into and through hose 109, through the port, and into sanitizing chamber 103. One advantage of the alternative configurations is that they eliminate potential leakage points presented by the use of upper seal members 205a, 205b, lower seals members 207a, 207b. Unlike systems 200 and 300, however, the alternative configurations do not permit the distal end 113 of hose 109 to remain connected to other components of medical device 129 during a sanitizing operating. More specifically, when medical device 129 is a CPAP device and hose 109 is a CPAP hose, systems 200, 300 permit the distal end 113 of hose 109 to remain connected to a CPAP mask during a sanitizing operation—thus allowing the CPAP hose and mask to be easily sanitized without disassembly. In contrast, in the alternative configurations the distal end 113 of hose 109 is coupled to the port in base 203. Thus, prior to conducting a sanitizing operation, the distal end 113 of hose 109 is decoupled from other components of medical device 129 (e.g., a CPAP mask) and coupled to the port. Regardless, using the alternative configurations sanitization of the CPAP mask can still be easily and efficiently achieved by placing the CPAP mask within sanitizing chamber during a sanitizing operation and connecting the distal end of hose 109 to the port in base 203.

Systems 200, 300 can effectively sanitize various components of a medical device, including but not limited to a hose 109, a mask (optionally attached to hose 109), a medical device 129 (e.g., a reservoir such as a CPAP reservoir), and/or components disposed within a sanitizing chamber 103. Due to the nature of the sanitizing gas, however, it may be desirable to limit, avoid, or prevent the release of sanitizing gas into the surrounding environment, and/or to prevent a user from inhaling or otherwise being exposed to the sanitizing gas. Unintentional release, inhalation and/or exposure may result, for example due to leakage of the sanitizing gas from one or more components of the sanitizing system, leakage of the sanitizing gas at one or more seals of the sanitizing system, and/or user operation of the sanitizing system while the system is in an unsafe condition.

In systems 200 and 300 leakage of the sanitizing gas may occur due to complete or partial failure of the seal formed around the intermediate portion of hose 109, e.g., by upper seal member 205a and lower seal member 207a. Leakage may also occur due to failure of the seal around plug 213. Sanitizing gas may also be released into the surrounding environment if the system is operated in an unsafe condition, e.g., when lid 201 is open; when hose 109 is not present within receptacle(s) 221a, 221b; when filter 115 is defective or not present; when a user is using a medical device (in the context of system 300); combinations thereof, and the like.

Accordingly, aspects of the present disclosure relate to sanitizing systems that include one or more safety features that are generally designed to limit or even prevent the release of sanitizing gas into the environment, and/or to control (e.g., limit or prevent) the execution of a sanitization cycle when the sanitizing system is in an unsafe condition. Such safety features include, without limitation, one or more sensors that enable the sanitizing system (or, more specifically, a controller of the sanitizing system) to detect an unsafe condition, and/or to prevent or disable execution of a sanitization cycle in response to the detection of an unsafe condition. Aspects of the present disclosure also relate to improved components of a sanitizing system, including improved sanitizing chambers, improved filters, improved sealing systems, combinations thereof, and the like.

Figure 4A:
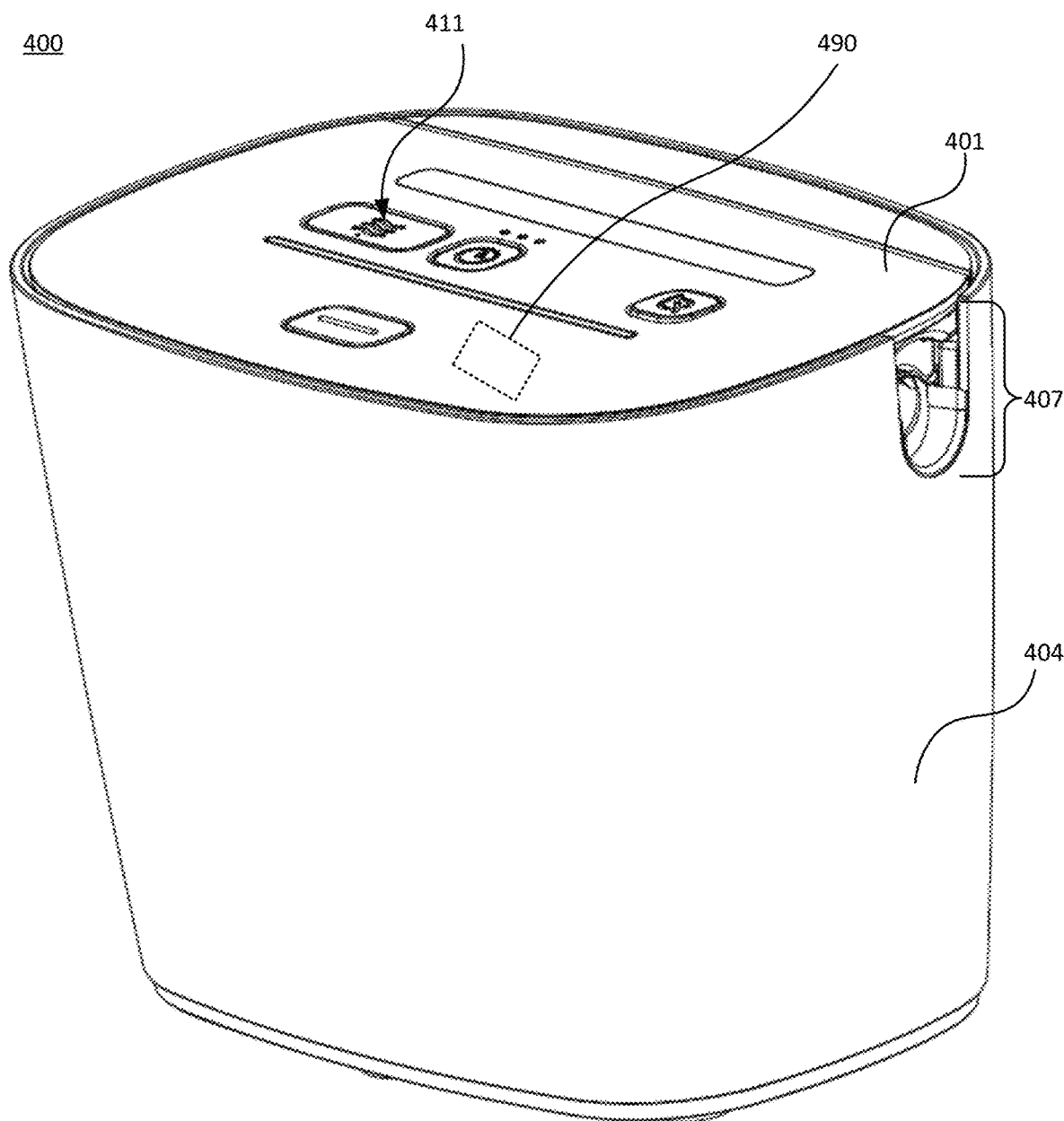
FIGS. 4A-4J depict various views of one example of a medical device and components thereof, consistent with the present disclosure.
Figure 4B:
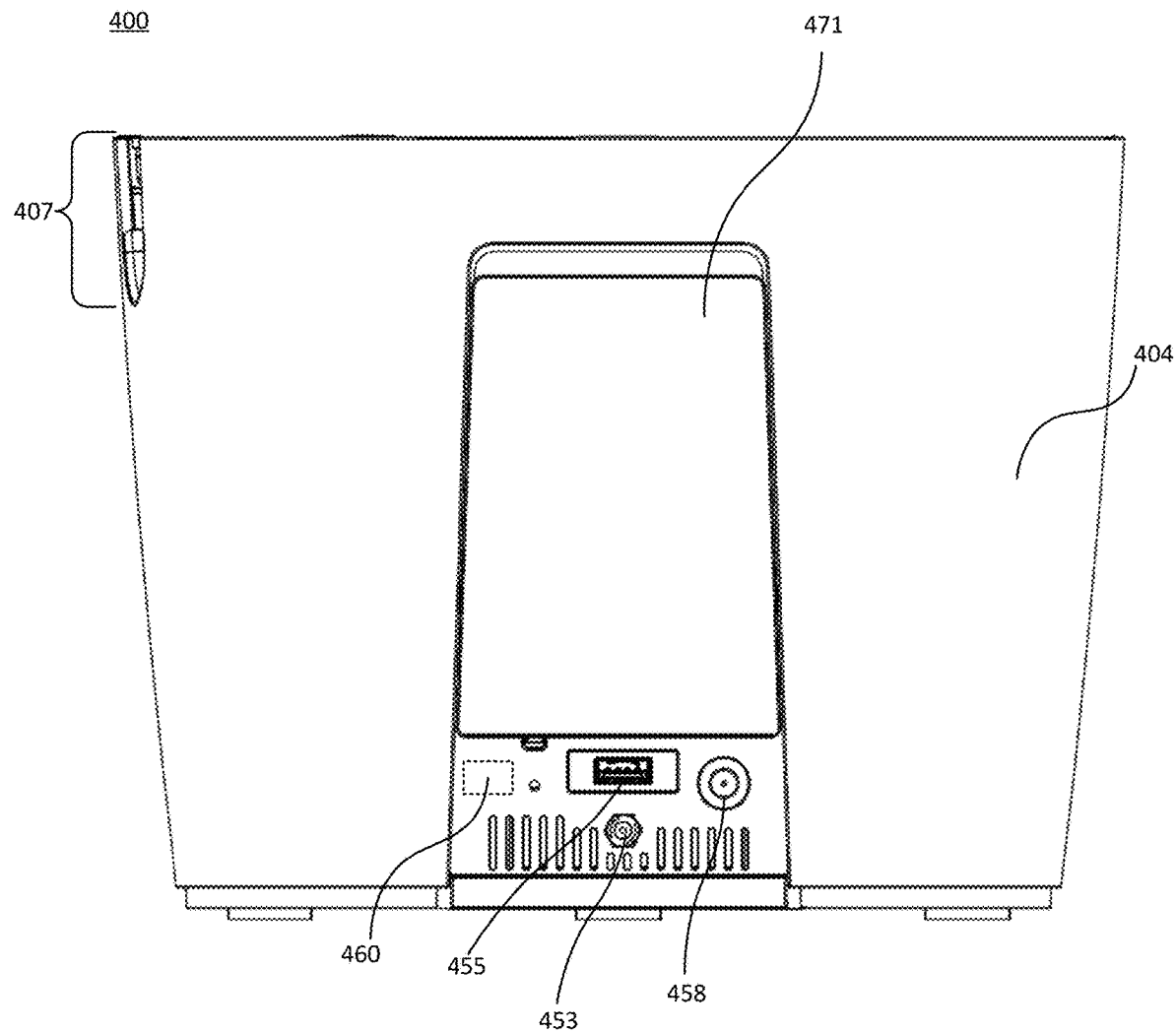
Figure 4C:
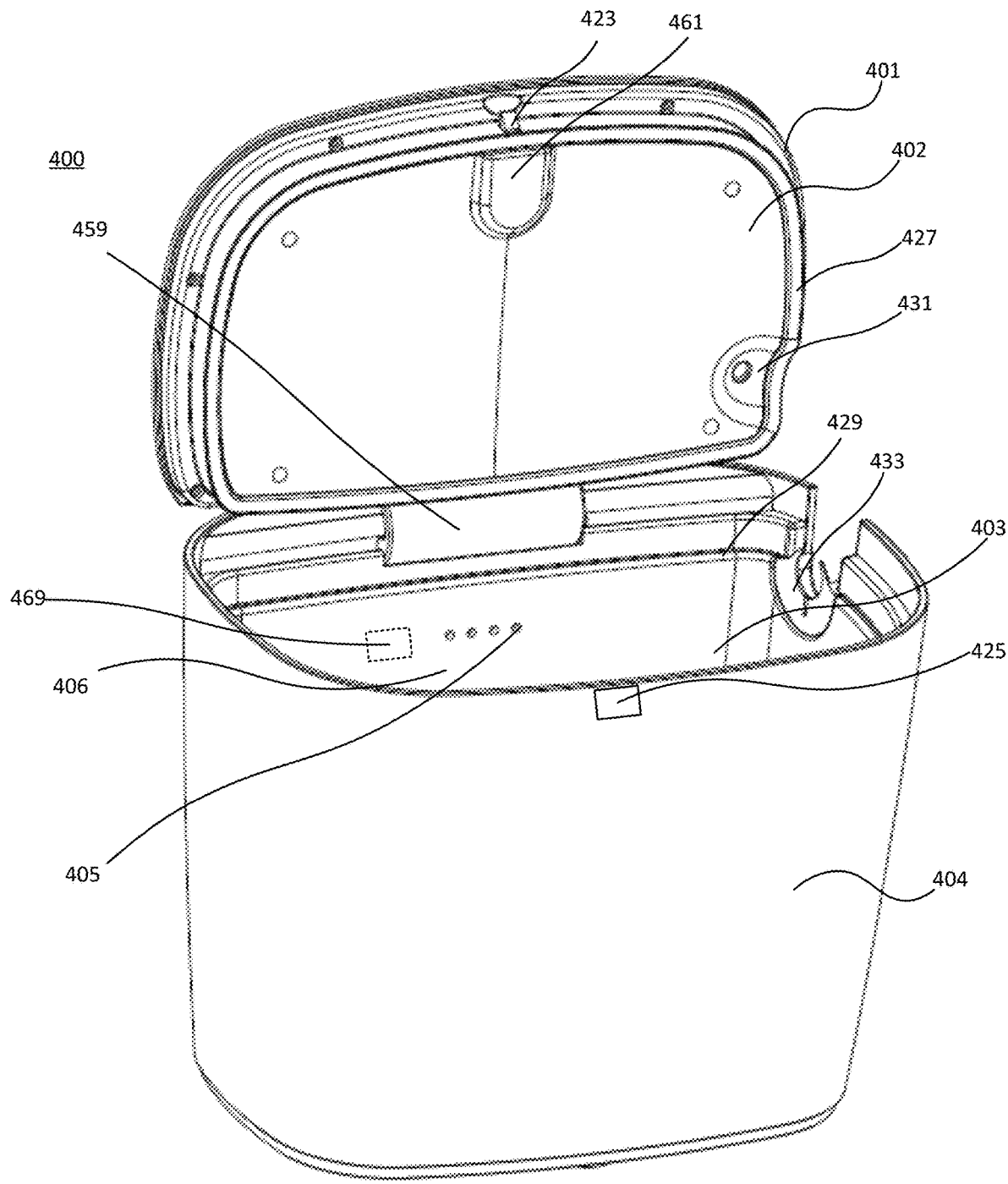
Figure 4D:
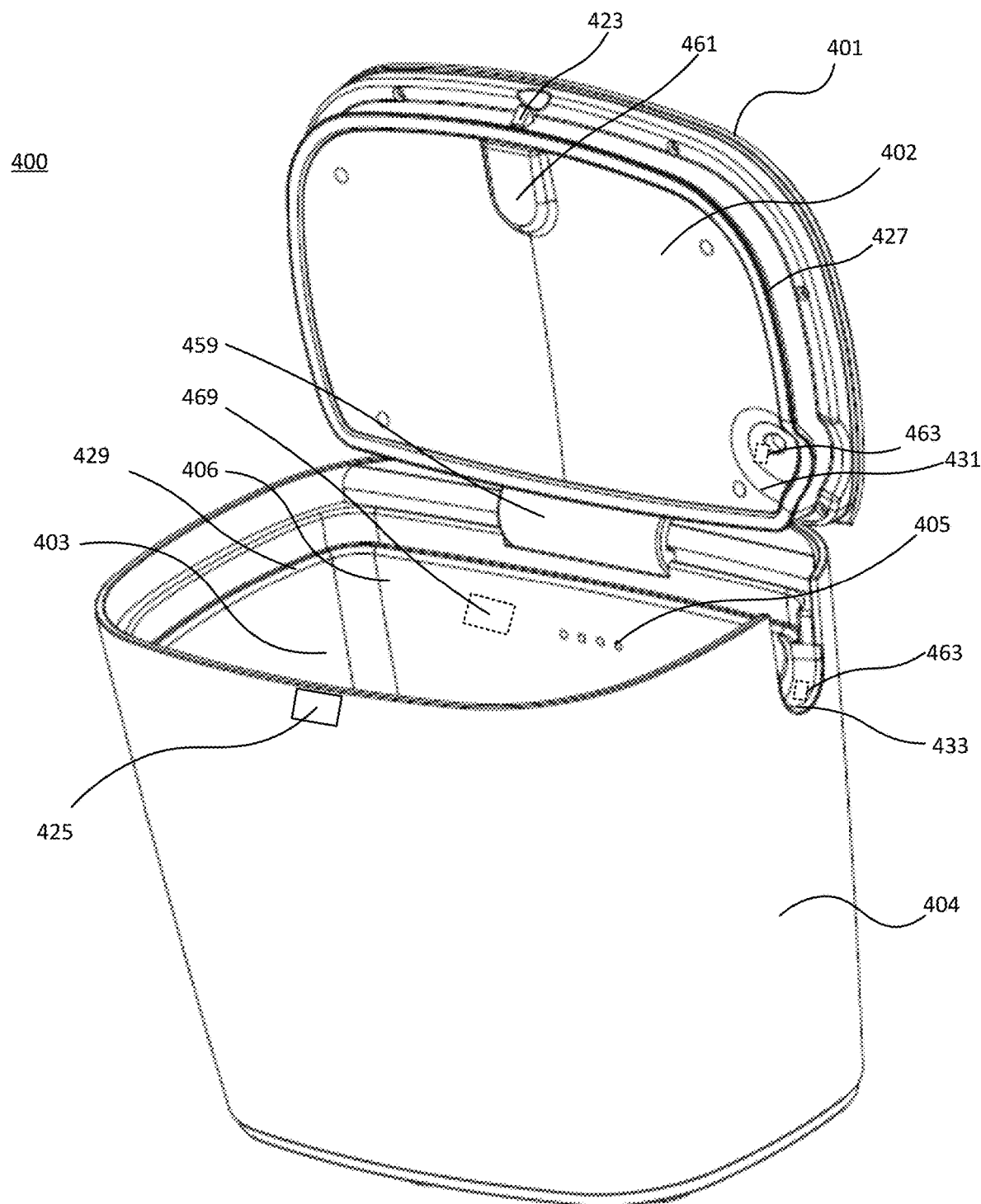
Figure 4E:
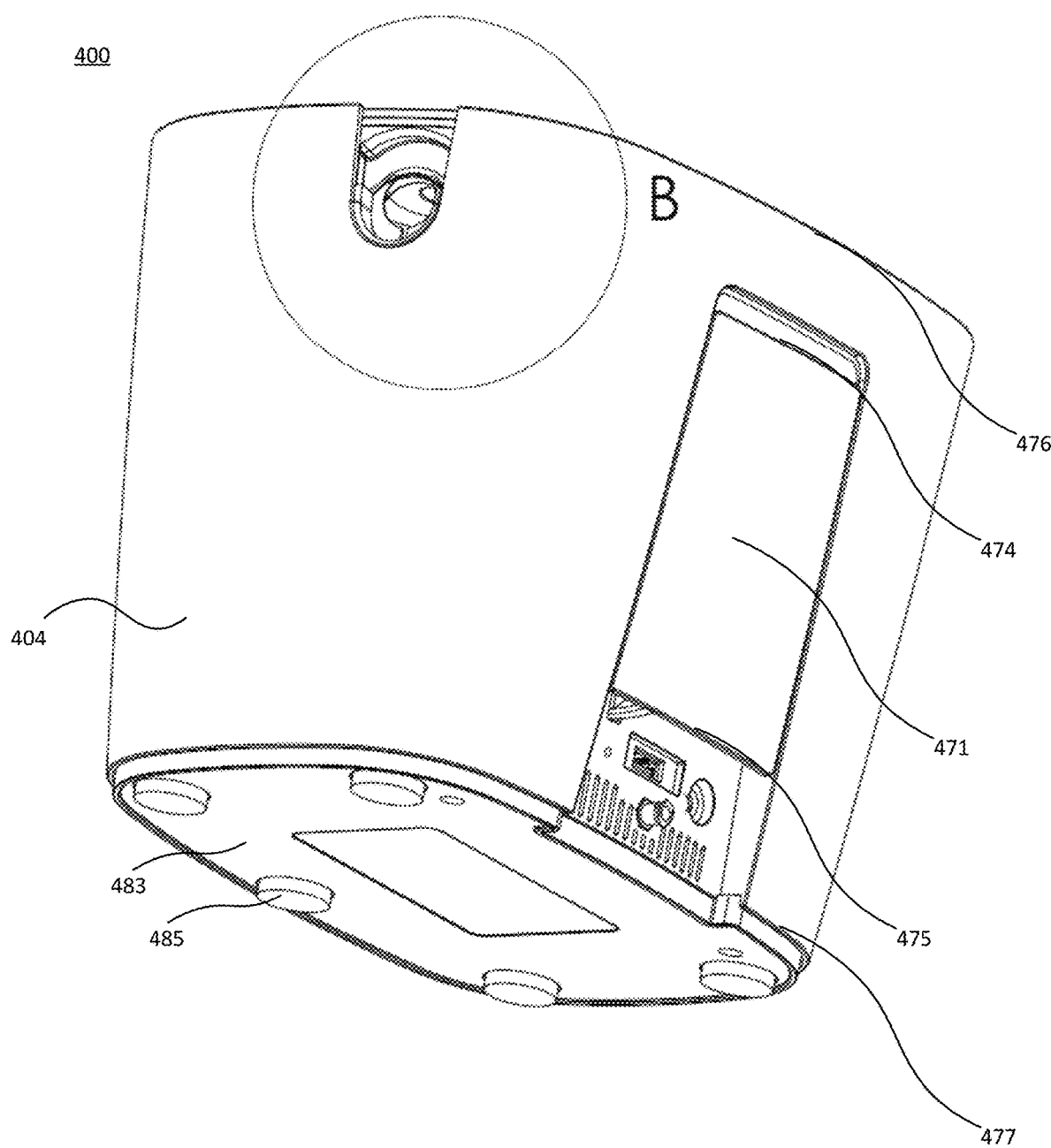
Figure 4F:
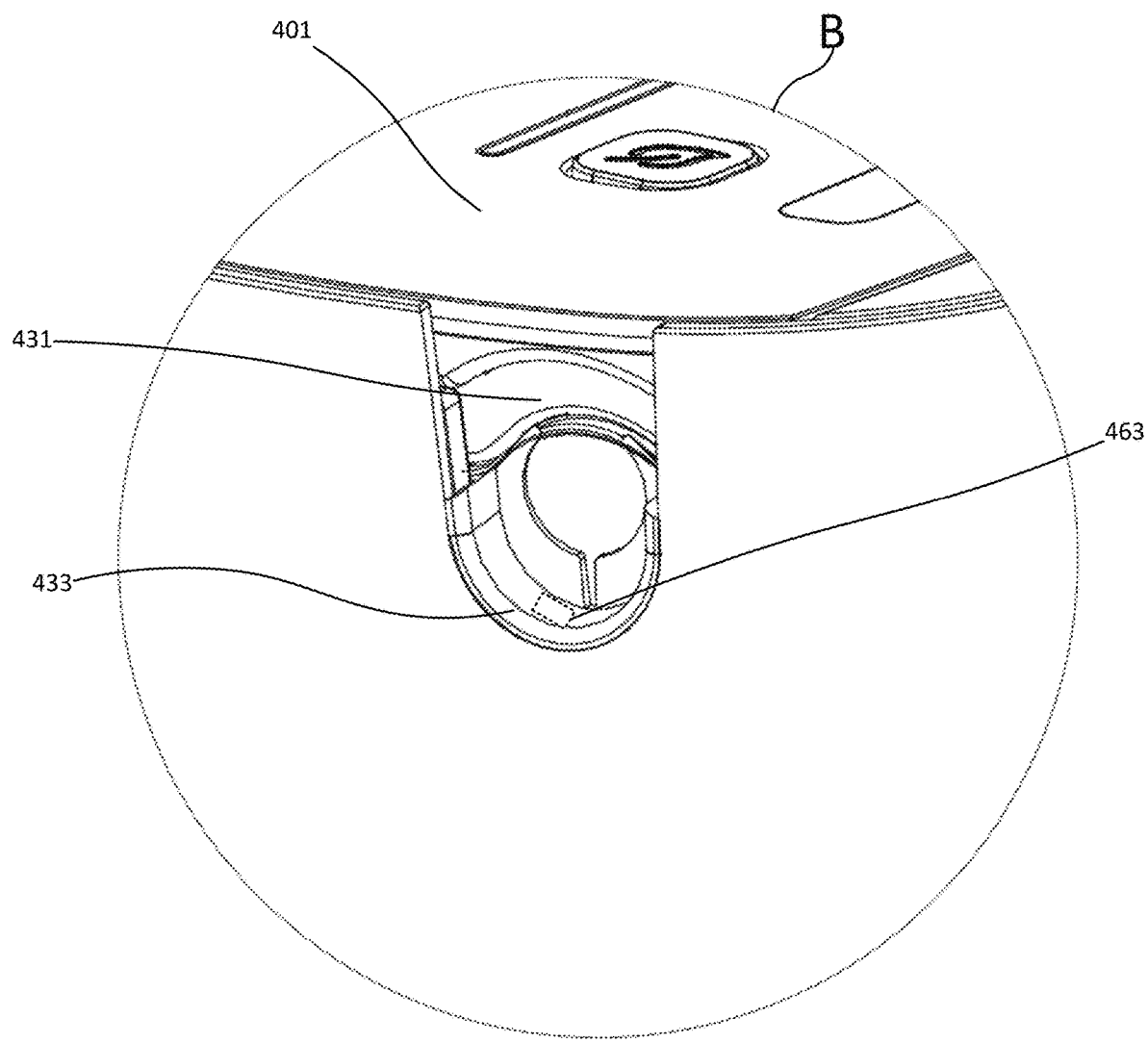

FIGS. 4A-4J depict one example of a sanitizing system consistent with the present disclosure. As shown, system 400 includes a lid 401, a base 404, and a receptacle 407. Base 404 is defined by one or more (e.g., 1, 2, 3, 4, 5, or more) sidewalls, and is coupled to or integral with a bottom 483, as best shown in FIG. 4E. One or more optional feet 485 may be integral with or coupled to the bottom 483, as also shown in FIG. 4E.

Lid 401 is coupled to base 404 in any suitable manner, and is movable between an open position and a closed position as best shown by comparison of FIGS. 4A, 4C and 4D. In the illustrated embodiments lid 401 is coupled to base 404 via hinge 459, but lid 401 may be coupled to base 404 in any suitable manner In the illustrated embodiments, lid 401 may rotate about an axis extending through hinge 459 as it moves between the closed and open positions as shown in FIGS. 4A and 4C, respectively.

Lid 401 may be retained in the closed position by a locking system that includes closing member 423 and receiver 425, the operation of which may be controlled by a controller 490. In embodiments closing member 423 is in the form of an electronically actuatable bolt that may be engaged and disengaged (e.g., inserted and retracted) from receiver 425, e.g., in response to a control signal from a controller. In such instances receiver 425 may be in the form of a latch, slot, or other suitable structure that is configured to receive the closing member 423. In some embodiments closing member 423 includes a bolt and a solenoid configured to actuate the bolt between locked and unlocked positions in response to a control signal, and receiver 425 is in the form of a slot that is configured to receive the closing member bolt.

In the locked position closing member 423 may be at least partially disposed within (e.g., engaged within) receiver 425. In that position closing member 423 and receiver 425 may mechanically interfere, preventing or hindering the movement of lid 401 from the closed to open position. In the unlocked position, closing member 423 may be withdrawn from (e.g., disengaged from) receiver 425, allowing lid 401 to move from the closed to the open position.

System 400 further includes a sanitizing chamber 403, which is best shown in FIGS. 4C and 4D. In the illustrated embodiment sanitizing chamber 403 is defined at least in part by base 404 and lid underside 402 when lid 401 is in the closed position. Lid 401 includes an inner peripheral edge (not labeled) that is configured to abut or cooperate with a corresponding inner peripheral edge (also not labeled) of sanitizing chamber 403. As shown in FIGS. 4C and 4D, a lid seal 427 extends around the inner peripheral edge of lid 401, and a base seal 429 extends around the inner peripheral edge of sanitizing chamber 403. When lid 401 is moved to the closed position, lid seal 427 is urged against base seal 429 to form a first gas tight seal proximate the inner peripheral edge of the lid and the inner peripheral edge of the sanitizing chamber 403. As used herein, the term "gas tight" when used in conjunction with a seal, means that the seal is configured to prevent the passage of sanitizing gas, or to limit the passage of sanitizing gas therethrough to below a threshold amount over a fixed amount of time. In embodiments leakage of sanitizing gas (e.g., ozone) through a gas tight seal is less than 0.05 parts per million (ppm) over a defined time period (e.g. 3-5 hours), and in embodiments leakage of sanitizing gas through a gas tight seal is 0 ppm over that period.

Lid seal 427 and base seal 429 may include or be formed of any suitable material that facilitates the formation of the first gas tight seal, such as materials commonly used to form gaskets, O-rings, and the like. Non-limiting examples of suitable materials that may be used to form lid seal 427 and base seal 429 include synthetic and natural elastomeric materials, such as one or more (optionally low durometer) elastomeric polymers (e.g., silicone), rubbers, and the like.

Sanitizing chamber 403 is generally sized and configured to house one or a plurality of medical devices and/or medical device components therein. In embodiments sanitizing chamber 403 is sized and configured to house one or more components of a continuous positive airway pressure (CPAP) device, including but not limited to one or more CPAP masks, CPAP nose pillows, CPAP hoses, combinations thereof, and the like. Sanitizing chamber 403 may also be configured to house to other types of medical devices and/or device components (e.g., respirators, breathing masks, nasal pillows, combinations thereof and the like).

Non-limiting examples of such devices and components include hoses, tubes, surgical instruments, irrigation systems for sterile instruments in sterile tissues, endoscopes and endoscopic biopsy accessories, duodenoscopes, endotracheal tubes, bronchoscopes, laryngoscopes blades and other respiratory equipment, esophageal manometry probes, diaphragm fitting rings and gastrointestinal endoscopes, infusion pumps, ventilators, combinations thereof, and the like.

System 400 further includes one or a plurality of exhaust ports 405, as best shown in FIGS. 4C and 4D. In the illustrated embodiment four exhaust ports 405 are shown, but any suitable number (e.g., 1, 2, 3, 4, 5 or more) exhaust ports 405 may be used. Regardless of their number, each exhaust port 405 may be sized and configured to facilitate removal of sanitizing gas (e.g., ozone) from sanitizing chamber 403, e.g., during or following execution of a sanitization cycle.

The exhaust ports 405 generally function to fluidly couple the interior of sanitizing chamber 403 with a filter 500. Thus, in embodiments each exhaust port 405 extends through one or more walls forming the inward facing surface 406 of sanitizing chamber 403. More specifically, each exhaust port 405 forms a channel for conveying sanitizing gas to a filter 500 from sanitizing chamber 403. In embodiments, exhaust ports 405 are configured to enable the removal of ozone or other sanitizing gas from sanitizing chamber 403, while regulating the backpressure of sanitizing gas within system 400 and/or the flow of sanitizing gas to filter 500.

While FIGS. 4C and 4D depict exhaust ports 405 in the form of holes, exhaust ports 405 may have any suitable geometry. For example, exhaust ports 405 may be in the form of one or more geometrically shaped openings (e.g., triangular, quadrilateral, circular, etc.), slots (e.g., ellipse, oval, etc.), irregular shaped openings, combinations thereof, and the like.

System 400 further includes a receptacle 407, as best shown in FIGS. 4A, 4B, and 4D-4F. Like receptacles 221a, 221b, receptacle 407 is generally configured to receive and form a seal around an intermediate portion of a hose of a medical device, such as a CPAP hose. In embodiments, receptacle 407 is configured to form a gas tight seal around an intermediate portion of a CPAP or other medical device hose, either alone or in conjunction with a portion of lid 201.

As will be discussed in detail with reference to FIGS. 6A-10B, 15A-15D, and 22A-22E, in embodiments receptacle 407 is defined at least in part by an upper seal member 431 and a lower seal member 433. As shown in FIGS. 4C and 4D, the upper seal member 431 may be defined at least in part by lid 401. For example, in embodiments upper seal member 431 is defined at least in part by lid seal 427. In different terms, in embodiments at least a portion of lid seal 427 forms or is part of upper seal member 431. In contrast lower seal member 433 is integral with or coupled to an opening formed through a sidewall of base 404. In embodiments and as discussed in detail regarding FIGS. 6A-10B, 15A-15D and 22A-22E, lower seal member 433 is in the form of a sealing insert that is coupled to base 404, e.g., by one or more lower seal retention members.

Figure 4G:
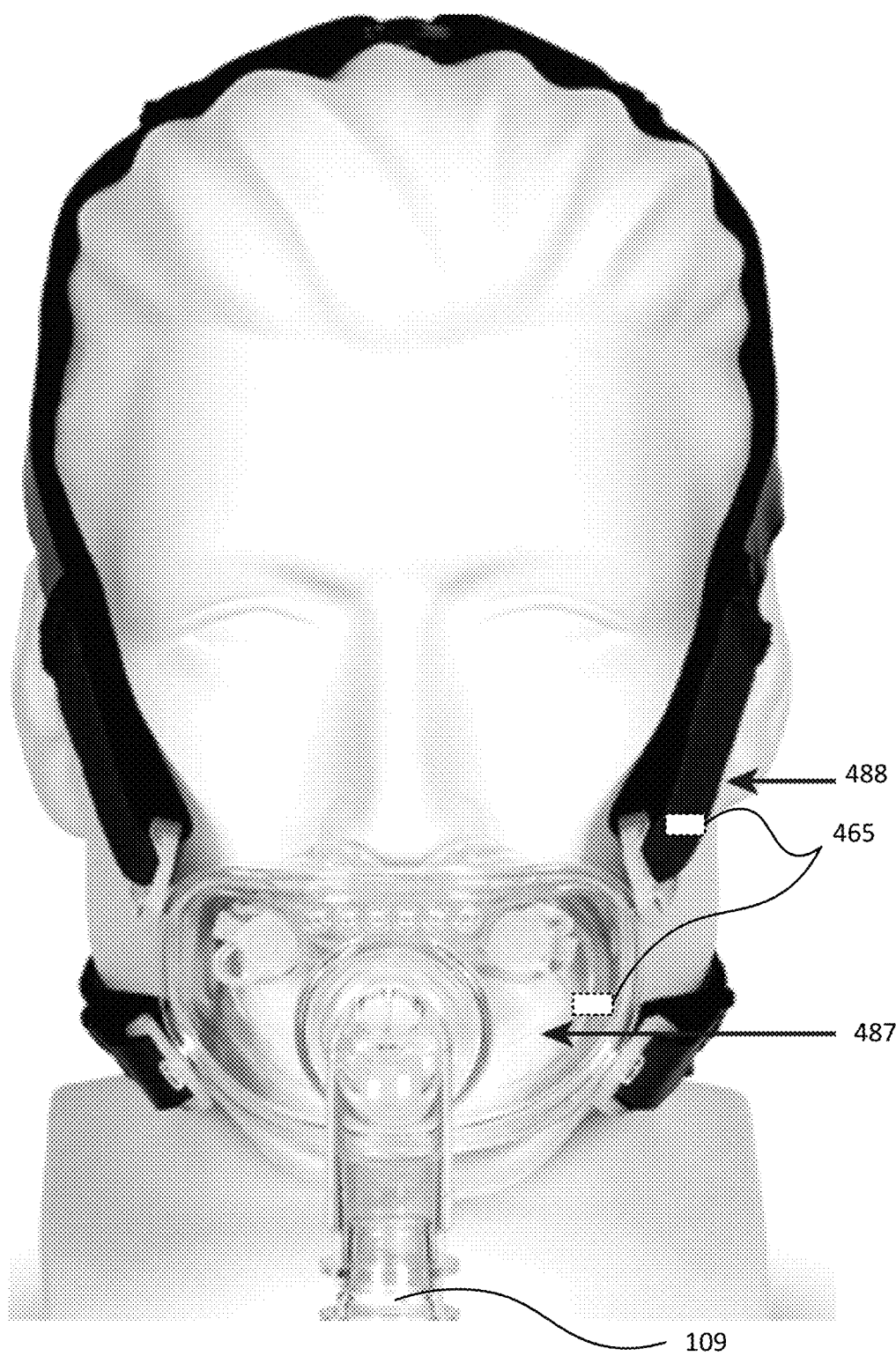
Figure 4H:
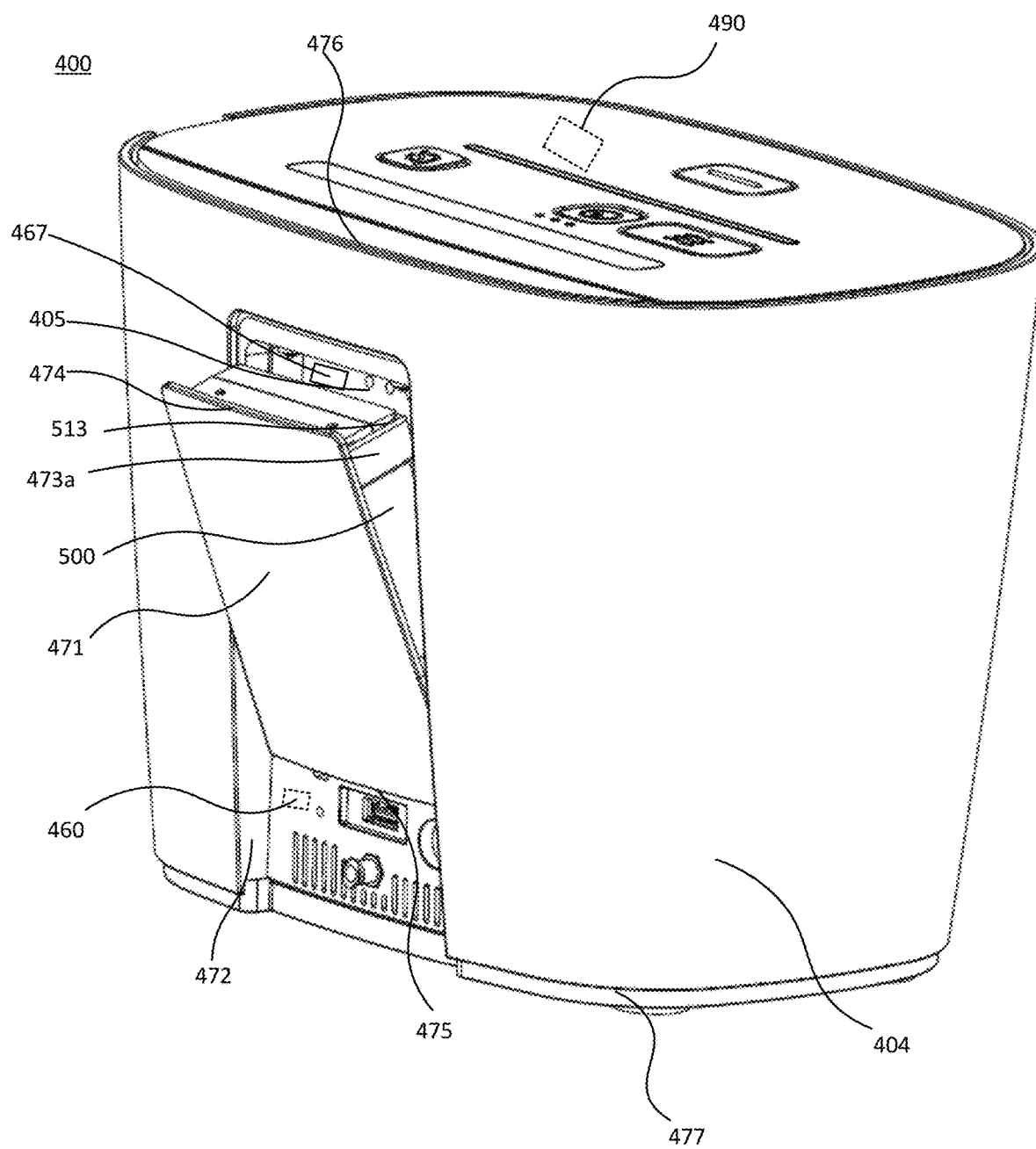
Figure 4I:
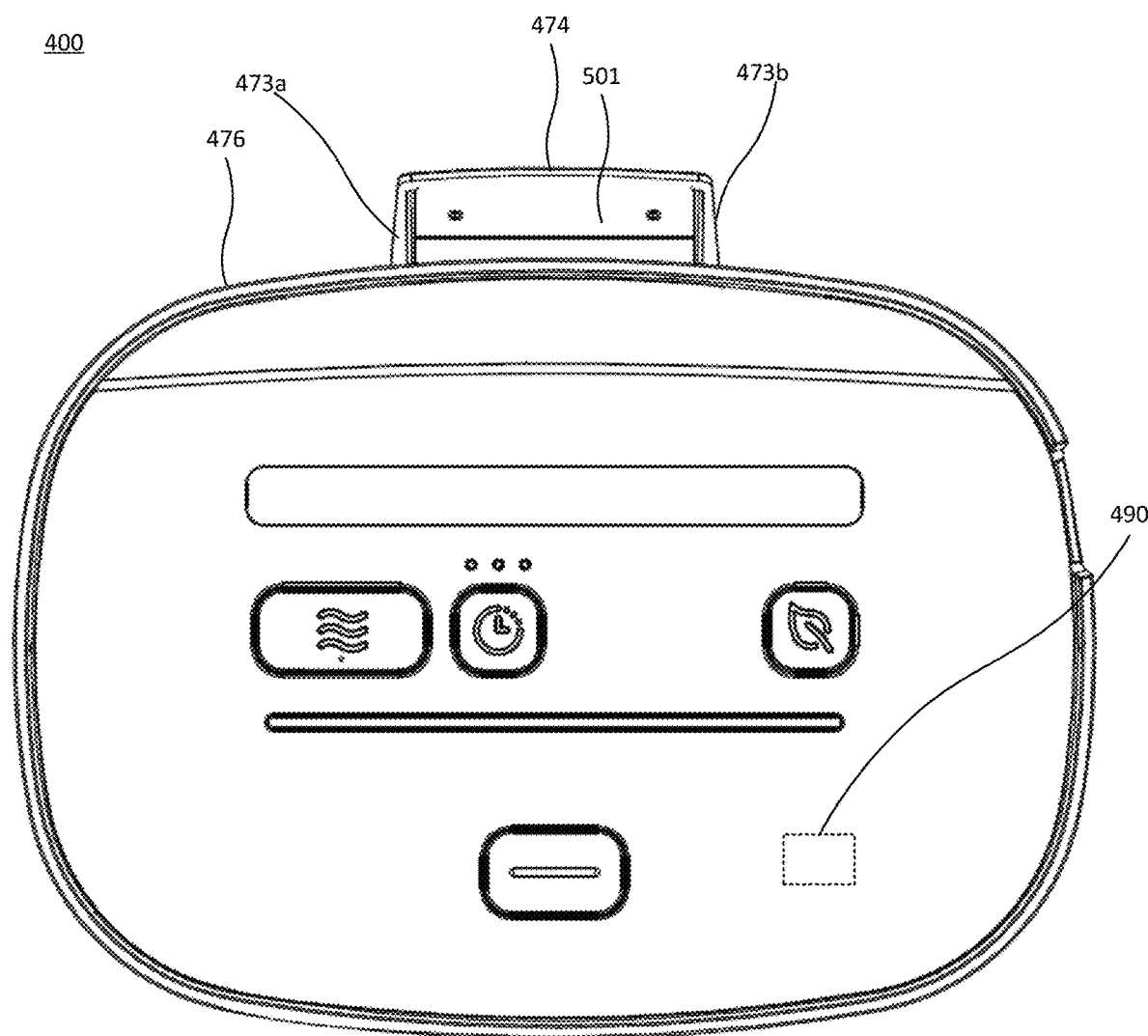
Figure 4J:
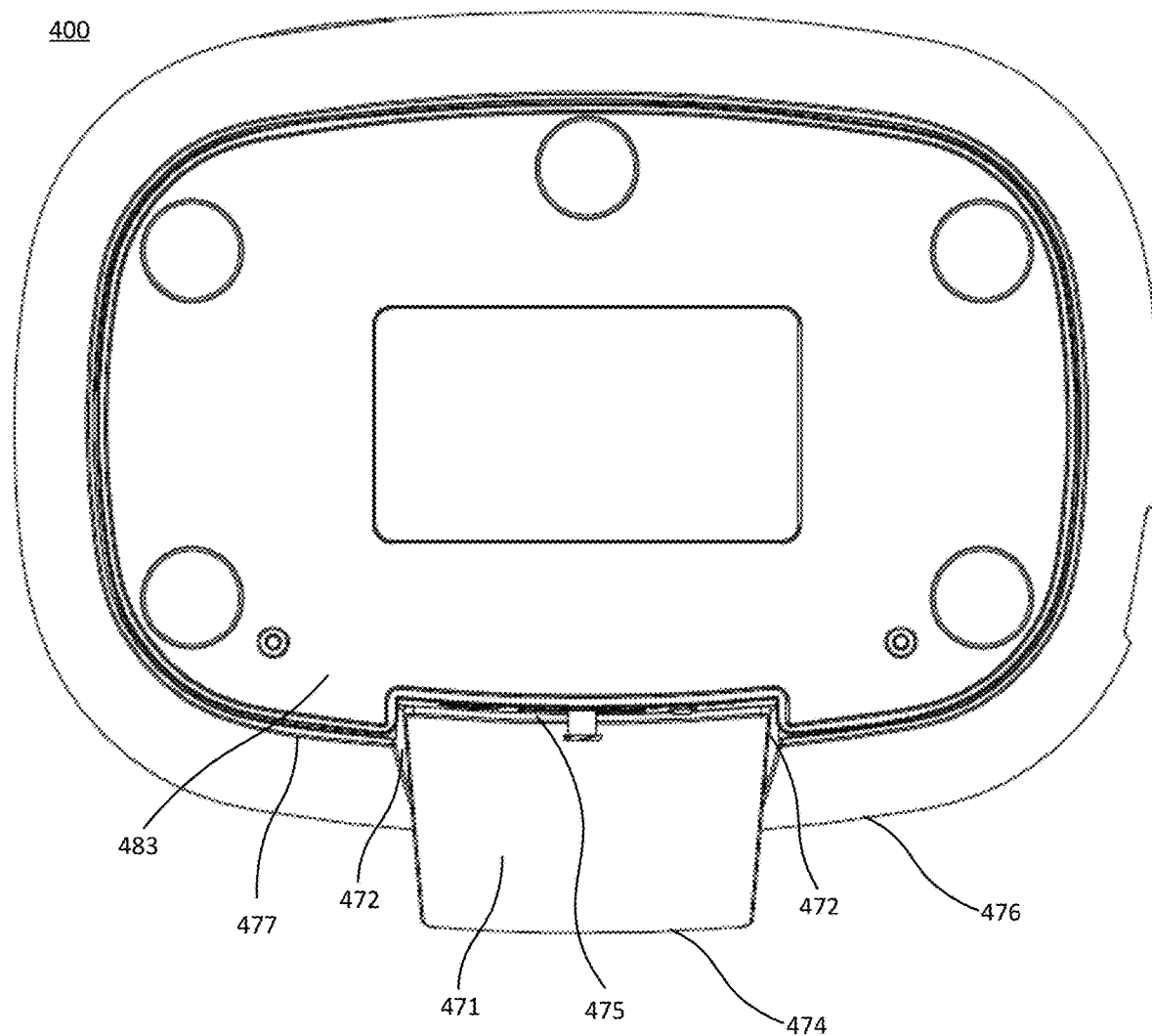
Figure 4K:
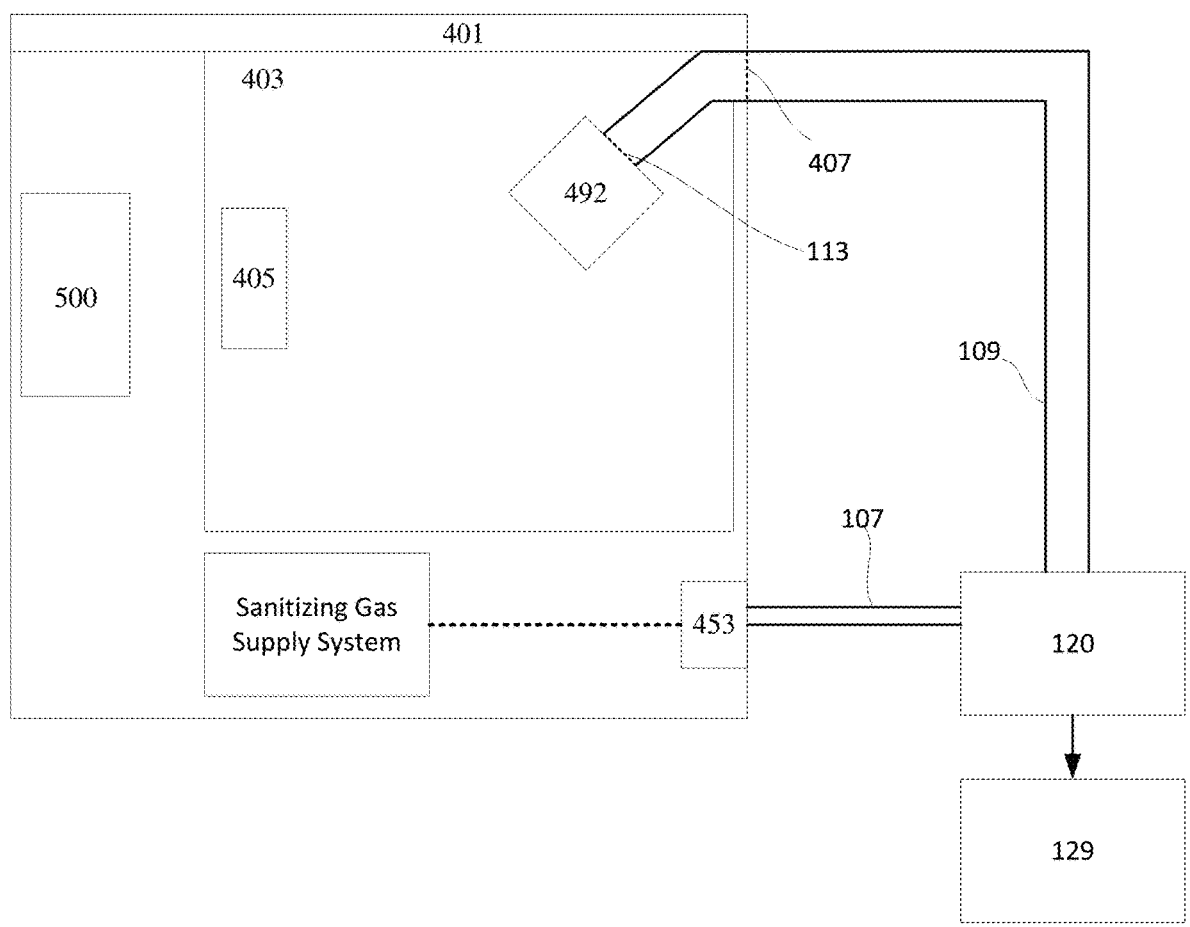
FIG. 4K is a block diagram of one configuration of a sanitizing system consistent with the present disclosure.
Figure 4L:
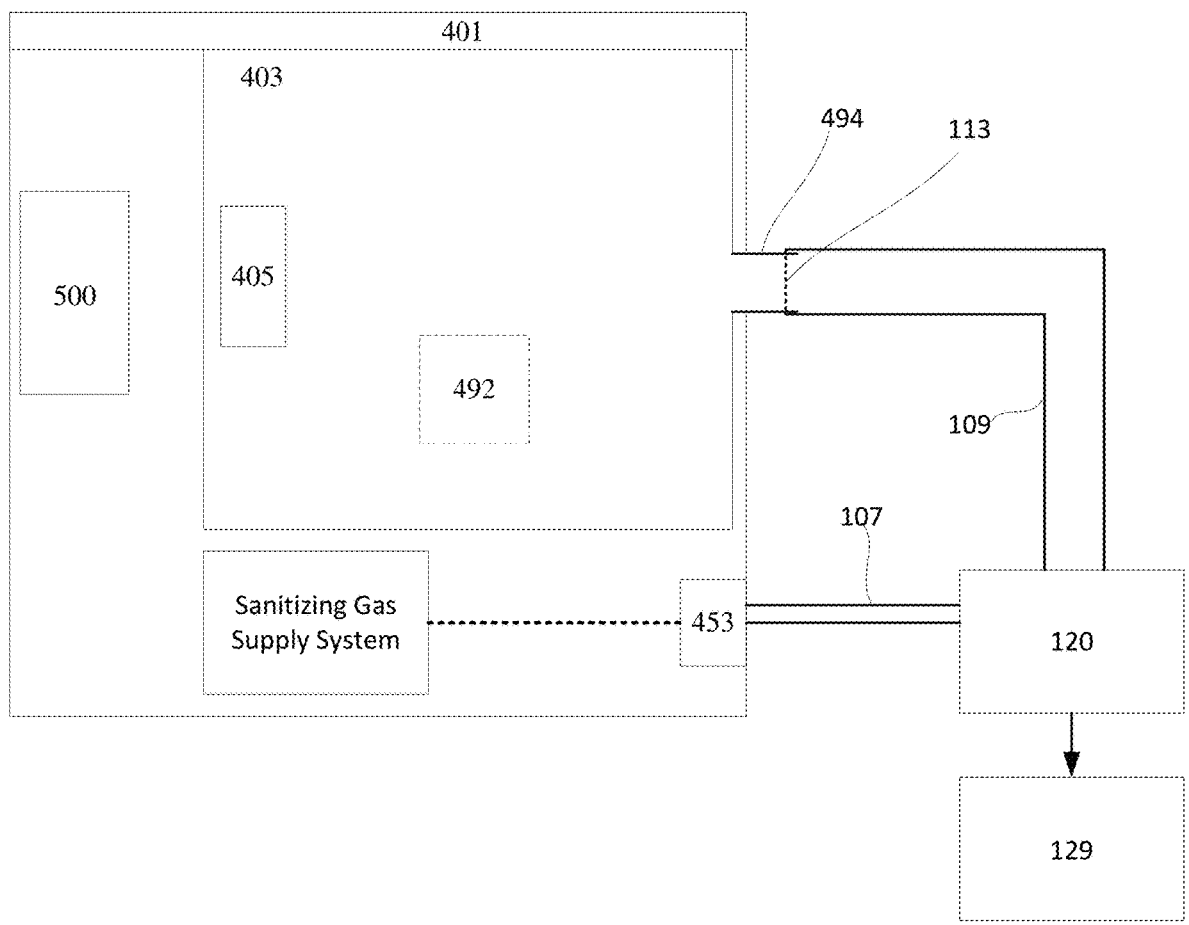
FIG. 4L is a block diagram of another configuration of a sanitizing system consistent with the present disclosure.

As shown in FIGS. 4K and 4L, system 400 further includes a sanitizing gas supply system. In embodiments the sanitizing gas supply system is housed within base 404, e.g., below a floor/bottom of sanitizing chamber 403. For example, the sanitizing gas supply system may be disposed between bottom 483 and a floor/bottom of sanitizing chamber 403. In such instances, bottom 483 may be in the form of a tray and the sanitizing gas supply system may be sized to fit in a space between bottom 483 of base 404 and an outside surface of the bottom of sanitizing chamber 403 (not shown). In any case, the sanitizing gas supply system is configured to generate or otherwise provide a sanitizing gas, as well as one or more pumps/fans for circulating the sanitizing gas. In some embodiments the sanitizing gas supply system includes or is in the form of an ozone operating system that is configured to generate or otherwise supply ozone gas as a sanitizing gas.

Turning to FIG. 4B, system 400 further includes a sanitizing gas outlet 453, an input/output (I/O) port 455, and a power supply connector 458. Sanitizing gas outlet 453 is configured to couple a sanitizing gas generator (disposed within or provided separately from base 404) to a distribution line, as will be described further below.

I/O port 455 is generally configured to couple system 400 to an external computing device (e.g., a desktop computer, laptop computer, mobile device, server, etc.). In embodiments, I/O port 455 is configured to charge one or more external devices, and/or to receive an electrical charge from one or more external devices. Alternatively or additionally, I/O port 455 may be configured to allow software, firmware, etc. of system 400 to be updated via wired (e.g., universal serial bus) communication with an external device. System 400 (e.g., I/O port 455 or a controller thereof) may also include one or more wireless communication chips that enable system 400 to communicate with an external computing device using one or more current or future developed wireless communications protocols such as near field communication (NFC), BLUETOOTH®, ZIGBEE®, WIFI, cellular (e.g., 2G, 3G, 4G, 5G, etc.) combinations thereof, and the like.

Power supply connector 458 is configured to couple system 400 to a suitable source of electric power, such as but not limited to a wall electrical socket. Of course, system 400 is not limited to embodiments in which an external source of electric power is used. For example, system 400 may include one or more batteries, in which case power supply connector 458 may be included or omitted.

System 400 further includes a filter tray 471, as best shown in FIGS. 4B, 4E, and 4H-4J. Filter tray 471 is generally configured to house a (removable) filter 500 therein, and to align an inlet of the filter 500 with exhaust ports 405 as discussed further below. Filter tray 471 may be coupled to base 404 in any suitable manner. In embodiments base 404 includes a recess formed in one of its sidewalls and extends inwardly towards sanitizing chamber 403, as best shown in FIG. 4J. In such instances filter tray 471 may be coupled to sidewalls 472 of said recess, as also shown in FIG. 4J. In any case filter tray 471 may be movable between a closed position (shown in FIGS. 4B, and 4E) and an open position (shown in FIGS. 4H-4J). For example filter tray 471 may be coupled to base 404 by one or more pins, hinges, pivots, etc. that allow filter tray to move between an open and closed position.

In embodiments the filter tray 471 includes an external surface that is substantially coplanar with a corresponding external surface of base 404. For example filter tray 471 may be coupled to sidewalls 472 of a recess formed in a first side of base 404. In such instances the filter tray 471 has an external surface that is complimentary to an external surface of a first side of base 404 proximate to said recess. In that context, "complimentary to" means that the external surface of the filter tray is shaped and contoured in the same manner as the external surface of the first side of base 404, such that the external surface of the filter tray and the first side of base 404 have the same or similar appearance.

In embodiments the filter tray 471 has an upper edge 474 and a lower edge 475. As best shown in FIG. 4E, when filter tray 471 is in the closed position the upper edge 474 extends along and is aligned with an upper edge 476 of base 404, and the lower edge 475 extends along and is aligned with a lower edge 477 of base 404. As shown in FIGS. 4H-4J, when filter tray 471 is in the open position the upper edge 474 is out of alignment with the upper edge 476 of base 404, and lower edge 475 is out of alignment with lower edge 477 of base 404.

As shown in FIGS. 4H and 4I, filter tray 471 further includes tray arms 473a, 473b. While the illustrated embodiment depicts filter tray 471 with two tray arms 473a, 473b, any suitable number of tray arms (e.g., 0, 1, 2, 3, 4, 5, or more) may be used. In the illustrated embodiment, tray arms 473a, 473b extend from an outward facing surface of filter tray 471 generally towards base 404 when filter tray 471 is in the closed position. Filter tray 471 and base 404 may further include a retention system that is configured to retain the filter tray 471 in the closed position. For example, filter tray 471 and base 404 may include one or more magnets (not shown) of opposing polarity, wherein such magnets interact to create a force (e.g., a pulling force) that biases the filter tray 471 toward the base 404 and urges a filter inlet seal (described later) against and/or around one or more of exhaust ports 405.

As noted above filter tray 471 is generally configured to house a (removable) filter 500 and to align an inlet of the filter 500 with exhaust ports 405, such that the filter 500 is fluidly coupled to the exhaust ports 405 when the filter tray 471 is in the closed position. FIGS. 5A-5F depict various views of a filter 500 consistent with the present disclosure. As shown filter 500 includes filter shell having a top 501, bottom 502 front 503, sides 505a, 505b, and back 507. The filter shell may be of single or multiple piece construction. In embodiments the filter shell is formed by or includes a first piece and a second piece, wherein the first piece forms a first part of the top 501, bottom 502, front 503, sides 505a, 505b, and back 507, and the second piece forms a second part of the top 501, bottom 502 front 503, sides 505a, 505b, and back 507. The first and second parts may be coupled together to form the filter shell in any suitable manner. For example, the first and second parts may be coupled by an interference fit, press fit, mechanical fasteners, adhesive, combinations thereof, and the like. In embodiments, the first piece includes one or a plurality of fingers that extend from one or more sides of the first piece, and the second piece includes a corresponding one or plurality of recesses formed at corresponding positions of corresponding sides of the second piece. In such instances the fingers of the first piece may be inserted and mechanically engage with the inserts of the second piece, e.g., to form one or more interference joints that retain the first and second parts together.

The filter shell is generally configured to house a filter media 515. In embodiments the filter media 515 is in the form of or includes a material that facilitates the conversion of a sanitizing gas such as ozone to a breathable gas such as oxygen. For example the filter media 515 may be in the form of a reticulated foam that is formed from, includes, and/or is coated with a material that facilitates the conversion of sanitizing gas to breathable gas. Non-limiting examples of such materials include activated carbon and magnesium oxide (either alone or in combination with activate carbon), though other materials may also be used.

Filter 500 further includes one or more filter inlet openings, a filter inlet seal, and one or more filter outlet openings. That concept is best shown in FIGS. 5B-5E, which illustrate filter 500 as including a plurality of filter inlet openings 508, a filter inlet seal 509, and a plurality of filter outlet openings 511. While the illustrated embodiment depicts the use of four (4) filter inlet openings 508 and eleven (11) filter outlet openings 511, any suitable number of filter inlet openings 508 and filter outlet openings 511 may be used. For example, filter 500 may include one or more (e.g., 1, 2, 3, 4, 5, 6, 7, 8, 9, 10, 15, 20, or more) filter inlet openings 508 and one or more (e.g., 1, 2, 3, 4, 5, 6, 7, 8, 9, 10, 15, 20, or more) filter outlet openings 511. In embodiments, filter 500 includes 3-6 (e.g., 4) filter inlet openings 508, and 1 to 5 (e.g., 3) filter outlet openings 511.

While the illustrated embodiment depicts filter inlet openings 508 as having a generally circular shape and filter outlet openings 511 in the form of slots defined by "teeth" in the lower part of a wall 512 of filter back 507 and bottom 502, the filter inlet openings 508 and filter outlet openings 511 may have any suitable shape and may be positioned at any suitable location. In embodiments filter inlet openings 508 are positioned such that they align with one or more exhaust ports 405 when filter 500 is disposed within filter tray 471 and filter tray 471 is in the closed position.

Filter inlet seal 509 is generally configured to form a (e.g., gas tight) seal around exhaust ports 405 when filter 500 is inserted in filter tray 471 and filter tray 471 is in the closed position. More specifically, filter inlet seal 509 is configured to form a seal with an external surface of the sanitizing chamber 403 disposed around exhaust ports 405, or a corresponding sealing element disposed on the surface of sanitizing chamber around exhaust ports 405. In that regard filter inlet seal 509 may be formed from any material that is suitable for forming a gas tight seal. In embodiments, filter inlet seal 509 is formed from or includes a flexible material, such as a (e.g., low durometer) natural or synthetic polymer (e.g., silicone), rubber, combinations thereof, and the like. In embodiments, filter inlet seal may include a flange extending at an angle from a peripheral surface thereof, wherein the flange is configured to engage and seal with a corresponding portion of base 404 proximate the outlet side of exhaust ports 405. As noted above, magnets or other closing means may facilitate the formation of a seal between filter inlet seal 509 and a region around exhaust ports 405, e.g., by biasing the filter inlet seal 509 towards base 404 when the filter tray is in the closed position.

To facilitate the formation of a seal by filter inlet seal 509, filter tray 471 may be biased towards sanitizing chamber 403 when filter tray 471 is in the closed position. Such biasing of the filter tray 471 may be accomplished mechanically (e.g. via one or more springs), magnetically, or in any other suitable manner. Alternatively or additionally, filter tray 471 may be retained in the closed position in another, such as but not limited to one or more fasteners, detents, or the like.

In embodiments filter 500 includes alignment features that facilitate the alignment of filter inlet openings 508 and filter inlet seal 509 with exhaust ports 405 when filter 500 is inserted in filter tray 471 and filter tray 471 is in the closed position. Such alignment features may include or be in the form of one or more shoulders that abut a corresponding upper edge of tray arms 473a, 473b when filter 500 is inserted into filter tray 471. That concept is best shown in FIGS. 5C and 5D, which depict an embodiment in which a peripheral edge of the top 501 of filter 500 extends beyond a peripheral edge of the front 503, sides 505a, 505b, and back 507, resulting in the formation of a shoulder 513 that extends completely or partially around the upper periphery of filter 500.

As shown in FIG. 4H, at least a portion of the shoulder 513 abuts an upper edge of each of the tray arms 473a, 473b when filter 500 is inserted into filter tray 471. In such embodiments the filter inlet openings 508, filter inlet seal 509, shoulder 513, and upper surface of the tray arms 473a, 473b are configured such that the filter inlet openings 508 and filter inlet seal 509 are aligned with exhaust ports 405 when at least a portion of shoulder 513 abuts the upper surface of the tray arms 473a, 473b and filter tray 471 is in the closed position. It is noted that the illustrated configuration is but one example of how filter inlet openings 508 and filter inlet seal 509 may be aligned with exhaust ports 405, and the present disclosure is not limited to such configurations. Indeed, the present disclosure envisions and encompasses embodiments in which the filter tray 471 and filter 500 are configured in any other manner to align the filter inlet openings 508 and filter inlet seal 509 with exhaust ports 405.

The shell of filter 500 may have any suitable shape, including but not limited to a geometric (e.g., triangular, quadrilateral, pentagonal, hexagonal, etc.) shape or irregular shape. In embodiments, the shell of filter 500 has a geometric or irregular shape having a width that tapers from the top 501 to the bottom 502 thereof, or vice versa. For example, the shell of filter 500 may have a first width (W1) proximate the top 501 and a second width W2 proximate the bottom 502, wherein W1 and W2 are the same or different. In embodiments, W1 is greater than W2, or W2 is greater than W1, such that the filter shell tapers from the top to the bottom or vice versa. One example of that concept is shown in FIG. 5D, which illustrates an embodiment in which filter 500 has a first width W1 proximate the top 501 and a second width W2 proximate the bottom 502, wherein W1 is greater than W2.

Figure 5A:
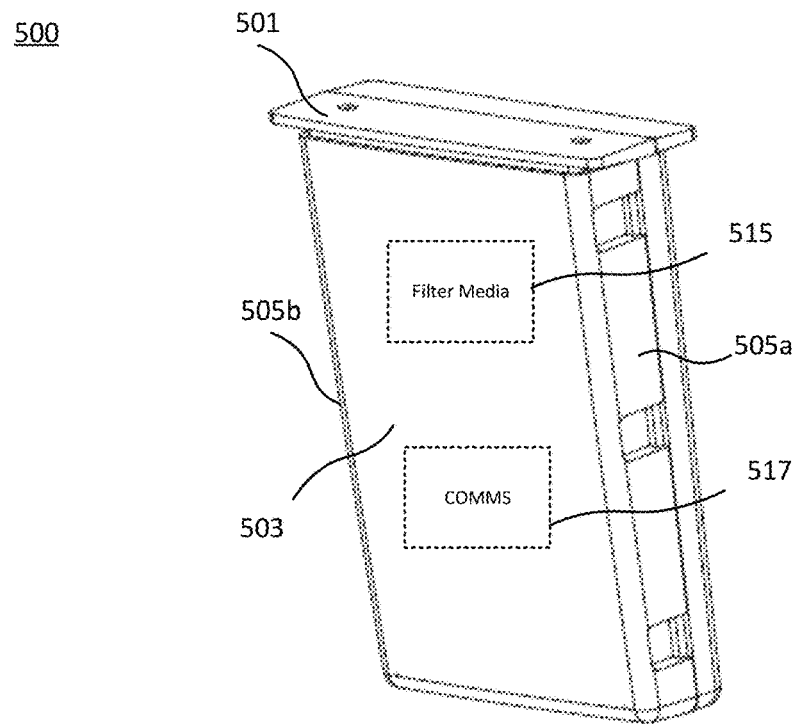
FIGS. 5A-5F depict various views of one example of a filter cartridge consistent with the present disclosure.
Figure 5B:
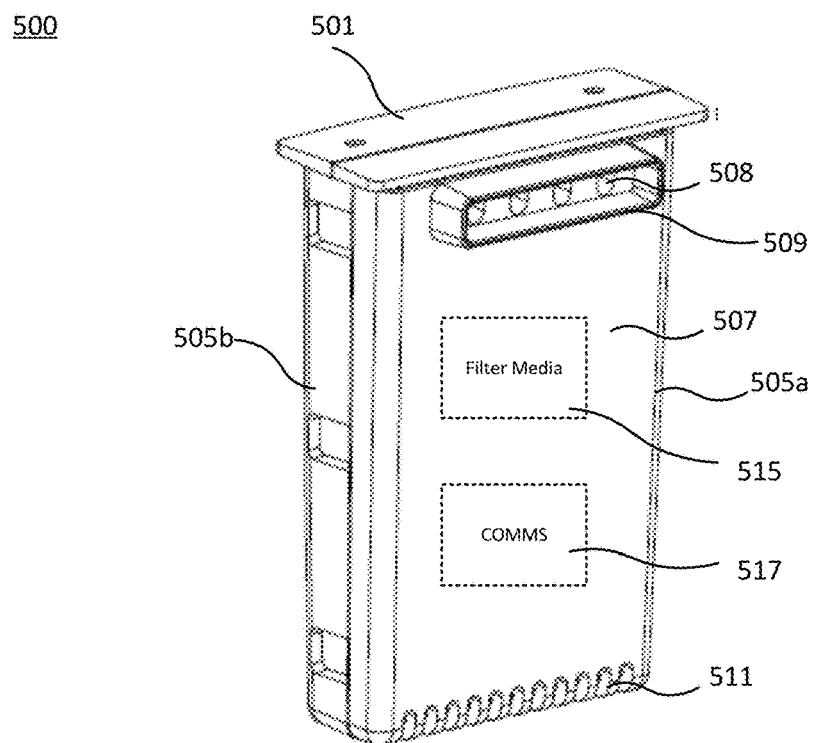
Figure 5C:
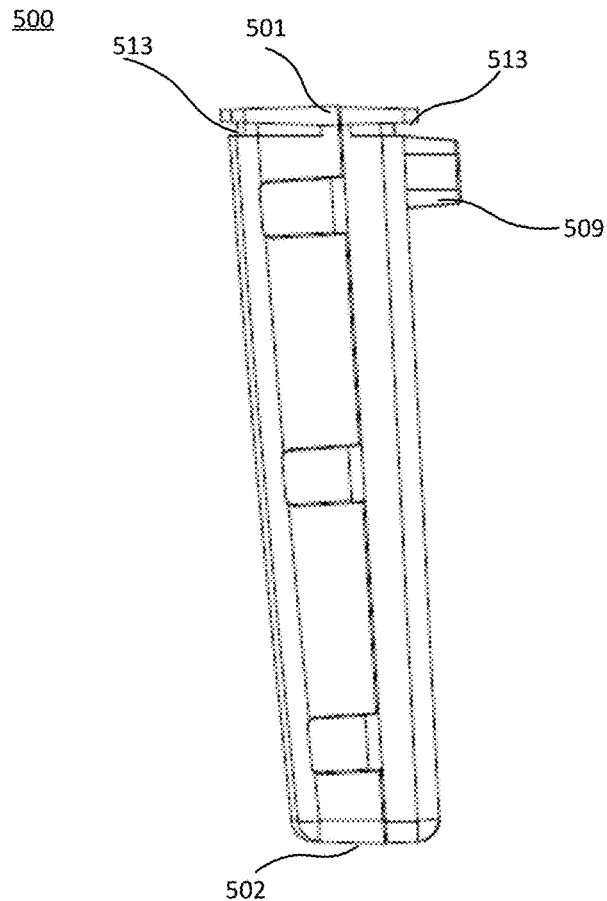
Figure 5D:
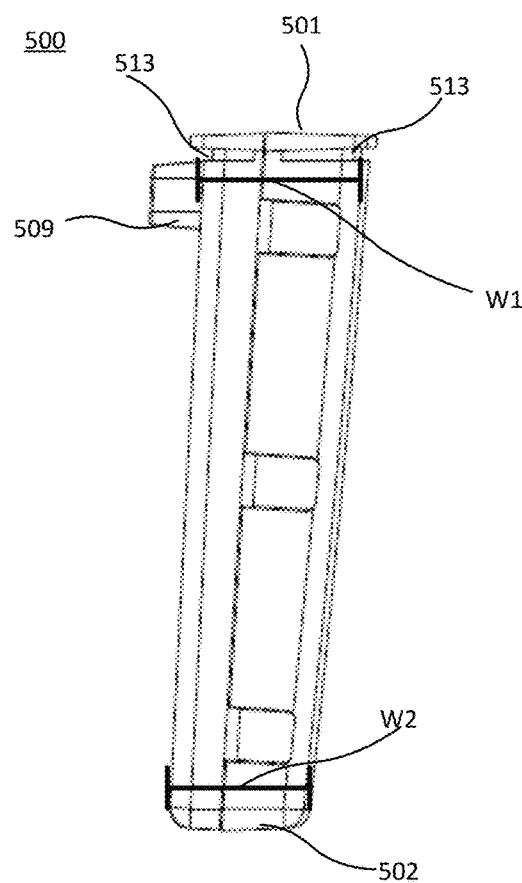
Figure 5E:
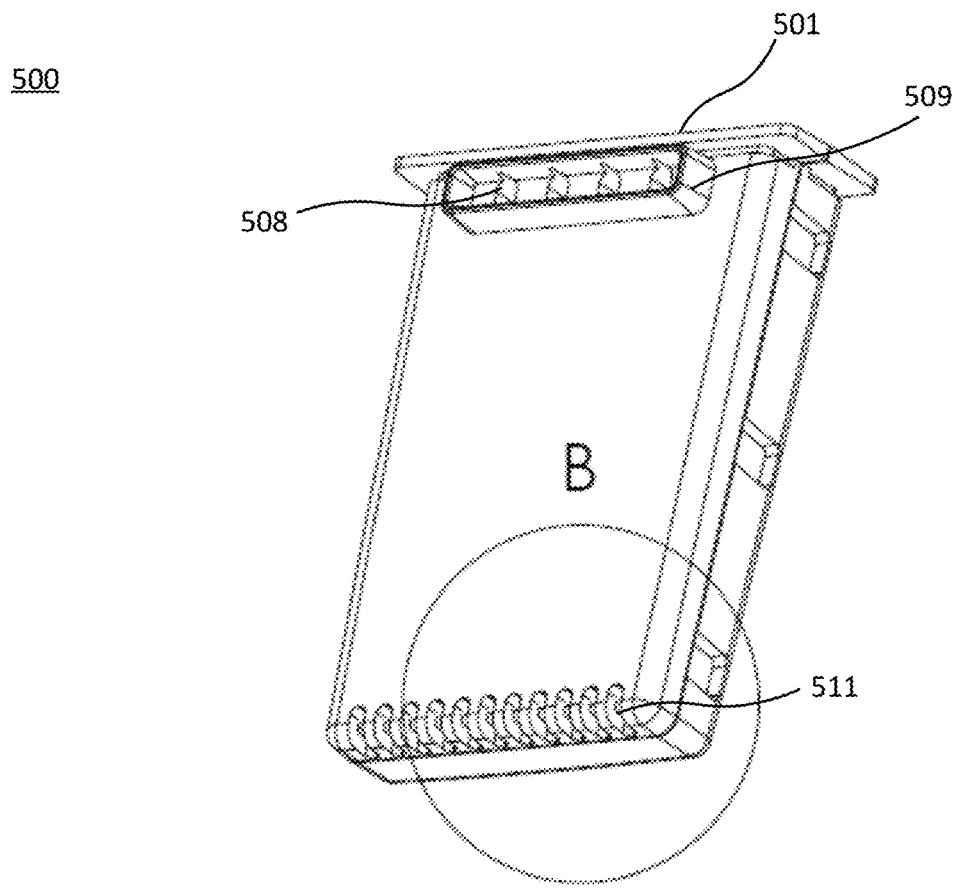
Figure 5F:
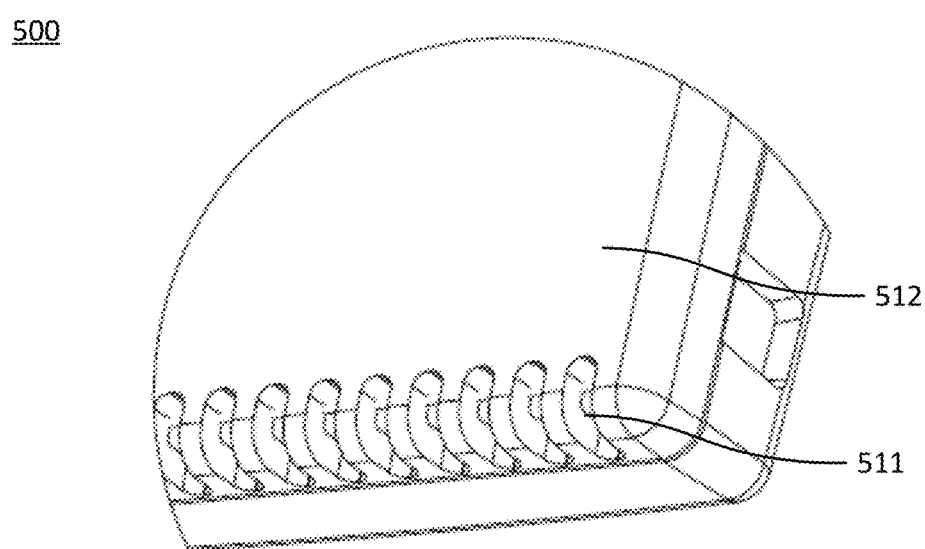

In embodiments filter 500 includes communication circuitry (COMMS) 517, as best shown in FIGS. 5A and 5B. When used, COMMS 517 is configured to enable communication between filter 500 and an external component (e.g., corresponding communication circuitry of base 404 (or more specifically, controller 490)) via any current or future developed wired or wireless communication protocol. In embodiments, COMMS 517 is configured to communicate wirelessly using a near field communication (NFC), BLUETOOTH®, ZIGBEE®, WIFI, or other wireless communication protocol. Without limitation, in embodiments COMMS 517 is or includes a radio frequency identification (RFID) circuit, and is configured to communicate wirelessly using an RFID or other NFC communication protocol. Further operations of COMMS 517 are described later in conjunction with the operations of controller 490.

As noted above and shown in FIGS. 4K and 4L, system 400 includes a sanitizing gas supply system that includes one or more fans/pumps that facilitate the flow of sanitizing gas (e.g., ozone) from the sanitizing gas supply system (e.g., an ozone generator) to one or more components of a medical device. The sanitizing gas supply system may be disposed within base 404 as shown in FIGS. 4K and 4L, or it may be provided separately from base 404. In embodiments the sanitizing gas generator is disposed within base 404, e.g., above, below, or to a side of sanitizing chamber 403.

With further reference to FIG. 4K, when system 400 is used to sanitize a medical device such as a CPAP device, a proximal end of a distribution line 107 may be connected to sanitizing gas outlet 453. A distal end of distribution line 107 may be fluidly coupled to a medical device 129 (e.g., a CPAP device or a water or other reservoir thereof) and a hose 109 (e.g., a CPAP hose) in any suitable manner, such as with a connector unit 120 as shown. Alternatively, connector unit 120 may be configured to couple directly to sanitizing gas outlet 453, in which case distribution line 107 may be omitted.

In operation, the sanitizing gas generator may generate sanitizing gas (e.g., ozone). A fan/pump within the sanitizing gas generator may cause the sanitizing gas to flow towards sanitizing gas outlet 453 and ultimately to components that are fluidly coupled to sanitizing gas outlet 453. For example and as described above, sanitizing gas may flow from sanitizing gas outlet 453, through a distribution line 107, and into connector unit 120. Alternatively, when distribution line 107 is omitted, sanitizing gas may flow directly from sanitizing gas outlet 453 to connector unit 120. In any case the sanitizing gas introduced into the connector unit 120 may be dispersed into the hose 109, into the medical device 129, or a combination thereof. For example, when medical device 129 is a CPAP device that includes a reservoir, sanitizing gas introduced into the connector unit 120 may flow into reservoir, as well as into the hose 109. For example, in embodiments sanitizing gas flows into a first passageway in the connector unit 120, from the first passageway into the reservoir, from the reservoir into a second passageway in the connector unit 120, and then into hose 109. Alternatively or additionally, at least a portion of the sanitizing gas introduced into the connector unit 120 may flow into the hose 109.

In embodiments and as shown in FIG. 4K, an intermediate portion of the hose 109 may pass through receptacle 407 such that a distal end 113 of the hose 109 is disposed within sanitizing chamber 403. As shown, a medical device component 492 (e.g., a CPAP mask, a CPAP nose pillow, etc.) may remain attached to the distal end 113 in this configuration. In operation, sanitizing gas introduced into the hose 109 may flow into sanitizing chamber 403 and—when medical device component 492 is attached to distal end 113—sanitizing gas may flow through medical device component 492 into sanitizing chamber 403. Once in sanitizing chamber 403, the sanitizing gas may convert into a breathable gas and/or may be carried through exhaust port(s) 405 into a filter 500 (described later) disposed within filter tray 471. Of course, medical device component 492 need not be attached to distal end 113 in order to conduct a sanitizing operation using this configuration.

Figure 4M:
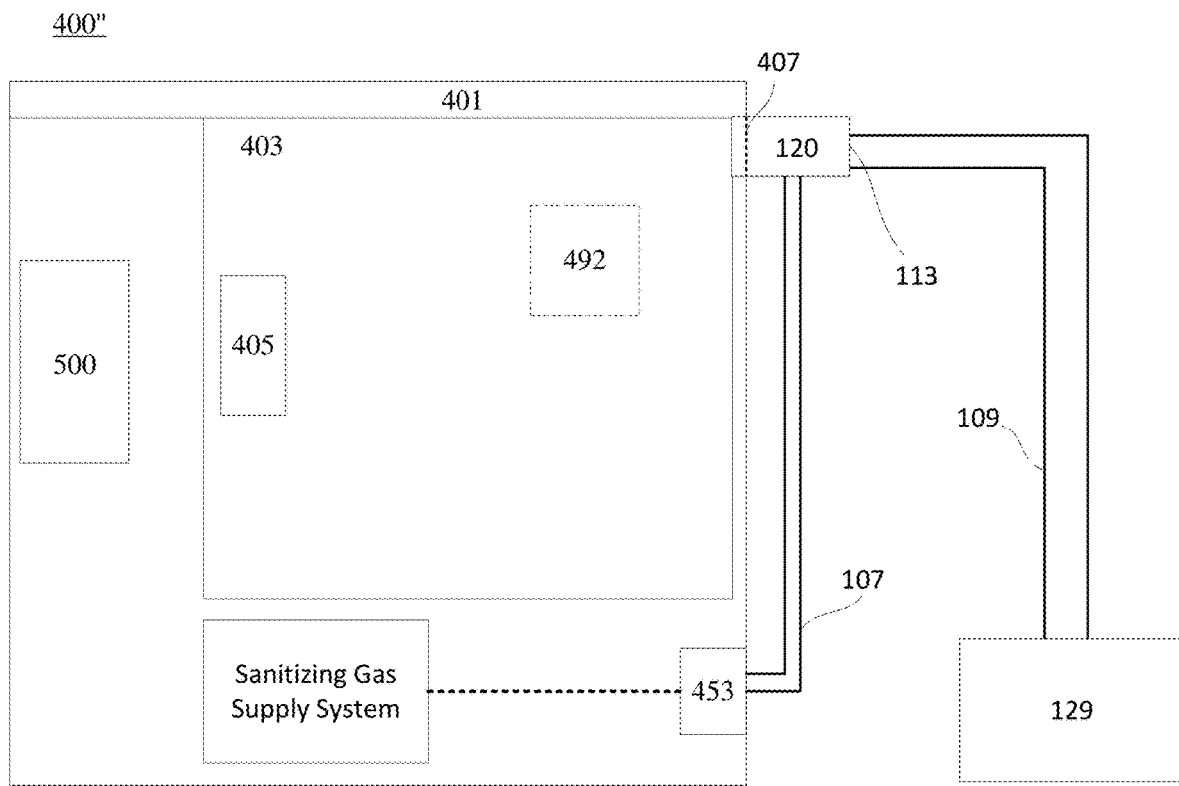
FIG. 4M is a block diagram of another configuration of a sanitizing system consistent with the present disclosure.
Figure 4N:
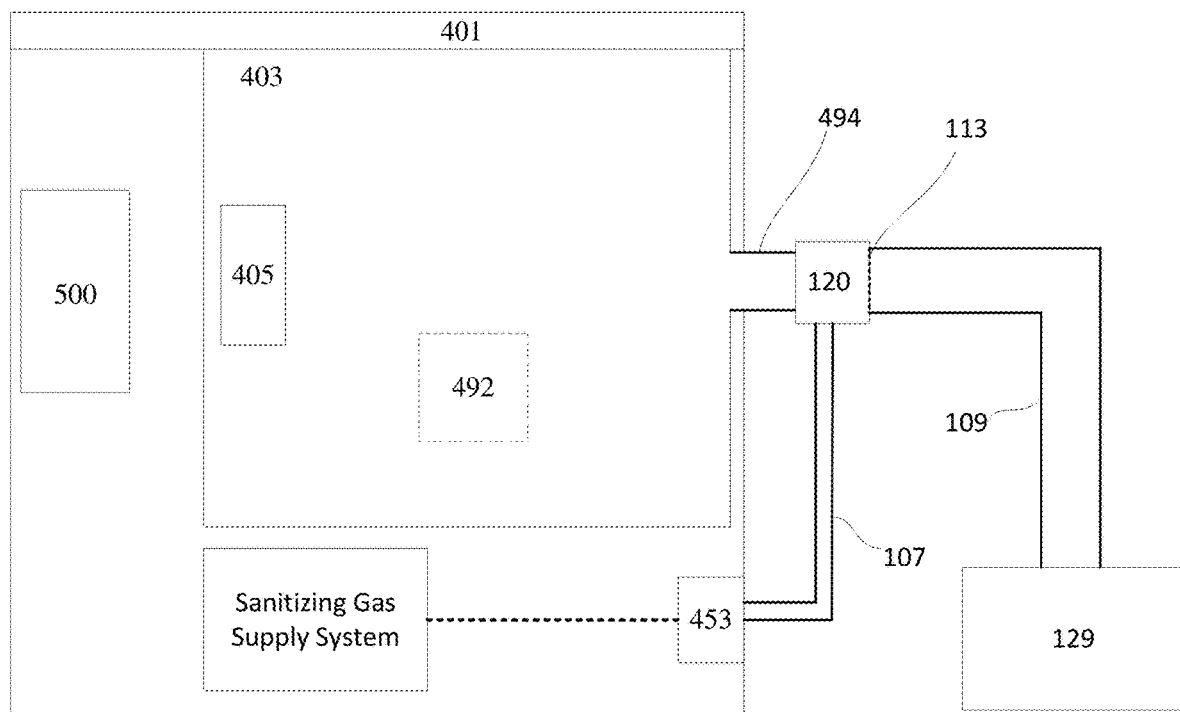
FIG. 4N is a block diagram of another configuration of a sanitizing system consistent with the present disclosure.

As noted above FIG. 4K depicts an embodiment in which an intermediate portion of the hose 109 is disposed within receptacle 407 and the distal end 113 of the hose is disposed inside sanitizing chamber 103. Although useful, such a configuration is not required and hose 109 may be fluidly coupled to the sanitizing chamber 403 in any suitable manner. For example and as shown in FIG. 4L, base 404 may include a port 494 that extends through a sidewall thereof, such as in the alternative configurations discussed above in the context of systems 200, 300. Like those previous embodiments, the port 494 may include a first end and a second end with a fluid passageway there between. In general, the fluid passageway enables the flow of a fluid (e.g., sanitizing gas) from a position outside base 404 (e.g., from hose 109) to inside sanitizing chamber 403. In that regard the first end of the port 494 may be configured to fluidly couple with the distal end 113 of the hose, either directly or via one or more intermediate components. For example and as shown in FIG. 4L, the first end of the port 494 may be configured to form a gas tight seal with the distal end 113 of hose 109, while allowing sanitizing gas to flow from hose 109 into the fluid passageway within port 494. Alternatively and as shown in FIG. 4N, in embodiments connector unit 120 may be configured to connect directly to the port 494, such that connector unit 120 is between the distal end of hose 109 and the port 494. In some embodiments, connector unit 120 in FIG. 4N is configured to only convey sanitizing gas towards port 494 and/or sanitizing chamber 403. In such embodiments hose 109 may be removed from between connector unit 120 and port 494, and hose 109 may be sanitized by placing it inside sanitizing chamber 403 during a sanitizing operation.

Notably, the configuration of system 400' in FIG. 4L allows for the elimination of receptacle 407 and the upper and lower seal members 431, 433. To accommodate the removal of such components, the lid seal 427 and base seal 429 may be configured to form a gas tight seal about the periphery of the lid 401 when lid 401 is in the closed position. However, prior to conducting a sanitizing operation using the configuration of FIG. 4L, the distal end 113 of the hose 109 may be coupled to medical device component 492, e.g., a CPAP hose. To conduct a sanitizing operation, medical device component 492 may be separated from distal end 113 and optionally placed within sanitizing chamber 403. The distal end 113 may then be connected to the first end of the port 494. Alternatively, hose 109 and medical device component 492 may be placed in sanitizing chamber 403 and connector unit 120 may be connected directly to port 494. In either case, a sanitizing operation may then be performed. During such an operation, a sanitizing gas (e.g., ozone) generated by the sanitizing gas generator may be introduced into the connector unit 120, e.g., via a distribution line 107 coupled to sanitizing gas outlet 453. The sanitizing gas introduced into the connector unit 120 may also optionally migrate into medical device 129. Alternatively or additionally, the sanitizing gas may migrate into and through port 494 (e.g. via hose 109 or directly from connector unit 120), and into sanitizing chamber 403.

FIGS. 4K and 4L focus on embodiments in which a connector unit 120 is disposed between a medical device 129 and a hose 109, and is configured to direct the flow of sanitizing gas into one or more of the medical device 129 and/or hose in a desired manner. While such embodiments are useful, as noted previously the present disclosure envisions and encompasses alternative configurations in which connector unit 120 is eliminated and/or is utilized in a different manner. For example and as shown in FIGS. 4M and 4N, in embodiments connector unit 120 is configured to fluidly couple to distribution line 107, distal end 113 of hose 109, and to sanitizing chamber 403. For example, the connector unit 120 may include a first connector 121 configured to fluidly couple with distribution line 107, a second connector 127 configured to fluidly couple with a distal end 113 of hose 109, and a third connector 133 configured to fluidly couple with sanitizing chamber 403. This is unlike the embodiments of FIGS. 4K and 4L, wherein connector unit 120 is configured to fluidly couple to distribution line 107, proximal end 111 of hose 109, and medical device 129.

As shown in FIG. 4M, connector unit 120 may be configured to fluidly couple to sanitizing chamber 403, e.g., via a receptacle 407. In such instances, the exterior of connector unit 120 may be configured such that a gas tight seal can be formed between receptacle 407 (and/or one or more sealing elements thereof) and connector unit 120, e.g., in the same manner as described herein concerning the formation of a gas tight seal with an intermediate portion of a medical device hose. Alternatively and as shown in FIG. 4N, the base 404 may include a port 494, and connector unit 120 may be configured to fluidly couple to the sanitizing chamber 403 via the port 494. In that regard, the connector unit 120 may include a first connector 121 configured to fluidly couple with distribution line 107, a second connector 127 configured to fluidly couple with a distal end 113 of hose 109, and a third connector 133 configured to fluidly couple with port 494 and, in turn, to sanitizing chamber 403.

In the embodiments of 4K to 4N the connector unit 120 may be configured to direct the flow of sanitizing gas during a sanitizing operation in any desired manner. For example, during a sanitizing operation a sanitizing gas (e.g., ozone) may be generated or otherwise provided by a sanitizing gas supply system. The sanitizing gas may be introduced into the connector unit 120, e.g. via distribution line 107. In embodiments, the connector unit 120 is configured such that all or a portion of the sanitizing gas introduced into the connector unit is conveyed into the sanitizing chamber 403, into the hose 109, into medical device 129, and/or a combination thereof. For example, connector unit 120 may be configured in the manner shown in any one of FIG. 19A-19G, 20, or 21, which are described later.

Figure 19A:
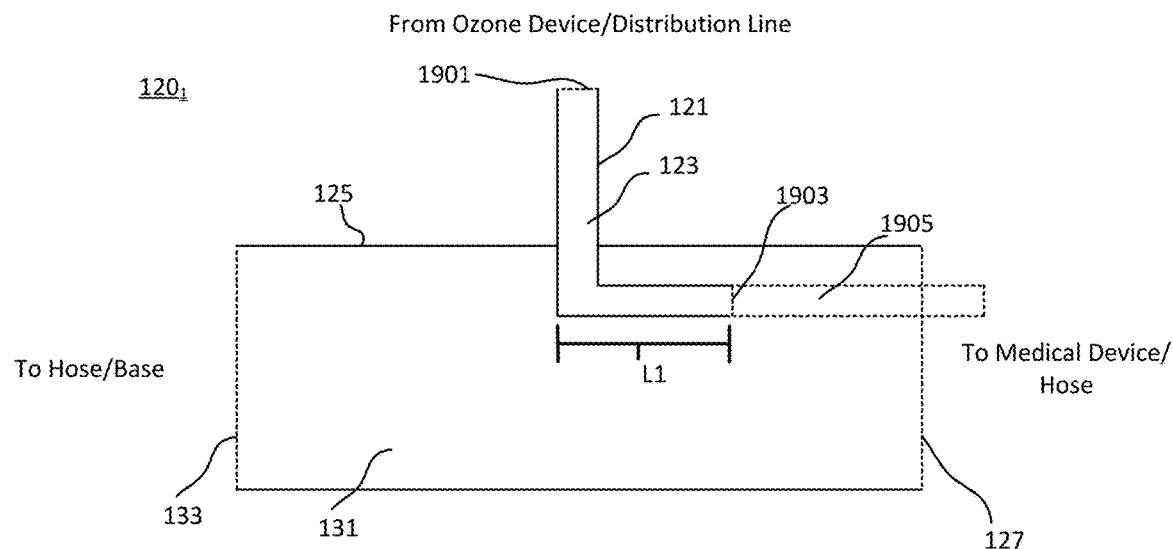
FIG. 19A depicts one example of a connector unit consistent with the present disclosure.
Figure 19B:
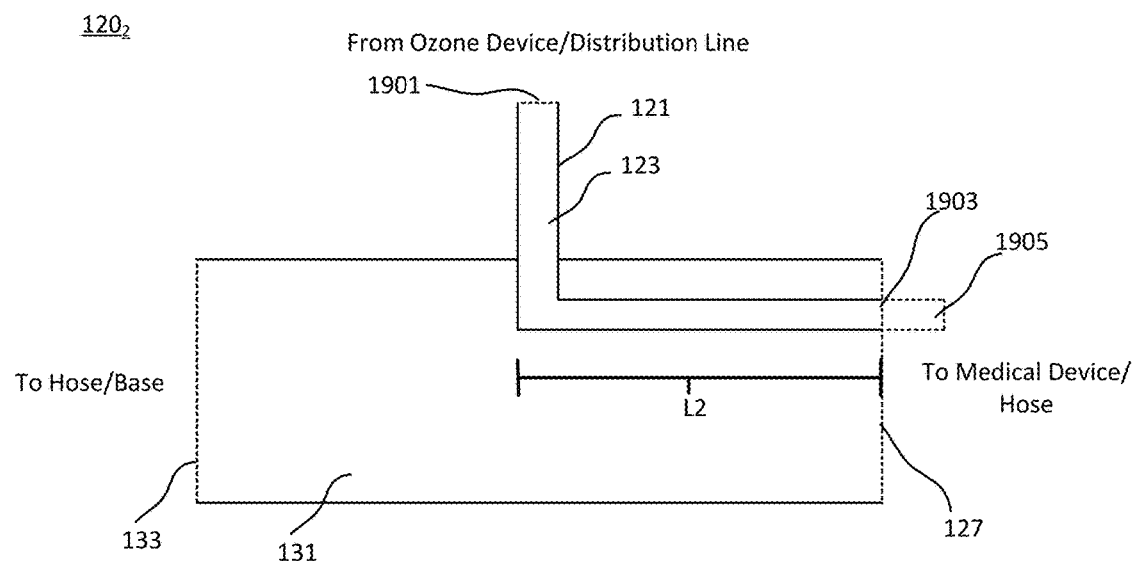
FIG. 19B depicts another example of a connector unit consistent with the present disclosure.
Figure 19C:
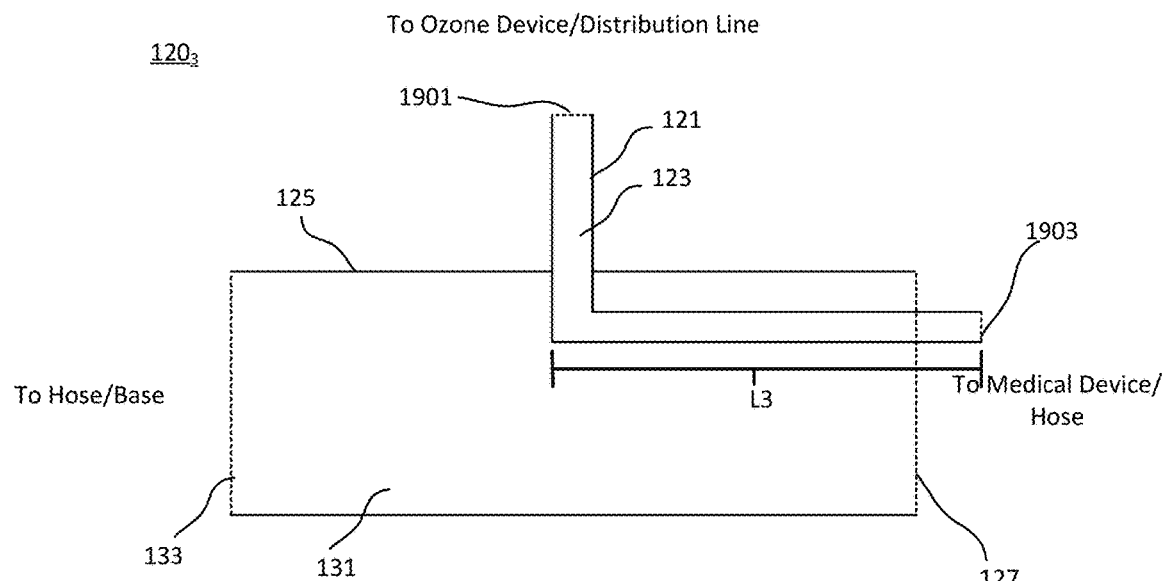
FIG. 19C depicts another example of a connector unit consistent with the present disclosure.

For example when connector unit 120 is configured in the manner shown in FIG. 19A, 19B, or 19C, during a sanitizing operation sanitizing gas may be introduced into the connector unit 120 via a proximal end 1901 of first connector 121 and flow into first passageway 123. Due to the configuration of first passageway 123 in such embodiments, sanitizing gas may initially flow from first passageway 123 towards medical device 129 (in the case of systems 400, 400') or towards hose 109 (in the case of systems 400" and 400'"). However, the amount of sanitizing gas that flows into hose 109, medical device 129, and/or chamber 403 may depend on various factors, such as the length of first passageway 123, the size and configuration of the distal end 1903, the length of hose 109, the flow rate/velocity of the sanitizing gas, etc. Thus, depending on such factors, in some embodiments all or a portion of the sanitizing gas may or may not flow into hose 109 and/or medical device 129, but rather may flow in a substantially opposite direction (e.g., towards hose 109 (in the case of systems 400, 400') or sanitizing chamber 403 (in the case of systems 400", 400'").

Figure 19D:
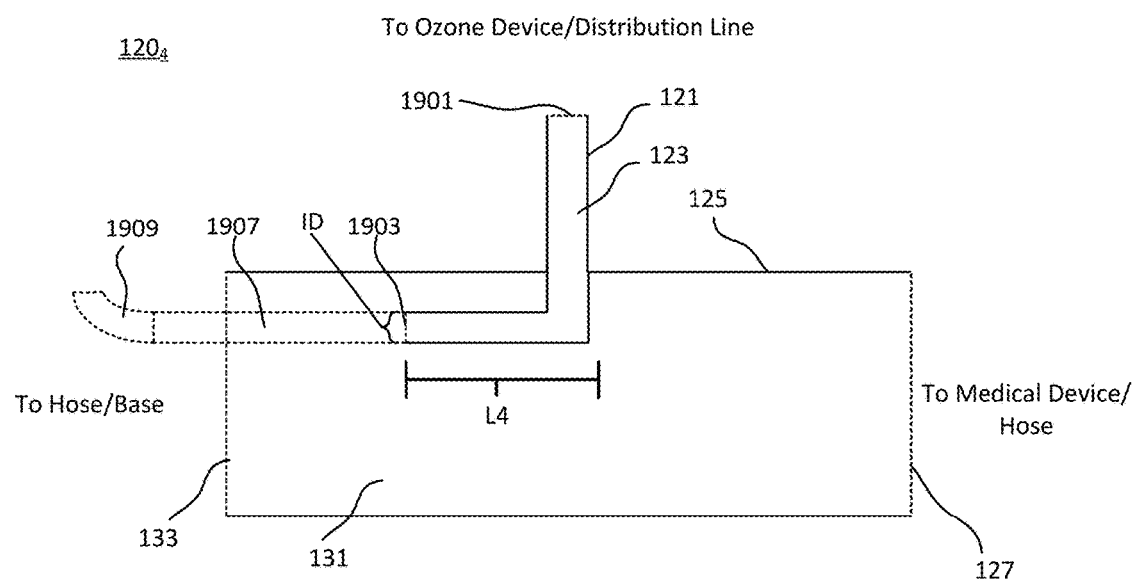
FIG. 19D depicts one example of a connector unit with a reverse jet, consistent with the present disclosure.
Figure 19E:
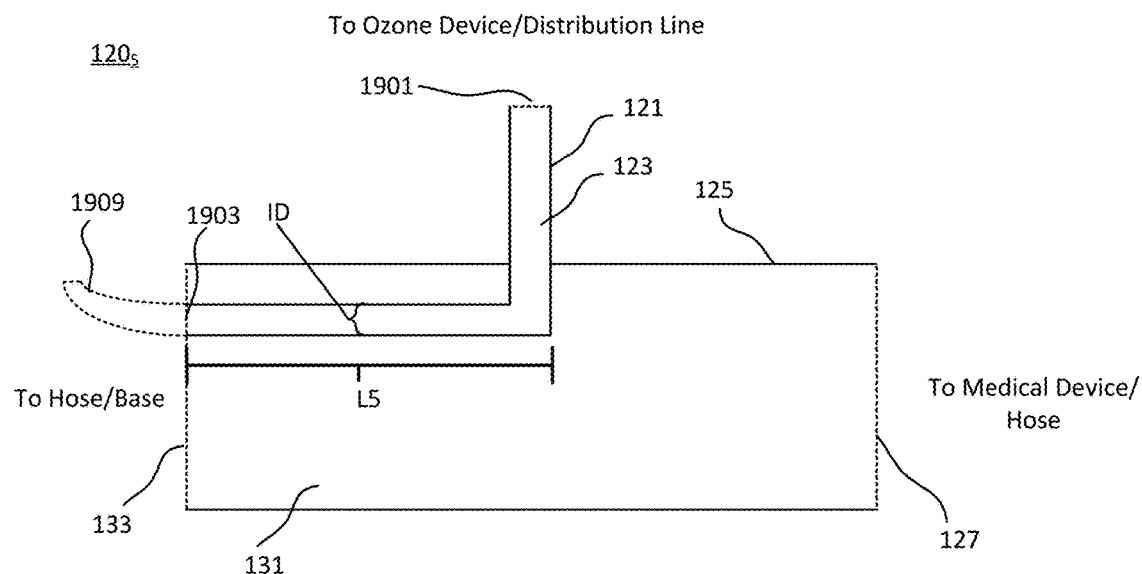
FIG. 19E depicts another example of a connector unit with a reverse jet, consistent with the present disclosure.
Figure 19F:
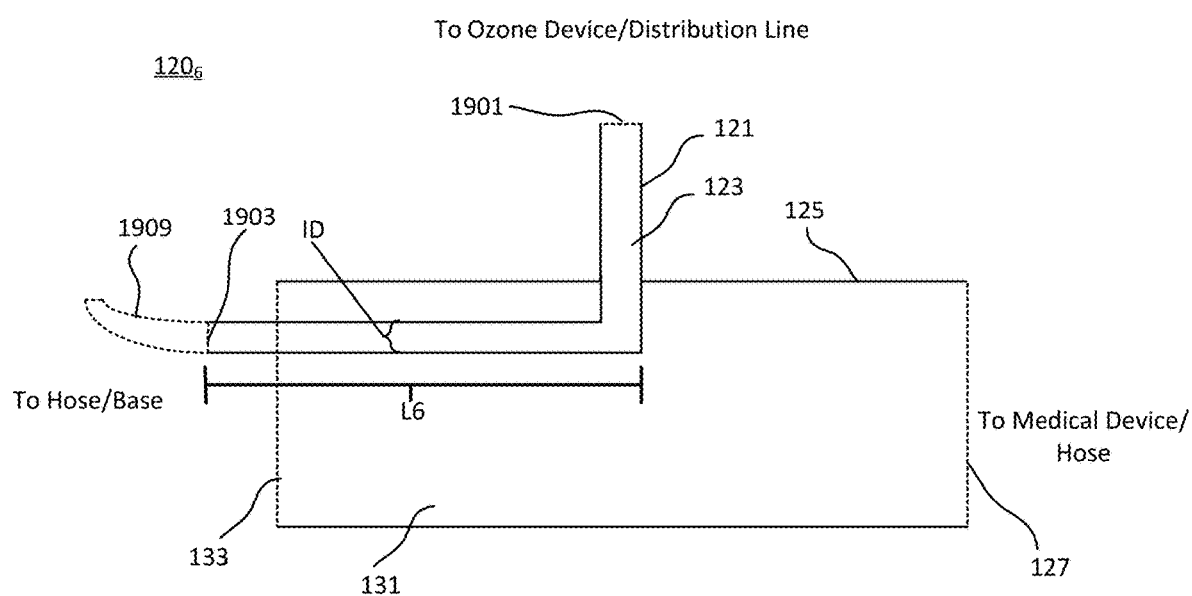
FIG. 19F depicts another example of a connector unit with a reverse jet, consistent with the present disclosure.

In alternative embodiments connector unit 120 is configured in the manner shown in FIGS. 19D-19F. In such instances, during a sanitizing operation sanitizing gas may be introduced into the connector unit 120 via a proximal end 1901 of first connector 121, and flow into first passageway 123. Due to the configuration of first passageway 123 in such embodiments, sanitizing gas may initially flow from first passageway 123 towards hose 109 (in the case of systems 400, 400') or towards sanitizing chamber 403 (in the case of systems 400" and 400'"). Like the previous embodiments, however, the amount of sanitizing gas that flows into hose 109, medical device 129, and/or sanitizing chamber 403 may depend on various factors, such as the length of first passageway 123, the flow rate/velocity of the sanitizing gas, use of an extension, etc. Thus, depending on such factors, in some embodiments all or a portion of the sanitizing gas may or may not flow into hose 109 and/or medical device 129. Because of the orientation of the first passageway 123 in FIGS. 19D-19F, such figures may be understood to show a connector unit with a "reverse jet" configuration.

Figure 20:
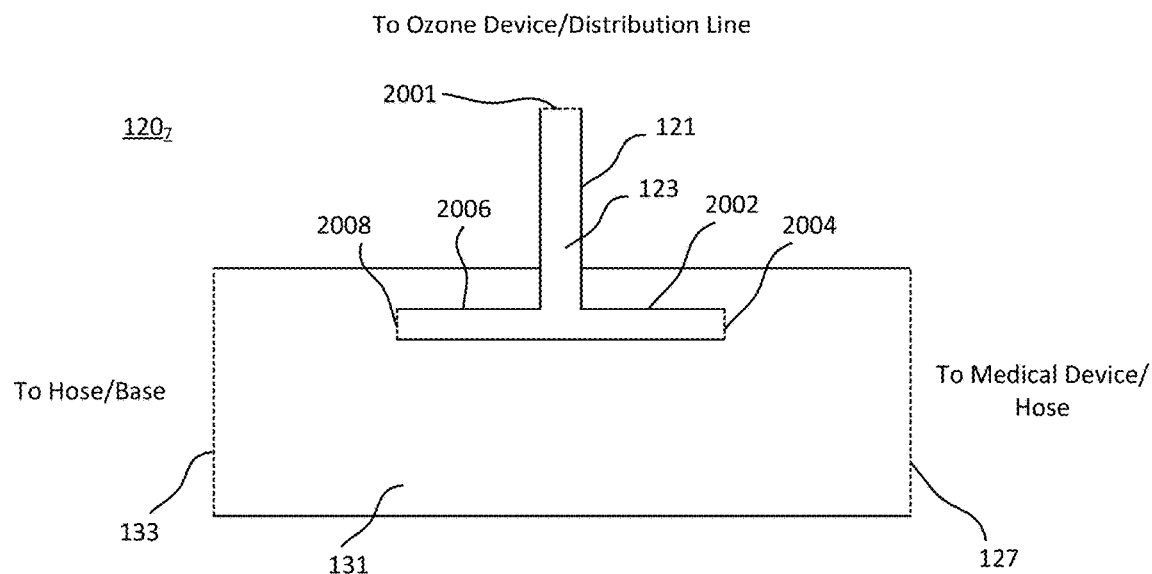
FIG. 20 depicts another example of a connector unit consistent with the present disclosure.

In further alternative embodiments connector unit 120 is configured in the manner shown in FIG. 20. In such instances, during a sanitizing operation sanitizing gas may be introduced into the connector unit 120 via a proximal end 1901 of first connector 121, and flow into first passageway 123. At least a portion of the sanitizing gas may flow into the first branch 2002 and the second branch 2006 of the first passageway. Sanitizing gas exiting the first distal end 2004 (of the first branch 2002) may flow initially towards second connector/open end 127 (e.g., towards hose 109 and/or medical device 129), and sanitizing gas exiting the second distal end 2008 may flow initially towards third connector/open end 133 (e.g., towards hose 109 or sanitizing chamber 403). Like the previous embodiments, however, the amount of sanitizing gas that flows into hose 109, medical device 129, and/or sanitizing chamber 403 may depend on various factors, such as the length of first passageway 123, the flow rate/velocity of the sanitizing gas, the size and configuration of the first branch 2002 and the second branch 2006, etc.

Figure 21:
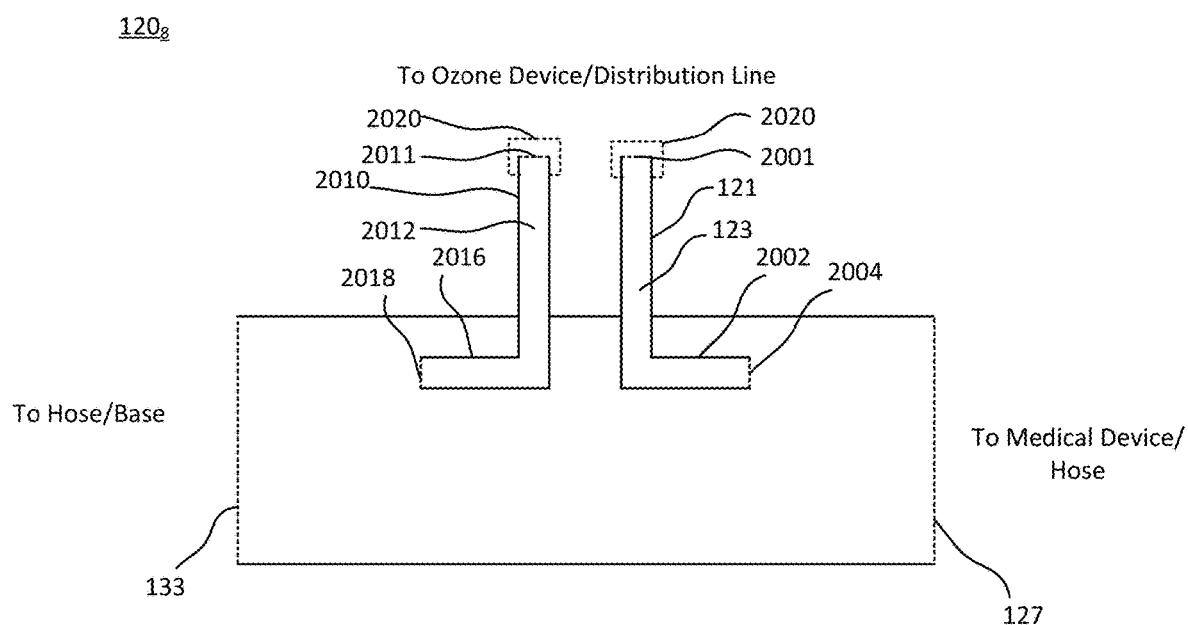
FIG. 21 depicts another example of a connector unit consistent with the present disclosure.

In still further alternative embodiments connector unit 120 is configured in the manner shown in FIG. 21. In such instances, during a sanitizing operation sanitizing gas may be introduced into the connector unit 120 via a proximal end 2001 of first connector 121 and a proximal end 2011 of a fourth connector 2010. Sanitizing gas introduced into first connector 121 may flow into first passageway 123, which has a distal end 2004 oriented towards second connector/open end 127. Sanitizing gas introduced into fourth connector 2010 may flow into a third passageway 2012 that has a distal end 2018 oriented towards third connector/open end 133. Sanitizing gas exiting the distal end 2004 may flow initially towards second connector/open end 127 (e.g., towards hose 109 and/or medical device 129), and sanitizing gas exiting the distal end 2018 may flow initially towards third connector/open end 133 (e.g., towards hose 109 or sanitizing chamber 403). Like the previous embodiments, however, the amount of sanitizing gas that flows into hose 109, medical device 129, and/or sanitizing chamber 403 may depend on various factors, such as the length of first passageway 123, the length of the third passageway 2012, the amount, flow rate and/or velocity of sanitizing gas introduced into the first passageway 123 and/or the third passageway 2012, etc. As may be appreciated, configuring connector unit 120 in the manner shown in FIG. 21 may allow for finer control over the amount of sanitizing gas that is directed in a particular manner, e.g., by allowing for independent control of the amount of sanitizing gas that is initially directed towards the second connector/open end 127 and/or towards the third connector/open end 133.

The sanitization systems described herein may be used to sanitize a wide variety of medical devices, including but not limited to several different types of CPAP equipment. With that in mind it may be desirable to direct the flow of sanitizing gas by the system, e.g., to ensure the flow of sanitizing gas into certain medical device components, and/or to avoid or limit exposure of certain medical device components to the sanitizing gas. For example, when the systems described herein are used to sanitize CPAP equipment, it may or may not be desirable for the sanitizing gas to enter into certain components of the CPAP equipment, such an air outlet, reservoir, or a combination thereof. For example, some CPAP devices may include seals or other components that may react with and/or be degrade by a sanitizing gas, such as ozone. In such instances it may be desirable to control or otherwise direct the flow of sanitizing gas in such a way as to limit or prevent contact of the sanitizing gas with such components. Alternatively, some CPAP devices may include components (e.g. water reservoirs, CPAP hoses, etc.) that are prone to fouling with bacteria and other pathogens. In such instances it may be desirable to control or otherwise direct the flow of sanitizing gas so as to ensure adequate exposure of such components to the sanitizing gas.

With the foregoing in mind, aspects of the present disclosure relate to connector units (e.g., CPAP connector units) that can direct the flow of sanitizing gas (e.g., ozone) in a desired manner during the performance of a sanitizing operation with the sanitization systems described herein. In that regard references is made to FIGS. 19A-19C, which depict several example connector units consistent with the present disclosure. As shown, connector units $120_1$, $120_2$, and $120_3$ each include a first connector 121, a second connector 127, and a third connector 133. In general, first connector 121 is configured to fluidly couple with a sanitizing gas supply system, either by directly coupling with a sanitizing gas outlet 453, or be coupling to a distribution line 107 that is fluidly coupled to a sanitizing gas supply system. In this context, "fluidly couple" means that sanitizing gas may flow into first connector 121 and into a first passageway 123 therein. In the illustrated embodiment, first connector 121 includes a proximal end 1901 that includes an opening that permits the flow of sanitizing gas into first passageway 123.

Second connector 127 is generally configured to fluidly couple to a CPAP device, e.g., directly or with the aid of an adapter (not shown). For example, second connector 127 may be configured to fluidly couple to an outlet from a CPAP device, such as by not limited to an air outlet (which may also be referred to as a tubing connector). The CPAP device may or may not include a reservoir. When the CPAP device includes a reservoir, the air outlet/tubing connector may be fluidly coupled to the reservoir, and the second connector may be fluidly coupled to the reservoir. In this context, "fluidly coupled" means that a gas may flow from the CPAP device into the second connector 127 and into a second passageway 131 in the connector unit 120₁. Accordingly, second connector 127 includes an opening that permits the flow of gas therethrough and into second passageway 131.

Third connector 133 is generally configured to fluidly couple with a sanitizing chamber of a sanitizing system consistent with the present disclosure. In embodiments and as discussed above, third connector 133 may be configured to connect to a proximal end of a hose (e.g. a CPAP hose). In such instances a distal end 113 of the hose may be disposed within sanitizing chamber 403 (e.g., as shown in FIG. 4K), or coupled to a port 494 as shown in FIG. 4L. Alternatively, third connector 133 may be configured to couple directly to a base 404, e.g., via a port 494—in which case coupling of the hose to the third connector is not required.

First connector 121 includes or defines a first passageway 123. The first passageway 123 extends through a sidewall 125 that extends between the openings formed in second connector 127 and third connector 133, such that at least a portion of the first passageway 123 is disposed within the second passageway 131. In this context, "at least partially disposed within" means that at least a portion of a wall defining the first passageway 123 extends into (e.g., occludes, narrows, etc.) the second passageway 131. In embodiments a gap is present between sidewall 125 and part of the wall defining the first passageway 123 (e.g., as shown in FIG. 19A), but such a gap need not be present for the first passageway to be disposed at least partially within the second passageway 131. Indeed, all or a portion of the first passageway 123 (or a wall thereof) may be integral with sidewall 125, yet first passageway 123 may be disposed at least partially within second passageway 131.

In FIGS. 19A-19C the distal end 1903 of first passageway 123 is oriented towards second connector 127. Such an orientation may direct the flow of sanitizing gas passing through first passageway 123 towards the second connector 127 and, hence, towards any medical device or hose that may be fluidly coupled to second connector 127. Depending on the volume and flow rate of the sanitizing gas, orienting distal end 1903 toward second connector 127 may ensure that at least a portion of sanitizing gas conveyed through first passageway 123 flows into a medical device or hose coupled to second connector 127, e.g., a CPAP device such as a CPAP reservoir or a CPAP hose. As shown in FIGS. 19A-19C, an optional second distribution line 1905 may be coupled to distal end 1903 to facilitate the conveyance of sanitizing gas into the medical device coupled to second connector 127.

In embodiments at least a portion of sanitizing gas introduced into first passageway 123 may flow through second passageway 131 towards third connector 133 and a hose 109 or base 404 coupled thereto. For example, sanitizing gas may flow from distal end 1903, into a medical device coupled to second connector 127 (e.g., a CPAP reservoir), from the CPAP reservoir into second passageway 131, and from second passageway 131 into a hose 109 or base 404 coupled to third connector 133. Alternatively or additionally, at least a portion of the sanitizing gas flowing through first passageway 123 may exit distal end 1903 and flow into second passageway 131 towards third connector, e.g., without entering a medical device coupled to second connector 127.

Connector units 120₁ (FIG. 19A), 120₂ (FIG. 19B) and 120₃ (FIG. 19C) differ from each other only in the length of the distal portion (nozzle) of their respective first passageways 123. That is, the nozzle of first passageway 123 of connector unit 120₁ has a length L1, the nozzle of first passageway 123 of connector unit 120₂ has a length L2, and the nozzle of first passageway 123 of connector unit 120₃ has a length L3, wherein L3>L2>L1. Because the length of the distal portion of the first passageway 123 may impact the amount of sanitizing gas that is conveyed from the first passageway 123 into a medical device or hose coupled to second connector 127, it may be desirable to set the length of the distal portion of the first channel based to expose a medical device coupled to the second connector 127 to a desired amount of sanitizing gas. In embodiments, the length of the nozzle (distal portion) of first passageway 123 range from 3 mm to 25 mm, such as from 6 mm to 19 mm Such lengths are enumerated for the sake of example, however, and the length of the nozzle of the first passageway 123 is not limited thereto.

FIGS. 19A-19C depict embodiments in which a proximal portion of first passageway 123 extends perpendicularly through sidewall 125, and a distal portion (nozzle) of first passageway 123 extends at a 90 degree angle relative to the proximal portion of the first channel in a direction towards the second connector 127. Although useful, such a configuration is not required and first passageway 123 may be configured in any suitable manner. For example, first connector 121 may be oriented at an angle such that proximal end 1901 is disposed closer to third connector 133 than it is to second connector 127, and first passageway 123 may extend in a straight line (i.e., without a bend) though sidewall 125 and at least partially into second passageway 131. Alternatively or additionally, first passageway 123 may bent or curved at an angle greater than or less than 90 degrees, as desired. Moreover, first passageway 123 may include more than one bend, such as 2, 3, 4, or more bends.

FIGS. 19D-19F illustrate additional examples of connector units consistent with the present disclosure. Connector units 120₄ (FIG. 19D), 120₅ (FIG. 19E), and 120₆ (FIG. 19F) generally include the same components as connector units 120₁-120₃. As the nature and function of the bulk of such components is the same as described above in connection with FIGS. 19A-19C, such description is not reiterated. Unlike connector units 120₁-120₃, connector units 120₄₋₆ include a first passageway 123 with a distal end that is oriented towards third connector 133 and towards components that may be fluidly connected to third connector 133. Such a configuration may be useful in instances in which it may be desirable to limit or even prevent the flow of sanitizing gas into medical device components that are fluidly connected to second connector 127, e.g., when medical equipment fluidly coupled to second connector 127 does not require sanitization, and/or is sensitive to (e.g., adversely impacted) exposure to the sanitizing gas used in a sanitizing operation. For example, some CPAP devices (e.g. CPAP devices that do not include a reservoir) may not require sanitization, and/or may include components that may be adversely affected by exposure to a sanitizing gas such as ozone. In such instances it may be desirable to limit or prevent the flow of sanitizing gas (e.g., ozone) into the CPAP device, while enabling the flow of sanitizing gas into other components, such as a hose 109 or base 404 fluidly coupled to third connector 133.

In that regard first passageway 123 (or, more particularly, the distal end (nozzle) thereof) in connector units $120_4$-$120_6$ is configured to enable a desired flow of sanitizing gas towards components that are downstream of third connector 133, while limiting or preventing flow of sanitizing gas through second connector 127. In general, first passageway 123 facilitates such flow by directing sanitizing gas towards components downstream of third connector 133 (e.g. towards a hose 109 or base 404 fluidly coupled to third connector 133), and by allowing sanitizing gas to flow through distal end 1903 at a flow volume and flow rate that limits or prevents flow of sanitizing gas through second connector 127.

Directing the flow of sanitizing gas towards components downstream of third connector 133 may be accomplished by controlling the position and/or orientation of the distal end 1903 of first passageway 123. In embodiments and as shown in FIGS. 19D-19F, the distal end 1903 may be oriented to face towards components downstream of third connector 133. In FIGS. 19D-19F, the distal end 1903 includes an opening that is oriented parallel to an opening in third connector 133, such a configuration is not required. Moreover, the relative position of distal end 1903 to third connector 133 is not limited, and may be selected to suit a particular application. This is demonstrated by FIGS. 19D-19F, in which connector units $120_4$-$120_6$ have different nozzle lengths, L4, L5, and L6 respectively, wherein L6>L5>L4, and L4, L5, and L6 may each range from about 3 to about 25 mm, such as from about 6 mm to about 19 mm, or even above 6 mm to about 14 mm In embodiments, the length of the first passageway 123 and/or the nozzle thereof is selected such that a desired flow volume and flow velocity of sanitizing gas is achieved at distal end 1903 during a sanitizing operation.

In embodiments, connectors $120_4$-$120_6$ are configured such that ozone flowing through first passageway 123 is directed along a flow path presented by components that are fluidly coupled to third connector 133. For example when third connector 133 is fluidly coupled to a hose (e.g., a CPAP hose), first passageway 123 may be configured such that sanitizing gas flowing through distal end 1903 is directed along a flow path within an interior of the hose, and/or an interior of an adapter used to connect the hose to third connector 133. Alternatively, one or more optional extensions 1907 and/or flow guides 1909 may be coupled to distal end 1903 and used to further direct the flow of sanitizing gas into a component downstream of third connector 133.

Put differently, first passageway 123 may, alone or in combination with optional extensions 1907 and/or flow guides 1909, be configured to enable laminar or substantially laminar flow of sanitizing gas into components downstream of third connector 133. This may be accomplished, for example, by positioning and orienting the opening in distal end 1903 (and/or extensions 1907/flow guides 1909) such that sanitizing gas exiting such openings is not directed at a steep angle (e.g., greater than about 45 degrees) towards a sidewall at least partially defining a flow path into and/or through components downstream of third connector 133. For example, in embodiments third connector 133 may be coupled to a proximal end of a CPAP hose, wherein the proximal end includes a relatively sharp bend (e.g., a bend with a radius less than 35 mm) proximate to third connector 133. In such instances, the distal end 1903 of first passageway 123 may be configured to extend into the hose and at least partially into or through the bend, such that the distal end 1903 is oriented to face a straight or relatively straight section of the interior of the hose. Alternatively when first passageway 123 is relatively short (e.g., as in FIG. 19D), one or more extensions 1907 and/or flow guides 1909 may be coupled to distal end 1903 and used to direct the flow of sanitizing gas into a relatively straight section of the hose. As may be appreciated, if the flow of sanitizing gas is directed into the relatively sharp bend, the flow of sanitizing gas through the hose may be impeded. Consequently, a portion of the sanitizing gas flowing from the first passageway may flow through second passageway 131 towards and potentially through second connector 127.

As noted above the flow volume and flow velocity of the sanitizing gas at the distal end 1903 can also impact how sanitizing gas flows through connector units $120_4$-$120_6$. In Accordingly, in embodiments first passageway 123 is configured to permit sanitizing gas to flow through distal end 1903 at a desired flow volume and flow velocity during a sanitizing operation. Without limitation, in embodiments first passageway 123 (and more particularly distal end 1903) is configured to permit sanitizing gas to flow at a flow volume ranging from about 1 to about 2 liters per minute (LPM) (e.g., from about 1.1 to about 1.7 LPM, or even about 1.2 to about 1.5 LPM), and at a flow velocity ranging from about 14 (e.g., 14.5) meters per second (m/s) to about 60 m/s (e.g., from about 15 to about 50 m/s or even from about 17 (e.g., 17.4) to about 50 m/s) during a sanitizing operation. Without limitation, in embodiments first passageway 123 (and more particularly distal end 1903) is configured to permit sanitizing gas to flow at a flow volume ranging from 1.2 to 1.5 LPM and at a flow velocity of 17.4 to 50 m/s during a sanitizing operation. Such volumes and flow rates may also be used in passageways of connector units that are configured differently, such as those shown in FIGS. 20 and 21.

Figure 19G:
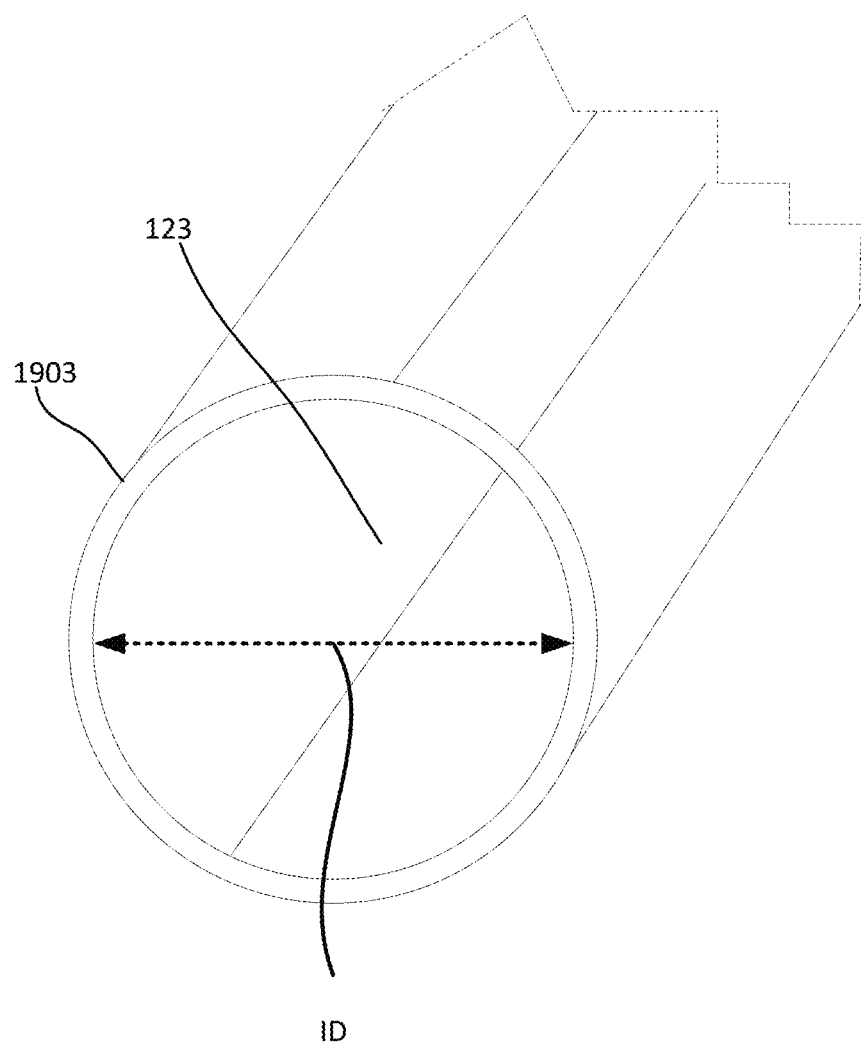
FIG. 19G depicts one example of a distal end of a first passageway of a connector unit, consistent with the present disclosure.

The geometry of distal end 1903 may affect the flow volume and flow velocity of sanitizing gas there through. Accordingly, it may be desirable to select the geometry of distal end 1903 in order to enable sanitizing gas to flow there through at a desired volume and velocity. With the foregoing in mind and as shown in FIG. 19G, in embodiments distal end 1903 has a circular (round) cross section with an internal diameter (ID) ranging from about 0.7 to about 1.5 mm, such as from about 0.8 to about 1.3 mm, or even from about 0.8 to about 1.2 mm That being said, distal end 1903 need not have a circular (round) cross section, and may have any suitable geometry (e.g., an ellipsoidal, triangular, quadrilateral, pentagonal, hexagonal, other geometric, or irregular shape) that allows for a flow rate and flow velocity of sanitizing gas within the above noted ranges. Such configurations may also be applied to passageways of other connector units, such as passageway 123 in FIGS. 20 and 21, and passageway 2012 in FIG. 21.

The position of distal end 1903 relative to sidewall 125 is not limited. In embodiments, the distance between distal end 1903 and the sidewall 125 ranges from greater than 0 to about 25 mm or more, such as from greater than 0 to about 20 mm, greater than 0 to about 15 mm, greater than 0 to about 10 mm, greater than 0 to about 5 mm, greater than 0 to about 1 mm, or even greater than 0 to about 0.5 mm In embodiments, distal end 1903 is about 0.5 mm from the sidewall 125. In other embodiments, distal end 1903 is centered within second passageway 131.

Like the embodiments of FIGS. 19A-19C, FIGS. 19D-19F show connector units that include a first passageway that includes a relatively sharp bend. Such a configuration is not required, and the first passageway 123 of connector units 120$_{4-6}$ may be configured in another manner. For example, in embodiments the first passageway 123 may be substantially straight (i.e., without any bends). In other embodiments, the first passageway 123 may include a single bend (e.g., as shown in FIGS. 19D-19F) or more than one (e.g., 2, 3, 4, etc.) bend.

FIGS. 19A-19F focus on connector units that include a single proximal end and a single distal end, so as define a single first passageway 123. The connector units of the present disclosure are not limited to such configurations, however, and may include any suitable number of proximal and distal ends, as well as any suitable number of channels. For example, the connector units described herein may include a first connector with a first passageway having a single proximal end and multiple distal ends. That concept is shown in FIG. 20, which illustrates a connector unit 1207 that includes a first connector 121 having a first passageway 123, wherein the first passageway 123 has a single proximal end 2001, and branches into a first branch 2002 with a first distal end 2004, and a second branch 2006 with a second distal end 2008. In such embodiments, the configuration of the first and second branches 2002, 2006 and the configuration of the first and second distal ends 2004, 2008 may be selected to control the relative amount of sanitizing gas that is directed toward a medical device fluidly connected to second connector 127 and the relative amount of sanitizing gas that is directed towards components (e.g., a hose 109 and/or base 404) fluidly coupled to third connector 133 during a sanitizing operation. Like the embodiments of FIGS. 19A-19F, one or more optional distribution lines, extensions, and/or flow directors may be coupled to first distal end 2004 and/or second distal end 2008, so as to achieve a desired flow of sanitizing gas during a sanitizing operation.

In additional embodiments the connector units may include multiple discrete connectors (i.e., multiple inlet connectors). That concept is shown in FIG. 21, which depicts a connector unit 1208 that includes a first connector 121 (i.e., a first inlet), a second connector 127, a third connector 133, and a fourth connector (i.e., a second inlet) 2010. The first connector 121 includes a first passageway 123 that includes first branch 2002, and which extends between a first proximal end 2001 and a first distal end 2004 that is oriented towards second connector 127 (or, more particularly, towards components that are or will be fluidly connected downstream of second connector 127). The fourth connector 2010 includes a third passageway 2012 that includes a second branch 2016, and which extends between a second proximal end 2011 and a second distal end 2018 that is oriented towards third connector 133 (or, more particularly, towards components that are or will be fluidly connected to third connector 133.

In use, either or both the first connector 121 and fourth connector 2010 may be connected to a source of sanitizing gas, such as ozone. For example, either or both the first connector 121 and fourth connector 2010 may be fluidly coupled to a source of sanitizing gas, e.g., via one or more sanitizing gas distribution lines. As may be appreciated, when both the first connector 121 and the fourth connector 2010 are coupled to a source of sanitizing gas, the amount of sanitizing gas flowing towards components fluidly coupled downstream of second connector 127 and the amount of sanitizing gas flowing towards components fluidly coupled downstream of third connector may be controlled by controlling the flow volume and velocity of sanitizing gas at the first distal end 2004 relative to the flow volume and flow velocity of sanitizing gas at the second distal end 2018, and vice versa. This may be accomplished, for example, by adjusting the input of sanitizing gas into the first proximal end 2001 and/or second proximal end 2011. Alternatively or additionally, the flow volume and velocity of sanitizing gas at the first and second distal ends 2004, 2018 may be set or adjusted by the geometry of the first and third passageways 123, 2012 and/or the geometry of the first and second distal ends 2004, 2018, respectively.

As shown in FIG. 21, first and/or third passageways 123, 2012 may be sealed, e.g., with an optional cap 2020 that is configured to form a gas tight seal with first and/or second proximal ends 2001, 2011. This capability enables connector unit 1208 to be utilized in a wide variety of applications, including applications in which sanitizing gas may be directed in one or multiple directions, i.e., only towards components fluidly coupled to second connector 127, only towards components fluidly coupled to third connector 133, or towards both components that are fluidly coupled to second connector 127 and components that are fluidly coupled to third connector 133.

The connector units of FIGS. 19A-19F and 20-21 can be used in a variety of systems. For example, the connector units of FIGS. 19A-19F and 20-21 can be used as connector unit 120 in a system configured in the manner shown in FIGS. 4K-4N as discussed above.

To enhance the flow of sanitizing gas such as ozone in a desired direction, the systems described herein may include one or more auxiliary (i.e., secondary) fans/pumps. When used, such auxiliary fans/pumps may be positioned at any suitable location, and may be configured to facilitate the flow of sanitizing gas towards filter 500. For example, the system 400 may include a sanitizing gas generator that includes a primary fan/pump, and at least one secondary fan/pump. In such embodiments the primary and secondary fans/pumps may be co-located within base 404, e.g., as part of the sanitizing gas generator. Alternatively, in some embodiments the systems described herein include a primary fan/pump and a secondary fan/pump at different locations. For example, the systems described herein include a primary fan/pump as part of a sanitizing gas generator that is disposed within base 404, and a secondary fan/pump that is present in another location, e.g., downstream of filter 500.

The primary and secondary fans/pumps are each configured to push or draw sanitizing gas generated by the sanitizing gas generator towards sanitizing gas outlet 453 and, ultimately, towards filter 500. In embodiments system 400 includes a primary fan/pump that is configured to push or draw sanitizing gas out/through sanitizing gas outlet 453. In such instances, system 400 may include a secondary pump/fan that is located downstream of filter 500, and which is configured to draw or pull sanitizing gas towards filter 500.

Figure 16A:
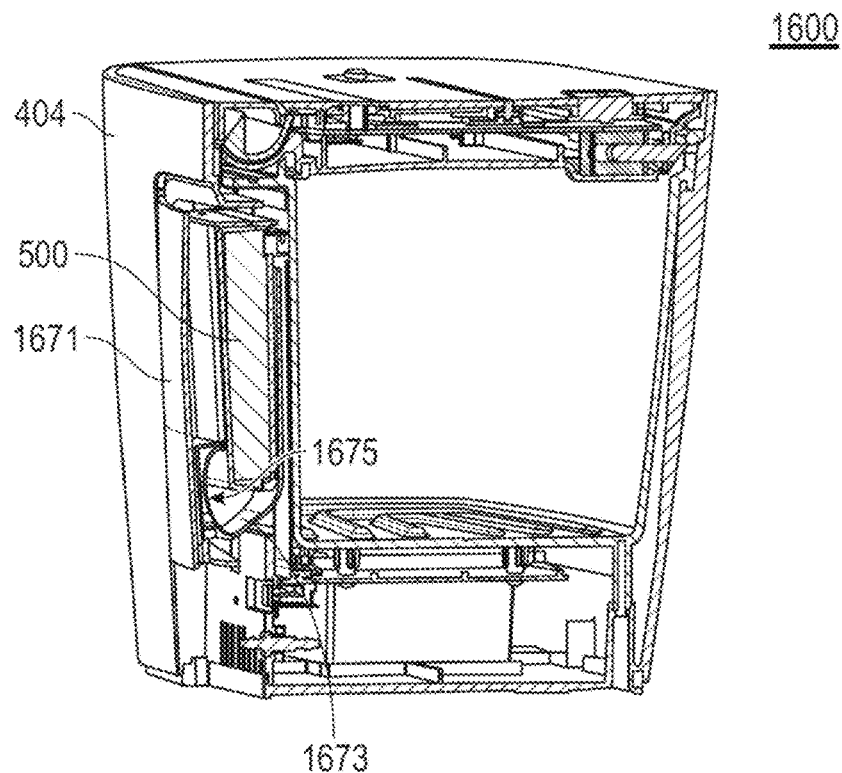
Figure 16B:
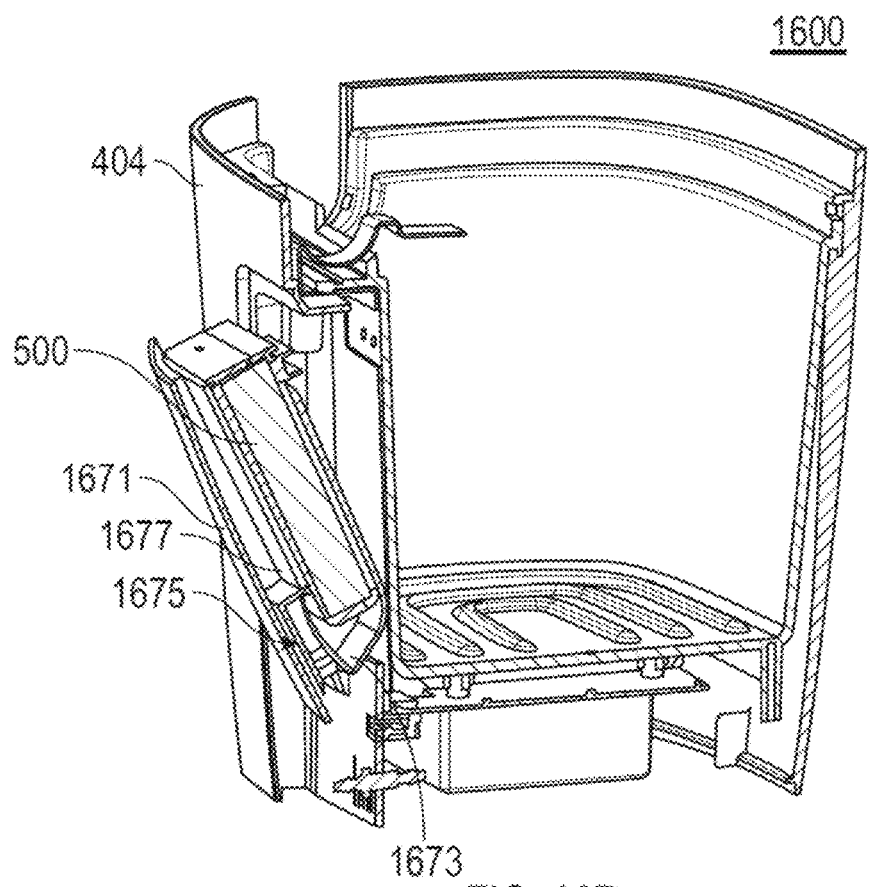
Figure 16C:
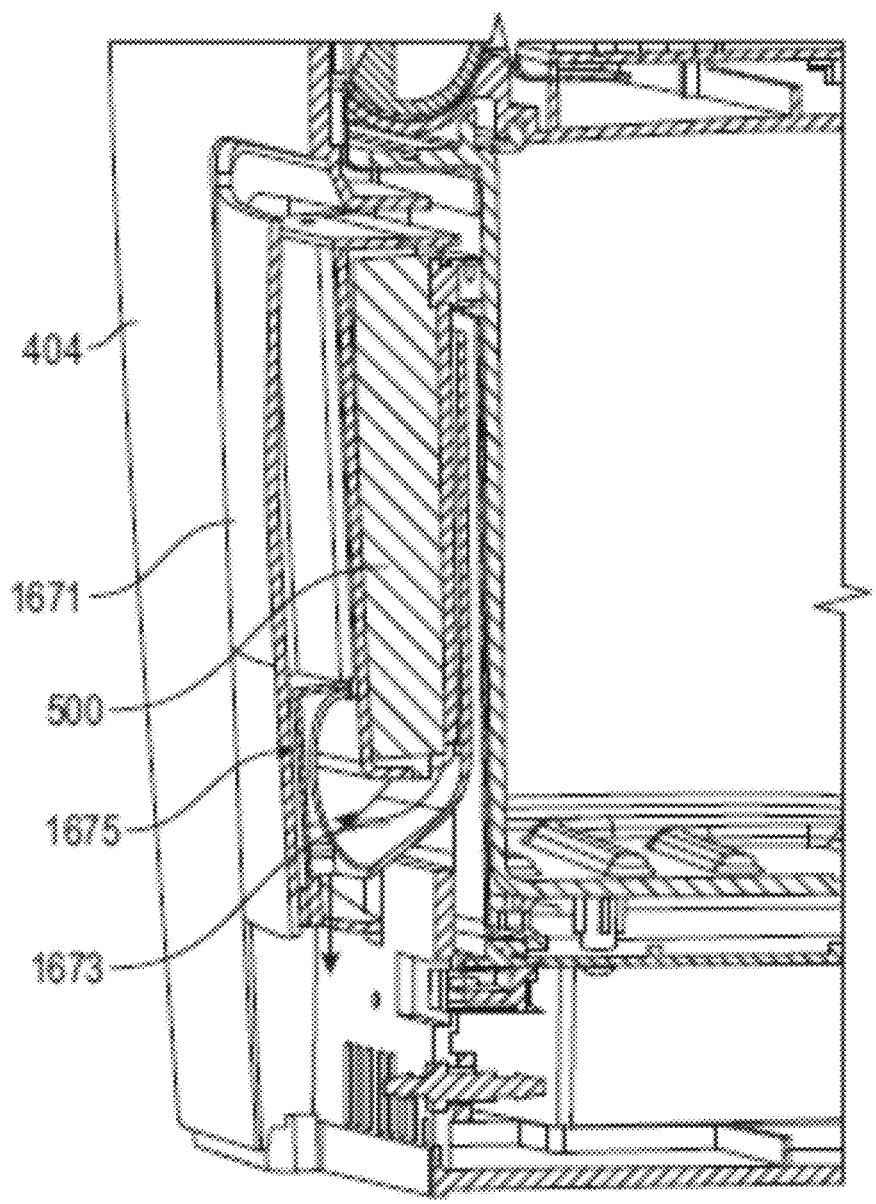
Figure 16G:
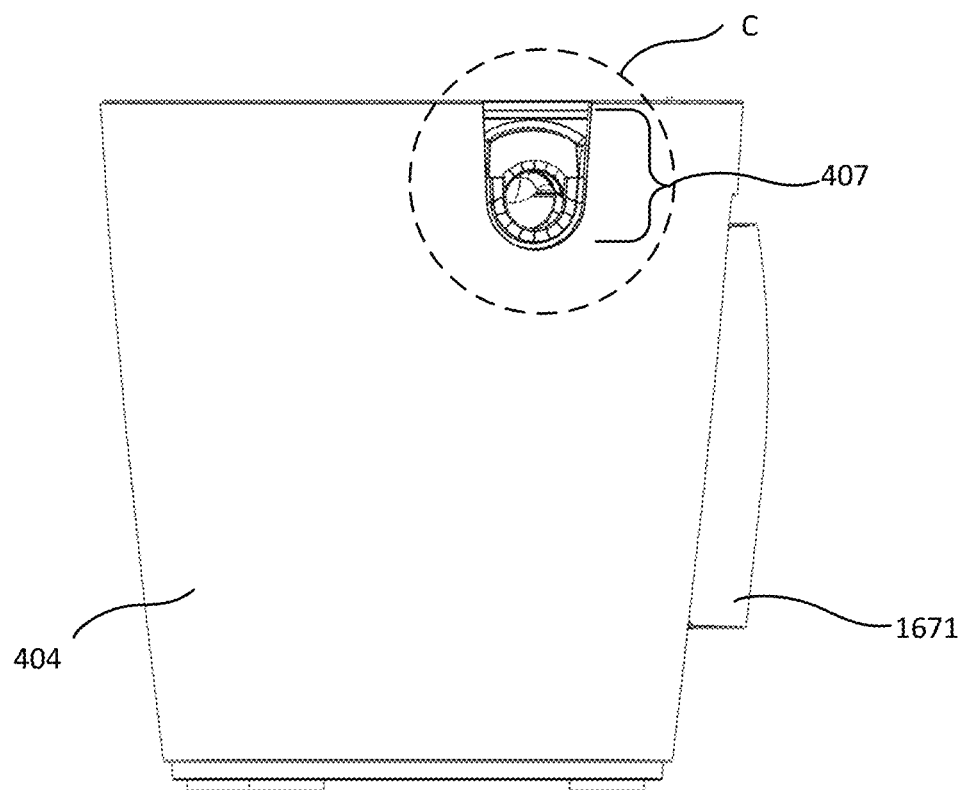

FIGS. 16A-16G depict one example of a system 1600 that includes an auxiliary (secondary) fan/pump consistent with the present disclosure. In this embodiment and as best shown in the cross-sectional views of FIGS. 16A and 16B, system 1600 includes a filter tray 1671, an airflow guide 1673, and an auxiliary fan/pump 1675. For clarity, system 400 is shown with a filter 500 installed within filter tray 1671. As best shown in FIG. 16C, auxiliary fan/pump 1675 is configured to draw (pull) air and/or sanitizing gas through filter 500, i.e., from the inlet of filter 500 towards the outlet of filter 500). When filter tray 1671 is in a closed position, the filter inlet seal 509 engages and seals around exhaust ports 405, as discussed previously. Operation of auxiliary fan/pump 1675 draws/pulls air/sanitizing gas from sanitizing chamber 403 into and through filter 500. Depending on its strength, the pulling/drawing force generated by auxiliary fan/pump 1675 may even draw air/sanitizing gas from the hose of medical device (a distal end of which is present in sanitizing chamber 403), and in some cases from a reservoir of the medical device that is fluidly coupled to the hose, e.g., via a connector unit.

Auxiliary fan/pump 1675 may be operated independently or in conjunction with a primary fan/pump, e.g., within a sanitizing gas generator used in system 400. For example, the primary fan/pump and auxiliary fan/pump 1675 may be configured in a "push/pull" configuration, in which the primary fan/pump "pushes" air/sanitizing gas such that it flows towards and through filter 500, whereas the secondary fan/pump 1675 "pulls" air/sanitizing gas towards and through filter 500. When operated simultaneously, the primary and secondary fans/pumps may increase the flow rate of air and sanitizing gas through filter 500, enhancing the evacuation of system 1600. While rapid evacuation of sanitizing gas may be desirable in some instances, it may shorten or otherwise limit exposure of medical device components to the sanitizing gas, potentially leading to inadequate sanitization. Operation of the auxiliary fan/pump 1675 and/or primary fan/pump may be managed to achieve a desired balance between sanitizing performance and evacuation of sanitizing gas from the system. For example, a controller (e.g., controller 490) may be used to dynamically manage operation of auxiliary fan/pump 1675, such that auxiliary fan/pump 1675 and/or the primary fan/pump (s) is/are activated at appropriate times and for appropriate durations to obtain desired performance.

In the embodiment of FIGS. 16A-16F, auxiliary fan/pump 1675 is in the form of an axial fan that includes an inlet and an outlet. As best shown in FIG. 16C, auxiliary fan/pump 1675 is configured to draw a flow of air/sanitizing gas (shown by arrows in FIG. 16C) from an outlet of filter 500 into an axial inlet on one side of the auxiliary fan/pump 1675, and to exhaust the flow via a perimeter outlet (i.e., an outlet in the perimeter of the fan). Filter tray 1671 includes an airflow guide that facilitates the flow of air/sanitizing gas into and through auxiliary fan/pump 1675.

Filter tray 1671 may be sized and shaped to accommodate the auxiliary fan/pump 1675. That concept is best shown in FIGS. 16D-16F, which show filter tray 1671 with an outer wall that is shaped to provide enough interior volume for auxiliary fan/pump 1675. More specifically and as best shown in FIG. 16B, filter tray 1671 may include an outer wall that is curved and laterally offset from an inner wall 1677, with a gap therebetween. In such instances auxiliary fan/pump 1675 is disposed at least partially within the gap between the inner wall 1677 and the outer wall of filter tray 1671, and is oriented substantially vertically (i.e., such that the axial sides of the auxiliary fan/pump 1675 are substantially parallel to an outer wall of base 404) when filter tray 1671 is in the closed position.

Figure 17A:
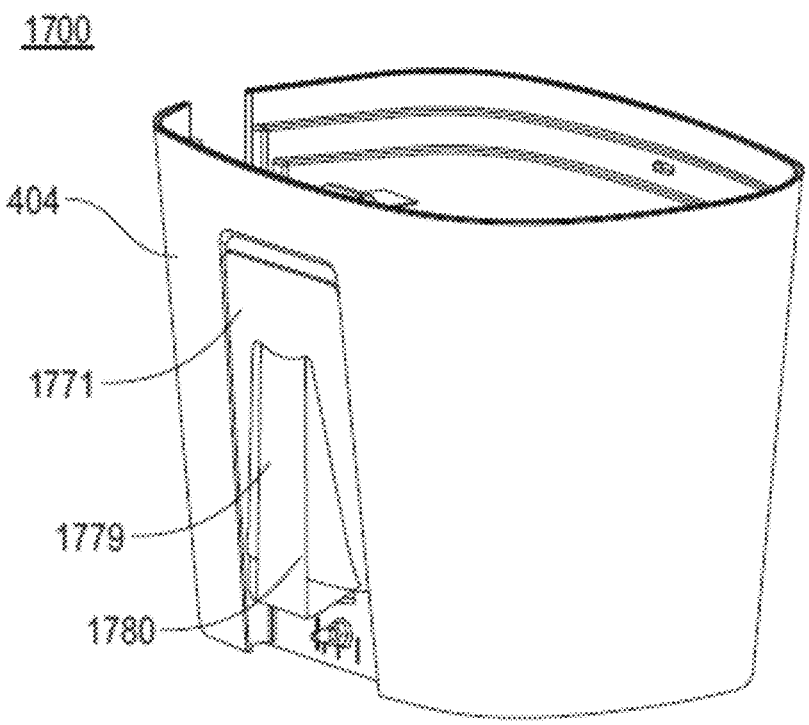
FIGS. 17A-17E depict various views of another example of a sanitizing device including an auxiliary fan, consistent with the present disclosure.
Figure 17B:
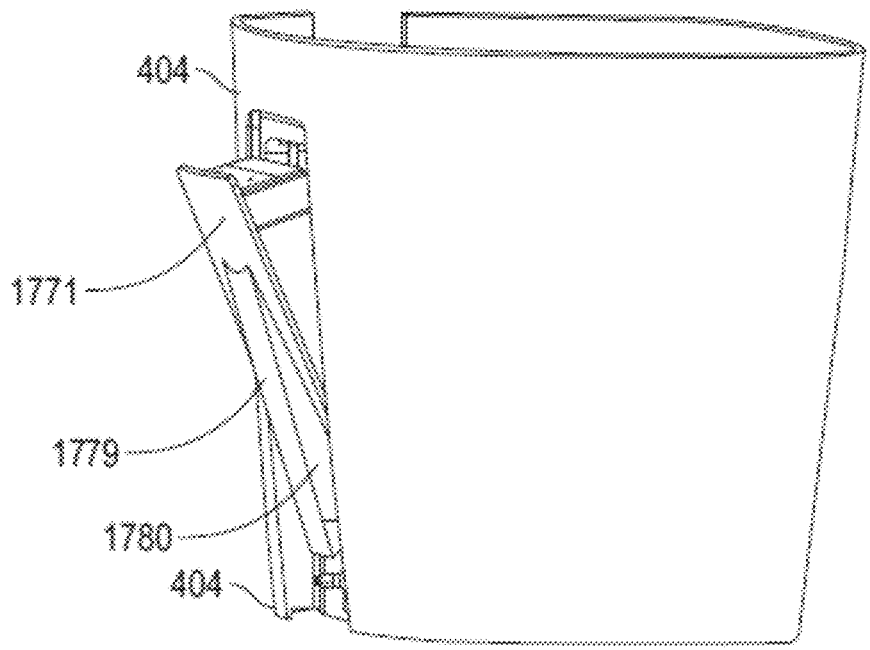
Figure 17C:
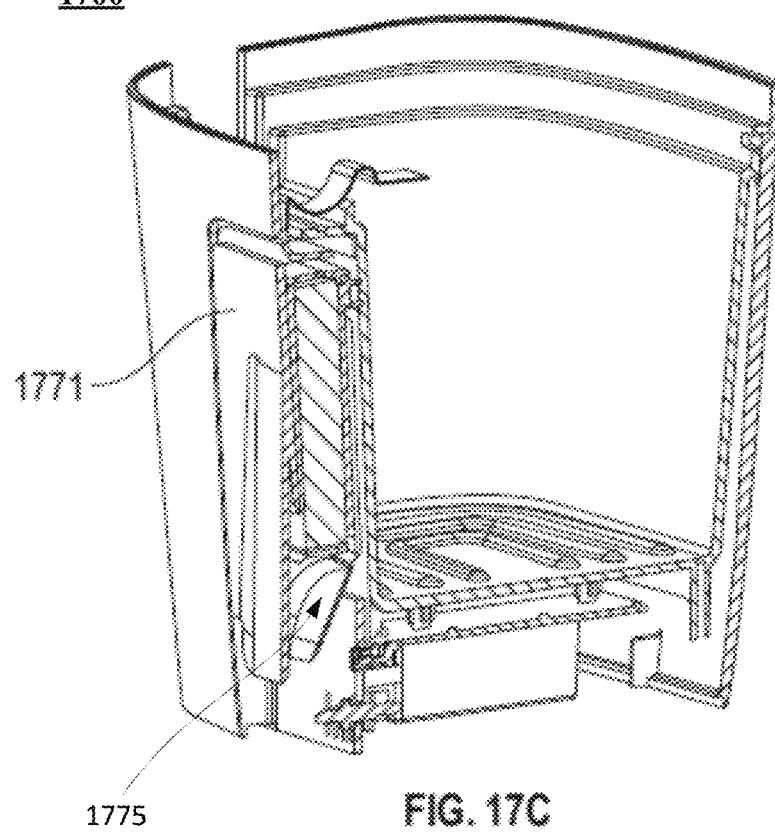
Figure 17D:
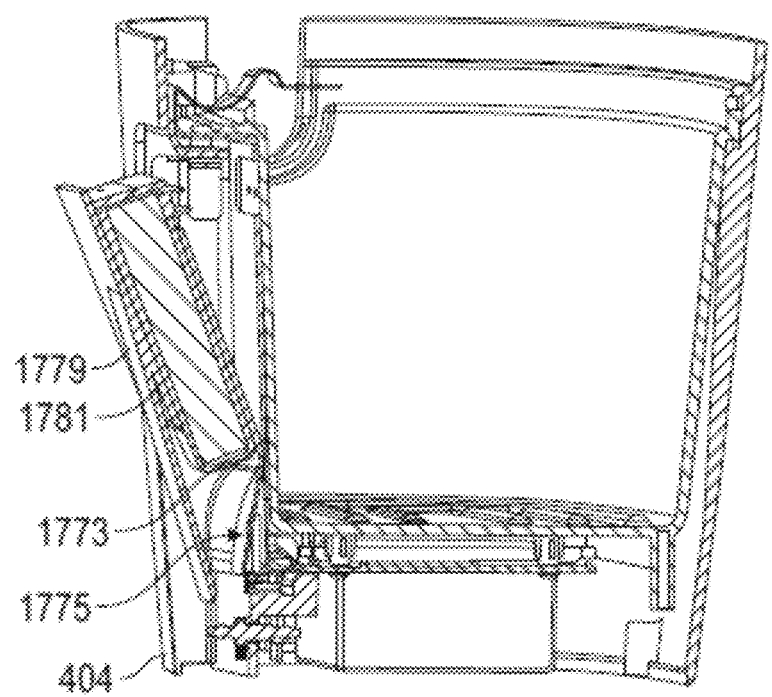

Other configurations that include an auxiliary fan/pump are possible and are envisioned and encompassed by the present disclosure. In that regard FIGS. 17A-17E depict another example of a sanitizing system that include an auxiliary fan/pump consistent with the present disclosure. Like the above described embodiments, system 1700 includes a base 404, a filter tray 1771, an airflow guide 1773, and an auxiliary fan/pump 1775. In this embodiment, however, filter tray 1771 includes a filter tray extension 1779. The filter tray extension 1779 includes at least one sidewall 1780 that extends from an outer wall (not labeled) of filter tray 1771 to an outer wall (not labeled) of filter tray extension 1779. In embodiments and as best shown in FIG. 17D, an optional shim 1781 may be present between an inner surface of filter tray extension 1779 and a filter 500 within filter tray 1771. As further shown in FIG. 17D, the filter tray extension 1779 is configured such that auxiliary fan/pump 1775 can be installed at an angle between an inner surface of the filter tray extension 1779 and an end of airflow guide 1773. More specifically, auxiliary fan/pump 1775 is installed such that when filter tray 1771 is in a closed position, the axial sides of auxiliary fan/pump 1775 are oriented at an offset angle relative to an outer wall of base 404. In embodiments, the offset angle is greater than or equal to about 2, 3, 4, 5, 10, or 15 degrees offset from vertical, or more.

Figure 17E:
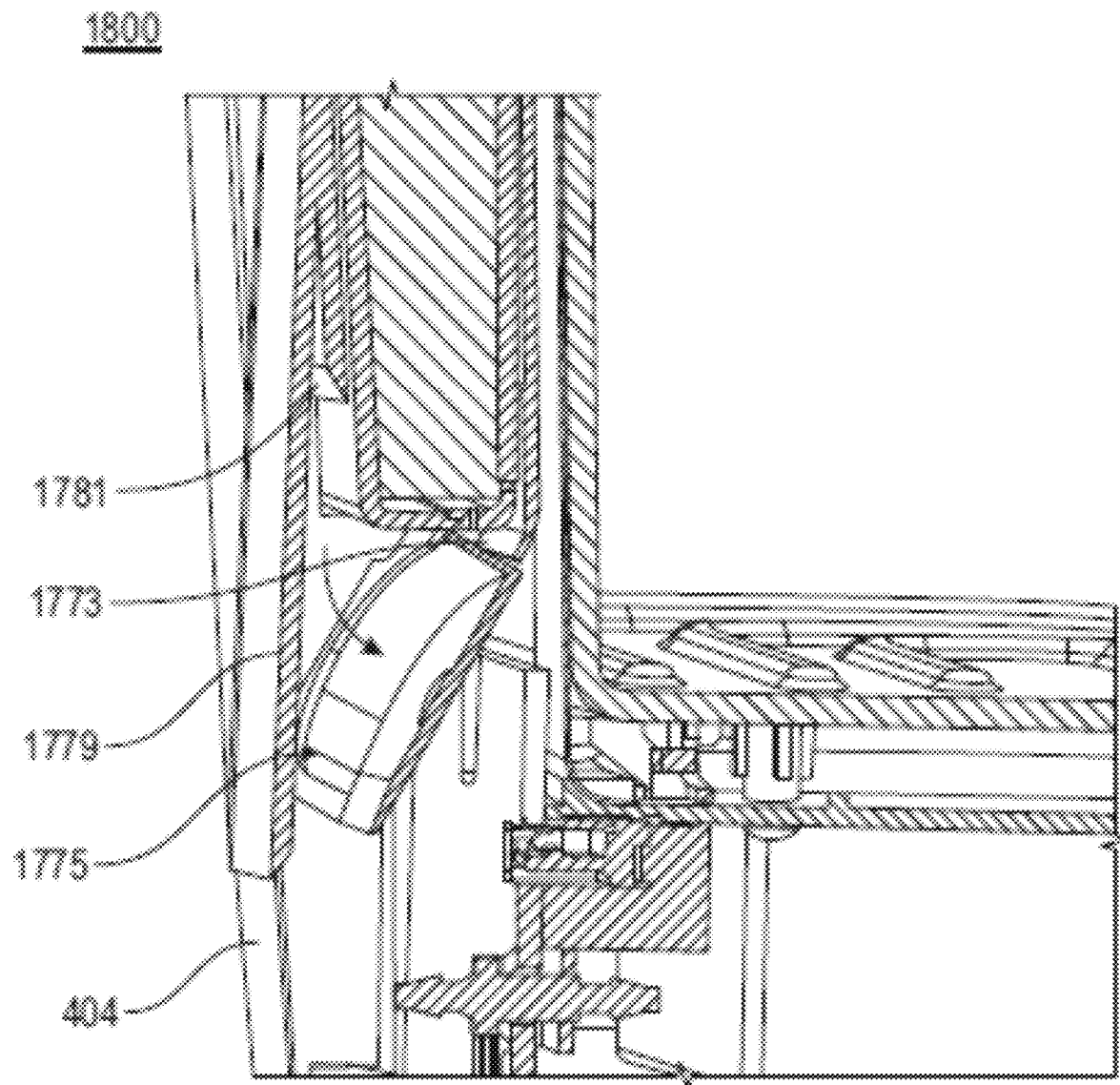

In the configuration shown in FIGS. 17A-17E, operation of the auxiliary fan/pump 1775 may draw an airflow through filter 500 when filter tray 1771 is in the closed position. That concept is best shown in FIG. 17E. Unlike the embodiment of FIGS. 16A-16F, auxiliary fan/pump 1775 may draw air into an axial inlet, and may exhaust air via an axial outlet. Without limitation, this may increase the amount of air flow passing through auxiliary fan/pump 1775, while also limiting the size of airflow guide 1773. Operation of the embodiment of FIGS. 17A-17D is substantially the same as the embodiment of FIGS. 16A-16F and therefore is not reiterated.

Figure 18A:
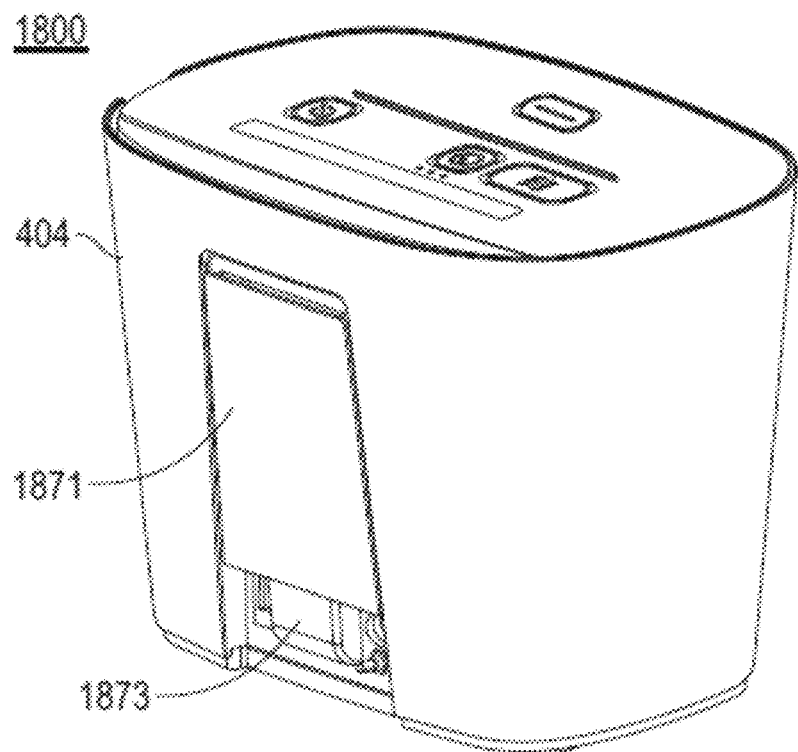
FIGS. 18A-18D depict various views of another example of a sanitizing device including an auxiliary fan, consistent with the present disclosure.
Figure 18B:
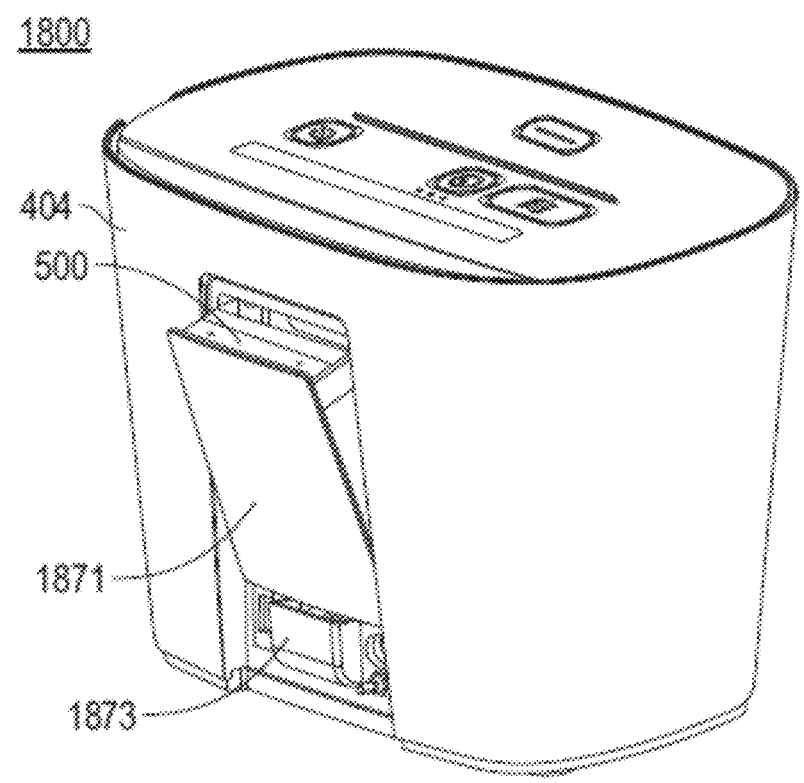
Figure 18C:
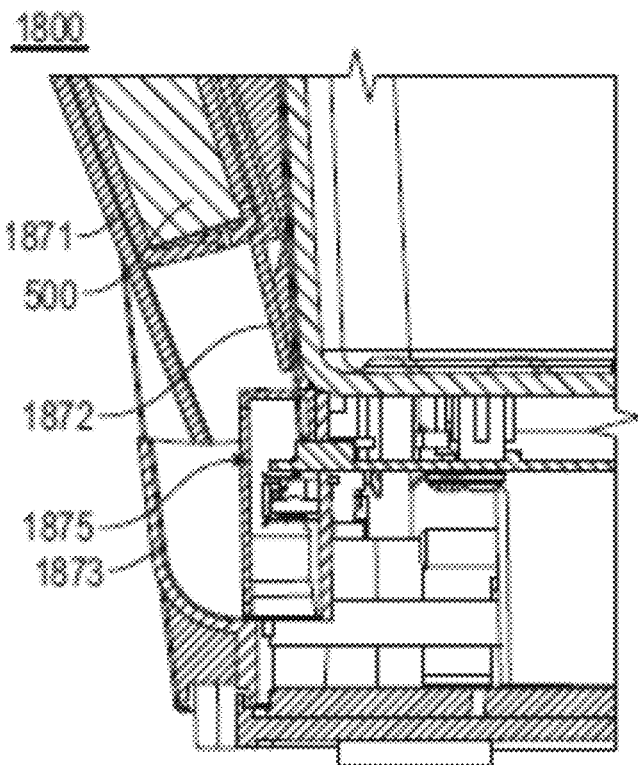
Figure 18D:
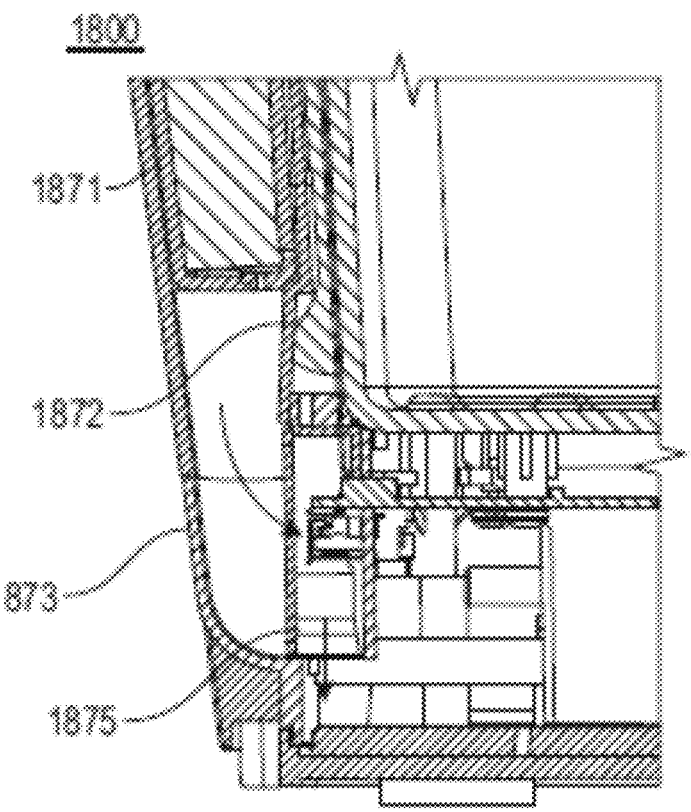

FIGS. 18A-18D depict another example of a system that includes an auxiliary pump/fan consistent with the present disclosure. Like the above described embodiments, system 1800 includes a base 404, a filter tray 1871, an airflow guide 1873, and an auxiliary fan/pump 1875. In this embodiment, however, filter tray 1871 is extended in length and includes an inner wall that forms an auxiliary (i.e., second) airflow guide. Moreover, in this embodiment auxiliary fan/pump 1875 is coupled to base 404, rather than being disposed within filter tray 1871. Consequently, auxiliary fan/pump 1875 remains stationary when filter tray 1871 is moved between the open and closed positions, potentially improving reliability and/or durability of power and/or control connections between auxiliary fan/pump 1875 and base 404/controller 490. Further, in this embodiment airflow guide 1873 is coupled to and/or is formed by part of base 404, as best shown in FIGS. 18A and 18B. As shown in FIG. 18C, when filter tray 1871 is in the open position an edge of inner wall 1872 and an edge of the outer wall of filter tray 1871 are displaced relative to corresponding parts (edges) of air flow guide 1873. When filter tray 1871 is in the closed position, however, the edges of the outer wall of filter tray 1871 and inner wall 1872 substantially align with corresponding parts (edges) of air flow guide 1873. Consequently, when auxiliary fan/pump 1875 is operated an air flow is drawn through filter 500, through air flow guide 1873, and into an axial inlet of auxiliary fan/pump 1875, as best shown in FIG. 18D. Auxiliary fan/pump 1875 may exhaust said air flow via a perimeter outlet as also shown in FIG. 18D. Alternatively, auxiliary fan/pump 1875 may include an axial inlet and an axial outlet. In such instances, base 404 may be configured such that an outlet channel is provided at proximate the axial outlet, so as to facilitate the flow of air from the axial outlet to the outside environment. In any case, the operation of the embodiment of FIGS. 18A-18D is the same as described above for the embodiment of FIGS. 16A-16F, and therefore is not reiterated.

FIGS. 16A-18D focus on embodiments in which an auxiliary fan/pump is located downstream of a filter 500, and is configured to draw sanitizing gas through the filter 500, e.g., during or after a sanitizing operation. While such configurations are useful, they are not required and the present disclosure envisions and encompasses systems in which an auxiliary fan is located in a different position. For example, in embodiments an auxiliary fan/pump may be located upstream of the inlet of the filter 500. In such instances, the auxiliary fan/pump may be configured to push and/or draw air and/or sanitizing gas towards the inlet of filter 500. In such instances the auxiliary fan/pump may facilitate the flow of air and/or sanitizing gas into the inlet of filter 500 and, ultimately, through filter 500.

FIGS. 16A-18D also focus on embodiments in which a single auxiliary fan/pump is used. Although useful the systems of the present disclosure are not limited to the use of a single auxiliary fan/pump. Indeed the systems may include any suitable number (e.g., 1, 2, 3, 4, 5, 6, 7, or more) auxiliary fans/pumps, wherein the auxiliary fan(s)/pump(s) is/are configured and positioned to facilitate the flow of air and/or sanitizing gas through filter 500. For example, in some embodiments the systems described herein include one or more auxiliary fans/pumps downstream of filter 500, and one or more auxiliary fans/pumps upstream of filter 500. In such embodiments, the auxiliary pumps/fans may function independently or in cooperation with one another to facilitate the flow of air and/or sanitizing gas through filter 500. The fans/pumps may also be operated to limit or present sanitizing gas from reaching certain components (e.g., a CPAP or other device, e.g., coupled to a connector unit), and/or to concentrate sanitizing gas at a certain part of the system (e.g., within a sanitizing chamber, a mask, a CPAP hose, combinations thereof, and the like)

As noted above receptacle 407 may be defined at least in part by an upper seal member 431 and a lower seal member 433. In general, the upper and lower seal members 431, 433 cooperatively function to form a seal around an intermediate portion of a hose of a medical device, such as a CPAP hose. Put in other terms, the upper and lower seal members 431, 433 form a sealing system that is configured to form a seal around an intermediate portion of a hose of a medical device.

Figure 6A:
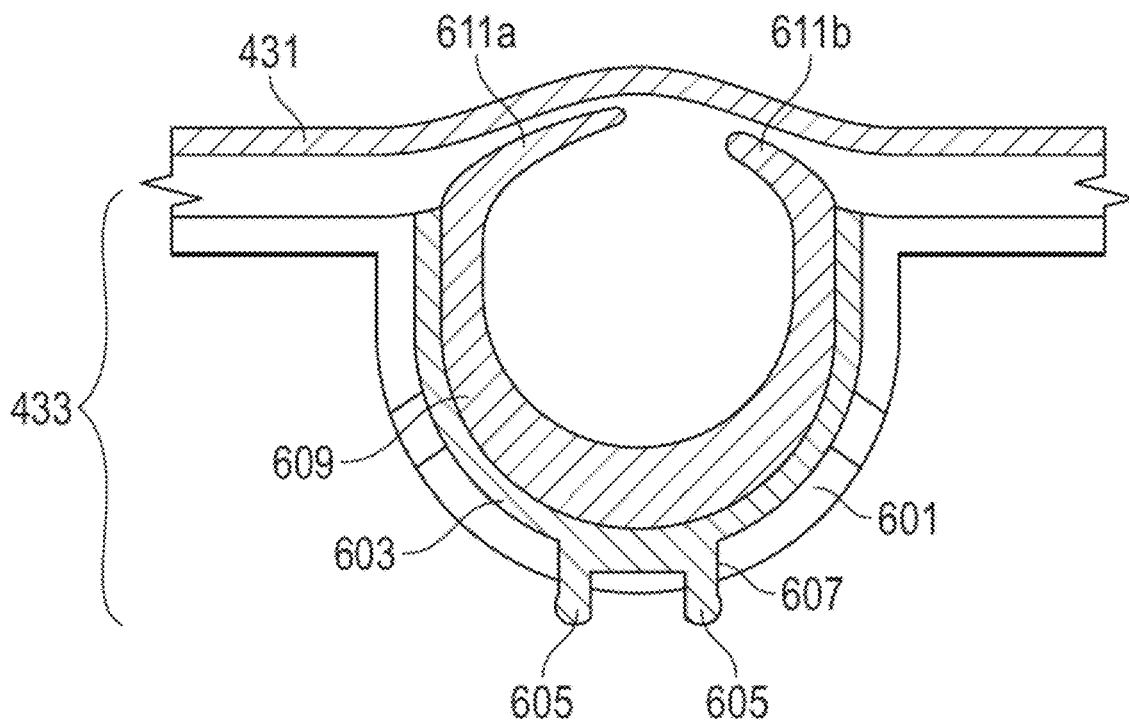
FIG. 6A depicts one example of a sealing system consistent with the present disclosure.
Figure 6B:
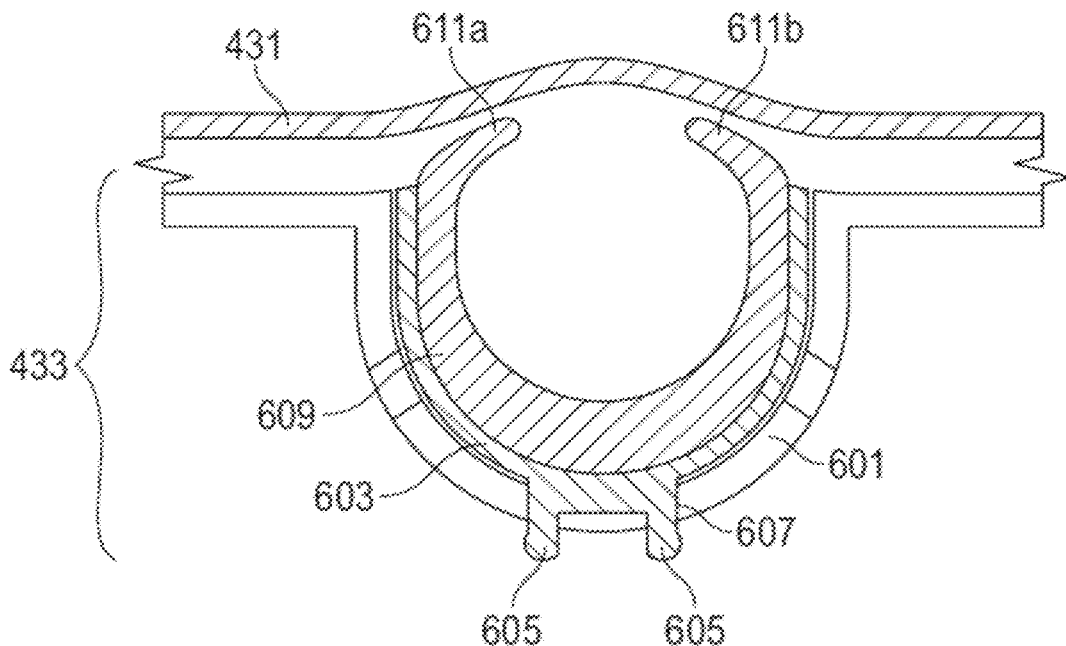
FIG. 6B depicts another example of a sealing system consistent with the present disclosure.
Figure 6C:
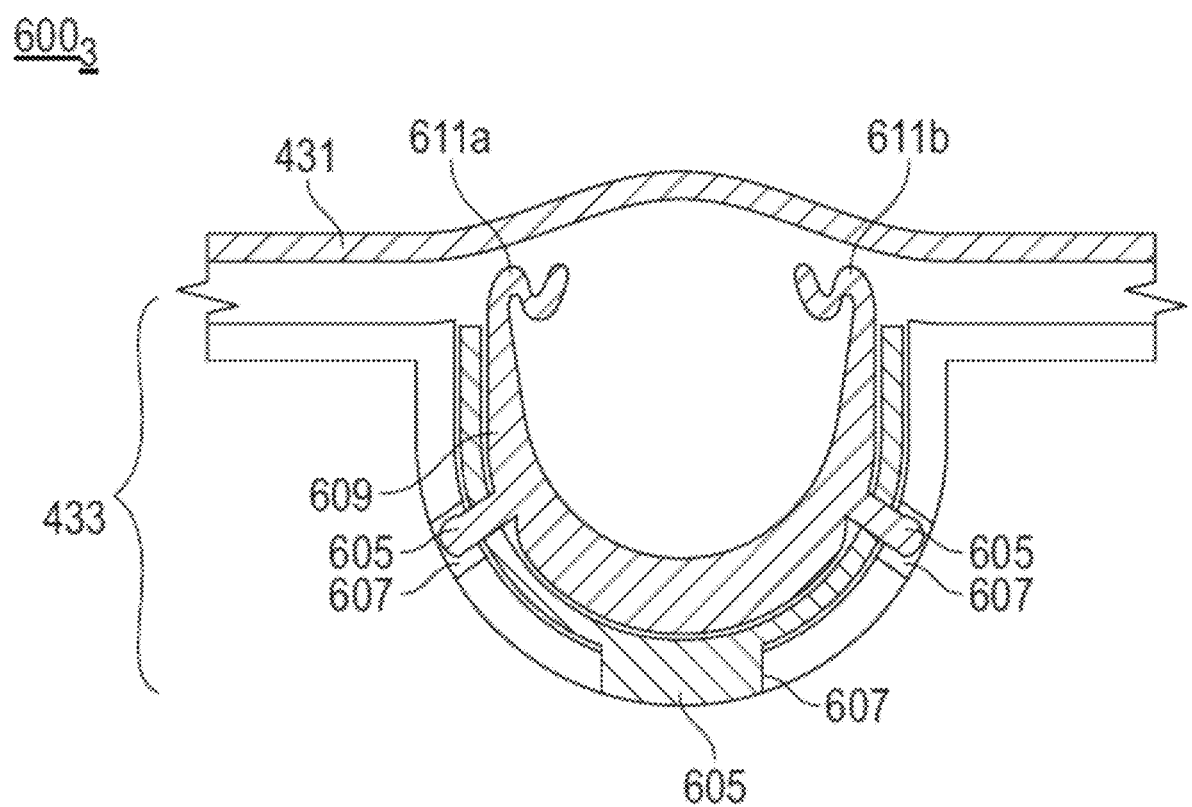
FIG. 6C depicts another example of a sealing system consistent with the present disclosure.

FIGS. 6A-6C depict several example sealing systems that may be used within or in conjunction with receptacle 407. As shown, sealing systems $600_1$, $600_2$, and $600_3$ each include an upper seal member 431 and lower seal member 433, wherein upper seal member 431 is formed at least in part by lid seal 427, as discussed above. In each embodiment, lower seal member 433 includes a lower seal body 603 and one or more lower seal retention members 605. The lower seal body 603 has an outer surface (not labeled) that compliments or is conformal to an inward facing surface 601 of receptacle 407.

The inward facing surface 601 includes at least one retention element receiver 607 (e.g., a recess, slot, groove, or the like), which is configured to receive lower seal retention member(s) 605. In embodiments, retention element receiver 607 is a slot, and lower seal retention member(s) 605 is (are) configured such that they may be inserted therein and mechanically retained by the edges of the retention element receiver 607. In that regard, lower seal retention members 605 may be formed from an elastomeric material, such that they can be compressed and inserted into retention element receiver 607. Once inserted the lower seal retention members 605 may expand to urge against the edges of a corresponding retention element receiver 607, thereby retaining lower seal member 433 within receptacle 407.

In the embodiments of FIGS. 6A and 6B, two lower seal retention elements 605 and a single retention element receiver 607 are used. Such a configuration is not required, however, and the lower seal member 433 may be retained within receptacle 407 in any suitable manner. For example, FIG. 6C depicts an embodiment in which lower seal member 433 includes a plurality of lower seal retention members 605, which are receivable within a corresponding plurality of retention element receivers 607 formed in the inner surface of receptacle 407.

In the embodiments of FIGS. 6A-6C the lower seal body 603 includes or defines a lower seal surface 609. In operation at least a portion of the lower seal surface 609 is configured to form a seal with a lower portion of a medical device hose when lid 401 is in the closed position. Lower seal surface 609 further includes first and second sealing fingers 611a, 611b, as shown. In the embodiment of FIG. 6A the first and second sealing fingers 611a, 611b are of different length, but such a configuration is not required. Indeed as shown in FIGS. 6B and 6C, sealing systems $600_2$, $600_3$ include sealing fingers 611a, 611b of equal length. Moreover, sealing fingers 611a, 611b may have any suitable shape. For example, FIGS. 6A and 6B depict embodiments in which sealing systems $600_1$, $600_2$ include sealing fingers 611a, 611b having a curvilinear shape. In contrast, FIG. 6C depicts a system $600_3$ that includes sealing fingers with an "S" or "inverse S" shape.

Regardless of their number, shape, and/or configuration, sealing fingers 611a, 611b generally function to form a seal with an upper portion of a medical device hose disposed within receptacle 407. For example, in operation sealing fingers 611a, 611b, may be compressed against an upper surface of a medical device hose when lid 401 is in a closed position. In that condition, sealing fingers 611a, 611b may form a seal with an upper portion of the hose while lower seal surface 609 forms a seal with a lower part of the hose.

Lower seal body 603, lower seal retention member 605, lower seal surface 609, and sealing fingers 611a, 611b may be formed from any suitable material. In embodiments, each of such components is formed from the same or different material, such as a natural or synthetic elastomeric material, such as a (e.g., low durometer) natural or synthetic elastomeric polymer, natural or synthetic rubber, or the like. In embodiments, the lower seal surface and sealing fingers may be configured to seal around the corrugated surface of a corrugated medical device hose.

Figure 7:
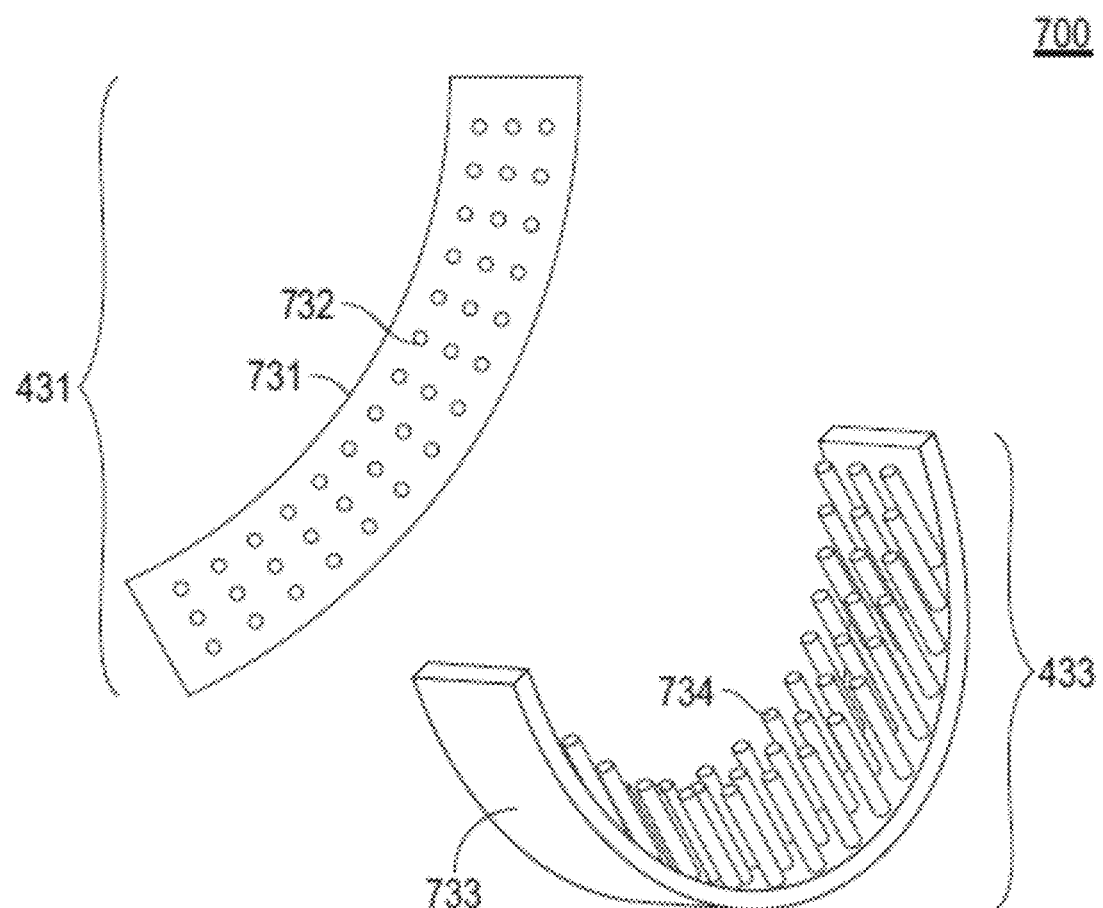
FIG. 7 depicts another example of a sealing system consistent with the present disclosure.

FIG. 7 depicts another example of a sealing system that may be used to seal around an intermediate portion of a hose. Sealing system 700 includes an upper seal member 431 and a lower seal member 433. In this embodiment, upper seal member 431 includes an upper base 731 and a plurality of upper protuberances 732 extending from upper base 731. Likewise, lower seal member 433 includes a lower base 733 and a plurality of lower protuberances 734 extending from lower base 733. Upper base 731, upper protuberances 732, lower base 733 and lower protuberances 734 may be formed from any suitable material. In embodiments, such components are formed form the same or different material, such as a natural or synthetic elastomeric polymer, natural or synthetic rubber, and/or ozone safe materials such as silicone.

In this embodiment upper seal member 431 may form part of lid seal 427, or may be discrete from lid seal 427. In either case, upper seal member 431 is (or, more particularly, upper protuberances 732 and upper base 731 are) configured to engage and form a seal with an upper portion of a medical device hose when lid 401 is in a closed position.

In this embodiment lower base 733 is generally configured to compliment and/or conform to an inner surface of receptacle 407 (e.g., as described above in connection with lower seal body 603 of FIGS. 6A-6C). In any case, lower seal member 433 is (or, more particularly, lower protuberances 734 and lower base 733 are) configured to engage and form a seal with a lower portion of a medical device hose when lid 401 is in a closed position.

Figure 8:
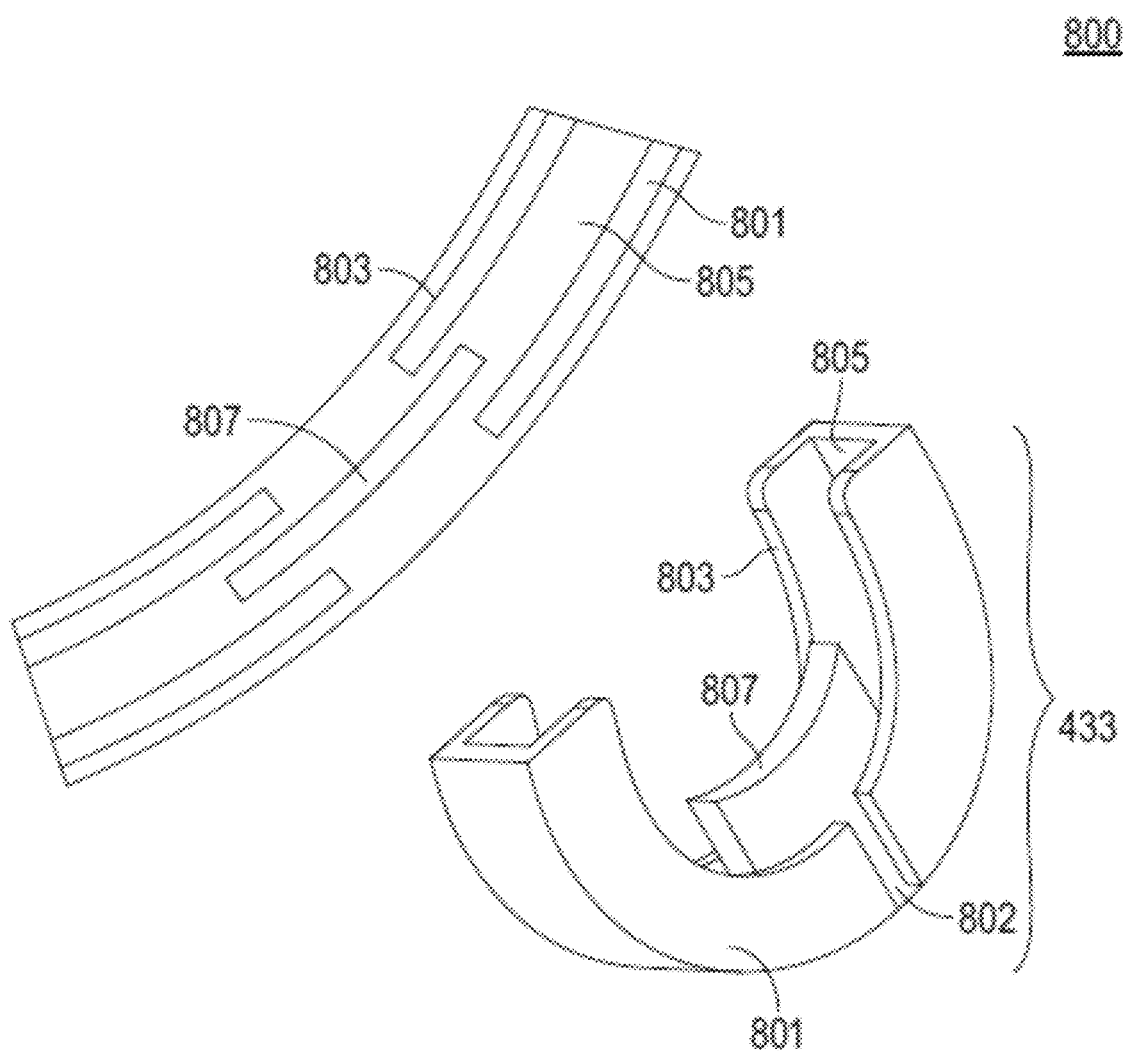
FIG. 8 depicts another example of a sealing system consistent with the present disclosure.

FIG. 8 depicts another example of a sealing system that may be used to seal around an intermediate portion of a hose. Sealing system 800 includes an upper seal member 431 that is formed by part of lid seal 427, and a lower seal member 433. In this embodiment lower seal member 433 includes lower outer seal 801, a lower inner seal 803, and an intermediate sealing element 807 disposed in a channel 805 between lower outer seal 801 and lower inner seal 803. A lower outer gap 802 is present between opposing halves of lower outer seal 801, but may be omitted. In this context, lower outer seal 801 is an "outer seal" because it is oriented away from sanitizing chamber 403 when lower seal member 433 is disposed within receptacle 407. Likewise, lower inner seal 803 is an "inner seal" because it is oriented towards sanitizing chamber when lower seal member 433 is disposed within receptacle 407.

In general, lower outer seal 801, lower inner seal 803, and intermediate sealing element 807 are configured to be disposed and seal around a reinforcement (e.g., a winding) of a medical device hose. For example, when lid 401 is moved to a closed position and a hose is disposed in receptacle 407, lower outer seal 801 and intermediate sealing element 807 may be disposed on opposing sides of a first reinforcement (e.g., a first winding/winding turn) of said hose, and said intermediate sealing element and said lower inner seal 803 may be disposed on opposing sides of the first reinforcement or on opposing sides of a second reinforcement of said hose (e.g. a second winding/winding turn). In such instances the first reinforcement may be pinched between intermediate sealing element 807 and lower outer seal 801 to form a first seal, and the first (or second) reinforcement may be pinched between intermediate sealing element 807 and lower inner seal 803 to form a second seal.

In embodiments lower outer seal 801, lower inner seal 803, channel 805, and intermediate sealing element 807 may have a pitch that is configured to match or substantially match a pitch of the reinforcement (e.g., winding) of the hose. For example, in some embodiments such components have a helical pitch that is configured to match or substantially match a helical pitch of a winding about a CPAP or other medical device hose.

Figure 9A:
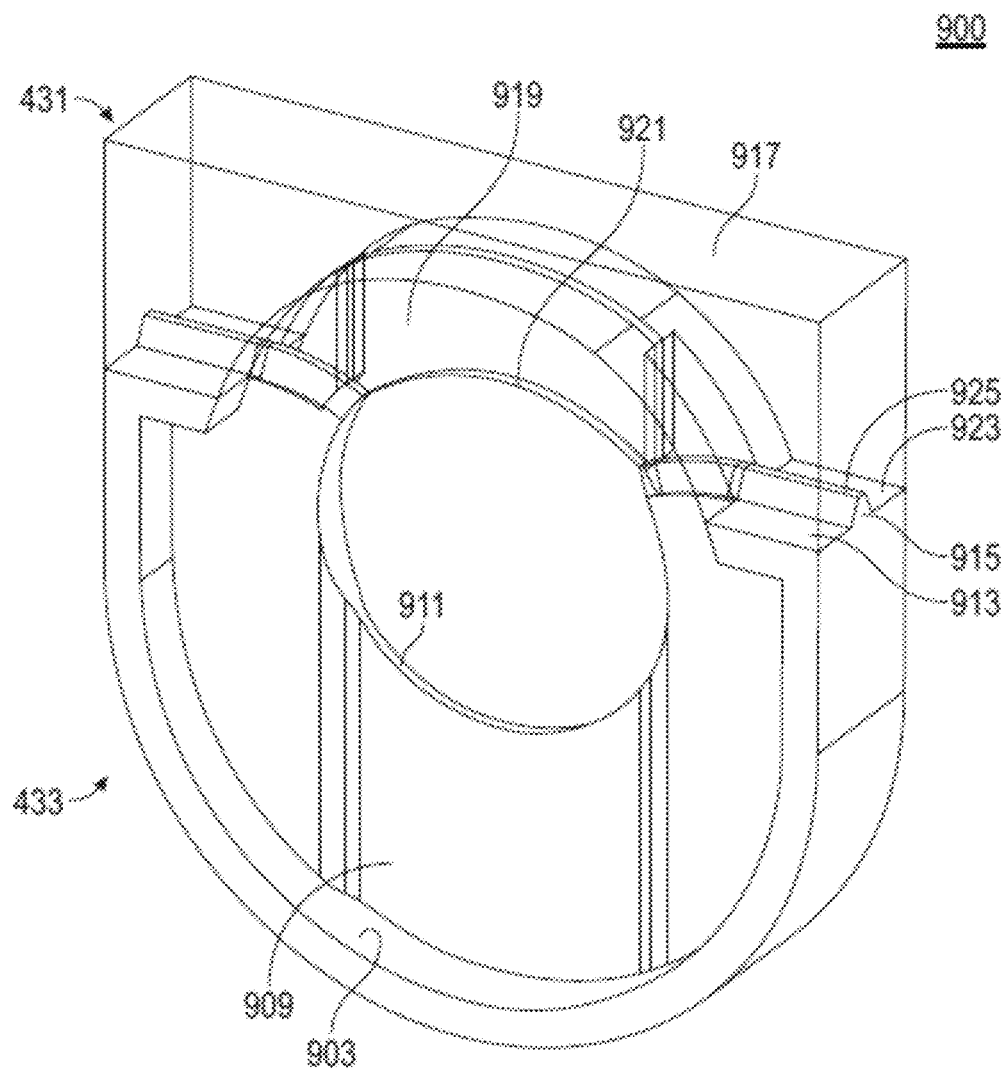
FIG. 9A depicts another example of a sealing system consistent with the present disclosure.

FIG. 9A depicts another example of a sealing system that may be used to seal around an intermediate portion of a hose. Sealing system 900 includes an upper seal member 431 and a lower seal member 433. The lower seal member 433 includes a lower seal body 903, a lower seal surface 909 and a lower seal edge 911. The upper seal member 431 includes an upper seal body 917, and upper seal surface 919, and an upper seal edge 921. As may be appreciated, in this embodiment upper seal member 431 is not formed by part of lid seal 427, but rather is discrete from lid seal 427. Accordingly, upper seal member 431 (or, more particularly, upper seal body 917) in this embodiment may be mounted or coupled to lid 401 in any suitable manner. Likewise, lower seal body 903 may be coupled to or otherwise retained within receptacle 407 in any suitable manner.

In this embodiment the lower seal edge 911 has a thickness that varies from its base (bottom) towards its top (left and right). Although not shown, upper seal edge 921 may have a thickness that varies similarly, albeit from the top toward the bottom (left and right) thereof. In embodiments, the thickened portions of lower and upper seal edges 911, 921 are configured to fit between and form a seal with a reinforcement (e.g., a winding) of a medical device hose, such as a CPAP hose. Consequently, at least the thickened portions of lower and upper seal edges 911, 921 may have a pitch that is configured to match or substantially match the pitch of a reinforcement (e.g., winding) of a medical device hose. In contrast, the thinned regions of lower and upper seal edges 911, 921 are configured to conform to the shape of the hose.

Upper and lower seal members 431, 433 of sealing system 900 further include elements that facilitate element thereof when lid 401 is moved to a closed position. In that regard, lower seal member 433 includes at least one lower seal shoulder 913 that extends from a portion of lower seal body 903 towards an opening extending through sealing system 900 when lid 401 is in a closed position. Upper seal member 431 includes at least one corresponding upper seal shoulder 923 that extends from a portion of upper seal body 917. At least one lower seal rib 915 extends from a facing surface of lower seal shoulder 913 towards upper seal member 431. Upper seal member further includes an upper seal groove 925 formed within upper seal shoulder 923. Lower seal shoulder 913, lower seal rib 915, upper seal shoulder 923, and upper seal groove are configured such that when lid 401 is in a closed position, lower seal rib 915 is disposed within upper seal groove 925, thereby aligning upper seal member 431 to lower seal member 433. Of course, other configurations of sealing system 900 are also envisioned and encompassed by the present disclosure. For example, sealing system 900 may be configured such that a groove is formed in lower seal shoulder 913 and a rib extends from upper seal shoulder.

Figure 9B:
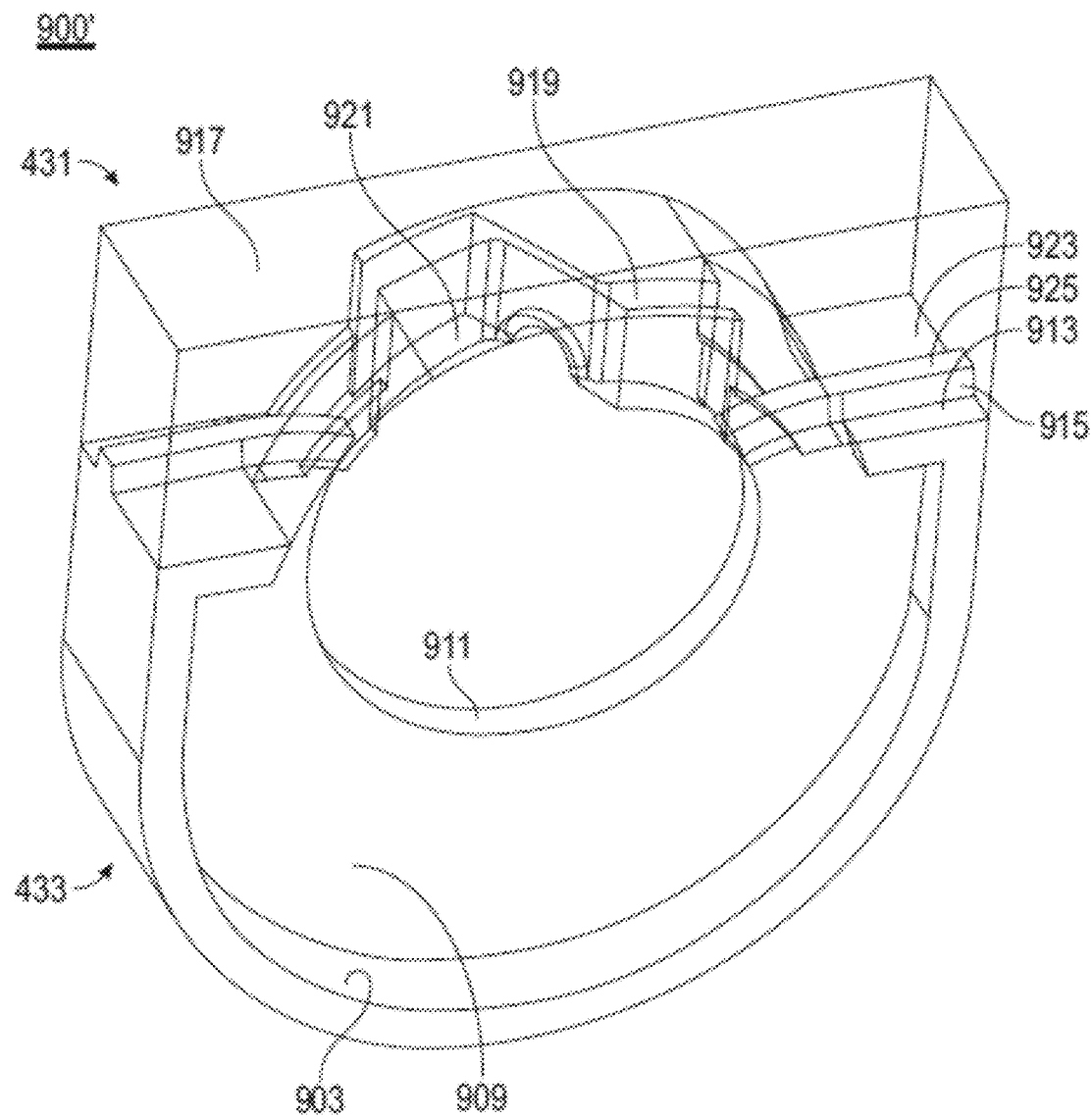
FIGS. 9B and 9C depict another example of a sealing system consistent with the present disclosure.
Figure 9C:
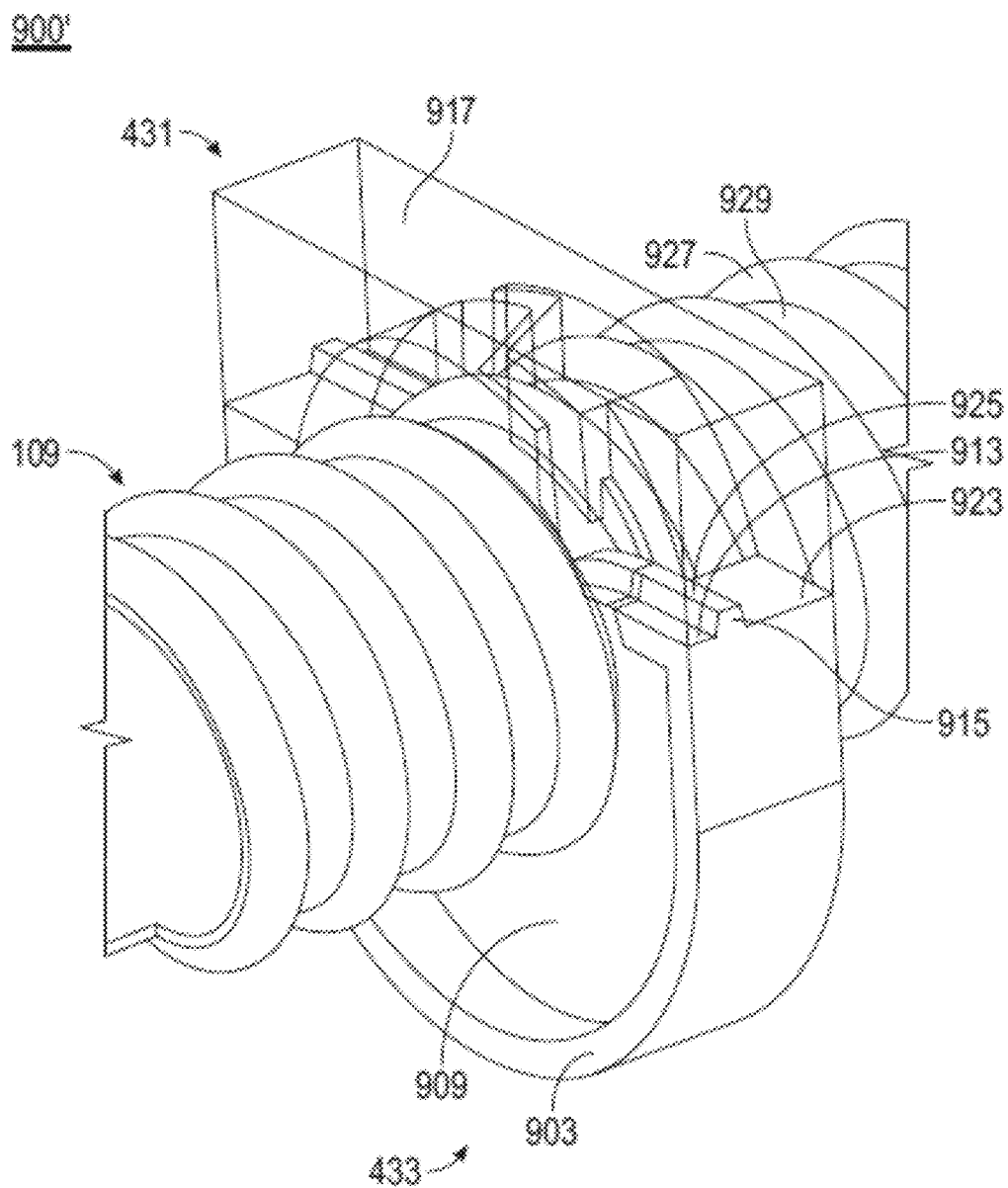

FIGS. 9B and 9C depict another example of a sealing system that may be used in or in conjunction with receptacle 407. Sealing system 900' includes the same elements as sealing system 900, so such elements are not described again in the interest of brevity. Like sealing system 900, sealing system 900' is configured to form a seal around and between a reinforcement (e.g., between two winding turns of a winding) of a medical device hose. In that regard, lower seal edge 911 and upper seal edge 921 each have a pitch that matches or substantially the pitch of a winding or other reinforcement of a medical device hose. Thus, when a hose is inserted into receptacle 407 and lid 401 is advanced to the closed position, upper seal member 431 and lower seal member 433 of sealing system 900' each form a seal between a winding or other reinforcement of the hose and a thin bridge section of the upper and lower seal members forms a seal against the winding/reinforcement. That concept is shown in FIG. 9C, which depicts sealing system 900' as it is used to form a seal around a hose 109. As shown, a helical reinforcement winding 927 is disposed around hose 109. A reinforcement channel 929 is present between each turn of winding 927. As shown, sealing system 900' is configured such that lower seal edge 911 and upper seal edge 921 are disposed and form a seal within a reinforcement channel 929.

Figure 10A:
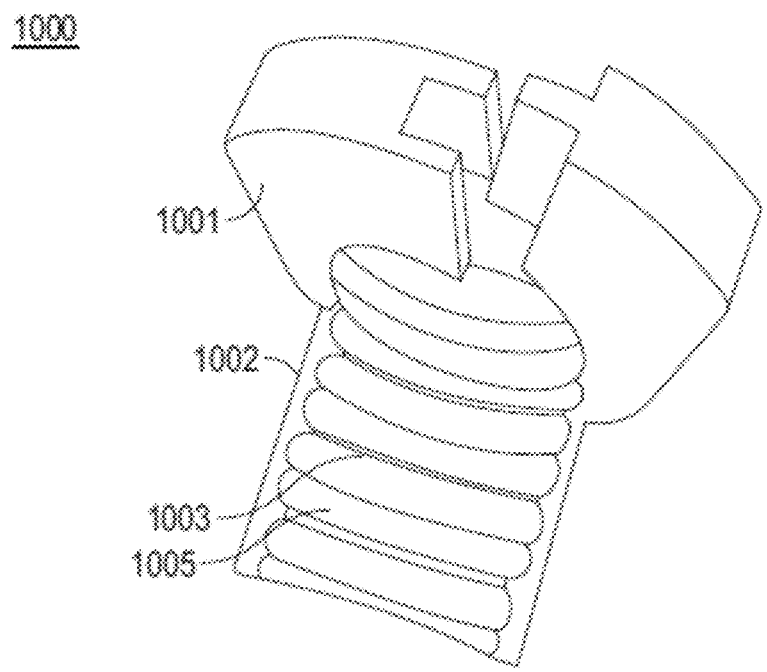
FIGS. 10A and 10B depict another example of a sealing system consistent with the present disclosure.
Figure 10B:
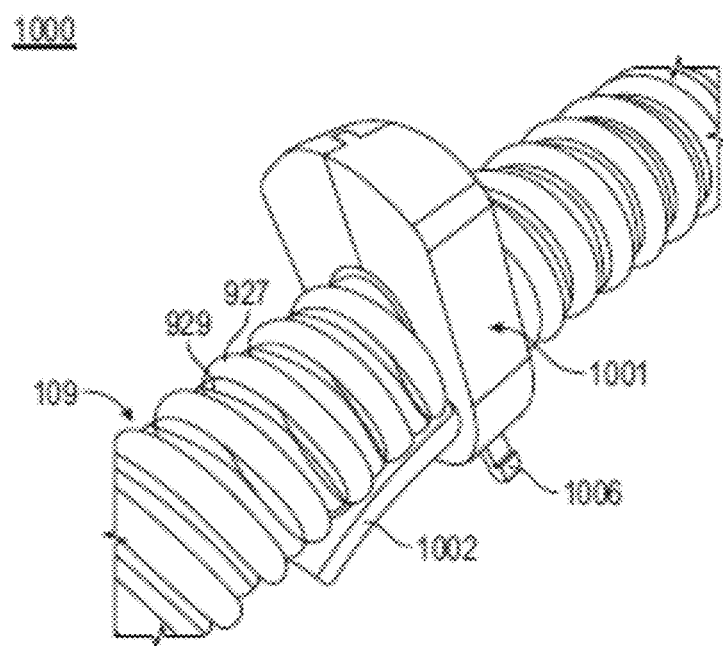

FIGS. 10A and 10B depict another example of a sealing system that may be used in system 400. Unlike the previous embodiments, sealing system 1000 does not include discrete upper and lower seal members 431, 433. Rather, sealing system 1000 includes a unitary sealing body 1001, which may be retained within receptacle 407 in any suitable manner. For example, sealing system may include retention members 1006 that may be disposed and retained within corresponding retention element receivers in an inward facing surface of receptacle 407, e.g., in the manner discussed above in conjunction with FIGS. 6A-6C. In this case, the unitary sealing body 1001 is in the form of a split ring that is configured to extend around an entire circumference of a medical device hose while allowing a medical device hose to be disposed therein, as shown in FIG. 10B.

A seal extension 1002 may extend from all or a portion of unitary sealing body 1001, as shown in FIGS. 10A and 10B. It is noted that FIGS. 10A and 10B depict an embodiment in which seal extension 1002 only extends from a lower portion of sealing body 1001. While such an embodiment is useful, seal extension 1002 may extend from all or other portions of unitary sealing body 1001. In embodiments, sealing system 1000 includes seal extensions 1002 that extend from the top, bottom, side(s), both the top and bottom, both sides, or both the top, bottom, and one or more sides of unitary sealing body 1001.

Seal extension 1002 is generally configured to strengthen the seal formed by sealing system 1000 when lid 401 is in the closed position. In embodiments, an inner surface of seal extension 1002 includes a plurality of extension ridges 1003 and extension valleys 1005, which have a pitch that is configured to match or substantially match a pitch of a reinforcement winding around hose 109. For example, extension ridges 1003 may be disposed between the reinforcement winding (e.g., within reinforcement channels), and the extension valleys 1005 may receive the reinforcement winding therein when lid 401 is in a closed position. Further, in embodiments seal extension 1002 supports the medical device hose, e.g., to improve the seal between the hose and the upper and lower seal members without excessive flexing of the hose.

FIGS. 15A-15D depict various views of another example of a sealing system that may be used to seal around an intermediate portion of a hose. Sealing system 1500 includes an upper seal member 431 and a lower seal member 433. The lower seal member includes a lower seal body 1503 and a plurality of lower seal retention members 1505 that are configured to retain the lower seal member 433 within a corresponding receptacle. Likewise, the upper seal member 431 includes an upper seal body 1517 and an upper seal retention member 1518 that is configured to retain upper seal member 431, e.g. to a lid of a sanitizing device. The lower seal body 1503 includes a plurality of lower seal abutment surfaces 1521, and the upper seal body 1517 includes a plurality of upper seal abutment surfaces 1523. The upper seal abutment surfaces 1523 may abut the lower seal abutment surfaces 1521 when the lid of a sanitizing device is in a closed position, resulting in the formation of a plurality of channels 1525 that extend around a circumference of an opening that extends through sealing system 1500.

Lower seal body 1503 further includes one or more guide ribs 1531, and upper seal member 431 further includes one or more guide surfaces 1533. In general, the guide rib(s) 1531 and guide surface(s) 1533 are configured to cooperate as a lid of a sanitizing system is moved to the closed position, facilitating contact between the upper and lower seal abutment surfaces 1523, 1521, respectively, as well as alignment of channels 1525. That concept is best shown by comparison of FIGS. 15A, 15C (which depict sealing system 1500 in a disengaged state) with FIGS. 15B, 15D, which depict sealing system 1500 in an engaged state.

Figure 15A:
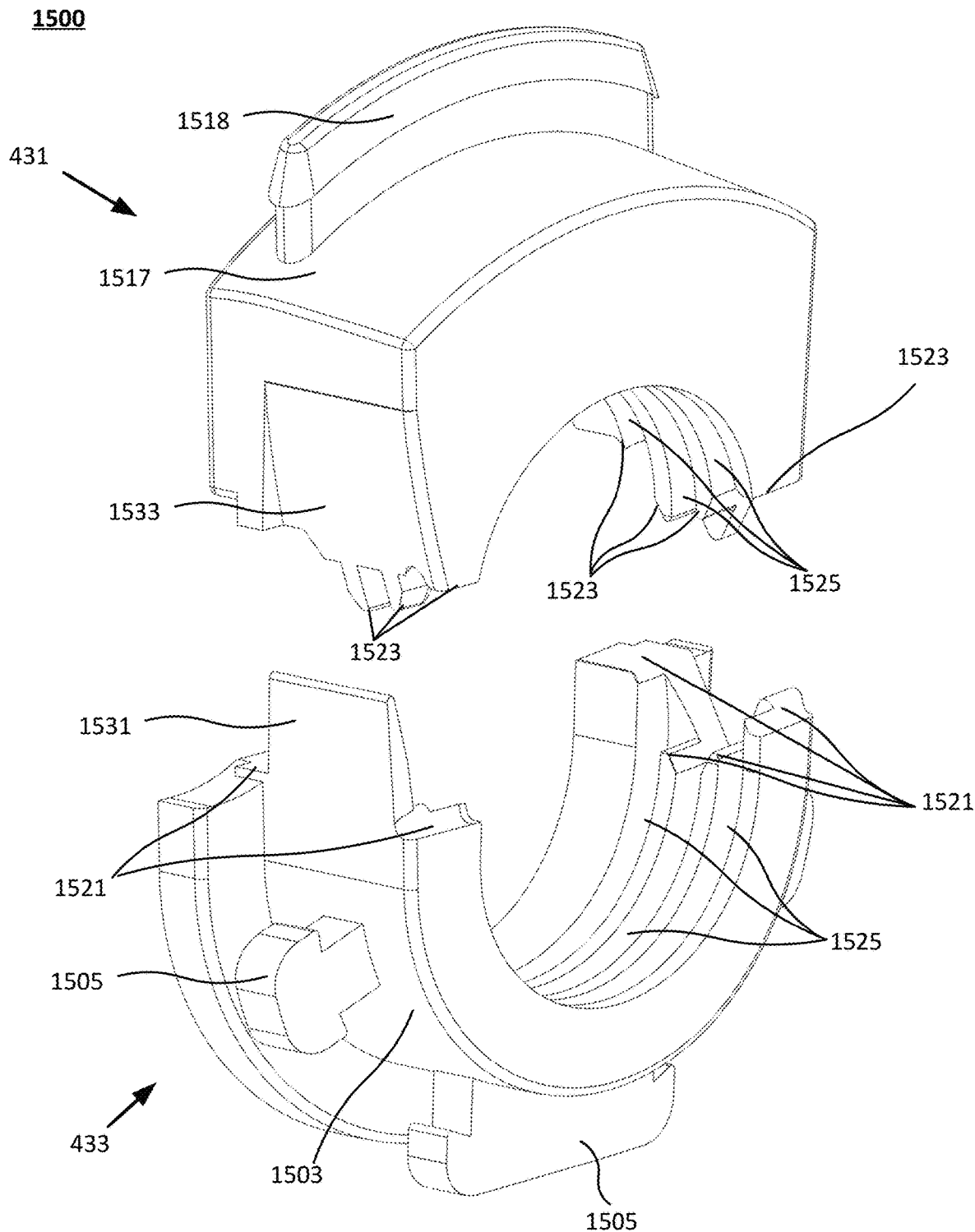
FIGS. 15A-15D depict various views of another example of a sealing system consistent with the present disclosure.
Figure 15B:
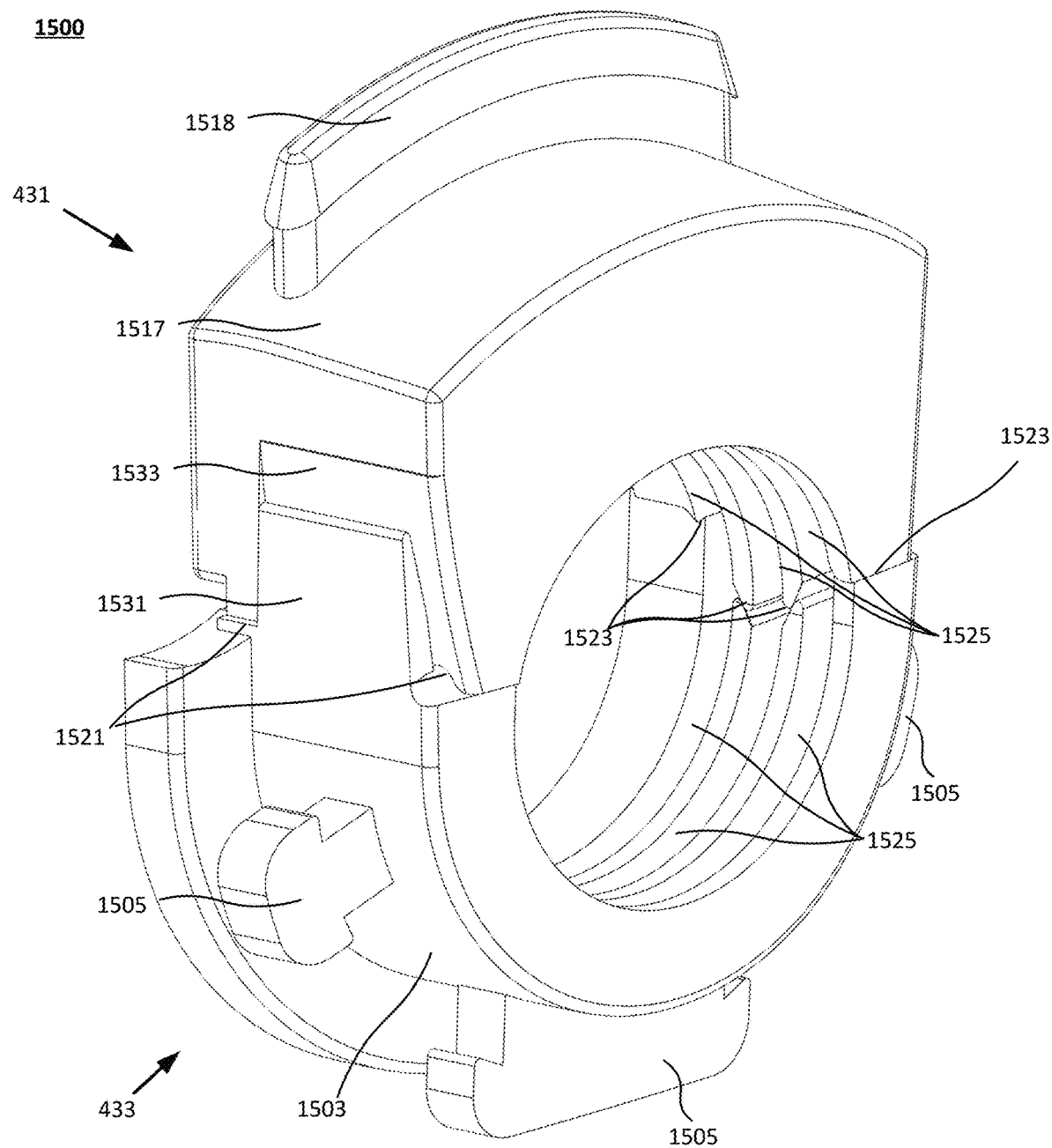
Figure 15C:
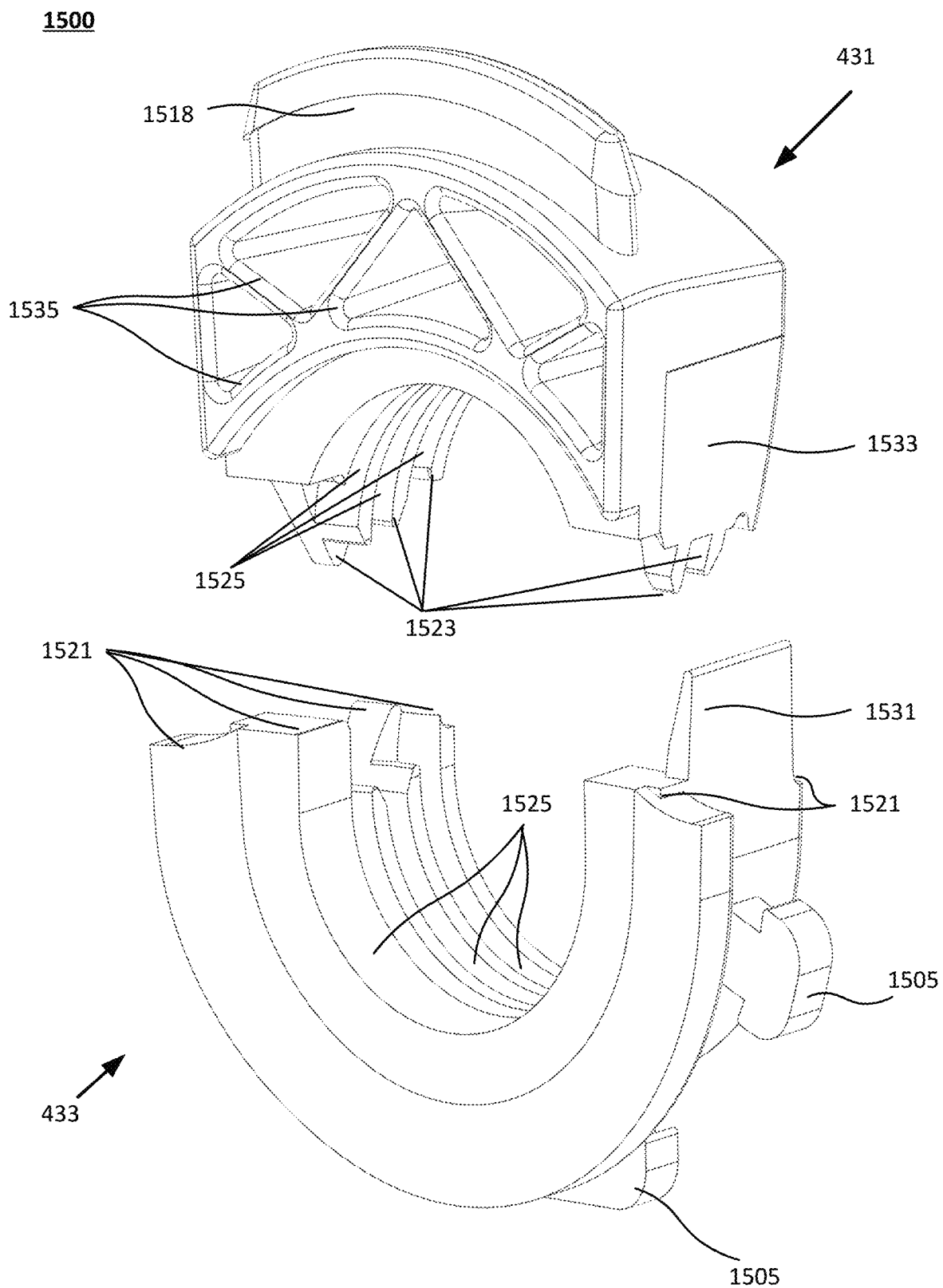
Figure 15D:
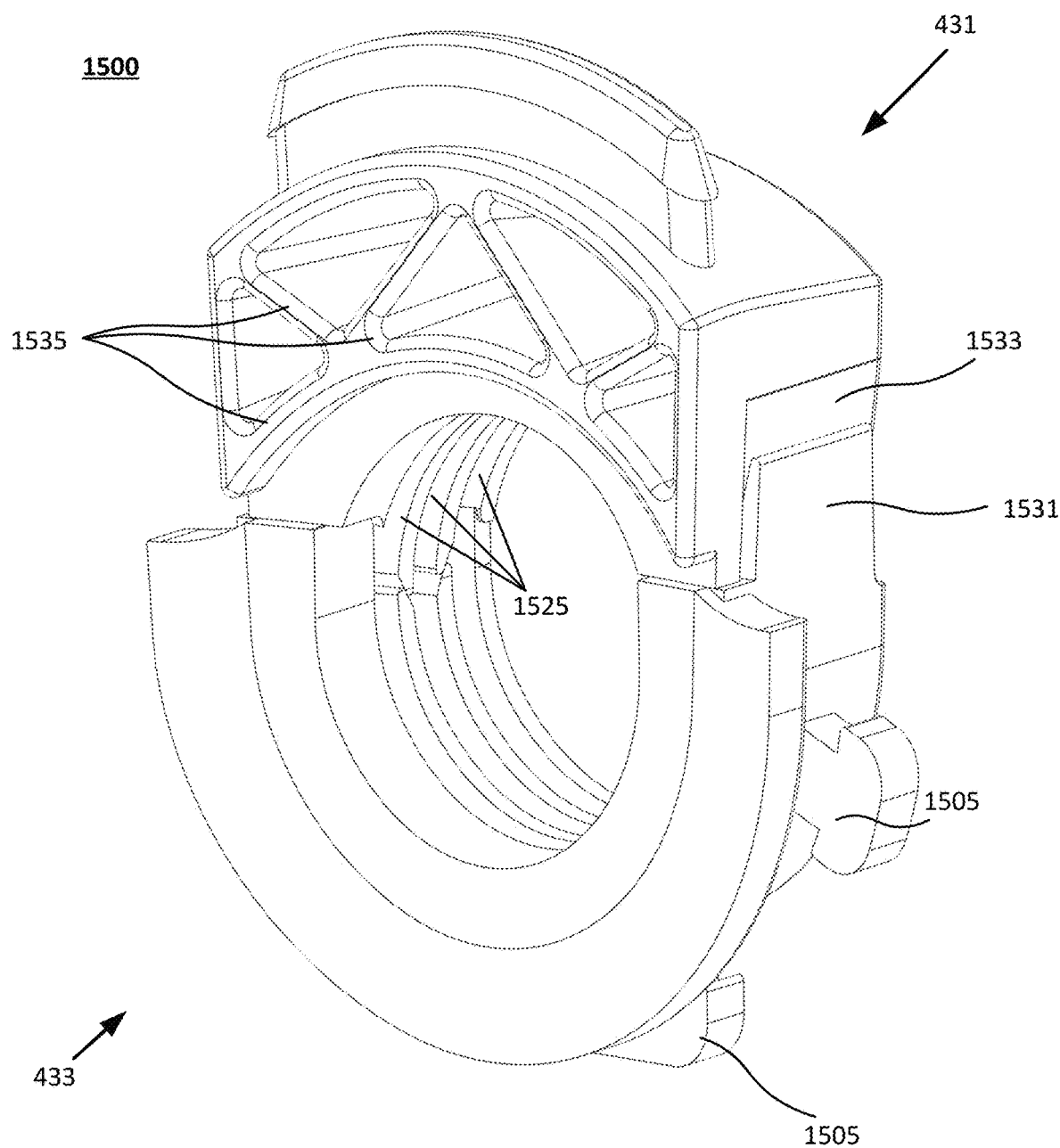

Upper seal body 1517 may further include one or more reinforcements 1535, as shown in FIGS. 15B and 15D. In general, reinforcements 1535 are configured to stiffen or otherwise reinforce portions of upper seal body 1517, such that a sufficient sealing force may be applied to sealing system 1500 without collapsing or degrading the integrity of upper seal body 1517.

In use, when sealing system 1500 is in the engaged state shown in FIGS. 15B and 15D, channels 1525 are disposed around a reinforcement (e.g. a winding) of a medical device hose. In such instances the surfaces of channels 1525 may abut and form a seal around the reinforcement of the hose, as well as with the body of the hose between the reinforcement. To enhance the seal, multiple channels 1525 may be used to seal around multiple reinforcements, as shown in FIGS. 15A-15D. However, any suitable number of channels (e.g., 1, 2, 3, 4, 5, 6, 7, 8, 9, 10, or more) may be used. Moreover, channels 1525 may be omitted in instances where sealing system 1500 is to be used with a smooth medical device hose, i.e., a hose that does not include an external reinforcement such as an external winding.

FIGS. 22A-22G depict various views of another example of a sealing system that may be used to seal around an intermediate portion of a hose. Sealing system 2200 is shown in connection with system 1600 (described later in conjunction with FIGS. 16A-16G), but it should be understood that sealing system 2200 may be used in other systems consistent with the present disclosure, including but not limited to systems 400 and 1600. As shown, sealing system 2200 includes an upper seal member 431 and a lower seal member 433. The lower seal member 433 includes a front lower lip 2201 and a rear lower lip 2205, and the upper seal member 431 includes a front upper lip 2203 and a rear upper lip 2207. The upper and lower lips, 2201, 2203, 2205, and 2207 are generally configured to conform to and seal around the outside of a hose (e.g., a CPAP hose) inserted into receptacle 407. In that regard, the upper and lower lips, 2201, 2203, 2205, and 2207 may be made from a conformable (e.g., elastomeric) material that can withstand exposure to a sanitizing gas (e.g., ozone), and which can conform to and form a gas tight seal with the outside of a hose, such as a CPAP hose. Non-limiting examples of suitable materials that may be used to form upper and lower seal members 431, 433 (or, more specifically, upper and lower lips 2201, 2203, 2205, and 2207) include natural and/or synthetic polymers (e.g., natural or synthetic rubber such as ethylene propylene diene monomer (EPDM) rubber, ozone resilient materials such as silicone, e.g., having a durometer in the range of about 30 to about 60, such as from about 40 to about 55, or even about 45 to 55. In embodiments the upper and lower seal members 431, 433 (or, more specifically, upper and lower lips 2201, 2203, 2205, and 2207) are formed from silicone, such as silicone with a durometer of about 40 to about 60, or even from about 45 to about 55. In specific embodiments, the upper and lower seal members 431, 433 (or, more specifically, upper and lower lips 2201, 2203, 2205, and 2207) are each formed from silicone having a durometer of about 45 to about 55.

As noted above, upper and lower lips 2201, 2203, 2205, and 2207 are generally configured to conform to and seal against the outer surface of a hose 109 inserted into receptacle 407. To facilitate such conformance and the formation of a seal, upper and lower lips 2201, 2203, 2205, and/or 2207 may be canted at an angle relative to a plane that extending through and parallel to the opening between upper and lower seal members 431, 433. For example, front lower lip 2201 and front upper lip may each be canted away from sanitizing chamber 403 (i.e., towards the outside of base 404), and rear lower lip 2205 and rear upper lip 2207 may each be canted towards the interior of sanitizing chamber 403. Alternatively or additionally, one or more slits 2209 may be formed in all or a portion of the upper and lower lips 2201, 2203, 2205, and/or 2207. When used, the slits 2209 may extend fully or partially through the thickness of the corresponding lips. In embodiments, a plurality of slits 2209 are provided in each of upper and lower lips 2201, 2203, 2205, and/or 2207, and extend fully through the thickness thereof. In general, slits 2209 may function to increase the flexibility of lips 2201, 2203, 2205, and/or 2207, enabling them to better conform to the outer surface of a hose. The number of slits used is not limited, and may be selected to achieve a desired flexibility for one or more of lips 2201, 2203, 2205, 2007, while also maintaining the integrity of the seal formed by such lips with a hose. Moreover, the number of slits formed in each of lips 2201, 2203, 2205, and 2007 may be the same or different. For example, a one or a plurality (e.g., 2, 3, 4, 5, 10, or more) slits may be formed in one or a plurality of lips 2201, 2203, 2205, 2207, wherein the number of slits formed in each of said lips is the same or different from the number of slits formed in another of said lips.

Sealing system 2200 further includes a plurality of retention members 2211 that are configured to retain the upper seal member 431 and/or lower seal member 433 within a corresponding receptacle 407 and/or to another portion of a sanitizing system, such as a lid. Retention members 2211 may be in the form of posts, slots, etc. which engage with corresponding members of other portions of a sanitizing system, such as a lid or base thereof.

Figure 22A:
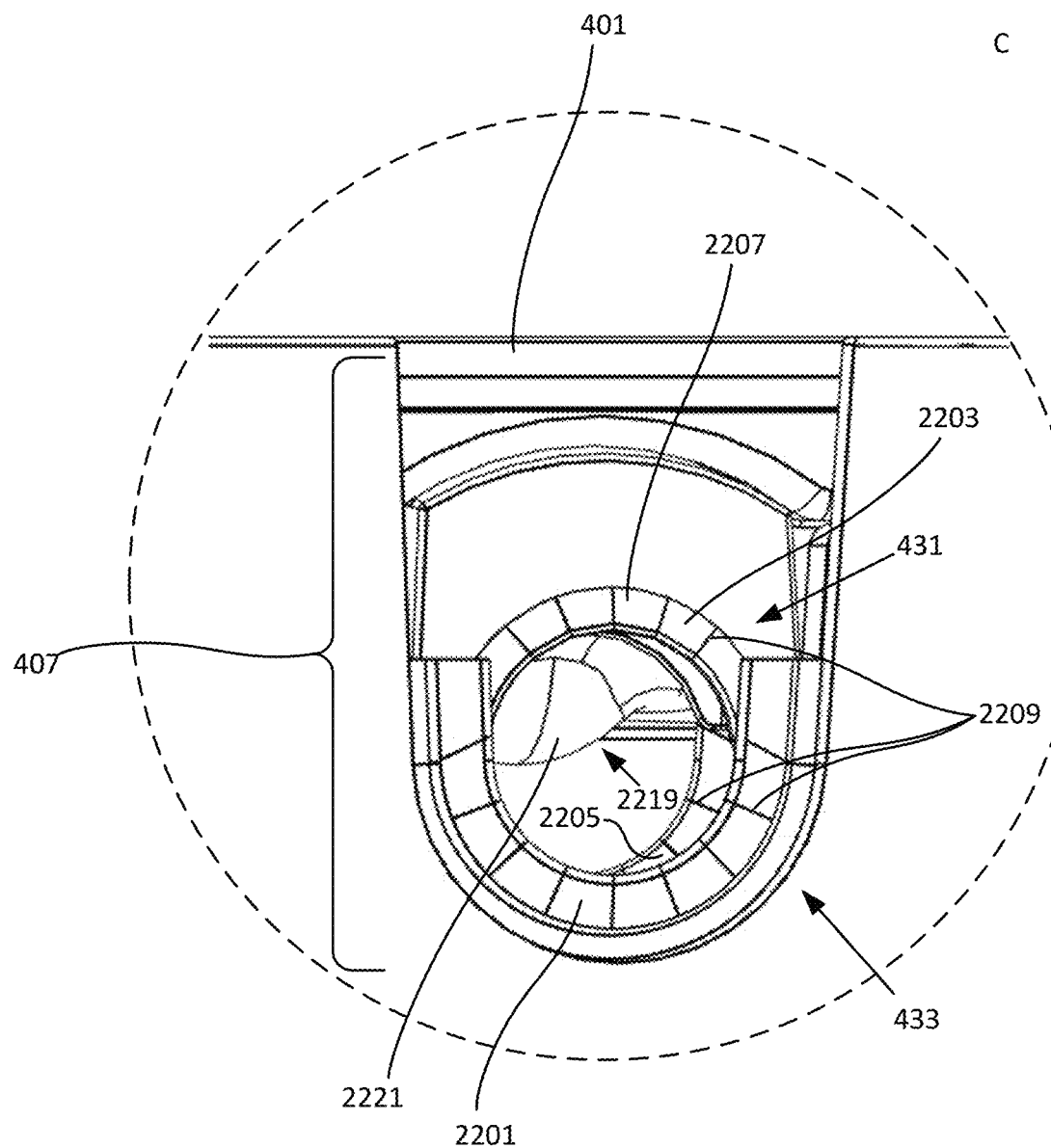
FIGS. 22A-22G depict various views of another example of a sealing system consistent with the present disclosure.
Figure 22B:
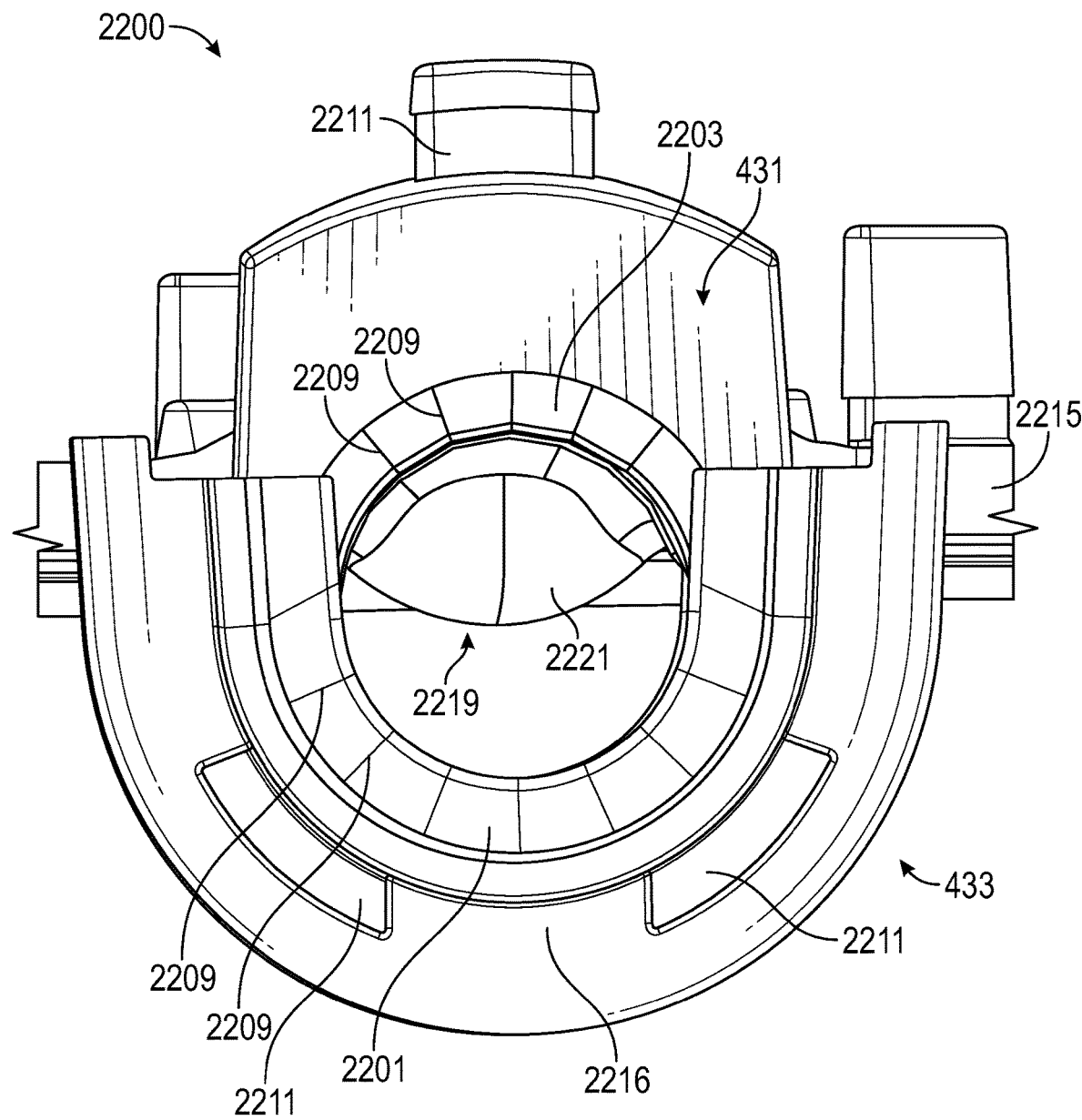
Figure 22C:
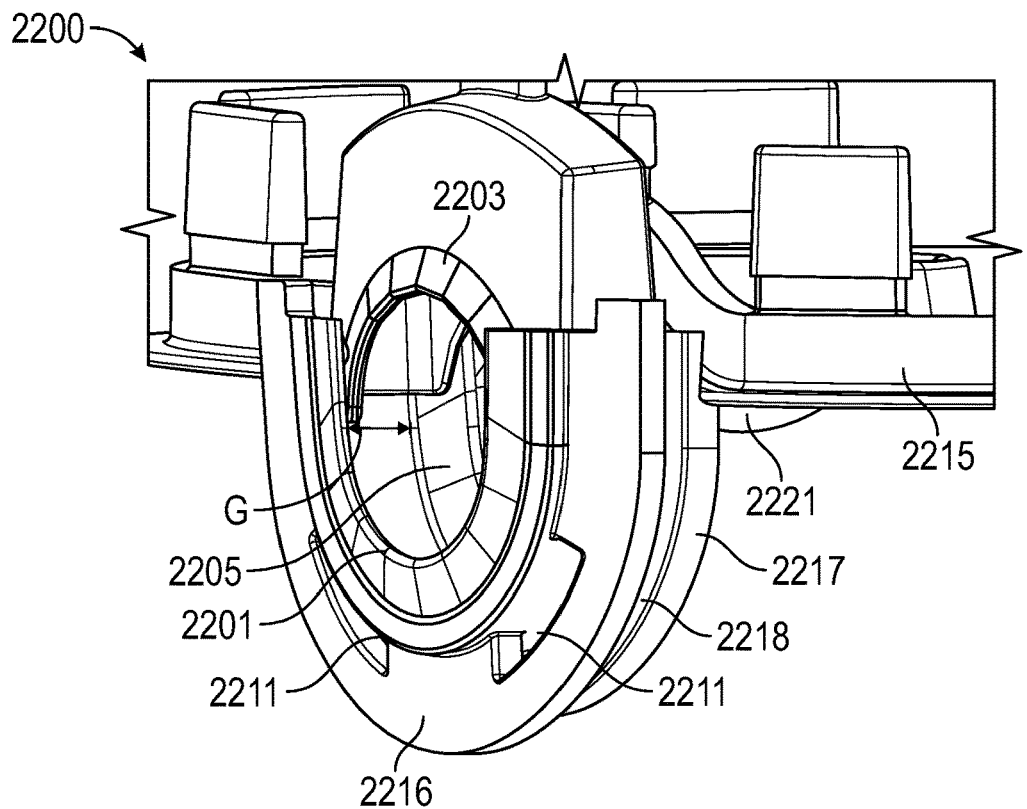
Figure 22D:
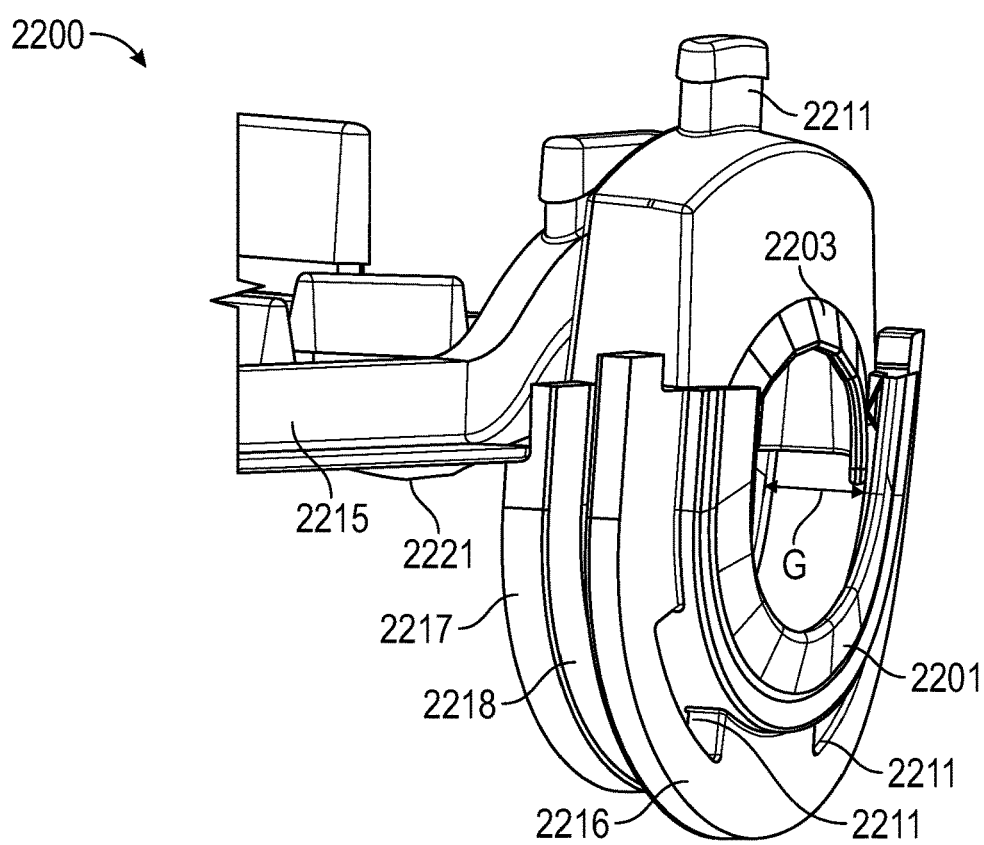
Figure 22E:
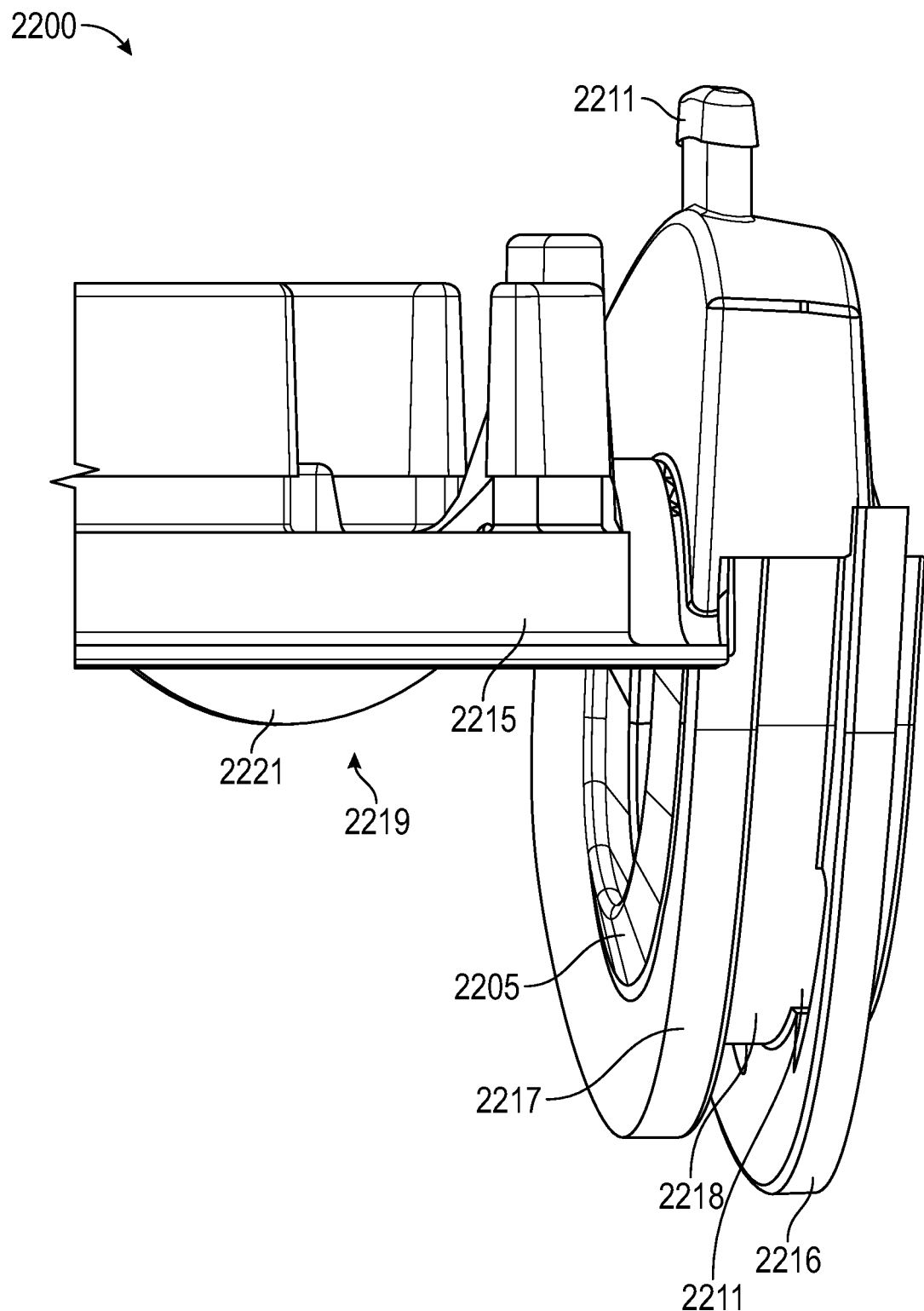
Figure 22F:
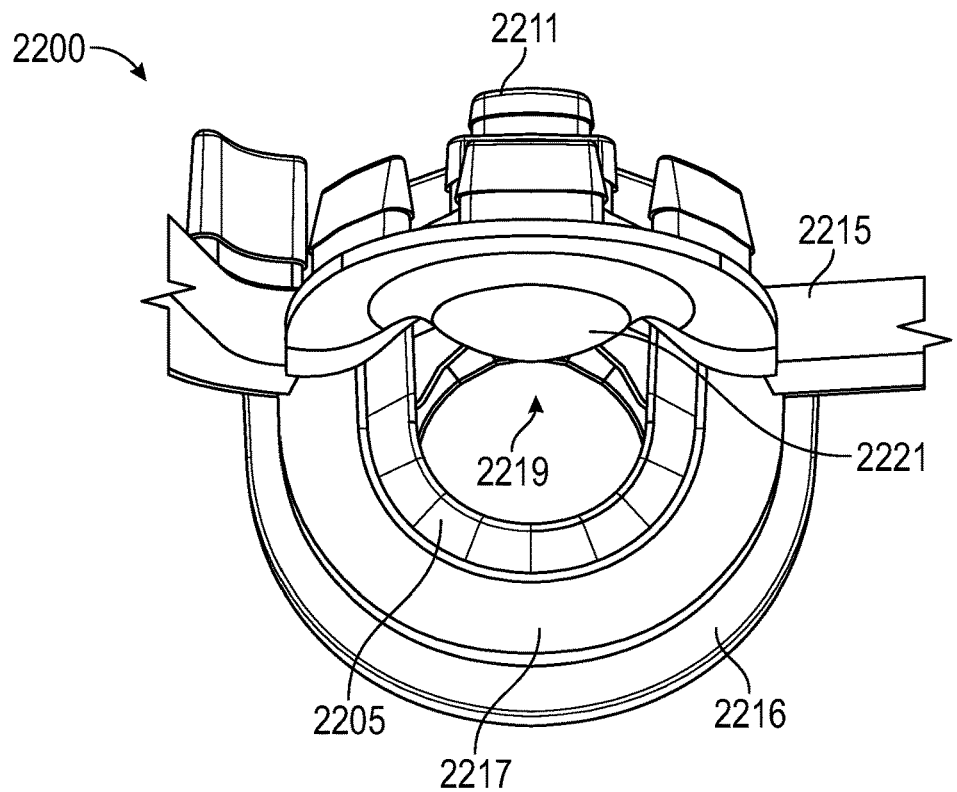

As best shown in FIGS. 22C and 22D, a gap G is present between the front lower lip 2201 and rear lower lip 2205, and a similar gap is present between front upper lip 2203 and rear upper lip 2207. In general, the gap G is configured allow sealing system 2200 (or, more particularly, lips 2201, 2203, 2005, 2007) to conform to the outside surface of a hose, such as a CPAP hose. For example when a hose (e.g., a CPAP hose) having an external winding is passed through receptacle 407, the GAP G may be configured such that one or multiple passes of the winding may be present therein, such that lips 2201, 2203, 2005, 2007 can abut and seal with portions of the hose that are between one or more passes of the winding.

As also best shown in FIGS. 22C and 22D, lower seal member 433 includes a front mounting flange 2216 and a rear mounting flange 2217, with a channel 2218 there between. In general, the front mounting flange 2216, rear mounting flange 2217, and channel 2218 are configured to engage with edges of an opening in the base of a sanitizing system (e.g., with edges of a receptacle 407) so as to retain the lower seal member therein. In contrast, the upper seal member 431 may be integral with or coupled to a mounting frame 2215, which may be configured to retain (in addition to retention members 2211) the upper seal member 431 to a lid of a sanitizing system.

In use, when sealing system 2200 is in an engaged state and a hose (e.g., a CPAP hose) is disposed through receptacle 407, lips 2201, 2203, 2205, and 2207 abut and seal with the outer surface of the hose. To enhance the seal, the lid 401 may bias the upper seal member 431 in a direction towards the hose, increasing the pressure between the hose and lips 2201, 2203, 2205, and 2207.

As noted above, adequate exposure of a medical device or medical device components to a sanitizing gas is desired to ensure adequate sanitization thereof. With that in mind, portions of medical devices within sanitizing chamber 403 may be in contact with the bottom, sides, or other features of the sanitizing chamber 403. For example when sanitizing chamber 403 has a flat bottom, a significant portion of the surface area of a medical device (e.g., a CPAP mask) may rest on that flat bottom surface. As a result, the portion of the medical device in connect with the bottom surface may be obscured during a sanitizing operation—potentially resulting in inadequate exposure to the sanitizing gas. Similar issues are present regarding portions of a medical device that contact the sidewalls of sanitizing chamber 403, other medical devices within sanitizing chamber 403, combinations thereof, and the like.

Figure 11A:
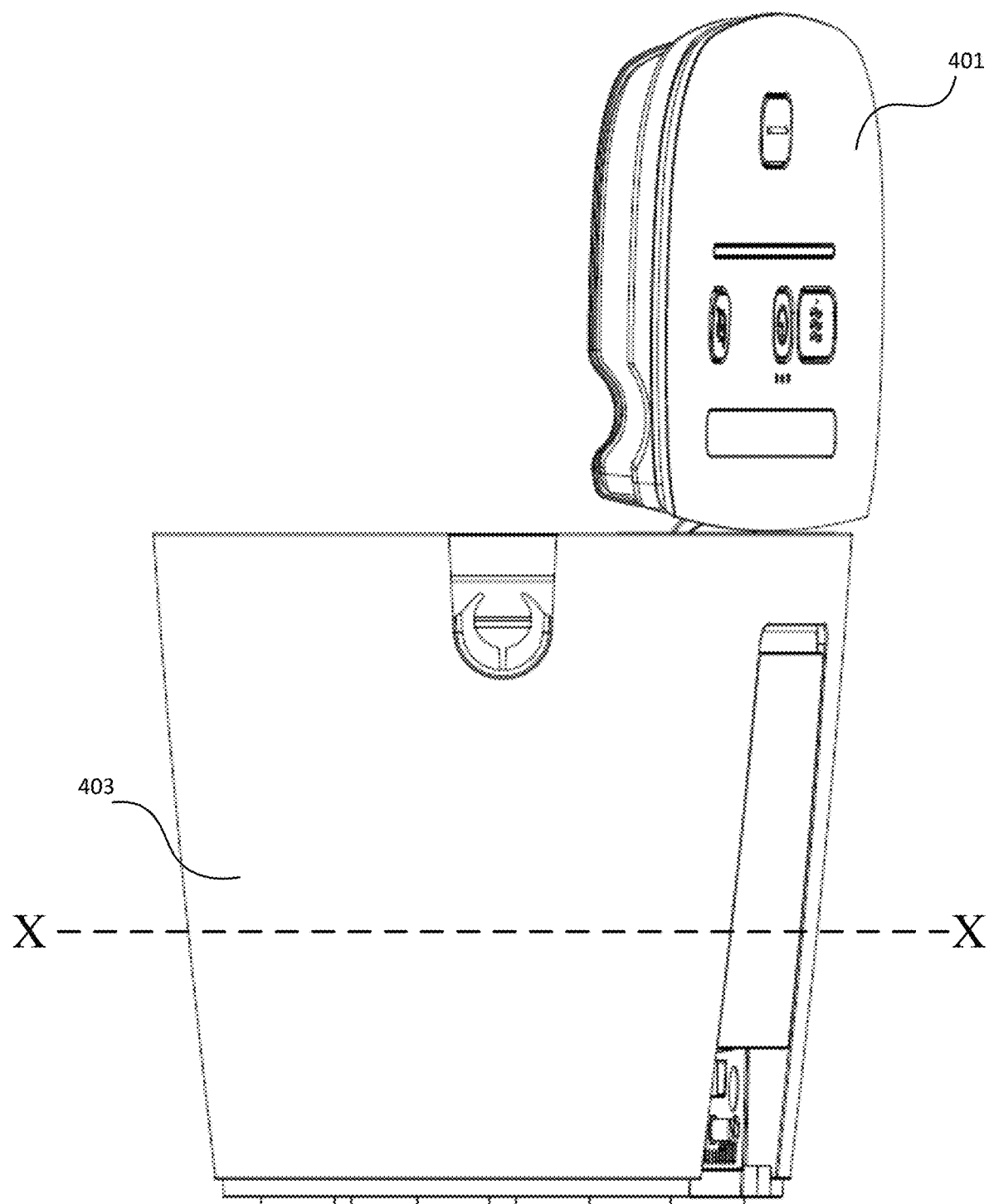
FIGS. 11A-11C depict various views of an example sanitizing system including one or more positioning elements, consistent with the present disclosure.
Figure 11B:
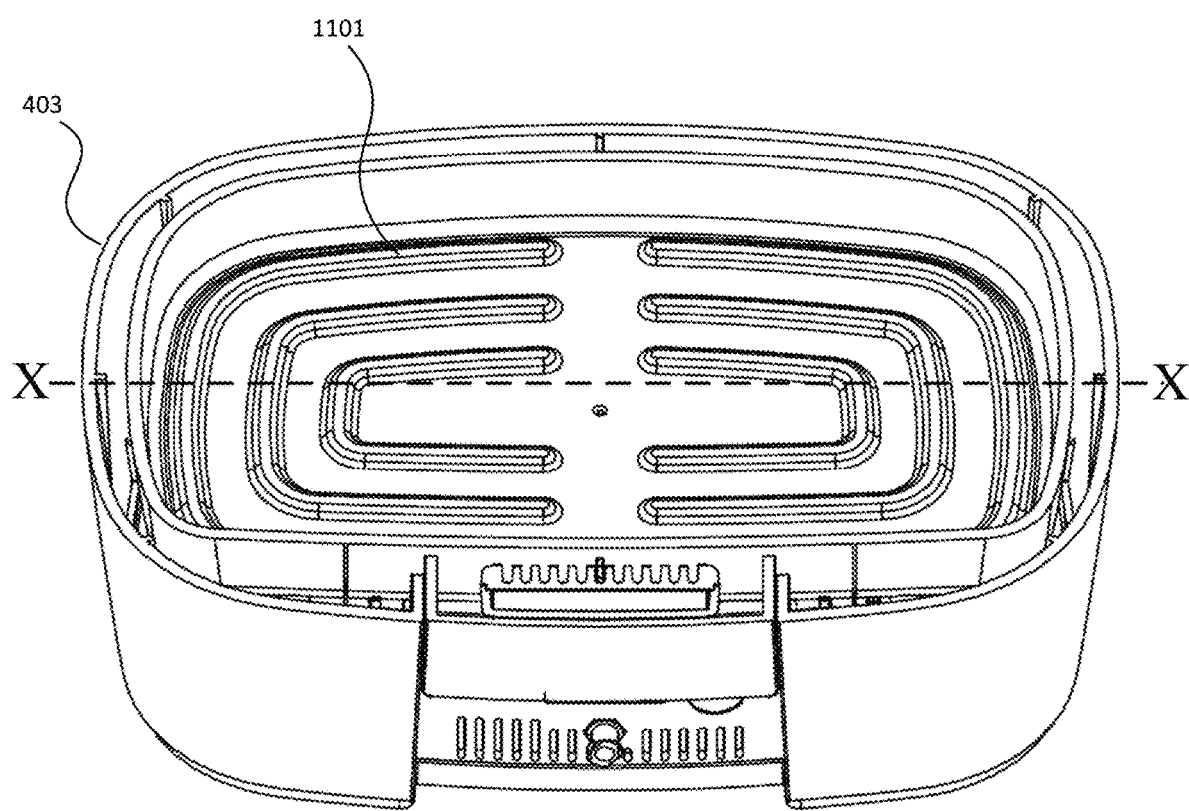
Figure 11C:
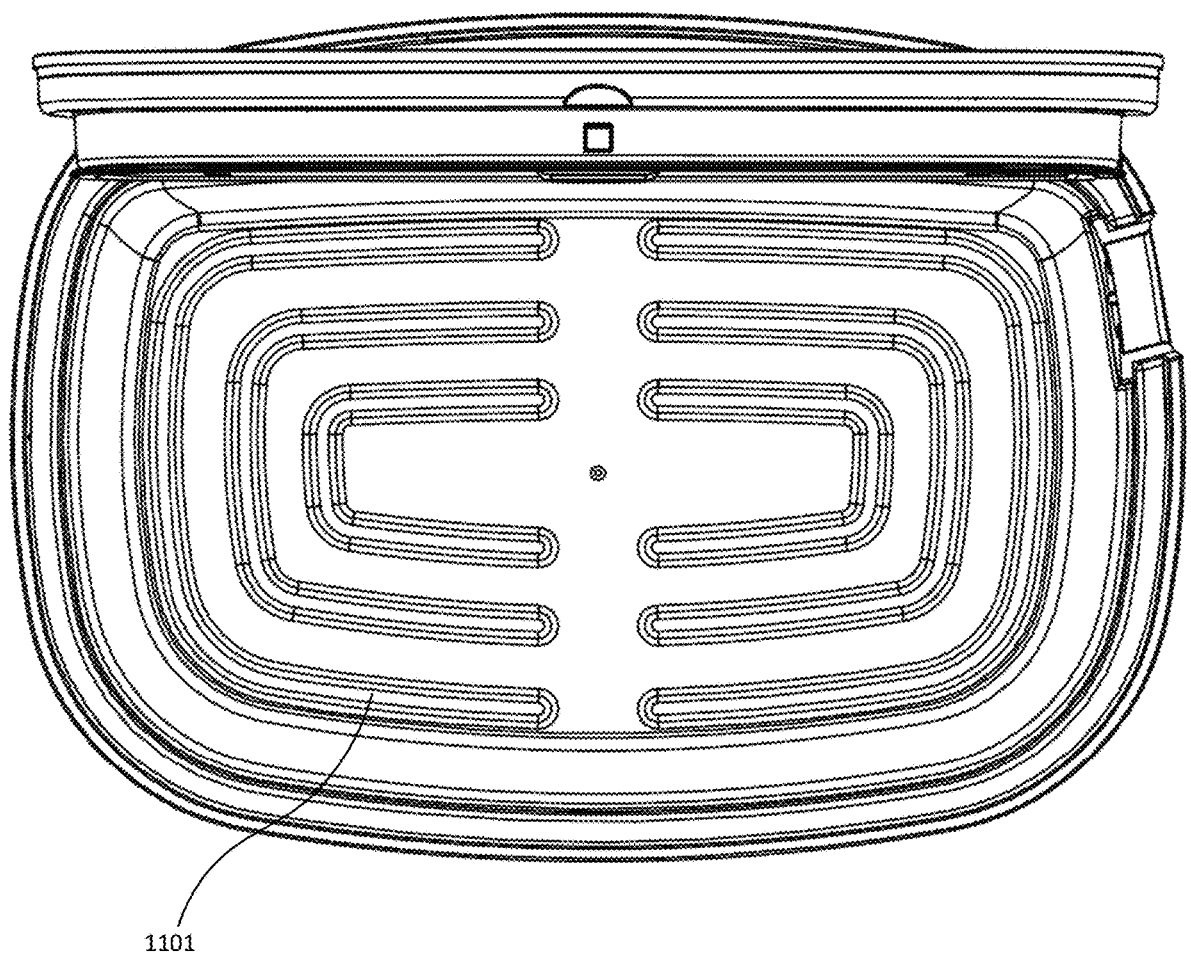

Accordingly, another aspect of the present disclosure relates to positioning elements that are configured to enhance exposure of medical devices within sanitizing chamber 403 to a sanitizing gas. In embodiments, such positioning elements include standoffs that are configured to lower or minimize the amount of surface area of a medical device or component thereof that is obscured during performance of a sanitizing operation. Reference is therefore made to FIGS. 11A, 11B, and 11C, which depict an embodiment of system 400 that includes standoffs 1101 formed on a bottom surface of sanitizing chamber 403. For clarity, FIG. 11B is a sectional view along axis X, enabling a perspective view of standoffs 1101. FIG. 11C is a top down view depicting standoffs 1101.

As shown, standoffs 1101 are in the form of a plurality of ridges that are disposed on or extend from a bottom of sanitizing chamber 403. In embodiments, standoffs 1101 are in the form of ridges that extend from a base of an insert tray (not shown) that is configured to be inserted within sanitizing chamber 403, e.g., to rest on a bottom thereof. In this embodiment, standoffs 1101 are generally C-shaped, but standoffs 1101 may have any suitable shape. For example, standoffs 1101 may have a linear, wavy, curvilinear, geometric, irregular, or other shape, as desired. The thickness and surface profile of the ridges forming standoffs 1101 may also be varied.

Of course, standoffs 1101 need not be in the form of ridges, and may take any other suitable form. For example, standoffs may be in the form of discrete protuberances that extend from a bottom of sanitizing chamber 403 or a suitable insert tray. Alternatively, standoffs 1101 may be specifically designed to support or cradle specific medical devices within sanitizing chamber 403, while minimizing the surface area of the medical device that is obscured. For example, standoffs 1101 may be in the form of hooks, stands, protuberances, etc. that are designed to support a CPAP hose or nose pillow within sanitizing chamber 403, while limiting and/or minimizing the surface area of such components with which standoffs 1101 are in contact.

The systems described herein may also include other positioning elements that are designed to facilitate exposure of a medical device to a sanitizing gas. In that regard, system 400 may include one or more clips, hooks, etc. that couple to a sidewall of sanitizing chamber 403 and/or to lid underside 402. In such instances, such elements may be configured to suspend a medical device/component such as a CPAP hose above the bottom of sanitizing chamber 403 (i.e., such that the medical device/component does not contact the bottom and/or sides of sanitizing chamber 403. In embodiments, such components (or other positioning elements) may be configured to rotate or otherwise move a medical device/component within sanitizing chamber 403, facilitating exposure of the surfaces of the medical device/component to a sanitizing gas during a sanitizing operation.

System 400 may be used to perform a sanitization cycle on medical devices in much the same manner as systems 200 and 300 described above. For clarity and ease of understanding, the performance of a sanitization cycle on a CPAP hose and/or a CPAP reservoir will now be described. Various safety features that may be included in system 400 will be described thereafter.

To perform a sanitization cycle on a CPAP device, an intermediate portion of a CPAP hose may be disposed within receptacle 407 while lid 401 is in the open position, such that a distal end of the CPAP hose is disposed within the sanitizing chamber 403. In embodiments system 400 is set up in substantially the same manner as system 200 discussed above. In such embodiments the proximal end of the CPAP hose is coupled to a distal end of a distribution line (not shown), wherein the proximal end of the distribution line is coupled to sanitizing gas outlet 453. In other embodiments system 400 is set up in substantially the same manner as system 300 discussed above. In such embodiments the proximal end of the CPAP hose is coupled to a connector unit, which in turn is coupled to a reservoir of the CPAP device and a distribution line coupled to sanitizing gas outlet 453. In either configuration, a filter 500 is present within filter tray 471, and filter tray 471 may be positioned in the closed position.

Lid 401 may then be advanced to the closed position, and a user may initiate a sanitization cycle with system 400 via user interface 411. During the sanitization cycle, the sanitizing gas supply system within system 400 produces sanitizing gas, e.g., ozone. The sanitizing gas is output through sanitizing gas outlet 453 and into the distribution line. Depending on the configuration, the sanitizing gas flows from the distribution line directly into the CPAP hose, or into a CPAP reservoir via a first passageway in a connector unit, as previously described in connection with systems 200, 300. In instances where sanitizing gas is introduced into a reservoir, sanitizing gas will flow from the reservoir through a second passageway in the connector unit to the CPAP hose, as previously described in connection with system 300. Sanitizing gas within the CPAP hose will then flow into the sanitizing chamber 403. The sanitization cycle may be allowed to continue for enough time to attain a desired level of sanitization.

During or after execution of the sanitization cycle, sanitizing gas (e.g., ozone) may convert to breathable gas (e.g., oxygen) naturally or with the aid of filter 500. In that regard, sanitizing gas within sanitizing chamber 403 may flow through exhaust ports 405 and into filter inlet openings 508. While within filter 500 the sanitizing gas (e.g., ozone) encounters filter media 515, which facilitates complete or partial conversion of the sanitizing gas to breathable gas (e.g., oxygen). Put differently, filter 500 is configured to receive an inlet flow containing a first concentration of sanitizing gas, and to produce an outlet flow with a second concentration of sanitizing gas, wherein the second concentration is less than the first concentration. In embodiments, the second concentration is below a threshold amount of sanitizing gas, such as less than 0.05 parts per million over a defined time period, such as 3 to 5 hours. And in still further embodiments, the second concentration is zero.

In embodiments system 400 includes one or more safety features that are designed to hinder or prevent execution of a sanitizing operation when the sanitization system is in an unsafe condition. As used herein, the term "unsafe condition" is used to describe a condition in which sanitizing gas is leaking or will leak from system 400, and/or a condition in which there is an elevated chance that a user may be exposed to the sanitizing gas. Non-limiting examples of unsafe conditions include: 1) execution of a sanitizing operation while lid 401 is in the open position; 2) opening of lid 401 while a sanitizing operation is being performed; 3) execution of a sanitizing operation when a plug or hose is not present within receptacle 407 (or a corresponding port in base 404); 4) leakage of sanitizing gas through receptacle 407 (or a corresponding port in base 404); 5) execution of a sanitizing operation while filter tray 471 is in an open position; 6) movement of filter tray 471 to the open position while a sanitizing operation is being performed; 7) execution of a sanitizing operation when a filter 500 is not present in filter tray 471; 8) execution of a sanitizing operation when filter 500 is an unauthorized filter; 9) the presence of an unacceptable amount of sanitizing gas downstream of filter 500; 10) execution of a sanitizing operation while a medical device (e.g., a CPAP mask) coupled to the system is being used by a user; combinations thereof, and the like.

In general the safety features include a controller and at least one sensor. The at least one sensor is configured to monitor a condition of the sanitization system and to output a sensor signal indicative of the monitored condition to the controller. In embodiments, one or more sensors are used to monitor: 1) a position of lid 401; 2) the presence of a hose or plug within receptacle 407 (or a corresponding port in base 404); 3) the leakage of sanitizing gas (e.g., ozone) through receptacle 407 (or a corresponding port in base 404); 4) the position of filter tray 471; 5) the presence of filter 500; 6) the type of filter 500; 7) the presence and/or concentration of sanitizing gas downstream of filter 500; 8) use of a medical device (e.g., CPAP mask or nose pillow) coupled to the sanitization system by a user; combinations thereof, and the like.

The controller is configured, in response to the sensor signal, to determine whether the sanitization system is in an unsafe or safe condition. Alternatively or additionally, the controller may transmit a status signal to an external computing system (e.g. a server) via wired or wireless communication. The status signal may be configured to cause the external computing system to determine whether the system is in an unsafe or safe condition, and to transmit a safety signal to the controller. In such instances the controller may be configured to determine whether the system is in a safe or unsafe condition based at least in part on the safety signal.

In any case when it is determined that the sanitization system is in an unsafe condition, the controller is configured to take appropriate action. For example, the controller may prevent initiation of a sanitizing operation, stop an executing sanitizing operation, disable operation of a sanitizing gas supply system (e.g., an ozone generator), prevent a lid and/or filter tray from being opened, combinations thereof, and the like. The controller may also cause a warning message or indicator to display (e.g., via a user interface), thus informing a user of the detected unsafe condition.

With the foregoing in mind, in embodiments system 400 includes a controller 490, as best shown in FIGS. 4A, 4H and 4I. As discussed above, controller 490 is generally configured to determine whether system 400 is in an unsafe condition or a safe condition, and to take appropriate action. Any suitable current or future developed controller may be used for that purpose. Non-limiting examples of such controllers include programmable controllers, application specific integrated circuits, combinations thereof, and the like. While controller 490 is shown as included in lid 401, controller 490 may be physically located at any suitable location.

Figure 12A:
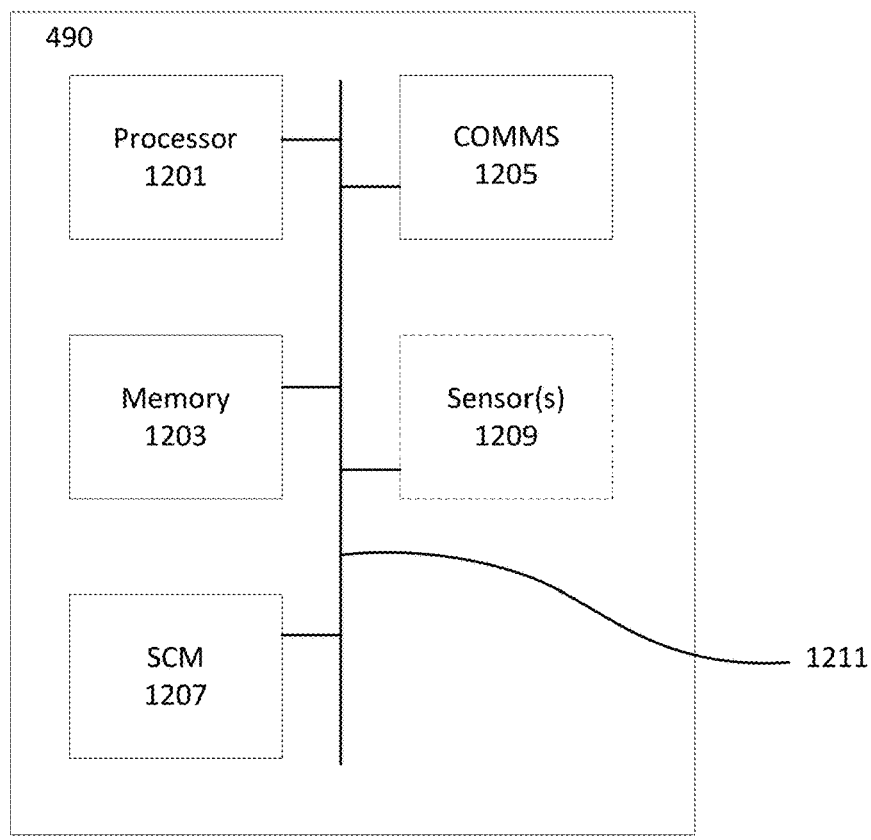
FIG. 12A is a block diagram of one example of a sanitizing system controller consistent with the present disclosure.

FIG. 12A is a block diagram of one example of a suitable controller that may be used in system 400. As shown, controller 490 includes a processor 1201, memory 1203, communications circuitry (COMMS) 1205, a safety control module (SCM) 1207 and optionally one or more sensors 1209 that are local to or remote from controller 490. Such components may be communicative coupled with one another via a bus 1211, as understood in the art.

Processor 1201 may be any suitable general-purpose processor or application specific integrated circuit, and may be configured to execute one or multiple threads on one or multiple processor cores. Without limitation, in some embodiments processor 1201 is a general-purpose processor, such as but not limited to the general-purpose processors commercially available from INTEL® Corp., ADVANCED MICRO DEVICES®, ARM®, NVIDIA®, APPLE®, and SAMSUNG®. While FIG. 12A illustrates the use of a single processor $120_1$, multiple processors may also be used.

Memory 1203 may be any suitable type of computer readable memory. Examples of memory types that may be used as memory 1203 include but are not limited to: programmable memory, non-volatile memory, read only memory, electrically programmable memory, random access memory, flash memory (which may include, for example NAND or NOR type memory structures), magnetic disk memory, optical disk memory, phase change memory, memristor memory technology, spin torque transfer memory, combinations thereof, and the like. Additionally or alternatively, memory 1203 may include other and/or later-developed types of computer-readable memory.

COMMS 1205 may include hardware (i.e., circuitry), software, or a combination of hardware and software that is configured to allow system 400 (or, more specifically, controller 490) to transmit and receive messages via wired and/or wireless communication. Communication between COMMS 1205 and a remote device (e.g., a server, a filter, etc.) may occur, for example, over a wired or wireless connection using one or more currently known or future developed communication standards. COMMS 1205 may include hardware to support such communication, e.g., one or more transponders, antennas, BLUETOOTH™ chips, personal area network chips, near field communication chips, wired and/or wireless network interface circuitry, combinations thereof, and the like.

SCM 1207 is generally configured to perform safety operations consistent with the present disclosure. In embodiments, safety operations include receiving one or more sensor signals from one or more sensors, determining whether system 400 is in a safe or unsafe condition based at least in part on such sensor signal(s), and issuing one or more control signals in response to that determination.

As used herein, the term "module" refers to software, firmware, circuitry, and/or combinations thereof that is/are configured to perform one or more operations consistent with the present disclosure. Software may be embodied as a software package, code, instructions, instruction sets and/or data recorded on non-transitory computer readable storage mediums. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, data machine circuitry, software and/or firmware that stores instructions executed by programmable circuitry. Any modules described herein may, collectively or individually, be embodied as circuitry.

In some embodiments, one or more of the modules described herein may be in the form of logic that is implemented at least in part in hardware to perform safety operations or other operations consistent with the present disclosure. In embodiments, SCM 1207 is in the form of software that is executable by processor 1201. Alternatively, SCM 1207 may by the form of circuitry (e.g., an application specific integrated circuit) that is configured to perform safety operations consistent with the present disclosure.

Figure 12B:
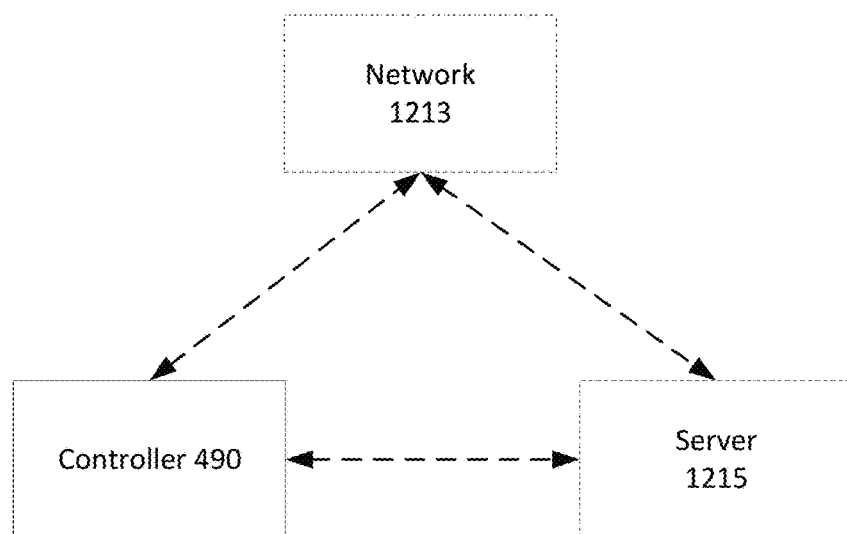
FIG. 12B is a schematic diagram of a control system including a sanitizing system controller consistent with the present disclosure.

In embodiments SCM 1207 is configured, in response to receipt of a sensor signal from a sensor, to independently determine whether system 400 is in a safe or unsafe condition. Alternatively, SCM 1207 is configured to transmit a status signal (or, more specifically to cause COMMS 1205 to transmit a status signal) to an external computing system such as a server 1215 via wired or wireless communication. For example, controller 490 may communicate with server 1215 directly or through a network 1213 (e.g., a local area network, wide area network, ZIGBEE® network, etc.), as shown in FIG. 12B. In any case the status signal may be configured to cause server 1215 (or, more specifically, a server safety control module (SSCM—not shown)) to determine whether system 400 is in an unsafe or safe condition, and to transmit a safety signal to the controller 490. In response, controller 490 is configured to determine whether the system is in a safe or unsafe condition based at least in part on the safety signal. In any case when it is determined that the sanitization system is in an unsafe condition, the controller 490 is configured to take appropriate action.

In embodiments the sanitization systems of the present disclosure include a lid detection sensor that enables controller 490 (or an external computing device) to determine a position of lid 401 prior to, during, or after execution of a sanitizing operation. In that regard reference is made to FIGS. 4C and 4D, which depict an embodiment in which system 400 includes a lid detection sensor 461. In general, lid detection sensor 461 functions to detect a position of lid 401 relative to base 404. In the illustrated embodiment lid detection sensor 461 is located on or within the lid underside 402 and proximate to closing member 423, but lid detection sensor 461 may be positioned at any suitable location. For example, lid detection sensor 461 may be positioned along a peripheral edge of lid 401, base 404, or a combination thereof.

Any suitable type of sensor may be used as lid detection sensor 461. Non-limiting examples of such sensors include electro-optical (e.g., visible, infrared, etc.) sensors, magnetic sensors, conductivity sensors, combinations thereof, and the like. In embodiments, lid detection sensor 461 is an electro-optical sensor that converts light, or a change in light, into a sensor signal. In such instances, lid detection sensor 461 may be positioned such that when lid 401 is moved from the open to the closed position (and vice versa), the amount of light impinging on lid detection sensor 461 changes and causes a corresponding change in the lid detection signal output by lid detection sensor 461. Alternatively or additionally, lid detection sensor 461 is in the form of or includes a magnetic sensor that enables detection of the position of lid 401 based on change in a magnetic field.

In any case, lid detection sensor 461 outputs a lid position sensor signal to controller 490. In response to receipt of the lid position sensor signal, controller 490 may determine whether lid 401 is in an open position or a closed position, independently or with the assistance of an external computing device as noted above. Controller 490 may then determine whether system 400 is in a safe or unsafe condition.

Prior to execution of a sanitizing operation, controller 490 may determine that system 400 is in an unsafe condition when lid 401 is in the open position. In such instances, controller 490 may prevent initiation of a sanitizing operation while lid 401 is in the open position. Controller 490 may prevent initiation of a sanitizing operation in any suitable manner. For example, controller 490 may lock out user interface 411 when lid 401 is in the open position, thus preventing a user from initiating a sanitizing operation via user interface 411. Alternatively or additionally, controller 490 may issue a sanitizing gas lockout signal (SGLS) that prevents a sanitizing gas supply system from generating or otherwise providing a sanitizing gas to system 400. For example where system 400 includes an ozone operating system including an ozone generator, the SGLS may be configured to disable the ozone operating system completely, or to disable only the ozone generator (e.g., allowing fans and/or pumps within the ozone operating system to circulate air). When it is determined that lid 401 is in the closed position, however (and no other unsafe conditions are detected), controller 490 may permit execution of a sanitizing operation.

During execution of a sanitizing operation (or within a threshold time following execution of a sanitizing operation), controller 490 may determine that system 400 is in an unsafe condition when lid 401 is in the closed position. In such instances, controller 490 may prevent lid 401 from being opened by a user. For example, controller 490 may transmit a locking control signal to an electronically controllable actuator that is responsible for moving closing member 423 between an unlocked and locked position. When it is determined that system 400 is in an unsafe condition the locking control signal may cause the electronically controllable actuator to maintain closing member 423 in the locked position, preventing or hindering the movement of lid 401 to the open position.

Controller 490 may later issue an unlocking control signal to move closing member 423 to an unlocked position. In embodiments, issuance of the unlocking control signal may be conditioned on the expiration of a threshold amount of time that is selected to allow enough conversion of sanitization gas to breathable gas. Alternatively or additionally, issuance of the unlocking control signal may be conditioned on the presence and/or concentration of the sanitizing gas within sanitizing chamber 403. In that regard system 400 may further include a sanitizing gas sensor 469 within sanitizing chamber 403, as shown in FIG. 4C. In general, sanitizing gas sensor 469 is configured to detect the presence and/or concentration of sanitizing gas within sanitizing chamber 403.

Any suitable sanitizing gas sensor may be used as sanitizing gas sensor 469. In embodiments, the sanitizing gas produced by system 400 is ozone, and sanitizing gas sensor 469 is an ozone sensor. In embodiments the sanitizing gas sensor 469 is configured to merely detect a presence of the sanitizing gas within sanitizing chamber 403. In other embodiments, sanitizing gas sensor 469 is configured to detect a concentration of sanitizing gas within sanitizing chamber 403. In either case, sanitizing gas sensor 469 is generally configured to output a gas detection signal to controller 490, wherein the gas detection signal is indicative of the presence and/or concentration of sanitizing gas within sanitizing chamber 403. In response to receipt of the gas detection signal, controller 490 may determine (independently or with the aid of an external computing system) whether system 400 is in a safe or unsafe condition while lid 401 is in the closed position.

In embodiments, controller 490 may determine that system 400 is in an unsafe condition when lid 401 is closed and sanitizing gas is present within sanitizing chamber 403, or a concentration of sanitizing gas within sanitizing chamber exceeds a threshold amount. In such instances, controller 490 may issue a locking control signal to hinder or prevent movement of lid 401 to the open position, as discussed above. Controller 490 may determine that system 400 is in a safe condition when lid 401 is closed and the gas detection signal indicates that sanitizing gas is either not present within sanitizing chamber 403, or the concentration of sanitizing gas within sanitizing chamber 403 is below a threshold amount. In such instance, controller 490 may permit the movement of lid 401 to the open position (provided no other unsafe condition indicating that lid 401 should not be opened is detected), e.g., by issuing an unlocking control signal as discussed above.

In embodiments the sanitization systems of the present disclosure include a hose detection sensor that enables controller 490 (or an external computing device) to determine whether a hose or plug is present within receptacle 407 prior to, during, or after execution of a sanitizing operation. In that regard reference is made to FIGS. 4D and 4F, which depict an embodiment in which system 400 includes a hose detection sensor 463. In general, hose detection sensor 463 functions to detect the presence or absence of a hose or plug within receptacle 407, and to output a hose detection signal. In embodiments hose detection sensor 463 is located at the base (e.g., bottom) of receptacle 407, but hose detection sensor 463 may be positioned at any suitable location. For example, hose detection sensor 463 may be positioned on lid under 102 proximate upper seal member 431, on a side of receptacle 407, or a combination thereof, as also shown in FIG. 4D.

Any suitable type of sensor may be used as hose detection sensor 463. Non-limiting examples of such sensors include electro-optical (e.g., visible, infrared, etc.) sensors, magnetic sensors, conductivity sensors, combinations thereof, and the like. In embodiments, hose detection sensor 463 is an electro-optical sensor that converts light, or a change in light, into a sensor signal. In such instances, hose detection sensor 463 may be positioned such that insertion or removal of a hose or plug from receptacle 407 changes the amount of light impinging on hose detection sensor 463, resulting in a corresponding change in the hose detection signal. Alternatively or additionally, hose detection sensor 463 is in the form of or includes a magnetic sensor that enables detection of the presence of absence of a hose or plug within receptacle 407 based on change in a magnetic field.

One example of a hose sensor that may be used in the present disclosure is shown in FIGS. 22A-22G and FIGS. 23A and B. As shown in such FIGS. the hose sensor includes a hose sensor bulb 2219 and a distance sensor 2301. The hose sensor bulb 2219 is configured to transition from an expanded state (shown in FIG. 23A) to a compressed state (shown in FIG. 23B). In that regard hose sensor bulb 2219 may be formed from or include a resiliently flexible material, such as a natural or synthetic polymer (e.g., silicone). The hose sensor bulb 2219 may be configured and positioned relative to receptacle 407 (or a sealing system therein)

such that a hose facing side 2221 thereof obscures at least a portion of an opening through the receptacle/sealing system, as best shown in FIGS. 22A and 22B.

Figure 22G:
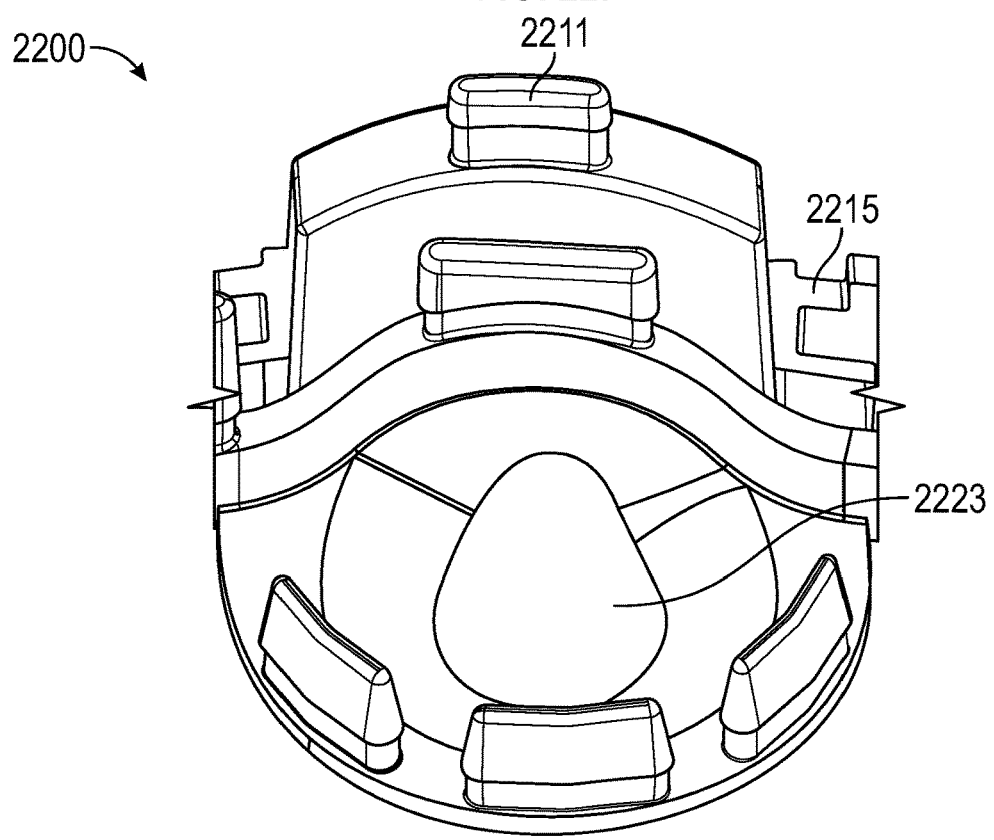
Figure 23A:
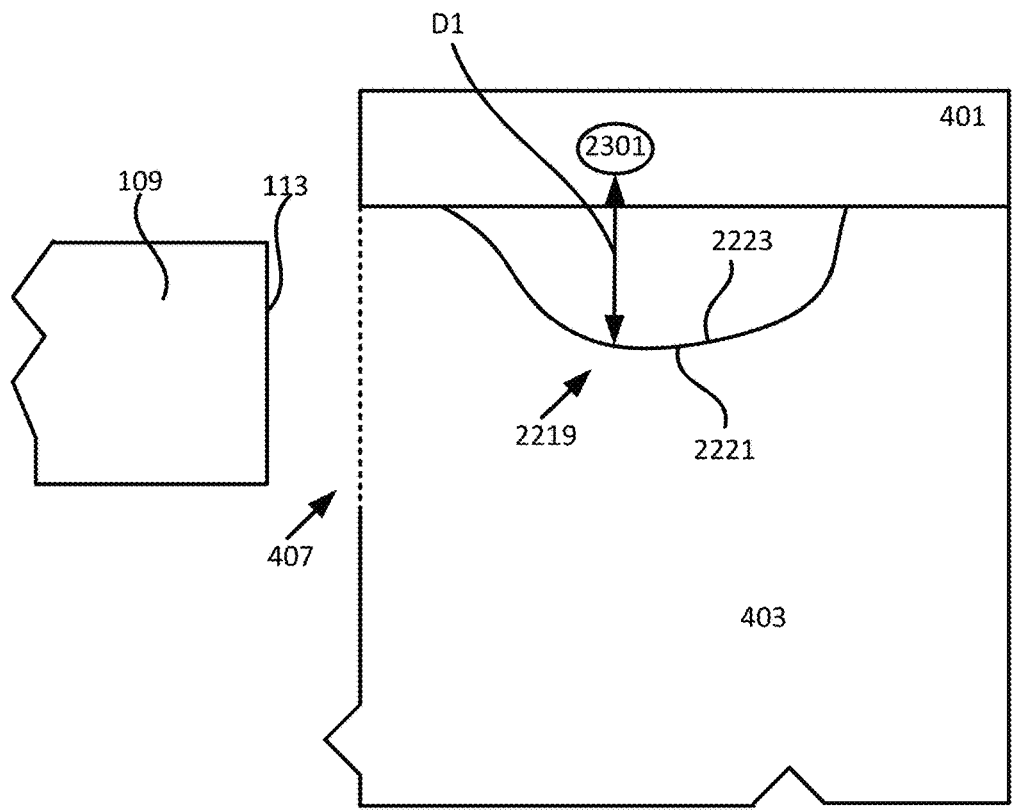
FIGS. 23A and 23B schematically illustrate the operation of one example of a hose detection sensor consistent with the present disclosure.

As best shown in FIGS. 22G and 23A and B, the hose facing side of 2221 of the hose sensor bulb 2219 may be oriented generally towards an interior of a sanitizing chamber 403 of a sanitizing system. The hose sensor bulb 2219 further includes a sensor facing side 2223 that is oriented towards distance sensor 2301. In general, distance sensor 2301 functions to sense a distance between it and the sensor facing side 2223 of hose sensor bulb 2219, and to output a sensor signal indicative of that sensed distance, e.g., to a controller 490. When the sensor signal indicates that the sensed distance is below a threshold distance, the controller may determine that a hose is present within receptacle 407, and/or within a sealing system consistent with the present disclosure.

Figure 23B:
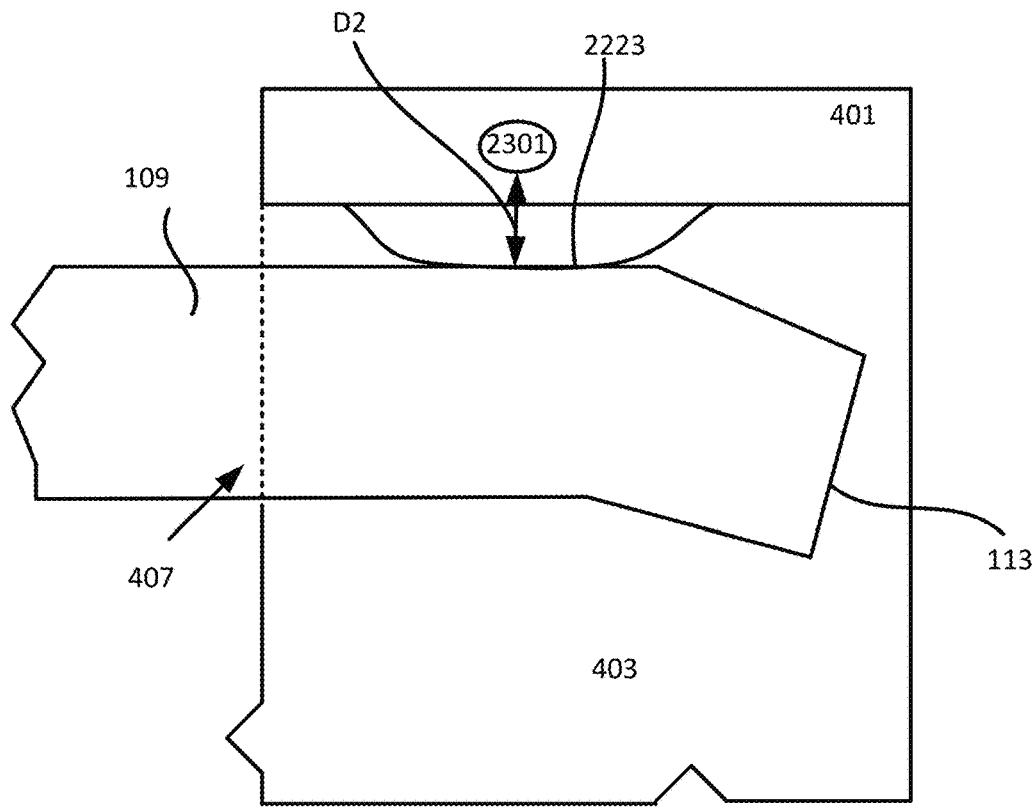

More specifically and as shown in FIG. 23A, when a hose 109 is not disposed through a receptacle 407, hose sensor bulb 2219 may be in the expanded state. In that state the distance D1 between the sensor facing side 2223 of the hose sensor bulb and the distance sensor 2301 may be relatively large. As shown in FIG. 23B, hose sensor bulb 2219 may be positioned and configured such that when hose 109 is inserted through receptacle 407, a portion of the outer surface of hose 109 contacts the hose facing side 2221 and causes the hose sensor bulb to move to a compressed state in which the distance D2 between distance sensor 2301 and the sensor facing side 2223 is relatively small. As discussed above, in operation distance sensor 2301 senses the distance between it and the sensor facing side 2223, and outputs a sensor signal indicated of a sensed distance to a controller. When the sensed distance is less than a threshold distance, the controller may determine that a hose is present within the receptacle 407.

Any suitable type of sensor may be used as distance sensor 2301. Non-limiting examples of such sensors include electro-optical (e.g., visible, infrared, etc.) sensors, magnetic sensors, conductivity sensors, combinations thereof, and the like. In embodiments, distance sensor 2301 is an electro-optical sensor that converts light, or a change in light, into a sensor signal. In such instances, the sensor facing side 2223 may be configured to enhance distance detection by distance sensor 2301. For example, the sensor facing side may be painted or otherwise coated with a colored and/or reflective coating, so as to enhance distance detection by distance sensor 2301.

In any case, hose detection sensor 463 outputs a hose detection signal to controller 490. In response to receipt of the hose detection signal, controller 490 may determine whether a hose or plug is present in receptacle 407, independently or with the assistance of an external computing device as noted above. Controller 490 may then determine whether system 400 is in a safe or unsafe condition.

Prior to execution of a sanitizing operation, controller 490 may determine that system 400 is in an unsafe condition when the hose detection signal indicates that a hose or plug is not present within receptacle 407 (i.e., the receptacle 407 is "open"). In such instances, controller 490 may prevent initiation of a sanitizing operation in any suitable manner. For example, controller 490 may lock out user interface 411 when receptacle 407 is open, thus preventing a user from initiating a sanitizing operation via user interface 411. Alternatively or additionally, controller 490 may issue a sanitizing gas lockout signal (SGLS) that prevents a sanitizing gas supply system from generating or otherwise providing a sanitizing gas to system 400 while receptacle 407 is open. For example where system 400 includes an ozone operating system including an ozone generator, the SGLS may be configured to disable the ozone operating system completely, or to disable only the ozone generator (e.g., allowing fans and/or pumps within the ozone operating system to circulate air) while receptacle 407 is open. When the hose detection signal indicates that a hose or plug is present within receptacle 407 (i.e., that receptacle 407 is "closed"), however, controller 490 may permit execution of a sanitizing operation, provided that no other unsafe condition is detected.

In embodiments the sanitization systems of the present disclosure include one or more sensors that enable controller 490 (or an external computing device) to determine whether system 400 is in a safe or unsafe condition based on the position of filter tray 471, the presence or absence of filter 500, and/or the use of an authorized or unauthorized filter. In that regard reference is made to FIG. 4H, which depicts an embodiment in which system 400 includes a tray position sensor 467. Tray position sensor 467 generally functions in much the same manner as lid detection sensor 461, except that it outputs a tray position signal that enables controller 490 to determine whether filter tray 471 is in an open or closed position. In the illustrated embodiment tray position sensor 467 is located within a recess formed in base 404 (e.g., on an outward facing side of sanitizing chamber 403), but tray position sensor 467 may be positioned at any suitable location. For example, tray position sensor 467 may be positioned on a sidewall 472 of said recess.

Any suitable type of sensor may be used as tray position sensor 467. Non-limiting examples of such sensors include electro-optical (e.g., visible, infrared, etc.) sensors, magnetic sensors, conductivity sensors, combinations thereof, and the like. In embodiments, tray position sensor 467 is an electro-optical sensor that converts light, or a change in light, into a sensor signal. In such instances, tray position sensor 467 may be positioned such that when filter tray 471 is moved from the open to the closed position (and vice versa), the amount of light impinging on tray position sensor 467 changes and causes a corresponding change in the tray position signal. Alternatively or additionally, tray position sensor 467 is in the form of or includes a magnetic sensor that enables detection of the position of filter tray 471 based on change in a magnetic field.

In any case, tray position sensor 467 outputs a tray position signal to controller 490. In response to receipt of the tray position signal, controller 490 may determine whether filter tray 471 is in an open position or a closed position, independently or with the assistance of an external computing device as noted above. Controller 490 may then determine whether system 400 is in a safe or unsafe condition.

Prior to execution of a sanitizing operation, controller 490 may determine that system 400 is in an unsafe condition when it is determined that filter tray 471 is in the open position. In such instances, controller 490 may prevent initiation of a sanitizing operation while filter tray 471 is in the open position. Controller 490 may prevent initiation of a sanitizing operation in any suitable manner, such as described above in connection with lid detection sensor 461 and hose detection sensor 463.

During execution of a sanitizing operation (or within a threshold time following execution of a sanitizing operation), controller 490 may determine that system 400 is in an unsafe condition while filter tray 471 is in the closed position. In such instances, controller 490 may prevent filter tray 471 from being moved to the open position. In embodiments system 400 includes electronically controllable tray locking components (not shown) that can maintain filter tray 471 in a closed and locked position. The tray locking components may be configured in much the same manner as closing member 423 and receiver 425, except that they function to lock filter tray 471 in the closed position. In such instances, controller 490 may transmit a tray locking control signal to an electronically controllable actuator that is responsible for moving a closing member of the tray locking components between an unlocked and locked position. When it is determined that system 400 is in an unsafe condition the tray locking control signal may cause the tray locking components to maintain filter tray 471 in a closed and locked position, preventing or hindering the movement of filter tray 471 to the open position.

Controller 490 may later issue a tray unlocking control signal to cause the locking components to unlock and allow filter tray 471 to be moved to the open position. In embodiments, issuance of the tray unlocking control signal may be conditioned on the expiration of a threshold amount of time that is selected to allow for enough conversion of sanitization gas to breathable gas. Alternatively or additionally, issuance of the tray unlocking control signal may be conditioned on the presence and/or concentration of the sanitizing gas within sanitizing chamber 403, e.g., as reported by sanitizing gas sensor 469 as discussed above. In embodiments, controller 490 may issue the tray unlocking signal when a sanitizing gas sensor signal issued by sanitizing gas sensor 469 indicates that a sanitizing gas not present within sanitizing chamber 403, or a concentration of sanitization gas within sanitizing chamber 403 is below a threshold amount.

In embodiments controller 490 may determine that system 400 is in an unsafe condition when filter tray 471 is moved from the closed position to the open position during execution of a sanitizing operation. Such movement may occur, for example, in instances where system 400 does not include tray locking components, and/or if system 400 includes such components but filter tray 471 is nonetheless moved to the open position during a sanitization cycle. In such instances, controller 490 may issue a shutdown command that is configured to discontinue an executing sanitization cycle. In embodiments, the shutdown command is configured to cause the sanitizing gas supply system to discontinue providing and/or generating sanitizing gas. For example, the shutdown command may turn off a sanitizing gas generator (e.g., an ozone generator) within the sanitizing gas supply system, and/or may disable sanitizing gas supply system completely.

In embodiments the sanitization systems of the present disclosure include a filter detection sensor that enables controller 490 (or an external computing device) to determine whether a filter 500 is present within filter tray 471. In that regard it is again noted that filter 500 may include communications circuitry (COMMS) 517 (as shown in FIGS. 5A and 5B) and that controller 490 also includes COMMS 1205. In embodiments, COMMS 517 is configured to communicate with COMMS 1205 in any suitable manner, such as via a currently known or future developed wired or wireless communication protocol. In embodiments, COMMS 517 is or includes a near field communication circuit, such as but not limited to a radio frequency identification (RFID) circuit. In such instances COMMS 1205 may be or include circuitry that can communicate with COMMS 517 via an RFID or other near field communication protocol.

In any case COMMS 517 is configured to provide a filter detection signal to controller 490. In embodiments the filter detection signal is configured merely to identify a presence of filter 500 within filter tray 471. Alternatively or additionally, the filter detection signal is also configured to enable controller 490 to determine whether filter 500 is an authorized filter. In such embodiments the filter detection signal may include a filter identifier, and controller 490 is configured to determine (independently or with the aid of an external computing device) whether filter 500 is an authorized filter based at least in part on said filter identifier. In embodiments, controller 490 may determine that filter 500 is an authorized filter when it determines that filter identifier is associated with a manufacturer of system 400, and/or an authorized manufacturer of replacement filters for system 400.

Controller 490 may determine whether filter 500 is an authorized filter in any suitable manner. For example, controller 490 may determine whether a filter identifier within filter detection signal is present within an authorized filter database stored in memory 1203. Alternatively, controller 490 may transmit a filter identification signal containing the filter identifier to a server 1215 (e.g., independently or with a status signal). In response to the filter identification signal, the server 1215 (which may be an external server) may determine whether the filter identifier is associated with a manufacturer of system 400 and/or authorized manufacturer of replacement filters. Based on that determination the server 1215 may transmit an authorization signal (independently or with a safety signal) to controller 490, wherein the authorization signal indicates that the filter identifier is associated with a manufacturer of system 400 or an authorized reseller of replacement filters. In such instances the controller 490 may determine whether the filter 500 is an authorized filter based at least in part on the authorization signal.

In embodiments controller 490 may determine that system 400 is in an unsafe condition when it determines that filter 500 is not present within filter tray 471. Controller 490 may make such a determination, for example, based on the failure of comms 1205 to receive a filter detection signal, e.g., before expiration of a threshold period of time. When such a determination is made prior to execution of a sanitization cycle, controller 490 may prevent the initiation of a sanitization cycle in any suitable manner, such as described above in connection with the lid detection sensor 461, hose detection sensor 463, and tray position sensor 467.

When such a determination is made during execution of a sanitization cycle (e.g., when filter 500 is removed during a sanitization cycle), controller 490 may issue a shutdown command to discontinue execution of the sanitization cycle, as discussed above. When such a determination is made following execution of a sanitization cycle (e.g., within a threshold time-period following an execution cycle), controller 490 may cause the issuance of a visual, auditory, or audiovisual warning signal, e.g. via user interface 411. The visual/auditory/audiovisual warning signal may encourage a user to insert a filter cartridge into filter tray 471, and to move filter tray 471 to the closed position.

Alternatively or additionally, controller 490 may issue a shutdown command that is configured to halt the operation of a sanitizing gas supply system, and to halt the flow of sanitizing gas through exhaust ports 405. Put differently, the controller 490 may issue commands that aim to retain the sanitizing gas within system 400 (i.e., within components upstream of exhaust ports 405). Doing so may prevent a user from being exposed to the sanitizing gas, and provides an opportunity for the sanitizing gas to convert to a breathable gas within components of system 400 that are upstream of exhaust ports 405.

In embodiments, controller 490 may also determine that system 400 is in an unsafe condition when it determines that filter 500 is present within filter tray 471, but is not an authorized filter. Controller 490 may make such a determination, for example, based at least in part on a filter identifier (in a filter detection signal provided by COMMS 517) and/or an authorization signal from server 1215. When such a determination is made prior to execution of a sanitization cycle, controller 490 may prevent the initiation of a sanitization cycle in any suitable manner, such as described above. When such a determination is made during execution of a sanitization cycle, however, controller 490 may issue a shutdown command to discontinue execution of the sanitization cycle as discussed above.

In embodiments controller 490 may determine that system 400 is in an unsafe condition when sanitizing gas is present downstream of filter 500, and/or whether a concentration of sanitizing gas downstream of filter 500 exceeds a threshold amount. In that regard reference is made to FIGS. 4B and 4H, which illustrate an embodiment in which system 400 includes a sanitizing gas sensor 460 downstream of filter 500. Sanitizing gas sensor 460 is configured to detect the presence and/or concentration of sanitizing gas within gas flow downstream of filter 500. Any suitable sanitizing gas sensor may be used as sanitizing gas sensor 460. In embodiments, the sanitizing gas produced by system 400 is ozone, and sanitizing gas sensor 460 is an ozone sensor.

In embodiments the sanitizing gas sensor 460 is configured to merely detect a presence of the sanitizing gas in a gas flow downstream of filter 500. In other embodiments, sanitizing gas sensor 460 is configured to detect a concentration of sanitizing gas in a gas flow downstream of filter 500. In either case, sanitizing gas sensor 460 is generally configured to output a filter efficacy signal (FES) to controller 490, wherein the FES is indicative of the presence and/or concentration of sanitizing gas within a gas flow downstream of filter 500. In response to receipt of the FES, controller 490 may determine (independently or with the aid of an external computing system) whether system 400 is in a safe or unsafe condition.

In embodiments controller 490 may determine that system 400 is in an unsafe condition when it determines (based at least in part on the FES) that sanitizing gas is present downstream of the filter 500, and/or a concentration of sanitizing gas downstream of the filter 500 exceeds a threshold amount. In either case, controller 490 may take appropriate action to maintain the safe operation of system 400. For example, when such a determination is made during execution of a sanitization cycle, controller 490 may issue a shutdown command that ceases execution of the sanitization cycle as discussed above.

As noted above controller 490 may disable execution of a sanitization cycle when it is determined that a filter is not detected in filter tray 471 and/or when an unauthorized filter is detected in filter tray 471. Alternatively, in some embodiments system 400 may not be configured to enable detection of the presence of filter 500 in filter tray 471, and/or may be unable to determine whether a filter within filter tray 471 is an authorized filter. In such instances controller 490 may be configured to determine whether a filter is present in filter tray 471 and is operating correctly (i.e., is converting sanitizing gas) based at least in part on the FES provided by sanitizing gas sensor 460.

For example, when the FES indicates the presence of sanitizing gas downstream of filter 500 (and/or a concentration of sanitizing gas exceeding a threshold level downstream of filter 500), controller 490 may determine that system 400 is in an unsafe condition due to the absence of filter 500, due to the failure of filter 500 to sufficiently convert sanitizing gas to breathable gas, and/or due to the use of an unauthorized filter. In such instances, controller 490 may disable execution of a sanitizing operation as discussed above, and/or issue a visible/auditory indicator (via user interface 411) that prompts a user to insert or replace filter 500.

Likewise, controller 490 may determine that system 400 is in a safe condition even if an unauthorized filter is present in filter tray 471, based at least in part on the FES. For example, controller 490 may determine that filter 500 is an unauthorized filter as described above, but may permit execution of a sanitizing operation for a limited time to allow sanitizing gas sensor 460 to generate an accurate FES. In response to receipt of the FES, controller 490 may determine whether sanitizing gas is present downstream of the filter 500, and/or is present at a concentration exceeding a threshold amount downstream of the filter 500. If the FES indicates that sanitizing gas is not present (or does not exceed the threshold amount) downstream of filter 500, controller 490 may permit execution of the sanitization cycle despite the use of an authorized filter. Otherwise, controller 490 may disable operation of the sanitization cycle as discussed above.

As may be appreciated, when system 400 is used to sanitizing a CPAP device and is configured in the same manner as system 300 (i.e., with a connector unit), a user may use the CPAP device while system 400 is connected to the hose 109 (e.g., a CPAP hose) and medical device 129. If a sanitization cycle is executed while the CPAP device is in use, the user may be undesirably exposed to the sanitizing gas. Accordingly, in embodiments controller 490 is configured to determine that system 400 is in an unsafe condition based at least in part on a determination that a user is using a medical device (e.g., a CPAP) coupled to system 400, and to take appropriate action in response to such a determination.

In that regard system 400 may include one or more wired or wireless sensors that are configured to detect contact between one or more components of a medical device and the skin of a user. As one non-limiting example of such a system, reference is made to FIG. 4G, which depicts a mask 487 (e.g., a CPAP mask) coupled to a hose 109 (e.g., a CPAP hose). As shown, mask 487 may be retained on a user's face by a strap 488. In the illustrated embodiment, one or more skin detection sensors 465 are disposed on mask 487 and/or strap 488. In general, skin detection sensor 465 is configured to detect contact with a user's skin, and to output a skin contact signal indicative of the presence or absence of skin contact to controller 490 via wired or wireless communication. Any suitable skin contact sensor may be used as skin contact sensor 465. Non-limiting examples of such sensors include conductivity sensors, capacitive sensors, haptic sensors, combinations thereof, and the like.

In such embodiments controller 490 may be configured to determine whether system 400 is in a safe or unsafe condition based at least in part on the skin contact signal. In embodiments, controller 490 may determine that system 400 is in an unsafe condition when skin contact signal indicates that a portion of a medical device (e.g., mask 487, strap 488) is in contact with a user's skin. In such instances, controller 490 may execute one or more safety operations to prevent the exposure of the user to the sanitizing gas. For example, controller 490 may prevent the execution of a sanitizing operation in any suitable manner, such as via the operations described previously in connection with the detection of an unsafe condition by controller 490.

It is noted that FIG. 4G depicts an embodiment in which two skin contact sensors are used as skin detection sensors 465, and such sensors are disposed on the mask 487 and strap 488 of a medical device. Such a configuration is not required, and the present disclosure encompasses embodiments in which any suitable number of skin contact sensors are used and are placed in any suitable location.

In embodiments, controller 490 may control operation of system 400 based at least in part on a determination as to whether a user of system 400 is or is not an authorized user. In that regard, one or more unique identifiers may be associated with a user of system 400 or a component thereof, such as filter 500. The association of the user with system 400 (or a component thereof) may be maintained locally or in server 1215, e.g., in accordance with required privacy regulations such as but not limited to the privacy requirements of the Health Insurance Portability and Accountability Act (HIPAA). In embodiments, server 1215 may maintain a user database (in the form of a lookup table or other data structure) that associates one or more users with system 400 or a component thereof, such as but not limited to filter 500. For example, the user database may associate a user with a system identifier that is unique to system 400 and is stored in memory 120$_3$. Alternatively or additionally, the user database may associate a user with a unique filter identifier that is stored in memory of COMMS 517 and which may be provided to controller 490 in a filter identification signal as discussed above.

Controller 490 may determine that a user of system 400 is an authorized user in any suitable manner. For example, before, during, or after initiation of a sanitization cycle, controller 490 may transmit an identification signal (e.g., independently or with a status signal) to server 1215 via wired or wireless communication. The identification signal may include a unique system identifier, a unique filter identifier, or a combination thereof. The identification signal is generally configured to cause server 1215 to determine whether a user is associated with the unique system identifier and/or unique filter identifier, and in some instances to determine whether that user is authorized to use system 400.

In embodiments, server 1215 may determine whether the user is authorized based on a payment status indicator associated with the user and/or unique system/filter identifier in the user database. For example, a user may rent or finance system 400 from a supplier pursuant to a rental or finance agreement that stipulates required payment terms in exchange for use of system 400. The payment terms may specify, for example, an allowed usage period in exchange for a specified payment, payment on a per use basis, periodic payments in association with a financing agreement, combinations thereof, or the like. In such embodiments, server 1215 may associate a payment status indicator with a user and/or the unique system identifier and/or filter identifier associated with the user. The payment status indicator may indicate whether a user is current on payments, or if payments are due on system 400 and/or filter 500.

In embodiments, server 1215 is configured to determine (responsive to an identification signal from controller 490) whether a user is authorized to use system 400 based at least in part on the payment status indicator. In embodiments, server 1215 may determine that a user is not authorized to use system 400 when the payment status indicator indicates that payment on system 400 and/or filter 500 is due or otherwise is not current. Conversely, server 1215 may determine that a user is authorized to use system 400 when the payment status indicator indicates that payment on system 400 is not due (i.e., is current).

In either case, server 1215 may transmit a user authorization signal (e.g., independently or with an authorization signal) to controller 490, via wired or wireless communication, as discussed above. In response, controller 490 may determine whether the user is authorized based at least in part on the user authorized signal. When controller 490 determines that the user is not authorized, it may prevent or disable the execution of a sanitization cycle in any suitable manner, such as the operations described above in connection with the detection of an unsafe condition. When controller 490 determines that the user is authorized, however, it may permit execution of a sanitization cycle provided no other unsafe conditions are detected.

It is noted that the above discussion focuses on embodiments in which a user database is maintained on server 1215, and in which server 1215 determines whether a user is authorized based on a payment status indicator. Such a configuration is not required, however, and user database may be maintained in another location. For example, user database may be maintained locally in memory 1203 of controller 490. In such instances, controller 490 may locally maintain the payment status indicator and determine whether a user is authorized based on the payment status indicator without the involvement of server 1215.

Figure 13:
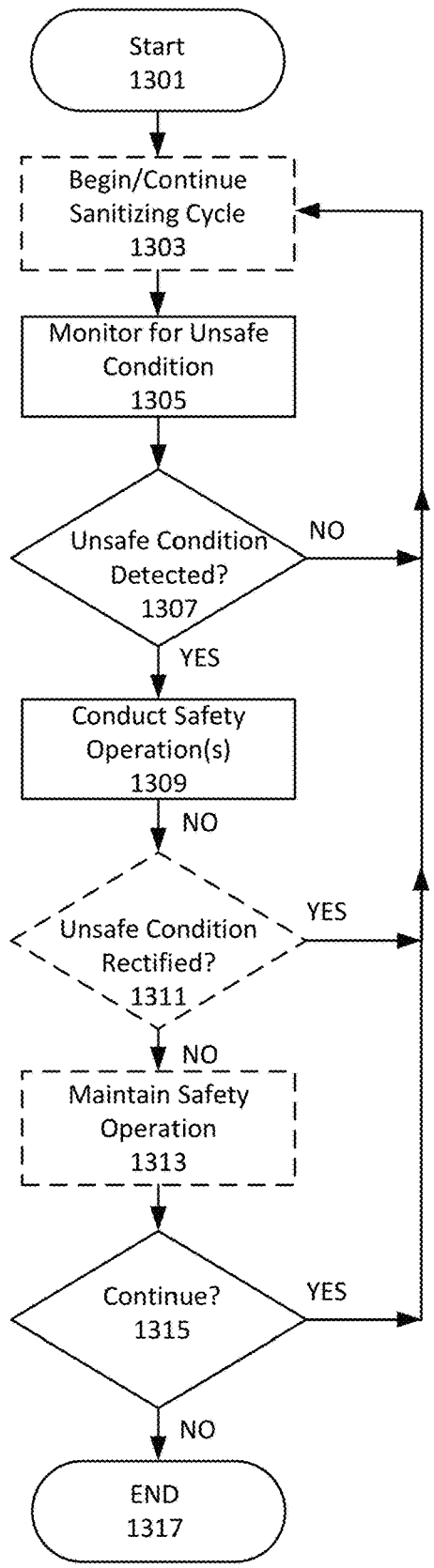
FIG. 13 is a flow diagram of exemplary operations in accordance with an example method of controlling a sanitizing system consistent with the present disclosure.

Other aspects of the present disclosure relate to methods of controlling a sanitization system. In that regard reference is made to FIG. 13, which is a flow chart of example operations of one example of a sanitization system control method consistent with the present disclosure. As shown, method 1300 begins at block 1301. The method proceeds to optional block 1303, pursuant to which a sanitization cycle is optionally initiated. Initiation of the sanitization cycle may be instigated by a user via user interface 411, as discussed above.

Following the operations of block 1303 (or if such operations are omitted), the method proceeds to block 1305, pursuant to which the sanitization system is monitored for the presence of an unsafe condition. Operations pursuant to block 1305 may include, for example, monitoring one or more sensor signals with a controller as discussed above.

The method may then proceed to block 1307, pursuant to which a decision is made (e.g., by a controller) as to whether an unsafe condition is detected. If not, the method loops back to optional block 1303. If an unsafe condition is detected, however, the method proceeds to block 1309, pursuant to which safety operations are conducted (e.g., by a controller). Operations pursuant to block 1305 may include, for example, any or a combination of the operations of controller 490 discussed above in response to detection of an unsafe condition.

During or following the operations of block 1309 the method may proceed to optional block 1311, pursuant to which a decision may be made (e.g., by a controller) as to whether the unsafe condition has been rectified. If so, the method loops back to optional block 1303. But if not, the method proceeds to optional block 1313, pursuant to which the safety operation(s) of block 1309 may be maintained. The method may then proceed to block 1315, pursuant to which a determination is made as to whether the method is to continue. If so, the method loops back to optional block 1303, but if not, the method proceeds to block 1317 and ends.

Figure 14:
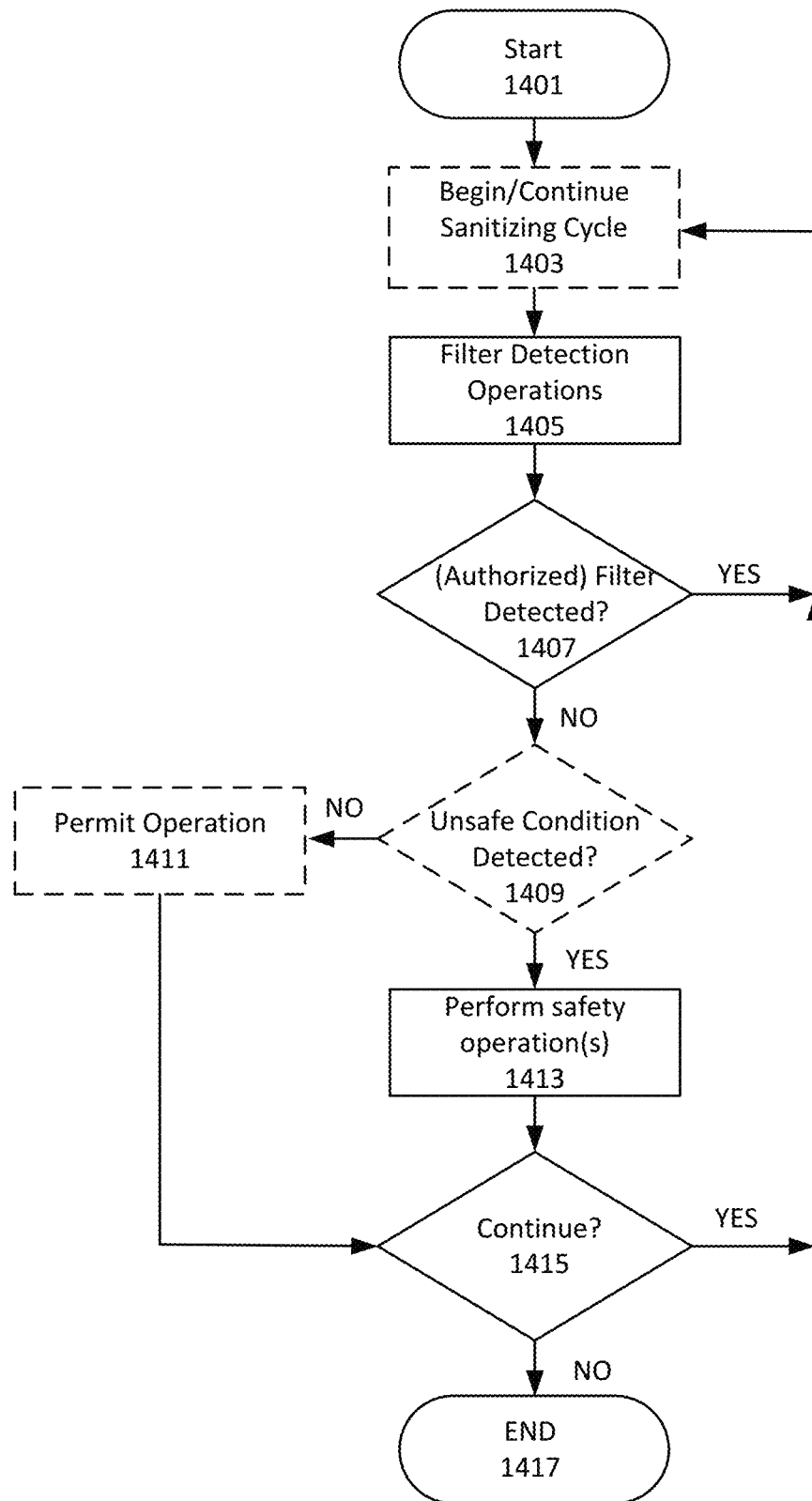
FIG. 14 is a flow diagram of exemplary operations in accordance with another example method of controlling a sanitizing system consistent with the present disclosure.

FIG. 14 is a flow diagram of exemplary operations of another method of controlling a sanitizing system consistent with the present disclosure. As shown, the method 1400 begins with block 1401. The method then proceeds to optional block 1403, pursuant to which a sanitization cycle may be initiated (e.g., by a user via user interface 411).

Following the operations of block 1403 or if such operations are omitted, the method proceeds to block 1405, pursuant to which filter detection operations may be performed (e.g., by a controller). Operations pursuant to block 1405 include, for example, determining whether a filter is present (e.g., within filter tray 471) and, in some instances whether a detected filter is an authorized filter. The method may then proceed to block 1407, pursuant to which a determination is made as to whether a filter is detected, and, in some instances, whether the detected filter is an authorized filter. If so (i.e., an (optionally authorized) filter is detected), the method may loop back to block 1403.

If not, however (i.e., if a filter is not detected and/or a filter is detected but not authorized), the method may proceed to optional block 1409, pursuant to which a determination is made (e.g., by a controller) as to whether an unsafe condition is detected. In embodiments the outcome of block 1409 may be conditioned on the detection of sanitizing gas downstream of the filter, and/or detection of a concentration of sanitizing gas downstream of the filter that exceeds a threshold amount. If sanitizing gas is not detected (or does not exceed the threshold amount), the method may proceed from block 1409 to block 1411, pursuant to which a sanitizing operation may be permitted (provided no other unsafe conditions are detected).

If an unsafe condition is detected (or the operations of block 1409 are omitted) however, the method may proceed to block 1413, pursuant to which one or more safety operations is performed (e.g., by a controller). Examples of such safety operations include any or a combination of the operations of controller 490 discussed above in response to detection of an unsafe condition. In any case, the method may proceed to block 1415, pursuant to which a determination may be made as to whether the method is to continue. If so, the method may loop back to block 1403, but if not, the method may proceed to block 1417 and end.

The following examples are provided as additional non-limiting embodiments of the present disclosure:

EXAMPLES

The following examples are provided as additional non-limiting embodiments of the present disclosure.

Example 1: According to this example there is provided a sanitization system, including: a base including a sanitizing chamber, the sanitizing chamber including at least one exhaust port; a sanitizing gas generator configured to supply a sanitizing gas and to fluidly couple to the sanitizing chamber; a primary fan or pump configured to push or draw at least a portion of the sanitizing gas from the sanitizing gas generator to the sanitizing chamber; and a secondary fan or pump configured to push or draw at least a portion of the sanitizing gas through the at least one exhaust port.

Example 2: This example includes any or all of the features of example 1, further including a filter fluidly coupled to the at least one exhaust port.

Example 3: This example includes any or all of the features of example 1 or example 2, wherein the secondary fan or pump is located upstream of the at least one exhaust port.

Example 4: This example includes any or all of the features of example 1 or example 2, wherein the secondary fan or pump is located downstream of the at least one exhaust port.

Example 5: This example includes any or all of the features of example 2, wherein the secondary fan or pump is located upstream of the filter.

Example 6: This example includes any or all of the features of example 2, wherein the secondary fan or pump is located downstream of the filter.

Example 7: This example includes any or all of the features of any one of examples 1, 2, 3, and 5, wherein the secondary fan or pump is configured to push at least a portion of the sanitizing gas through the at least one exhaust port.

Example 8: This example includes any or all of the features of example 5 or example 7, wherein the secondary fan or pump is configured to draw or push at least a portion of the sanitizing gas through the filter.

Example 9: This example includes any or all of the features of example 4 or example 6, wherein the secondary fan or pump is configured draw sanitizing gas through the filter.

Example 10: This example includes any or all of the features of any one of examples 1 to 9, wherein the base further includes the sanitizing gas generator, the primary fan or pump, and the secondary fan or pump.

Example 11: This example includes any or all of the features of any one of examples 1 to 10, further including a connector unit configured to fluidly couple with the sanitizing gas generator and the sanitizing chamber.

Example 12: This example includes any or all of the features of example 11, wherein the connector unit is further configured to couple or fluidly couple to a medical device.

Example 13: This example includes any or all of the features of example 11, wherein the connector unit is further configured to couple or fluidly couple to a medical device hose.

Example 14: This example includes any or all of the features of any one of examples 1 to 10, further including a medical device and a medical device hose, wherein: the connector unit includes a first connector fluidly coupled with the sanitizing gas generator; the connector unit includes a second connector coupled or fluidly coupled with the medical device; and the connector unit includes a third connector fluidly coupled to a proximal end of the medical device hose; and a distal end of the medical device hose is fluidly coupled with the sanitizing chamber.

Example 15: This example includes any or all of the features of example 10, further including a medical device and a medical device hose, wherein: the connector unit includes a first connector fluidly coupled with the sanitizing gas generator; the connector unit includes a second connector coupled or fluidly coupled with a distal end of the medical device hose; the connector unit includes a third connector fluidly coupled to the sanitizing chamber; and a proximal end of the medical device hose is fluidly coupled to the medical device.

Example 16: This example includes any or all of the features of example 14 or example 15, wherein the medical device is a continuous positive airway pressure (CPAP) device and the medical device hose is a CPAP hose.

Example 17: This example includes any or all of the features of any one of examples 14 to 16, wherein: the first connector includes a first opening; the second connector includes a second opening; the third connector includes a third opening; and the connector unit further includes a first passageway, the first passageway having a first proximal end and at least a first distal end.

Example 18: This example includes any or all of the features of example 17, wherein: the first proximal end of the first passageway is defined at least in part by the first opening; and the first distal end is oriented towards the second connector or the third connector.

Example 19: This example includes any or all of the features of example 17, wherein: the proximal end of the first passageway is defined at least in part by the first opening; the first passageway further includes a second distal end; the first distal end is oriented towards the second opening; and the second distal end is oriented towards the third connector.

Example 20: This example includes any or all of the features of any one of examples 17-19, wherein the second connector and the third connector are fluidly coupled by a second passageway.

Example 21: This example includes any or all of the features of example 20, wherein material of a sidewall of the first passageway is at least partially disposed within the second passageway.

Example 22: This example includes any or all of the features of example 17 or 18, wherein: the second connector and the third connector are fluidly coupled by a second passageway; the connector unit includes a fourth connector including a fourth opening; and the connector unit includes a third passageway including a second proximal end and a third distal end.

Example 23: This example includes any or all of the features of example 22, wherein: the second proximal end includes the fourth opening; and the third distal end is oriented towards the second connector or the third connector.

Example 24: This example includes any or all of the features of example 2, wherein: the filter is a filter cartridge including a shell and a filter media housed within the shell; the shell includes a filter inlet configured to fluidly couple to the at least one exhaust port; the shell further includes a filter outlet; and the filter media is configured to convert the sanitizing gas to a breathable gas.

Example 25: This example includes any or all of the features of example 24, wherein the sanitizing gas is ozone and the breathable gas is oxygen.

Example 26: This example includes any or all of the features of example 24 or example 25, wherein the filter cartridge further includes a filter inlet seal disposed around the filter inlet, the filter inlet seal configured to form a seal around the at least one exhaust port.

Example 27: This example includes any or all of the features of example 26, wherein the filter inlet seal includes a peripheral surface and a flange that extends at an angle from the peripheral surface.

Example 28: This example includes any or all of the features of example 24 or example 25, wherein: the base further includes a filter tray that is configured to receive the filter cartridge; the filter tray is movable between an open and a closed position; and when the filter cartridge is in the filter tray and the filter tray is in the closed position, the filter inlet is disposed proximate the at least one exhaust port.

Example 29: This example includes any or all of the features of example 28, wherein: the filter further includes a filter inlet seal disposed around the filter inlet; and when the filter cartridge is in the filter tray and the filter tray is in the closed position, the filter inlet seal forms a seal around the at least one exhaust port.

Example 30: This example includes any or all of the features of example 29, wherein the filter inlet seal includes a peripheral surface and a flange that extends at an angle from the peripheral surface.

Example 31: This example includes any or all of the features of any one of examples 24-30, wherein the secondary fan or pump is disposed downstream of the filter outlet.

Example 32: This example includes any or all of the features of any one of examples 1-31, wherein the sanitizing chamber includes a bottom and at least one side, and the system further includes one or more standoffs to position at least one medical device relative to the bottom, the at least one side, or a combination thereof.

Example 33: This example includes any or all of the features of any one of examples 1-31, further including a controller and at least one sensor, wherein the at least one sensor is configured to monitor a condition of the system and to output a sensor signal indicative of the monitored condition to the controller, and the controller is configured to permit or prevent the execution of a sanitizing operation with the system based at least in part on the sensor signal.

Example 34: This example includes any or all of the features of example 33, wherein the at least one sensor includes: a lid detection sensor configured to detect a position of a lid of the system; a hose detection sensor configured to detect a presence of a hose or plug within a receptacle of the system; a leakage sensor configured to detect leakage of sanitizing gas from the system; a tray position sensor configured to detect a position of a filter tray of the system; a filter detection sensor configured to detect a presence of a filter of the system; or a usage sensor configured to detect use of a medical device coupled to the system; or a combination of two or more thereof.

Example 35: This example includes any or all of the features of any one of examples 2 and 24-31, further including a controller and at least one sensor, wherein: the at least one sensor includes a filter detection sensor configured to detect the filter and to output a filter detection signal; and the controller is configured to determine whether the filter is an authorized filter based at least in part on the filter detection signal.

Example 36: This example includes any or all of the features of example 35, wherein the controller is configured to prevent or discontinue execution of a sanitizing cycle when it is determined that the filter is an unauthorized filter.

Example 37: This example includes any or all of the features of any one of examples 2 and 24-31, further including a controller and at least one sensor, wherein: the at least one sensor includes a filter detection sensor configured to detect the filter and to output a filter detection signal; and the controller is configured to determine whether the filter is present based at least in part on the filter detection signal.

Example 38: This example includes any or all of the features of example 37, wherein the controller is configured to prevent or discontinue execution of a sanitizing cycle when it is determined that the filter is not present.

Example 39: This example includes any or all of the features of any one of examples 2 and 24-31, further including a controller and at least one sensor, wherein: the at least one sensor includes a sanitizing gas sensor configured to detect a presence of the sanitizing gas downstream of the filter, and to output a filter efficacy signal (FES); and the controller is configured to determine whether sanitizing gas is present downstream of the filter based at least in part on the FES.

Example 40: This example includes any or all of the features of example 39, wherein the controller is configured to prevent or discontinue execution of a sanitizing cycle when it is determined that sanitizing gas is present downstream of the filter.

Example 41: This example includes any or all of the features of example 39, wherein the controller is further configured to determine a concentration of the sanitizing gas downstream of the filter based at least in part on the FES, and to prevent or discontinue execution of a sanitizing cycle when it is determined that the concentration of the sanitizing gas downstream of the filter is greater than or equal to a threshold concentration.

Example 42: This example includes any or all of the features of any one of examples 28-31, further including a controller and at least one sensor, wherein: the at least one sensor includes a tray position sensor configured to detect a position of the filter tray and to output a tray position signal; and the controller is configured to determine whether the filter tray is in the open position or the closed position based at least in part on the tray position signal.

Example 43: This example includes any or all of the features of example 42, wherein the controller is configured to prevent or discontinue execution of a sanitizing cycle when it is determined that the tray is in the open position.

Example 44: This example includes any or all of the features of example 33, further including a lid, wherein: the lid is movable between an open position and a closed position, wherein in the open position the lid permits access to the sanitizing chamber; the at least one sensor includes a lid detection sensor configured to detect a position of the lid and to output a lid position signal; and the controller is configured to determine whether the lid is in the open position or the closed position based at least in part on the lid position signal.

Example 45: This example includes any or all of the features of example 44, wherein the controller is configured to prevent or discontinue execution of a sanitizing cycle when it is determined that the lid is in the open position.

Example 46: This example includes any or all of the features of example 33, further including a receptacle for receiving at least a portion of a hose of a medical device, wherein: the at least one sensor includes a hose detection sensor configured to detect a presence or coupling of the medical device hose in or with the receptacle and to output a hose detection signal; and the controller is configured to determine whether the hose is present within the receptacle or coupled to the receptacle based at least in part on the hose detection signal.

Example 47: This example includes any or all of the features of example 46, wherein the controller is configured to prevent or discontinue execution of a sanitizing cycle when it is determined that the hose is not present within or coupled to the receptacle.

Example 48: This example includes any or all of the features of example 33, further including a lid and a receptacle for receiving at least a portion of a hose of a medical device, wherein: the lid is movable between an open position and a closed position, wherein in the open position the lid permits access to the sanitizing chamber; the at least one sensor includes a lid detection sensor configured to detect a position of the lid and to output a lid position signal; the at least one sensor further includes a hose detection sensor configured to detect a presence or coupling of the medical device hose in or with the receptacle and to output a hose detection signal; the controller is configured to determine to determine whether the lid is in the open position or the closed position based at least in part on the lid position signal; and the controller is further configured to determine whether the hose is present within the receptacle or coupled to the receptacle based at least in part on the hose detection signal.

Example 49: This example includes any or all of the features of example 33, wherein: the at least one sensor includes a skin contact sensor configured to output a skin contact signal; the controller is configured to determine whether a component of the medical device is in contact with skin of a user of a medical device coupled to the system based at least in part on the skin contact signal; and the controller is configured to prevent or discontinue execution of a sanitizing cycle when it is determined that the component of the medical device is in contact with skin of the user.

Example 50: According to this example there is provided a method of sanitizing, including: generating sanitizing gas with a sanitizing gas generator; with a primary fan or pump, pushing or drawing at least a portion of the sanitizing gas from the sanitizing gas generator to a sanitizing chamber in a base, the sanitizing chamber including at least one exhaust port; with a secondary fan or pump, pushing or drawing at least a portion of the sanitizing gas through the at least one exhaust port.

Example 51: This example includes any or all of the features of example 50, wherein the secondary fan or pump is located upstream of the at least one exhaust port.

Example 52: This example includes any or all of the features of example 50, wherein the secondary fan or pump is located downstream of the at least one exhaust port.

Example 53: This example includes any or all of the features of example 50, wherein a filter is fluidly coupled to the at least one exhaust port, and the secondary fan or pump is located upstream of the filter.

Example 54: This example includes any or all of the features of example 50, wherein a filter is fluidly coupled to the at least one exhaust port, and the secondary fan or pump is located downstream of the filter.

Example 55: This example includes any or all of the features of example 51, wherein the method further includes pushing at least a portion of the sanitizing gas through the at least one exhaust port with the secondary fan or pump.

Example 56: This example includes any or all of the features of example 51, wherein the method further includes drawing at least a portion of the sanitizing gas through the at least one exhaust port with the second fan or pump.

Example 57: This example includes any or all of the features of example 51 or 52, wherein the method further includes drawing at least a portion of the sanitizing gas through the filter.

Example 58: This example includes any or all of the features of any one of examples 50 to 57, wherein the base further includes the sanitizing gas generator, the primary fan or pump, and the secondary fan or pump.

Example 59: This example includes any or all of the features of any one of examples 50 to 58, wherein a connector unit is fluidly coupled to the sanitizing gas generator and the sanitizing chamber, and the method further includes receiving at least a portion of the sanitizing gas in the connector unit, and flowing at least a portion of the sanitizing gas from the connector unit into the sanitizing chamber.

Example 60: This example includes any or all of the features of example 59, wherein the connector unit is coupled or fluidly coupled to a medical device.

Example 61: This example includes any or all of the features of example 59, wherein the connector unit is fluidly coupled to one end of a medical device hose, and the method further comprise flowing at least a portion of the sanitizing gas from the connector unit into the medical device hose.

Example 62: This example includes any or all of the features of example 59, wherein: the connector unit includes a first connector fluidly coupled with the sanitizing gas generator; the connector unit includes a second connector coupled or fluidly coupled with a medical device; the connector unit includes a third connector fluidly coupled to a proximal end of a medical device hose; and a distal end of the medical device hose is fluidly coupled with the sanitizing chamber.

Example 63: This example includes any or all of the features of example 59, wherein: the connector unit includes a first connector fluidly coupled with the sanitizing gas generator; the connector unit includes a second connector coupled or fluidly coupled with a distal end of a medical device hose; the connector unit includes a third connector fluidly coupled to the sanitizing chamber; and a proximal end of the medical device hose is fluidly coupled to a medical device.

Example 64: This example includes any or all of the features of example 62 or example 63, wherein the medical device is a continuous positive airway pressure (CPAP) device and the medical device hose is a CPAP hose.

Example 65: This example includes any or all of the features of any one of examples 62 to 64, wherein: the first connector includes a first opening; the second connector includes a second opening; the third connector includes a third opening; the connector unit further includes a first passageway, the first passageway having a first proximal end and at least a first distal end; and the method includes flowing at least a portion of the sanitizing gas through the first passageway.

Example 66: This example includes any or all of the features of example 65, wherein: the first proximal end of the first passageway is defined at least in part by the first opening; and the first distal end is oriented towards the second connector or the third connector.

Example 67: This example includes any or all of the features of example 65, wherein: the proximal end of the first passageway is defined at least in part by the first opening; the first passageway further includes a second distal end; the first distal end is oriented towards the second opening; and the second distal end is oriented towards the third connector.

Example 68: This example includes any or all of the features of any one of examples 65 to 67, wherein the second connector and the third connector are fluidly coupled by a second passageway, and the method further includes flowing at least a portion of the sanitizing gas within the second passageway.

Example 69: This example includes any or all of the features of example 68, wherein material of a sidewall of the first passageway is at least partially disposed within the second passageway.

Example 70: This example includes any or all of the features of example 65 or 66, wherein: the second connector and the third connector are fluidly coupled by a second passageway; the connector unit includes a fourth connector including a fourth opening; the connector unit includes a third passageway including a second proximal end and a third distal end; and the method further includes flowing at least a portion of the ozone gas through the third passageway.

Example 71: This example includes any or all of the features of example 70, wherein: the second proximal end includes the fourth opening; and the third distal end is oriented towards the second connector or the third connector.

Example 72: This example includes any or all of the features of example 53, wherein: the filter is a filter cartridge including a shell and a filter media housed within the shell; the shell includes a filter inlet configured to fluidly couple to the at least one exhaust port; the shell further includes a filter outlet; and the method further includes converting at least a portion of the sanitizing gas to breathable gas with the filter media.

Example 73: This example includes any or all of the features of example 72, wherein the sanitizing gas is ozone and the breathable gas is oxygen.

Example 74: This example includes any or all of the features of example 72 or 73, wherein the filter cartridge further includes a filter inlet seal disposed around the filter inlet, and the method further includes forming a seal around the at least one exhaust port with the filter inlet seal.

Example 75: This example includes any or all of the features of example 74, wherein the filter inlet seal includes a peripheral surface and a flange that extends at an angle from the peripheral surface.

Example 76: This example includes any or all of the features of example 72 or 73, wherein: the base further includes a filter tray that is configured to receive the filter cartridge; the filter tray is movable between an open and a closed position; and when the filter cartridge is in the filter tray and the filter tray is in the closed position, the filter inlet is disposed proximate the at least one exhaust port.

Example 77: This example includes any or all of the features of example 76, wherein: the filter further includes a filter inlet seal disposed around the filter inlet; and the method further includes forming a seal around the at least one exhaust port with the filter inlet seal when the filter cartridge is in the filter tray and the filter tray is in the closed position.

Example 78: This example includes any or all of the features of example 77, wherein the filter inlet seal includes a peripheral surface and a flange that extends at an angle from the peripheral surface.

Example 79: This example includes any or all of the features of any one of examples 72 to 78, wherein the secondary fan or pump is disposed downstream of the filter outlet.

Example 80: This example includes any or all of the features of any one of examples 50 to 79, wherein the sanitizing chamber includes a bottom and at least one side, and the method further includes positioning, with at least one standoff, a component of a medical device relative to the bottom, the at least one side, or a combination thereof.

Example 81: This example includes any or all of the features of any one of examples 50 to 80, wherein the method further includes: monitoring, with at least one sensor, a condition of the system and outputting a sensor signal indicative of the monitored condition to a controller; and with the controller, permitting or preventing generation of the sanitizing gas by the sanitizing gas generator based at least in part on the sensor signal.

Example 82: This example includes any or all of the features of example 81, wherein the at least one sensor includes: a lid detection sensor configured to detect a position of a lid of the system; a hose detection sensor configured to detect a presence of a hose or plug within a receptacle of the system; a leakage sensor configured to detect leakage of sanitizing gas from the system; a tray position sensor configured to detect a position of a filter tray of the system; a filter detection sensor configured to detect a presence of a filter of the system; a usage sensor configured to detect use of a medical device coupled to the system; or a combination of two or more thereof.

Example 83: This example includes any or all of the features of any one of examples 51 and 72 to 79, further including: monitoring for the filter with at least one filter detection sensor and outputting a filter detection signal; and determining, with a controller, whether the filter is an authorized filter based at least in part on the filter detection signal.

Example 84: This example includes any or all of the features of example 83, wherein when it is determined that the filter is an unauthorized filter, the method further includes preventing or disabling generation of the sanitizing gas by the sanitizing gas generator with the controller.

Example 85: This example includes any or all of the features of any one of examples 51 and 72-79, wherein the method further includes: monitoring for the filter with at least one filter detection sensor and outputting a filter detection signal; and determining, with a controller, whether the filter is present based at least in part on the filter detection signal.

Example 86: This example includes any or all of the features of example 85, wherein when it is determined that the filter is not present, the method further includes preventing or disabling generation of the sanitizing gas by the sanitizing gas generator with the controller.

Example 87: This example includes any or all of the features of any one of examples 51 and 72 to 79, wherein the method further includes: monitoring for a presence of the sanitizing gas downstream of the filter with a sanitizing gas sensor and outputting a filter efficacy signal (FES); and determining, with a controller, whether sanitizing gas is present downstream of the filter based at least in part on the FES.

Example 88: This example includes any or all of the features of example 87, wherein when it is determined that sanitizing gas is present downstream of the filter, the method further includes preventing or disabling generation of the sanitizing gas by the sanitizing gas generator with the controller.

Example 89: This example includes any or all of the features of example 87, further including, with the controller: determining a concentration of the sanitizing gas downstream of the filter based at least in part on the FES; and preventing or disabling generation of the sanitizing gas by the sanitizing gas generator when it is determined when it is determined that the concentration of the sanitizing gas downstream of the filter is greater than or equal to a threshold concentration.

Example 90: This example includes any or all of the features of any one of examples 76 to 79, further including: monitoring a position of the filter tray with a tray position sensor and outputting a tray position signal; and determining, with a controller, whether the filter tray is in the open position or the closed position based at least in part on the tray position signal.

Example 91: This example includes any or all of the features of example 90, wherein when it is determined that the filter tray is in the open position, the method further includes preventing or disabling generation of the sanitizing gas by the sanitizing gas generator with the controller.

Example 92: This example includes any or all of the features of example 81, wherein the base further includes a lid that is movable between an open and a closed position, and the method further includes: monitoring a position of the lid with a lid detection sensor and outputting a lid detection signal; and determining, with a controller, whether the lid is in the open position or the closed position based at least in part on the lid position signal.

Example 93: This example includes any or all of the features of example 92, wherein when it is determined that the lid is in the open position, the method further includes preventing or disabling generation of the sanitizing gas by the sanitizing gas generator with the controller.

Example 94: This example includes any or all of the features of example 81, wherein: the monitoring includes monitoring for contact of a component of medical device with skin of a user with skin contact sensor, and outputting a skin contact signal; and the method further includes determining, with the controller, whether the component of the medical device is in contact with skin of the user based at least in part on the skin contact signal.

Example 95: This example includes any or all of the features of example 94, wherein the controller prevents generation of the sanitizing gas by the sanitizing gas generator when it is determined that the component of the medical device is in contact with skin of the user.

Example 96: According to this example there is provided a connector unit for a medical device, including: a first connector; a second connector; a third connector; a first passageway including a first proximal end and at least a first distal end, the first passageway including a first inlet including a first opening in the first connector; a second passageway extending between a second opening in the second connector and a third opening in the third connector; wherein the first passageway is configured to permit sanitizing gas to flow there through at a flow volume ranging from about 1 to about 2 liters per minute (LPM) at a flow velocity in a range of about 14 to about 60 meters/second (m/s).

Example 97: This example includes any or all of the features of example 96, wherein the first passageway is configured to permit sanitizing gas to flow at a flow volume ranging from about 1.2 to about 1.5 liters per minute (LPM) at a flow velocity in a range of about 17 to about 50 meters/second (m/s).

Example 98: This example includes any or all of the features of example 95 or 96, wherein the first distal end is oriented towards the third connector.

Example 99: This example includes any or all of the features of example 95 or 96, wherein the first passageway further includes a second distal end.

Example 100: This example includes any or all of the features of example 99, wherein the first distal end is oriented towards the third connector and the second distal end is oriented towards the second connector.

Example 101: This example includes any or all of the features of any one of examples 96 to 100, wherein the first connector is configured to fluidly couple to an ozone distribution line.

Example 102: This example includes any or all of the features of any one of examples 96 to 101, wherein the second connector is configured to fluidly couple to the medical device.

Example 103: This example includes any or all of the features of example 102, wherein the medical device is a continuous positive airway pressure (CPAP) device.

Example 104: This example includes any or all of the features of any one of examples 96 to 103, wherein the third connector is configured to fluidly couple to a proximal end of medical device hose.

Example 105: This example includes any or all of the features of example 104, wherein the medical device hose is a continuous positive airway pressure (CPAP) hose.

Example 106: This example includes any or all of the features of any one of examples 96 to 101, wherein the second connector is configured to fluidly couple to a distal end of a medical device hose.

Example 107: This example includes any or all of the features of example 106, wherein the medical device hose is a continuous positive airway pressure (CPAP) hose.

Example 108: This example includes any or all of the features of examples 96 to 101, 106, and 107, wherein the third connector is configured to couple with a base including a sanitizing chamber.

Example 109: This example includes any or all of the features of example 96, further including a fourth connector and a third passageway including a second proximal end and a second distal end.

Example 110: This example includes any or all of the features of example 109, wherein the first distal end is oriented towards the third connector and the second distal end is oriented towards the second connector.

Example 111: This example includes any or all of the features of example 109 or 110, wherein the first connector is configured to fluidly couple to an ozone distribution line.

Example 112: This example includes any or all of the features of example 109 or 110, wherein the second connector is configured to fluidly couple to the medical device.

Example 113: This example includes any or all of the features of example 112, wherein the medical device is a continuous positive airway pressure (CPAP) device and the medical device hose is a CPAP hose.

Example 114: This example includes any or all of the features of example 109 or 110, wherein the third connector is configured to fluidly couple to a proximal end of medical device hose.

Example 115: This example includes any or all of the features of example 109 or 110, wherein the second connector is configured to fluidly couple to a distal end of a medical device hose.

Example 116: This example includes any or all of the features of example 115, wherein the medical device hose is a continuous positive airway pressure (CPAP) hose.

Example 117: According to this example there is provided a filter for a sanitizing system, including: a filter shell including a top, bottom, front, back, a first side, and a second side; a filter media housed within the filter shell; at least one inlet opening positioned proximate the top of the filter shell, the at least one inlet opening configured to permit a gas inflow; at least one outlet opening positioned proximate the bottom of the filter shell, the at least one outlet opening configured to permit a gas outflow; and an inlet seal disposed around the at least one inlet opening.

Example 118: This example includes any or all of the features of example 117, wherein the filter has a first width W1 proximate the top of the filter and a second width proximate the bottom of the filter, wherein W1 differs from W2.

Example 119: This example includes any or all of the features of example 118, wherein W2 is less than W1.

Example 120: This example includes any or all of the features of any one of examples 117 to 119, further including a shoulder between the top of the filter and at least one of the front, first side, second side, and back of the filter.

Example 121: This example includes any or all of the features of example 120, wherein: the top of the filter includes a first peripheral edge; the shell includes a second peripheral edge that extends around the front, first side, second side, and back of the filter; and the shoulder is defined at least in part by a portion of the first peripheral edge that extends past one or more than one of the top of the filter and at least one of the front, first side, second side, and back of the filter.

Example 122: This example includes any or all of the features of any one of examples 117 to 121, wherein the at least one filter outlet opening includes a plurality of slots.

Example 123: This example includes any or all of the features of example 122, wherein the plurality of slots are formed in one or a combination of the back of the filter, the front of the filter, or the bottom of the filter.

Example 124: This example includes any or all of the features of example 122, wherein the slots are defined at least in part by teeth in the lower part of a wall of the back and bottom of the filter.

Example 125: This example includes any or all of the features of examples 117 to 124, wherein the filter shell includes a first piece, wherein the first piece forms a first part of the top, bottom, front, first side, second side, and back of the filter, and the second piece forms a second part of the top, bottom, front, first side, second side, and back of the filter, and the first and second parts are coupled together.

Example 126: This example includes any or all of the features of example 125, wherein the first and second parts are coupled by an interference fit connection, press fit connection, at least one mechanical fastener, an adhesive, or a combination thereof.

Example 127: This example includes any or all of the features of example 125, wherein: the first piece includes at least one finger that extends from the first part of the first side, second side, or both the first and second sides; the second piece includes at least one recess configured to receive the at least one finger; and the first and second pieces are coupled together at least in part by mechanical engagement of the at least one finger with the at least one recess.

Example 128: This example includes any or all of the features of any one of examples 117 to 127, further including communications circuitry, wherein the communications circuitry is configured to communicate with a controller via wired communication, wireless communication, or a combination thereof.

Example 129: This example includes any or all of the features of example 129, wherein the communication circuitry is configured to transmit a filter identifier to the controller.

Example 130: This example includes any or all of the features of example 131, wherein the filter identifier is indicative of whether the filter is an authorized filter.

Example 131: This example includes any or all of the features of

As used herein, the term "about" when used in reference to a value or a range means +/−5% of the value or the end points of the range.

As used herein, the term "fluidly coupled" when used in reference to two or more components means that a gas may flow between the indicated components, either directly or indirectly. In contrast, the term "coupled" when used in reference to two or more components means that the indicated components may are physically coupled to one another, either directly or through or more intervening components. Components that are coupled to one another may or may not also be fluidly coupled to one another.

The terms and expressions which have been employed herein are used as terms of description and not of limitation, and there is no intention, in the use of such terms and expressions, of excluding any equivalents of the features shown and described (or portions thereof), and it is recognized that various modifications are possible within the

What is claimed, is:

1. A sanitization system, comprising:
   a lid configured to transition between an open lid position and a closed lid position;
   a base comprising a sanitizing chamber, the sanitizing chamber comprising an opening and at least one exhaust port, wherein the lid is configured to extend across the opening when the lid is in the closed position;
   a sanitizing gas generator configured to supply a sanitizing gas and to fluidly couple to the sanitizing chamber;
   a primary fan or pump configured to push or draw at least a portion of said sanitizing gas from the sanitizing gas generator to the sanitizing chamber; and
   a secondary fan or pump configured to push or draw gas within the sanitizing chamber through the at least one exhaust port and outside of the sanitizing chamber when the lid is in the closed lid position;
   wherein:
   the base further comprises a filter tray that is configured to receive a filter therein, the filter comprising a filter inlet;
   the filter tray is movable between an open tray position and a closed tray position; and
   in the closed tray position, the filter tray is configured to position the filter such that the filter inlet is in fluid communication with the at least one exhaust port.

2. The sanitization system of claim 1, further comprising said filter.

3. The sanitization system of claim 2, wherein the filter is a filter cartridge comprising a shell and a filter media housed within the shell, the shell comprising said filter inlet and a filter outlet.

4. The sanitization system of claim 3, wherein when said filter cartridge is received by said filter tray, the secondary fan or pump is located upstream of said filter inlet.

5. The sanitization system of claim 3, wherein when said filter cartridge is received by said filter tray, the secondary fan or pump is located downstream of said filter outlet.

6. The sanitization system of claim 2, wherein when said filter is received by said filter tray, the secondary fan or pump is located upstream of said filter.

7. The sanitization system of claim 2, wherein when said filter is received by said filter tray, the secondary fan or pump is located downstream of said filter.

8. The sanitization system of claim 7, wherein the secondary fan or pump is configured draw sanitizing gas through said filter.

9. The sanitization system of claim 2, wherein said filter cartridge comprises a filter inlet seal disposed around said inlet.

10. The sanitization system of claim 9, wherein the filter inlet seal comprises a peripheral surface and a flange that extends at an angle from the peripheral surface.

11. The sanitization system of claim 1, wherein said sanitizing gas generator, said primary fan or pump, and said secondary fan or pump are housed within said base.

12. The sanitization system of claim 1, wherein the filter comprises a filter media that is configured to convert the sanitizing gas to a breathable gas.

13. The sanitization system of claim 12, wherein the sanitizing gas is ozone and the breathable gas is oxygen.

14. The sanitization system of claim 1, further comprising a controller and at least one sensor, wherein the at least one sensor is configured to monitor a condition of the system and to output a sensor signal indicative of the monitored condition to the controller, and the controller is configured to permit or prevent execution of a sanitizing operation with said system based at least in part on said sensor signal.

15. The sanitization system of claim 14, wherein the at least one sensor includes:
   a lid detection sensor configured to detect a position of the lid of said sanitizing chamber;
   a tray position sensor configured to detect a position of the filter tray;
   a filter detection sensor configured to detect the filter of said system; or
   a combination of two or more thereof.

16. The sanitization system of claim 15, wherein:
   the at least one sensor comprises a filter detection sensor configured to detect said filter and to output a filter detection signal;
   the controller is configured to determine whether said filter is an authorized filter based at least in part on said filter detection signal; and
   said controller is configured to permit, prevent, or discontinue execution of a sanitizing operation by said sanitization system based at least in part on said filter detection signal.

17. The sanitization system of claim 16, wherein said filter comprises communications circuitry, and said filter detection sensor is configured to produce said filter detection signal based on communication with said communications circuitry.

18. The sanitization system of claim 17, wherein said communications circuitry is configured to wirelessly communicate with said filter detection sensor.

19. The sanitization system of claim 15, wherein:
   the at least one sensor includes a tray position sensor configured to detect a position of said filter tray and output a filter tray detection signal;
   the controller is configured to detect a position of said filter tray based at least in part on said filter tray detection signal; and
   said controller is configured to permit, prevent or discontinue execution of a sanitizing cycle by said sanitization system based at least in part on the detected position of said filter tray.

* * * * *